US011746098B2

(12) United States Patent
Cullen et al.

(10) Patent No.: US 11,746,098 B2
(45) Date of Patent: Sep. 5, 2023

(54) PROTEASOME ACTIVITY ENHANCING COMPOUNDS

(71) Applicant: Proteostasis Therapeutics, Inc., Boston, MA (US)

(72) Inventors: Matthew Cullen, Braintree, MA (US); Sheila Hauck, Lincoln, MA (US); Megan Foley, Somerville, MA (US); Bradley Tait, North Andover, MA (US); Markus Haeberlein, Wellesley, MA (US)

(73) Assignee: Proteostasis Therapeutics, Inc., Boston, MA (US)

( * ) Notice: Subject to any disclaimer, the term of this patent is extended or adjusted under 35 U.S.C. 154(b) by 95 days.

(21) Appl. No.: 17/133,362

(22) Filed: Dec. 23, 2020

(65) Prior Publication Data

US 2021/0188802 A1 Jun. 24, 2021

Related U.S. Application Data

(63) Continuation of application No. PCT/US2019/039562, filed on Jun. 27, 2019.

(60) Provisional application No. 62/690,554, filed on Jun. 27, 2018.

(51) Int. Cl.
C07D 401/06 (2006.01)
C07D 207/333 (2006.01)
C07D 207/335 (2006.01)
C07D 403/06 (2006.01)
C07D 403/12 (2006.01)
C07D 403/14 (2006.01)
C07D 405/12 (2006.01)

(52) U.S. Cl.
CPC ....... C07D 401/06 (2013.01); C07D 207/333 (2013.01); C07D 207/335 (2013.01); C07D 403/06 (2013.01); C07D 403/12 (2013.01); C07D 403/14 (2013.01); C07D 405/12 (2013.01)

(58) Field of Classification Search
CPC .............. C07D 207/335; C07D 401/06; C07D 401/14; C07D 403/12; A61K 31/4025; A61K 31/40
See application file for complete search history.

(56) References Cited

U.S. PATENT DOCUMENTS 3,706,750 A 12/1972 Urberto et al.

FOREIGN PATENT DOCUMENTS

| CN | 104478780 A * | 4/2015 |
| GB | 1142508 A | 2/1969 |
| WO | 2011094545 A2 | 8/2011 |
| WO | 2012078902 A2 | 6/2012 |
| WO | 2012078909 A1 | 6/2012 |
| WO | 2012154880 A1 | 11/2012 |
| WO | 2012154967 A1 | 11/2012 |
| WO | 2013112651 A2 | 8/2013 |
| WO | 2013112699 A2 | 8/2013 |
| WO | 2013112706 A1 | 8/2013 |
| WO | 2014116228 A1 | 7/2014 |
| WO | 2014210159 A1 | 12/2014 |
| WO | 2015073528 A1 | 5/2015 |
| WO | 2015138909 A1 | 9/2015 |
| WO | 2015138934 A1 | 9/2015 |
| WO | 2015196071 A1 | 12/2015 |
| WO | 2016105468 A1 | 6/2016 |
| WO | 2016105477 A1 | 6/2016 |
| WO | 2016105484 A1 | 6/2016 |
| WO | 2016105485 A2 | 6/2016 |
| WO | 2016115090 A1 | 7/2016 |
| WO | 2017019589 A1 | 2/2017 |
| WO | 2017040606 A1 | 3/2017 |
| WO | 2017062581 A1 | 4/2017 |
| WO | 2017112853 A1 | 6/2017 |
| WO | 2017177124 A1 | 10/2017 |
| WO | 2017196843 A1 | 11/2017 |
| WO | 2017223188 A1 | 12/2017 |
| WO | 2018081377 A1 | 5/2018 |
| WO | 2018081378 A1 | 5/2018 |
| WO | 2018081381 A1 | 5/2018 |
| WO | 2018201126 A1 | 11/2018 |
| WO | 2019071078 A1 | 4/2019 |

OTHER PUBLICATIONS

Bundgaard, Design of Prodrugs, p. 1, 1985.*
Silverman, Prodrugs and Drug Delivery Systems, The Organic Chemistry of Drug Design and Drug Action, pp. 352-399, 1992.*
Banker et al., Prodrugs, Modern Pharmaceutics, Third Edition, Revised and Expanded, pp. 451 and 596 (1996).*
Wolff, Some consideration for prodrug design, Burger's Medicinal Chemistry and Drug Discovery, 5th Edition, vol. 1: Principles and Practice, pp. 975-977, 1995.*
Worsch et al., Separation of Enantiomers by Clathrate Formation, Topics in Current Chemistry, vol. 140, pp. 23-41, 1987.*
Simone, Oncology: Introduction, Cecil Textbook of Medicine, 20th Edition, vol. 1, pp. 1004-1010, 1996.*
Acute Leukemia, Merck Manual (Online Edition) 6 pages, pp. 1-6 (2013).*
Pearce et al., Failure modes in anticancer drug discovery and development, Cancer Drug Design and Discovery Edited by Stephen Neidle, Chapter 18, pp. 424-435 (2008).*
Gura et al., Systems for identifying new drugs are often faulty, Science, 278:1041-1042, 1997.*
Johnson et al., Relationships between drug activity in NCI preclinical in vitro and in vivo models and early clinical trials, British Journal of Cancer, 84(10):1424-1431, 2001.*
Damasio, Alzheimer's Disease and related dementias, Cecil Textbook of Medicine, 20th Edition, vol. 2, pp. 1992-1996, 1996.*

(Continued)

Primary Examiner — Deepak R Rao
(74) Attorney, Agent, or Firm — Armstrong Teasdale LLP

(57) ABSTRACT

The present invention is directed to compounds that inhibit Usp14, compositions thereof, and methods for the treatment of a condition associated with a dysfunction in proteostasis.

25 Claims, No Drawings

(56) References Cited

OTHER PUBLICATIONS

Layzer, Degenerative diseases of the nervous system, Cecil Textbook of Medicine, 20th Edition, vol. 2, pp. 2050-2057, 1996.*
Lack et al., Targeting the Binding Function 3 (BF3) Site of the Human Androgen Receptor through Virtual Screening, J. Med. Chem. 54, pp. 8563-8571 (2011).*
Lack et al., CAPLUS Abstract 156:564 (2011).*
Machine Translation of CN 104478780 A, 18 pages (2015).*
Wang et al., Copper-Catalyzed Oxidative Dehydrogenative C(sp)3-H Bond Amination of (cyclo)alkanes using NH-Heterocycles as amine sources, ChemSusChem, 10, pp. 3075-3082 (2017).*
Bocelli et al., "An inhibitor of the proteasomal deubiquitinating enzyme USP14 induces tau elimination in cultured neurons", J. Biol. Chem., 2017, vol. 292, No. 47, pp. 19209-19225.
Carson et al., "Aroyl(aminoacyl)pyrroles, a New Class of Anticonvulsant Agents", J. Med. Chem., 1997, vol. 40, pp. 1578-1584.
Di Santo et al., "Design, Synthesis, and Biological Activities of Pyrrolylethanoneamine Derivatives, a Novel Class of Monoamine Oxidases Inhibitors", J. Med. Chem., 2005, vol. 48, pp. 4220-4223.
Hesabi et al., "Light-induced Reactions of Heteroaryl N-Methylanilinomethyl Ketones: Formation of 3-Heteroaryl-1-phenylazetidin-3-ols", J. Chem. Society, Jan. 1980, vol. 11, pp. 2371-2373.
Database Registry [Online], Chemical Abstracts Service, Feb. 16, 2017, CAS Registry Nos. 2071559-65-2, 2071547-82-3, 2071391-64-3, 2071313-25-0, XP002793590, 2 pages.
Database Registry [Online], Chemical Abstracts Service, Sep. 7, 2011, CAS Registry Nos. 1329566-19-9, 1329566-08-6, 1329448-11-4, 1329393-64-7, 1329393-09-0, 1329334-69-1, SP-002793591, 3 pages.
Database Registry [Online], Chemical Abstracts Service, Sep. 6, 2011, CAS Registry Nos. 1328692-07-4, 1328691-95-7, XP-002793592, 1 page.
Database Registry [Online], Chemical Abstracts Service, Sep. 2, 2011, Database accession No. 1327009-43-7, XP-002793593, 1 page.
Database Registry [Online], Chemical Abstracts Service, Sep. 1, 2011, Database accession No. 1326694-91-0, XP-002793594, 1 page.
International Search Report and Written Opinion, PCT/US2019/039562, dated Nov. 13, 2019, 26 pages.
CAS Registry No. 1981490-43-0, SciFinder, 2023, 2 pages.

* cited by examiner

PROTEASOME ACTIVITY ENHANCING COMPOUNDS

CROSS REFERENCE TO RELATED APPLICATIONS

This application is a continuation of International Application No. PCT/US2019/039562, which was filed Jun. 27, 2019 and published as WO 2020/006269, the disclosure of which is hereby incorporated by reference as if set forth in its entirety. International Application No. PCT/US2019/039562 claims the benefit of priority to U.S. provisional application Ser. No. 62/690,554, filed Jun. 27, 2018, the disclosure of which is hereby incorporated by reference as if set forth in its entirety.

BACKGROUND OF THE INVENTION

Cells normally maintain a balance between protein synthesis, folding, trafficking, aggregation, and degradation, referred to as protein homeostasis, utilizing sensors and networks of pathways [Sitia et al., *Nature* 426: 891-894, 2003; Ron et al., *Nat Rev Mol Cell Biol* 8: 519-529, 2007], The cellular maintenance of protein homeostasis, or proteostasis, refers to controlling the conformation, binding interactions, location and concentration of individual proteins making up the proteome. Protein folding in vivo is accomplished through interactions between the folding polypeptide chain and macromolecular cellular components, including multiple classes of chaperones and folding enzymes, which minimize aggregation [Wiseman et al., *Cell* 131: 809-821, 2007], Whether a given protein folds in a certain cell type depends on the distribution, concentration, and subcellular localization of chaperones, folding enzymes, metabolites and the like [Wiseman et al.]. Human loss of function diseases are often the result of a disruption of normal protein homeostasis, typically caused by a mutation in a given protein that compromises its cellular folding, leading to efficient degradation [Cohen et al., *Nature* 426: 905-909, 2003], Human gain of function diseases are similarly frequently the result of a disruption in protein homeostasis, such as the accumulation of misfolded proteins, leading to protein aggregation [Balch et al. (2008), *Science* 319: 916-919].

The proteasome is a large protein complex of multiple subunits which acts as a protease to degrade misfolded proteins. Most proteasome substrates are targeted for degradation by the covalent attachment of ubiquitin moieties which are recognized by the proteasome [Lee et al. (2010), *Nature* 467(7312): 179-184], Proteins with longer ubiquitn chains tend to have a stronger association with the proteasome than those with smaller chains [Lee et al. (2010); Proctor et al. (2007), *BMC Systems Biology* 1: 17], The length of the ubiquitin chains is modulated, in part, by proteasome-associated deubiquitinating enzymes. One such mammalian deubiquitinating enzyme is Usp14 which has been shown to act as an inhibitor of the proteasome [Lee et al. (2010)].

Both proteasome dysfunction and dysfunction in proteostasis have been implicated in a diverse range of diseases including for example, neurodegenerative disease, metabolic diseases, inflammatory diseases, and cancer. In many such diseases and conditions, the proteasome has decreased ability to degrade misfolded or abnormal proteins, leading to the presence of toxic protein aggregates. In addition, the enhancement of proteasome activity can be therapeutic for any disease characterized by deficient proteasome activity, or deficient activity of other components of the ubiquitin-proteasome pathway including, but not limited to, von Hippel-Lindau disease, spinocerebellar ataxia 1, Angelman syndrome, giant axon neuropathy, inclusion body myopathy with Paget disease of bone and frontotemporal dementia (IBMPFD), and others [Lehman, N. L., (2009), Acta Neuropathologica, 118(3), 329-347; Weihl et al., (2007), Neuromuscular Disorders, 77, 87-87], Enhancing proteasome activity is also therapeutic for diseases in which proteasome substrates are involved and contribute to pathology, but which do not satisfy a strict definition of proteinopathies. For example, numerous oncoproteins are proteasome substrates and their ability to promote cancer can potentially be attenuated by enhancing proteasome activity.

Therefore, there is a need for compounds and pharmaceutical compositions to treat conditions associated with proteostasis dysfunction and/or that provide therapies based on enhancing proteasome activity.

SUMMARY OF THE INVENTION

The present invention is based, in part, on the discovery that compounds of the invention inhibit Usp14. The present invention is directed to compounds encompassed by the Formulae (I), (IIa), (IIb), (IIIa), (IIIb), (IV), (V), (VI), (VII), (VIII), (IX), or (X) or a pharmaceutically acceptable salt, solvate, clathrate or prodrug of any of thereof, compositions thereof, methods for the treatment of a condition associated with a dysfunction in proteostasis, methods for enhancing proteasome activity and methods for treating cancer or tumor.

In one embodiment, the invention is directed to a compound having the Formula (I):

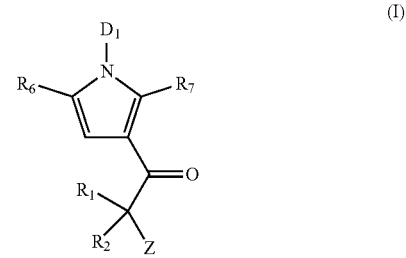

(I)

or a pharmaceutically acceptable salt, solvate, clathrate or prodrug thereof; wherein:

$D_1$ is selected from the group consisting of optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl and optionally substituted naphthyl;

each of $R_1$ and $R_2$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, $CN$, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $OC(O)R_c$, $(C=NR_d)R_c$, optionally substituted heterocyclic and optionally substituted heteroaryl;

each of $R_6$ and $R_7$ is independently selected from the group consisting of optionally substituted $C_1$-$C_4$ alkyl;

Z is selected from the group consisting of $NR_bR_b$, optionally substituted N-heterocyclic, and optionally substituted N-heteroaryl;

each $R_b$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; or two geminal $R_d$ groups are taken together with the nitrogen atom to which they are attached to form an optionally substituted heterocyclic or an optionally substituted heteroaryl; and each n is independently 0, 1 or 2.

In an additional embodiment, the invention is directed to a compound having the Formula (IIa) or (IIb):

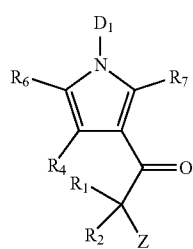

(IIa)

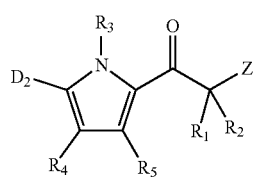

(IIb)

or a pharmaceutically acceptable salt, solvate, clathrate or prodrug thereof; wherein:

$D_2$ is selected from the group consisting of optionally substituted aryl and optionally substituted heteroaryl;

each of $R_1$ and $R_2$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, $N_3$, halo, $OR_c$, $NR_dR_d$, $C(O)OR_c$, $NO_2$, $CN$, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)R_c$, $OC(O)OR_c$, $(C=NR_d)R_c$, optionally substituted heterocyclic and optionally substituted heteroaryl;

each of $R_3$, $R_4$ and $R_5$ is independently selected from the group consisting of hydrogen and optionally substituted $C_1$-$C_{10}$ alkyl;

Z is selected from the group consisting of $NR_bR_b$, optionally substituted N-heterocyclic, and optionally substituted N-heteroaryl;

each $R_b$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; or two geminal $R_d$ groups are taken together with the nitrogen atom to which they are attached to form an optionally substituted heterocyclic or an optionally substituted heteroaryl; and each n is independently 0, 1 or 2.

In yet an additional embodiment, the invention is directed to a compound shown below in Table 1.

In some embodiments, the invention is directed to a compound having the formula (IIIa) or (IIIb):

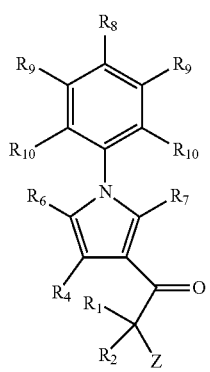

(IIIa)

-continued

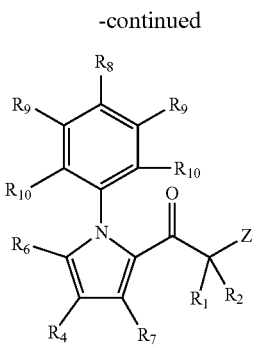

(IIIb)

or a pharmaceutically acceptable salt, solvate, clathrate or prodrug thereof; wherein:

each of $R_1$ and $R_2$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)R_c$, $OC(O)OR_c$, $(C{=}NR_d)R_c$, optionally substituted heterocyclic and optionally substituted heteroaryl;

$R_4$ is independently selected from the group consisting of hydrogen and optionally substituted $C_1$-$C_{10}$ alkyl;

each of $R_6$ and $R_7$ is independently selected from optionally substituted $C_1$-$C_4$ alkyl;

$R_8$ is selected from the group consisting of hydrogen, optionally substituted $C_1$-$C_{10}$ alkyl, optionally substituted $C_1$-$C_{10}$ alkenyl, halo, $OR_c$, $C(O)OR_c$, CN, $S(O)_nR_c$, and $S(O)_nNR_dR_d$;

each $R_9$ is independently selected from the group consisting of hydrogen and halo; each $R_{10}$ is selected from the group consisting of hydrogen and optionally substituted $C_1$-$C_{10}$ alkyl;

Z is selected from the group consisting of $NR_bR_b$, optionally substituted 6-membered N-heteroaryl, and optionally substituted N-heterocyclic;

each $R_b$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; or two geminal $R_d$ groups are taken together with the nitrogen atom to which they are attached to form an optionally substituted heterocyclic or an optionally substituted heteroaryl; and each n is independently 0, 1 or 2.

In some embodiments, the compound has the Formula (IV):

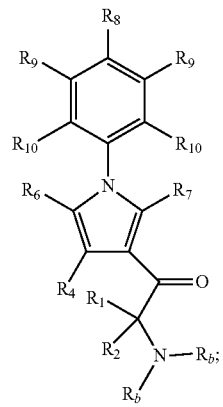

(IV)

or is a pharmaceutically acceptable salt, solvate, clathrate or prodrug thereof; wherein:

each of $R_1$ and $R_2$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)R_c$, $OC(O)OR_c$, $(C{=}NR_d)R_c$, optionally substituted heterocyclic and optionally substituted heteroaryl;

$R_4$ is independently selected from the group consisting of hydrogen and optionally substituted $C_1$-$C_{10}$ alkyl;

each of $R_6$ and $R_7$ is independently selected from optionally substituted $C_1$-$C_4$ alkyl;

$R_8$ is selected from the group consisting of hydrogen, optionally substituted $C_1$-$C_{10}$ alkyl, optionally substituted $C_1$-$C_{10}$ alkenyl, halo, $OR_c$, $C(O)OR_c$, CN, $S(O)_nR_c$, and $S(O)_nNR_dR_d$;

each $R_9$ is independently selected from the group consisting of hydrogen and halo;

each $R_{10}$ is selected from the group consisting of hydrogen and optionally substituted $C_1$-$C_{10}$ alkyl;

each $R_b$ is independently selected from the group consisting of hydrogen, —$CH_3$, —$CH_2CH_2OH$, —$CH_2CHOHCH_2OH$, cyclopropyl, cycloheptyl,

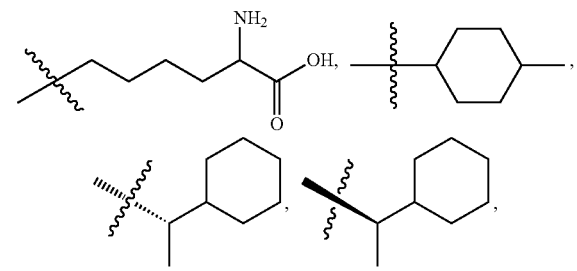

-continued

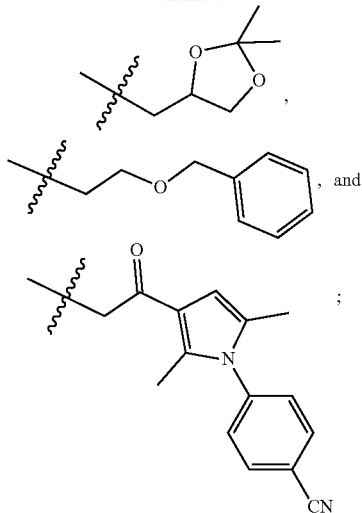

each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; or two geminal $R_d$ groups are taken together with the nitrogen atom to which they are attached to form an optionally substituted heterocyclic or an optionally substituted heteroaryl; and each n is independently 0, 1 or 2.

In some embodiments, the compound has the Formula (V):

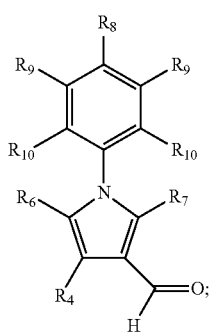

or is a pharmaceutically acceptable salt, solvate, clathrate or prodrug thereof; wherein $R_4$ is hydrogen or optionally substituted $C_1$-$C_4$ alkyl;

$R_6$ and $R_7$ are each independently selected from the group consisting of hydrogen, methyl, ethyl, methoxy, and cyclopropyl;

$R_8$ is selected from the group consisting of hydrogen, optionally substituted $C_1$-$C_{10}$ alkyl, optionally substituted $C_1$-$C_{10}$ alkenyl, halo, $OR_c$, $C(O)OR_c$, CN, $S(O)_nR_c$, and $S(O)_nNR_dR_d$;

each $R_9$ is independently selected from the group consisting of hydrogen and halo; and each $R_{10}$ is selected from the group consisting of hydrogen and optionally substituted $C_1$-$C_{10}$ alkyl.

In some embodiments, the invention is directed to a compound having the Formula (VI):

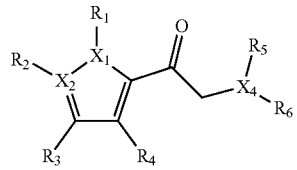

(VI)

or a pharmaceutically acceptable salt, solvate, clathrate or prodrug thereof; wherein:

$X_1$ and $X_2$ are independently carbon or nitrogen, wherein one of $X_1$ or $X_2$ is nitrogen;

$X_4$ is N or $C(R_7)$;

$R_1$ is hydrogen or $C_{1-4}$ alkyl; and $R_2$ is selected from the group consisting of hydrogen, optionally substituted $C_{1-4}$ alkyl, and optionally substituted $C_{3-8}$ cycloalkyl;

each $R_3$ and $R_4$ is independently selected from the group consisting of hydrogen, $C_{1-4}$ alkyl, and $C_{3-8}$ cycloalkyl;

each $R_5$ and $R_6$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl;

or $R_5$ and $R_6$ combine with $X_4$ to form an optionally substituted 5-membered heterocycle, an optionally substituted 6-membered heterocycle, an optionally substituted 5-membered heteroaryl, or an optionally substituted 6-membered heteroaryl; and $R_7$ is hydrogen or $C_{1-4}$ alkyl;

wherein substituents of optionally substituted $R_2$, $R_5$, and $R_6$ are each independently selected from the group consisting of $C_{1-4}$ alkyl optionally substituted with $OR_c$ or $NR_dR_d$; CN; halo; $C_{1-4}$ haloalkyl; $C_{2-4}$ alkynyl; $C_{4-6}$ cycloalkyl; 5-membered heterocyclyl optionally substituted with $C_{1-4}$ alkyl; $OR_c$; $COR_c$; $COOR_c$; $NR_dR_d$; $CONR_dR_d$; $OCONR_dR_d$; $S(O)_nR_c$; and $S(O)_nNR_dR_d$;

wherein each $R_c$ is independently selected from the group consisting of hydrogen, $C_{1-4}$ alkyl optionally substituted with phenyl or $CONR_dR_d$; $C_{1-4}$ haloalkyl; phenyl; and heteroaryl optionally substituted with —$CH_3$ or phenyl; and each $R_d$ is independently selected from the group consisting of hydrogen, $C_{1-4}$ alkyl, $COOC_{1-4}$ alkyl, $C_3$-$C_{12}$ cycloalkyl, and heteroaryl optionally substituted with —$OC_{1-4}$ alkyl;

or two $R_d$ together with nitrogen form a 3-6-membered heterocyclyl;

each n is independently 0, 1 or 2.

In some embodiments, the invention is directed to a compound having the Formula (VII):

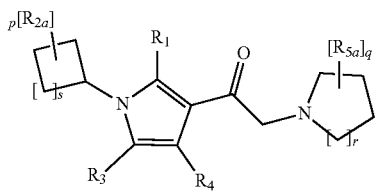

(VII)

or a pharmaceutically acceptable salt, solvate, clathrate or prodrug thereof; wherein:

each $R_1$, $R_3$, and $R_4$ is independently selected from the group consisting of hydrogen, $C_{1-4}$ alkyl, and $C_{3-8}$ cycloalkyl;

each of $R_{2a}$ is selected form the group consisting of hydrogen, $C_{1-4}$ alkyl, $C_{1-4}$ haloalkyl, halo, CN, $CONH_2$, COOH, and COO-benzyl;

each of $R_{5a}$ is selected form the group consisting of hydrogen and OH;

each n is independently 0, 1 or 2;

q is 0, 1 or 2;

r is 1 or 2; and s is 1, 2, or 3.

In some embodiments, the invention is directed to a compound having the Formula (VIII):

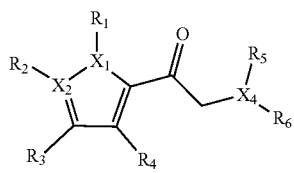

(VIII)

or a pharmaceutically acceptable salt, solvate, clathrate or prodrug thereof; wherein:

$X_1$ and $X_2$ are independently carbon or nitrogen, wherein one of $X_1$ or $X_2$ is nitrogen;

$X_4$ is N or $C(R_7)$;

$R_1$ is selected from the group consisting of optionally substituted $C_{1-4}$ alkyl, optionally substituted $C_{3-8}$ cycloalkyl, and optionally substituted $C_{5-6}$ aryl;

$R_2$ is hydrogen or $C_{1-4}$ alkyl;

each $R_3$ and $R_4$ is independently selected from the group consisting of hydrogen, $C_{1-4}$ alkyl, and $C_{3-8}$ cycloalkyl;

each $R_5$ and $R_6$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl;

or $R_5$ and $R_6$ combine with $X_4$ to form an optionally substituted 5-6-membered heterocycle, or an optionally substituted 5-6-membered heteroaryl; and $R_7$ is hydrogen or $C_{1-4}$ alkyl;

wherein substituents of optionally substituted $R_1$, $R_5$, and $R_6$ are each independently selected from the group consisting of $C_{1-4}$ alkyl optionally substituted with $OR_c$ or $NR_dR_d$; CN; halo; $C_{1-4}$ haloalkyl; $C_{2-4}$ alkynyl; $C_{4-6}$ cycloalkyl; 5-membered heterocyclyl optionally substituted with $C_{1-4}$ alkyl; $OR_c$; $COR_c$; $COOR_c$; $NR_dR_d$; $CONR_dR_d$; $OCONR_dR_d$; $S(O)_nR_c$ and $S(O)_nNR_dR_d$;

wherein each Reis independently selected from the group consisting of hydrogen, $C_{1-4}$ alkyl optionally substituted with phenyl or $CONR_dR_d$; $C_{1-4}$ haloalkyl; phenyl and heteroaryl optionally substituted with —$CH_3$ or phenyl; and each $R_d$ is independently selected from the group consisting of hydrogen, $C_{1-4}$ alkyl, $COOC_{1-4}$ alkyl, $C_3$-$C_{12}$ cycloalkyl, and heteroaryl optionally substituted with —$OC_{1-4}$ alkyl;

or two $R_d$ together with nitrogen form a 3-6-membered heterocyclyl;

each n is independently 0, 1 or 2.

In some embodiments, the invention is directed to a compound having the Formula (IX):

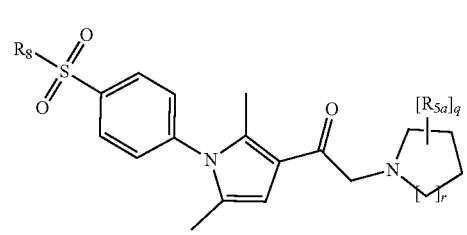

(IX)

or a pharmaceutically acceptable salt, solvate, clathrate or prodrug thereof, wherein:

$R_8$ is $C_{1-4}$alkyl or $NR_{8a}R_{8b}$, wherein $R_{8a}$ is selected from the group consisting of hydrogen, $C_{5-6}$ aryl and 5-6-membered heteroaryl, optionally substituted with —$OC_{1-4}$ alkyl.

each of $R_{5a}$ is selected form the group consisting of hydrogen, $C_{1-4}$ alkyl optionally substituted with $OR_c$ or $NR_dR_d$, halo, $C_{1-4}$ haloalkyl, $OR_c$, $COOR_c$, $NR_dR_d$, $CONR_dR_d$, $OCONR_dR_d$, and $S(O)_nR_c$;

each $R_c$ is independently selected from the group consisting of hydrogen, $C_{1-4}$ alkyl optionally substituted with phenyl or $CONR_dR_d$, $C_{1-4}$ haloalkyl, phenyl, and heteroaryl optionally substituted with —$CH_3$ or phenyl;

each $R_d$ is independently selected from the group consisting of hydrogen, $C_{1-4}$ alkyl, $COOC_{1-4}$ alkyl, $C_3$-$C_{12}$ cycloalkyl, and heteroaryl optionally substituted with —$OCH_3$;

or two $R_d$ together form a heterocyclyl;

each n is independently 0, 1 or 2;

q is 0, 1 or 2; and r is 1 or 2.

In some embodiments, the invention is directed to a compound having the Formula (X):

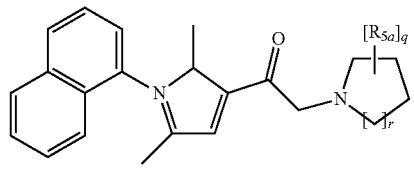

(X)

or a pharmaceutically acceptable salt, solvate, clathrate or prodrug thereof, wherein:

each of $R_{5a}$ is selected form the group consisting of hydrogen, $C_{1-4}$ alkyl optionally substituted with $OR_c$ or $NR_dR_d$, halo, $C_{1-4}$ haloalkyl, $OR_c$, $COOR_c$, $NR_dR_d$, $CONR_dR_d$, $OCONR_dR_d$, and $S(O)_nR_c$;

each $R_c$ is independently selected from the group consisting of hydrogen, $C_{1-4}$ alkyl optionally substituted with phenyl or CONR$_d$R$_d$, C$_{1-4}$ haloalkyl, phenyl, and heteroaryl optionally substituted with —CH$_3$ or phenyl;

each R$_d$ is independently selected from the group consisting of hydrogen, C$_{1-4}$ alkyl, COOC$_{1-4}$ alkyl, C$_3$-C$_{12}$ cycloalkyl, and heteroaryl optionally substituted with —OCH$_3$;

or two R$_d$ together form a heterocyclyl;

each n is independently 0, 1 or 2;

q is 0, 1 or 2; and r is 1 or 2.

In additional embodiments, the invention is directed to a pharmaceutical composition comprising a pharmaceutically acceptable carrier or excipient and a compound of Formula (I), (IIa), (IIb), (IIIa), (IIIb), (IV), (V), (VI), (VII), (VIII), (IX), or (X) or a pharmaceutically acceptable salt, solvate, clathrate or prodrug of any compound of any Formula thereof.

In an additional aspect, the invention is directed to a method of inhibiting the deubiquitination activity of a Usp14 protein comprising contacting the Usp14 protein with an effective amount of a compound of Formula (I), (IIa), (IIb), (IIIa), (IIIb), (IV), (V), (VI), (VII), (VIII), (IX), or (X) or a pharmaceutically acceptable salt, solvate, clathrate or prodrug of any compound of any Formula thereof, in an amount sufficient to inhibit the deubiquitination activity of the Usp14 protein.

In yet another embodiment, the invention is directed to a method of enhancing protein degradation by a proteasome in a cell comprising contacting the cell with an effective amount of a compound of Formula (I), (IIa), (IIb), (IIIa), (IIIb), (IV), (V), (VI), (VII), (VIII), (IX), or (X) or a pharmaceutically acceptable salt, solvate, clathrate or prodrug of any compound of any Formula thereof, in an amount sufficient to enhance protein degradation by the proteasome.

In additional embodiments, the invention encompasses a method of treating a patient suffering from a condition associated with a dysfunction in proteostasis comprising administering to said patient an effective amount of a compound of Formula (I), (IIa), (IIb), (IIIa), (IIIb), (IV), (V), (VI), (VII), (VIII), (IX), or (X) or a pharmaceutically acceptable salt, solvate, clathrate or prodrug of any compound of any Formula thereof.

In another aspect, the invention is directed to a method of enhancing proteasome function in a subject in need thereof comprising administering to said subject an effective amount a compound of Formula (I), (IIa), (IIb), (IIIa), (IIIb), (IV), (V), (VI), (VII), (VIII), (IX), or (X) or a pharmaceutically acceptable salt, solvate, clathrate or prodrug of any compound of any Formula thereof.

In a further embodiment, the invention is directed to a method for treating a condition characterized by deficient proteasome activity or deficiency of other components of the ubiquitin-proteasome pathway in a subject comprising administering to said subject an effective amount of a compound of Formula (I), (IIa), (IIb), (IIIa), (IIIb), (IV), (V), (VI), (VII), (VIII), (IX), or (X) or a pharmaceutically acceptable salt, solvate, clathrate or prodrug of any compound of any Formula thereof.

In yet another embodiment, the invention encompasses a method of treating cancer or a tumor in a subject in need thereof comprising administering to said subject an effective amount of a compound of Formula (I), (IIa), (IIb), (IIIa), (IIIb), (IV), (V), (VI), (VII), (VIII), (IX), or (X) or a pharmaceutically acceptable salt, solvate, clathrate or prodrug of any compound of any Formula thereof.

In a further aspect, the invention is a pharmaceutical composition comprising:

a pharmaceutically acceptable carrier or excipient;

an agent selected from the group consisting of a proteostasis regulator and a pharmacologic chaperone; and a compound of Formula (I), (IIa), (IIb), (IIIa), (IIIb), (IV), (V), (VI), (VII), (VIII), (IX), or (X) or a pharmaceutically acceptable salt, solvate, clathrate or prodrug of any compound of any Formula thereof.

DETAILED DESCRIPTION OF THE INVENTION

A description of preferred embodiments of the invention follows.

As used herein, the words "a" and "an" are meant to include one or more unless otherwise specified. For example, the term "a cell" encompasses both a single cell and a combination of two or more cells.

Compounds of Formula (I)

In some embodiments, the present invention is directed to compounds of Formula (I), or a pharmaceutically acceptable salt, solvate, clathrate or prodrug thereof, pharmaceutical compositions thereof, methods of use thereof in the treatment of conditions associated with a dysfunction in proteostasis, methods of enhancing proteasome activity and methods for treating cancer or a tumor.

In one embodiment, the invention is directed to a compound having the Formula (I):

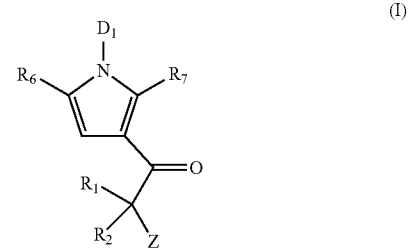

or a pharmaceutically acceptable salt, solvate, clathrate or prodrug thereof, wherein:

D$_1$ is selected from the group consisting of optionally substituted C$_1$-C$_{10}$ alkyl, optionally substituted C$_2$-C$_{10}$ alkenyl, optionally substituted C$_2$-C$_{10}$ alkynyl, optionally substituted C$_3$-C$_{12}$ cycloalkyl, optionally substituted C$_3$-C$_{12}$ cycloalkenyl and optionally substituted naphthyl;

each of R$_1$ and R$_2$ is independently selected from the group consisting of hydrogen, optionally substituted C$_1$-C$_{10}$ alkyl, optionally substituted C$_2$-C$_{10}$ alkenyl, optionally substituted C$_2$-C$_{10}$ alkynyl, optionally substituted C$_3$-C$_{12}$ cycloalkyl, optionally substituted C$_3$-C$_{12}$ cycloalkenyl, optionally substituted aryl, N$_3$, halo, OR$_c$, NR$_d$R$_d$, C(O)OR$_c$, NO$_2$, CN, C(O)R$_c$, C(O)C(O)R$_c$, C(O)NR$_d$R$_d$, NR$_d$C(O)R$_c$, NR$_d$S(O)$_n$R$_c$, N(R$_d$)(COOR$_c$), NR$_d$C(O)C(O)R$_c$, NR$_d$C(O)NR$_d$R$_d$, NR$_d$S(O)$_n$NR$_d$R$_d$, NR$_d$S(O)$_n$R$_c$, S(O)$_n$R$_c$, S(O)$_n$NR$_d$R$_d$, OC(O)OR$_c$, OC(O)R$_c$, (C=NR$_d$)R$_c$, optionally substituted heterocyclic and optionally substituted heteroaryl;

each of R$_6$ and R$_7$ is independently selected from optionally substituted C$_1$-C$_4$ alkyl;

Z is selected from the group consisting of NR$_b$R$_b$, optionally substituted N-heterocyclic, and optionally substituted N-heteroaryl;

each R$_b$ is independently selected from the group consisting of hydrogen, optionally substituted C$_1$-C$_{10}$ alkyl, optionally substituted C$_2$-C$_{10}$ alkenyl, optionally substituted C$_2$-C$_{10}$ alkynyl, optionally substituted C$_1$-C$_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; or two geminal $R_d$ groups are taken together with the nitrogen atom to which they are attached to form an optionally substituted heterocyclic or an optionally substituted heteroaryl; and each n is independently 0, 1 or 2.

In some embodiments, in compounds of Formula (I), substituents of optionally substituted Z, $D_1$, $R_1$, $R_2$, $R_6$, and $R_7$ are each independently selected from the group consisting of $C_{1-4}$ alkyl optionally substituted with $OR_c$ or $NR_dR_d$; CN; halo; $C_{1-4}$ haloalkyl; $C_{2-4}$ alkynyl; $C_{4-6}$ cycloalkyl; 5-membered heterocyclyl optionally substituted with $C_{1-4}$ alkyl; $OR_c$; $COR_c$; $COOR_c$; $NR_dR_d$; $CONR_dR_d$; $OCONR_dR_d$; $S(O)_nR_c$; and $S(O)_nNR_dR_d$;

wherein each $R_c$ is independently selected from the group consisting of hydrogen, $C_{1-4}$ alkyl optionally substituted with phenyl or $CONR_dR_d$; $C_{1-4}$ haloalkyl; phenyl; and heteroaryl optionally substituted with —$CH_3$ or phenyl; and each $R_d$ is independently selected from the group consisting of hydrogen, $C_{1-4}$ alkyl, $COOC_{1-4}$ alkyl, $C_3$-$C_{12}$ cycloalkyl, and heteroaryl optionally substituted with —$OC_{1-4}$ alkyl;

or two $R_d$ together with nitrogen form a 3-6-membered heterocyclyl;

each n is independently 0, 1 or 2.

In some embodiments, the invention is directed to a compound of Formula (I), wherein $D_1$ is optionally substituted $C_1$-$C_{10}$ alkyl, or a pharmaceutically acceptable salt, solvate, clathrate or prodrug thereof. In some embodiments, $D_1$ is optionally substituted methyl or optionally substituted ethyl. In some embodiments, D1 is —$CH_2CF_3$.

In yet additional embodiments, the invention is directed to a compound of Formula (I), wherein $D_1$ is optionally substituted $C_3$-$C_{12}$ cycloalkyl, or a pharmaceutically acceptable salt, solvate, clathrate or prodrug thereof. In some embodiments, $D_1$ is optionally substituted $C_3$-$C_6$ cycloalkyl. In additional embodiments, $D_1$ is optionally substituted cyclobutyl, optionally substituted cyclopentyl, or optionally substituted cyclohexyl. In certain embodiments, $D_1$ is an optionally substituted cyclohexyl. In some embodiments, the invention is directed to a compound of Formula (I), wherein $D_1$ is optionally substituted naphthyl.

In some embodiments, the invention is directed to a compound of Formula (I), or a pharmaceutically acceptable salt, solvate, clathrate or prodrug thereof, wherein $D_1$ is selected from the group consisting of.

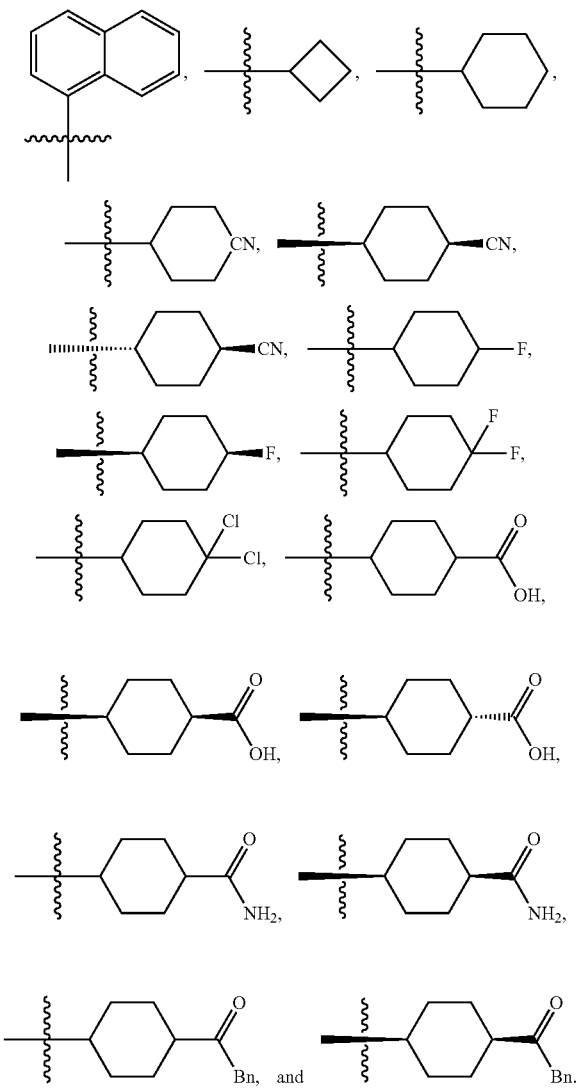

In certain aspects, the invention is directed to a compound of Formula (I), or a pharmaceutically acceptable salt, solvate, clathrate or prodrug thereof, wherein $D_1$ is optionally substituted naphthyl.

In some embodiments, the invention is directed to a compound of Formula (Ia) or Formula (Ib):

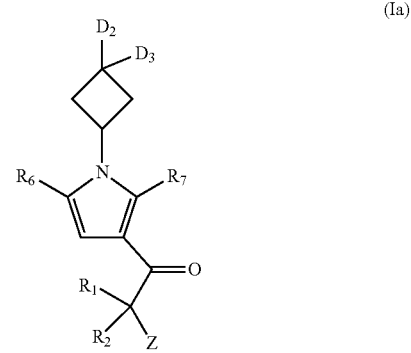

(Ia)

-continued (Ib)

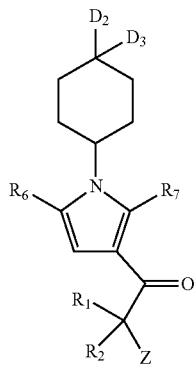

or a pharmaceutically acceptable salt, solvate, clathrate or prodrug thereof;

wherein:

each of $R_1$ and $R_2$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, $N_3$, halo, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $OC(O)R_c$, $(C=NR_d)R_c$, optionally substituted heterocyclic and optionally substituted heteroaryl;

each of $R_6$ and $R_7$ is independently selected from optionally substituted $C_1$-$C_4$ alkyl;

Z is selected from the group consisting of $NR_bR_b$, optionally substituted N-heterocyclic, and optionally substituted N-heteroaryl;

$D_2$ and $D_3$ are each independently selected from the group consisting of hydrogen, CN, fluoro, chloro, —COH, —CONH$_2$, and

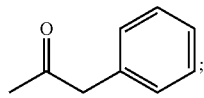

each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; or two geminal $R_d$ groups are taken together with the nitrogen atom to which they are attached to form an optionally substituted heterocyclic or an optionally substituted heteroaryl; and each n is independently 0, 1 or 2.

In some embodiments, in compounds of Formula (Ia) or (Ib), substituents of optionally substituted Z, $D_2$, $D_3$, $R_1$, $R_2$, $R_6$, and $R_7$ are each independently selected from the group consisting of $C_{1-4}$ alkyl optionally substituted with $OR_c$ or $NR_dR_d$; CN; halo; $C_{1-4}$ haloalkyl; $C_{2-4}$ alkynyl; $C_{4-6}$ cycloalkyl; 5-membered heterocyclyl optionally substituted with $C_{1-4}$ alkyl; OR; $COR_c$; $COOR_c$; $NR_dR_d$; $CONR_dR_d$; $OCONR_dR_d$; $S(O)_nR_c$; and $S(O)_nNR_dR_d$;

wherein each $R_c$ is independently selected from the group consisting of hydrogen, $C_{1-4}$ alkyl optionally substituted with phenyl or $CONR_dR_d$; $C_{1-4}$ haloalkyl; phenyl; and heteroaryl optionally substituted with —$CH_3$ or phenyl; and each $R_d$ is independently selected from the group consisting of hydrogen, $C_{1-4}$ alkyl, $COOC_{1-4}$ alkyl, $C_3$-$C_{12}$ cycloalkyl, and heteroaryl optionally substituted with —$OC_{1-4}$ alkyl;

or two $R_d$ together with nitrogen form a 3-6-membered heterocyclyl;

each n is independently 0, 1 or 2.

In yet additional embodiments, the invention is directed to a compound of Formula (I), (Ia), or (Ib), or a pharmaceutically acceptable salt, solvate, clathrate or prodrug thereof, wherein $R_6$ and $R_7$ are each independently selected from methyl and ethyl. In additional aspects, $R_6$ and $R_7$ are each methyl.

In some embodiments, the invention is directed to a compound of Formula (I), (Ia), or (Ib), or a pharmaceutically acceptable salt, solvate, clathrate or prodrug thereof, wherein each of $R_1$ and $R_2$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)R_c$, $OC(O)OR_c$, $(C=NR_d)R_c$, optionally substituted heterocyclic and optionally substituted heteroaryl. In yet additional embodiments, $R_1$ and $R_2$ are each independently selected from hydrogen and optionally substituted $C_1$-$C_{10}$ alkyl. In some aspects, $R_1$ and $R_2$ are each hydrogen.

In yet additional embodiments, the compound has the Formula (I), (Ia), or (Ib), or is a pharmaceutically acceptable salt, solvate, clathrate or prodrug thereof, wherein Z is $NR_bR_b$. In certain aspects, each $R_b$ is independently selected from the group consisting of hydrogen, optionally substituted $C_1$-$C_{10}$ alkyl, and optionally substituted $C_3$-$C_{12}$ cycloalkyl.

In some embodiments, the compound has the Formula (I), (Ia), or (Ib), or is a pharmaceutically acceptable salt, solvate, clathrate or prodrug thereof, wherein Z is an optionally substituted N-heterocyclic. In some aspects, Z is 1-pyrrolidinyl or 1-piperidinyl, each optionally substituted.

In some embodiments, the compound has the Formula (I), (Ia), or (Ib), or a pharmaceutically acceptable salt, solvate, clathrate or prodrug thereof, wherein Z is an optionally substituted 5-membered N-heterocyclic, optionally having an additional heteroatom selected from the group consisting of O, S, and N.

In some embodiments, the compound has the Formula (I), (Ia), or (Ib), or a pharmaceutically acceptable salt, solvate, clathrate or prodrug thereof, wherein Z is an optionally substituted 6-membered N-heterocyclic, optionally having an additional heteroatom selected from the group consisting of O, S, and N.

In additional embodiments, the compound has the Formula (I), (Ia), or (Ib), or is a pharmaceutically acceptable salt, solvate, clathrate or prodrug thereof, wherein Z is an optionally substituted 1-pyrrolidinyl or optionally substituted 1-piperidinyl, $R_6$ and $R_7$ are each methyl and $R_1$ and $R_2$ are each hydrogen.

In some aspects, the compound has the Formula (I), (Ia), or (Ib), or is a pharmaceutically acceptable salt, solvate, clathrate or prodrug thereof, wherein Z is selected from the group consisting of

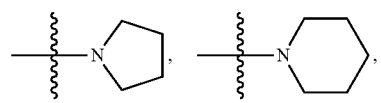

-continued

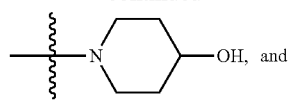

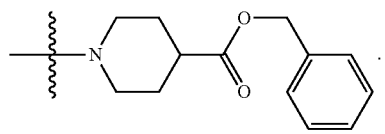

In some embodiments, the compound is selected from among those in the following Table 1:

TABLE 1

| Compound No. | Chemical Structure |
| --- | --- |
| 5 | 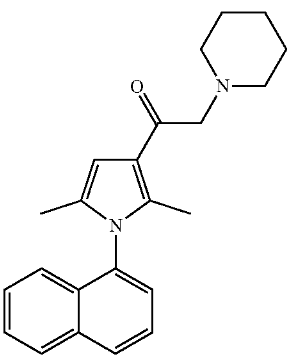 [SMILES: Cc1cc(C(=O)CN2CCCCC2)c(C)n1-c1cccc2ccccc12] |
| 8 | 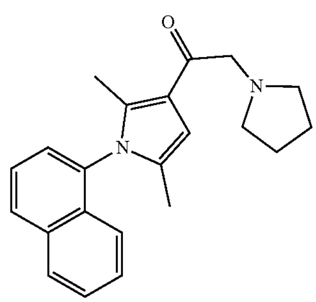 [SMILES: Cc1cc(C(=O)CN2CCCC2)c(C)n1-c1cccc2ccccc12] |
| 9 | 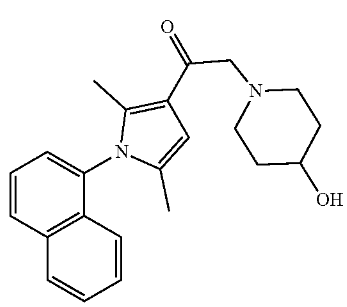 [SMILES: Cc1cc(C(=O)CN2CCC(O)CC2)c(C)n1-c1cccc2ccccc12] |

TABLE 1-continued

| Compound No. | Chemical Structure |
|---|---|
| 32 | 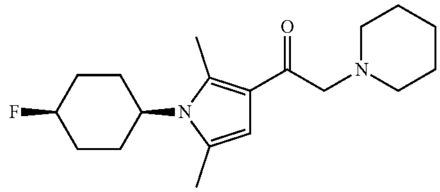 [SMILES: Cc1cc(C(=O)CN2CCCCC2)c(C)n1[C@H]1CC[C@@H](F)CC1] |
| 35 | 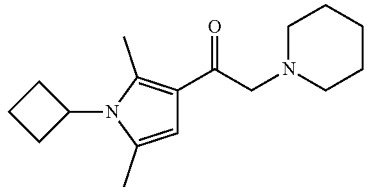 [SMILES: Cc1cc(C(=O)CN2CCCCC2)c(C)n1C1CCC1] |
| 36 | 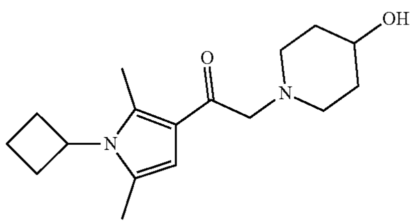 [SMILES: Cc1cc(C(=O)CN2CCC(O)CC2)c(C)n1C1CCC1] |
| 37 | 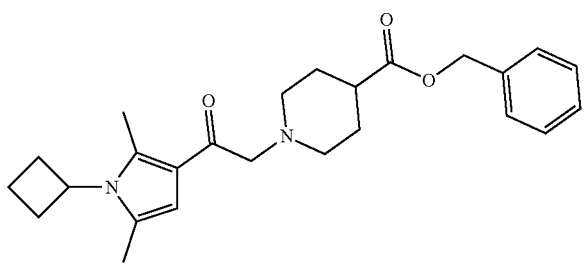 [SMILES: Cc1cc(C(=O)CN2CCC(C(=O)OCc3ccccc3)CC2)c(C)n1C1CCC1] |
| 45 | 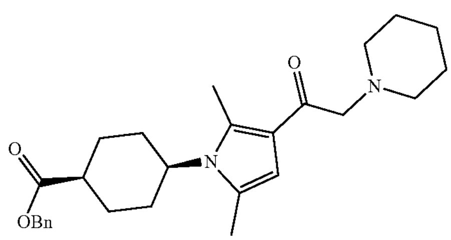 [SMILES: Cc1cc(C(=O)CN2CCCCC2)c(C)n1[C@H]1CC[C@@H](C(=O)OCc2ccccc2)CC1] |
| 46 | 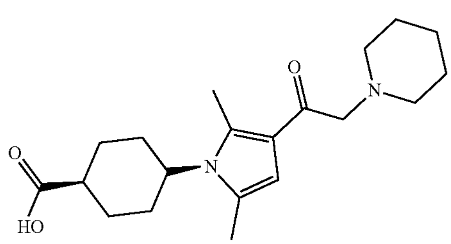 |
| 65 | 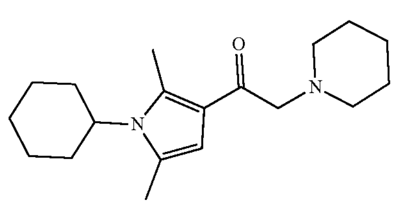 [SMILES: Cc1cc(C(=O)CN2CCCCC2)c(C)n1C1CCCCC1] |

TABLE 1-continued
| Compound No. | Chemical Structure |
|---|---|
| 76 | 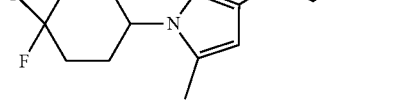 |
| 97 | 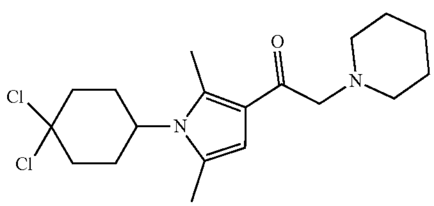 [SMILES: Cc1cc(C(=O)CN2CCCCC2)c(C)n1C1CCC(Cl)(Cl)CC1] |
| 103 | 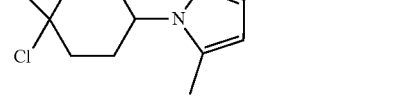 |
| 105 | 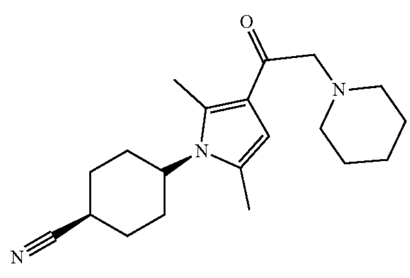 |
| 107 | 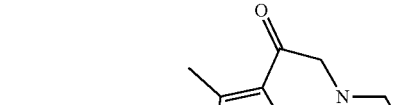 |

TABLE 1-continued
| Compound No. | Chemical Structure |
|---|---|
| 120 | 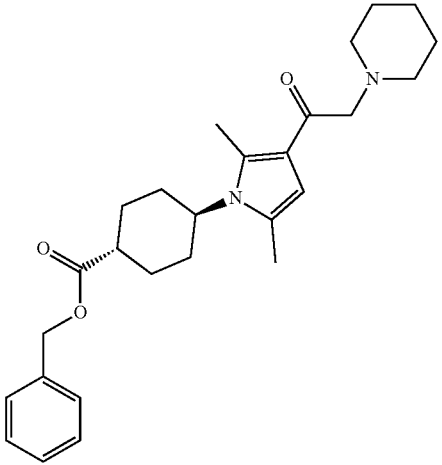 [SMILES: Cc1cc(C(=O)CN2CCCCC2)c(C)n1[C@H]1CC[C@H](C(=O)OCc2ccccc2)CC1] |
| 121 | 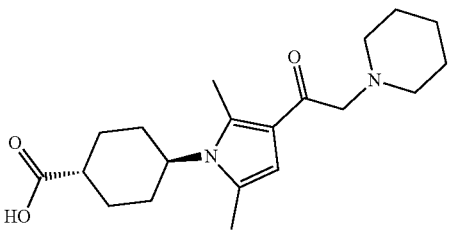 [SMILES: Cc1cc(C(=O)CN2CCCCC2)c(C)n1[C@H]1CC[C@H](C(=O)O)CC1] |
| 122 | 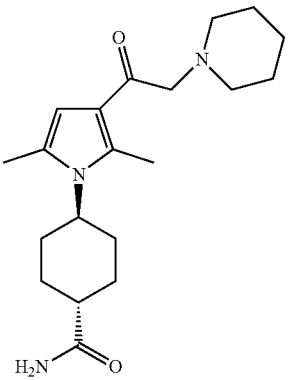 [SMILES: Cc1cc(C(=O)CN2CCCCC2)c(C)n1[C@H]1CC[C@H](C(N)=O)CC1] |
| 143 | 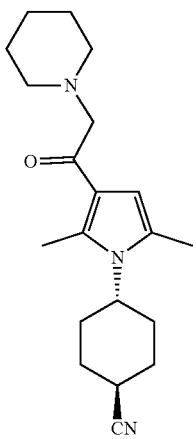 [SMILES: Cc1cc(C(=O)CN2CCCCC2)c(C)n1[C@H]1CC[C@H](C#N)CC1] |

Compounds of Formula (IIa) or (IIb)

In some embodiments, the present invention is directed to compounds of Formula (IIa) or (IIb), or a pharmaceutically acceptable salt, solvate, clathrate or prodrug thereof, pharmaceutical compositions thereof, methods of use thereof in the treatment of conditions associated with a dysfunction in proteostasis, methods of enhancing proteasome activity and methods for treating cancer or a tumor.

The invention additionally encompasses a compound having the Formula (IIa) or (IIb):

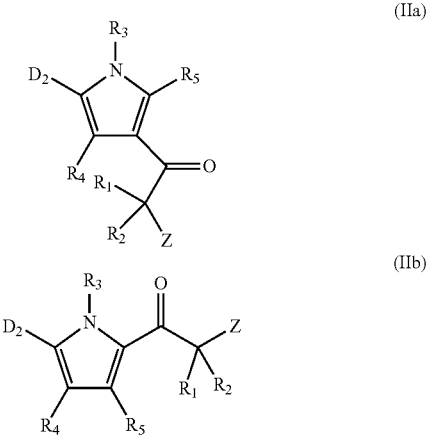

or a pharmaceutically acceptable salt, solvate, clathrate or prodrug thereof; wherein:

$D_2$ is selected from the group consisting of optionally substituted aryl and optionally substituted heteroaryl;

each of $R_1$ and $R_2$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, $N_3$, halo, $OR_c$, $NR_dR_d$, $C(O)OR_c$, $NO_2$, $CN$, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)R_C$, $OC(O)OR_c$, $(C=NR_d)R_c$, optionally substituted heterocyclic and optionally substituted heteroaryl;

each of $R_3$, $R_4$ and $R_5$ is independently selected from the group consisting of hydrogen and optionally substituted $C_1$-$C_{10}$ alkyl;

Z is selected from the group consisting of $NR_bR_b$, optionally substituted N-heterocyclic, and optionally substituted N-heteroaryl;

each $R_b$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; or two geminal $R_d$ groups are taken together with the nitrogen atom to which they are attached to form an optionally substituted heterocyclic or an optionally substituted heteroaryl; and each n is independently 0, 1 or 2.

In some embodiments, in compounds of Formula (IIa) or (IIb), substituents of optionally substituted Z, $D_2$, $R_1$, $R_2$, $R_3$, $R_4$, and $R_5$ are each independently selected from the group consisting of $C_{1-4}$ alkyl optionally substituted with $OR_c$ or $NR_dR_d$; CN; halo; $C_{1-4}$ haloalkyl; $C_{2-4}$ alkynyl; $C_{4-6}$ cycloalkyl; 5-membered heterocyclyl optionally substituted with $C_{1-4}$ alkyl; OR; $COR_c$; $COOR_c$; $NR_dR_d$; $CONR_dR_d$; $OCONR_dR_d$; $S(O)_nR_c$; and $S(O)_nNR_dR_d$;

wherein each $R_c$ is independently selected from the group consisting of hydrogen, $C_{1-4}$ alkyl optionally substituted with phenyl or $CONR_dR_d$; $C_{1-4}$ haloalkyl; phenyl; and heteroaryl optionally substituted with —$CH_3$ or phenyl; and each $R_d$ is independently selected from the group consisting of hydrogen, $C_{1-4}$ alkyl, $COOC_{1-4}$ alkyl, $C_3$-$C_{12}$ cycloalkyl, and heteroaryl optionally substituted with —$OC_{1-4}$ alkyl;

or two $R_d$ together with nitrogen form a 3-6-membered heterocyclyl;

each n is independently 0, 1 or 2.

In some embodiments, the invention is directed to a compound having the Formula (IIa) or (IIb), or a pharmaceutically acceptable salt, solvate, clathrate or prodrug thereof, provided that the compound is not:

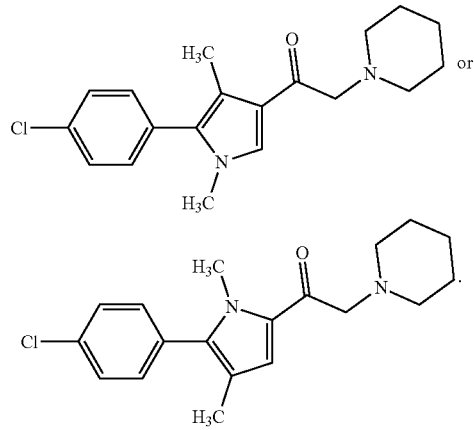

In some embodiments, the invention is directed to a compound of Formula (IIa) or (IIb), or a pharmaceutically acceptable salt, solvate, clathrate or prodrug thereof, wherein $D_2$ is an optionally substituted phenyl.

In some embodiments, the invention is directed to a compound of Formula (IIa) or (IIb), or a pharmaceutically acceptable salt, solvate, clathrate or prodrug thereof, wherein $D_2$ is

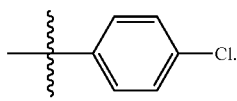 [SMILES: *c1ccc(Cl)cc1]

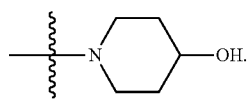

In some embodiments, the invention is directed to a compound of Formula (IIa) or (IIb), or a pharmaceutically acceptable salt, solvate, clathrate or prodrug thereof, wherein each of $R_1$ and $R_2$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $OR_c$, $NR_dR_d$, $C(O)OR_c$, $NO_2$, $CN$, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)R_c$, $OC(O)OR_c$, $(C=NR_d)R_c$, optionally substituted heterocyclic and optionally substituted heteroaryl. In yet additional embodiments, $R_1$ and $R_2$ are each independently selected from hydrogen and optionally substituted $C_1$-$C_{10}$ alkyl. In some embodiments, $R_1$ and $R_2$ are each hydrogen.

In some embodiments, the invention is directed to a compound of Formula (IIa) or (IIb), or a pharmaceutically acceptable salt, solvate, clathrate or prodrug thereof, wherein $R_5$ is hydrogen.

In some embodiments, the invention is directed to a compound of Formula (IIa) or (IIb), or a pharmaceutically acceptable salt, solvate, clathrate or prodrug thereof, wherein $R_3$ and $R_4$ are each independently selected from optionally substituted $C_1$-$C_4$ alkyl. In yet additional embodiments, $R_3$ and $R_4$ are each methyl.

In some embodiments, the invention is directed to a compound of Formula (IIa) or (IIb), or a pharmaceutically acceptable salt, solvate, clathrate or prodrug thereof, wherein Z is $NR_bR_b$.

In some aspects, each $R_b$ is independently selected from the group consisting of hydrogen, optionally substituted $C_1$-$C_{10}$ alkyl, and optionally substituted $C_3$-$C_{12}$ cycloalkyl.

In some embodiments, the invention is directed to a compound of Formula (IIa) or (IIb), or a pharmaceutically acceptable salt, solvate, clathrate or prodrug thereof, wherein Z is optionally substituted N-heterocyclic. In certain aspects, Z is optionally substituted 1-pyrrolidinyl or optionally substituted 1-piperidinyl.

In some embodiments, the invention is directed to a compound of Formula (IIa) or (IIb), or a pharmaceutically acceptable salt, solvate, clathrate or prodrug thereof, wherein Z is an optionally substituted 5-membered N-heterocyclic, optionally having an additional heteroatom selected from the group consisting of O, S, and N.

In some embodiments, the invention is directed to a compound of Formula (IIa) or (IIb), or a pharmaceutically acceptable salt, solvate, clathrate or prodrug thereof, wherein Z is an optionally substituted 6-membered N-heterocyclic, optionally having an additional heteroatom selected from the group consisting of O, S, and N.

In some embodiments, the invention is directed to a compound of Formula (IIa) or (IIb), or a pharmaceutically acceptable salt, solvate, clathrate or prodrug thereof, wherein Z is selected from the group consisting of

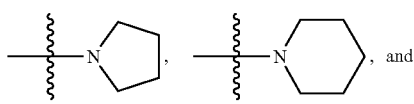

, and

The present invention additionally encompasses the compounds shown below in Table 2.

TABLE 2

| Compound No. | Chemical Structure |
|---|---|
| 92 | ![structure] |
| 94 | ![structure] |
| 95 | ![structure] |

Compounds of Formula (IIIa) or (IIIb)

In some embodiments, the present invention is directed to compounds of Formula (IIIa) or (IIIb), or a pharmaceutically acceptable salt, solvate, clathrate or prodrug thereof, pharmaceutical compositions thereof, methods of use thereof in the treatment of conditions associated with a dysfunction in proteostasis, methods of enhancing proteasome activity and methods for treating cancer or a tumor.

The invention additionally encompasses a compound having the Formula (IIIa) or (IIIb):

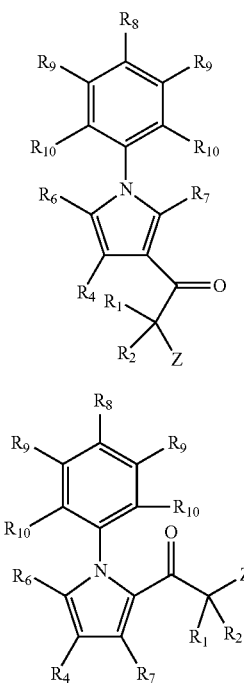

or a pharmaceutically acceptable salt, solvate, clathrate or prodrug thereof, wherein:

each of $R_1$ and $R_2$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)R_c$, $OC(O)OR_c$, $(C=NR_d)R_c$, optionally substituted heterocyclic and optionally substituted heteroaryl;

$R_4$ is independently selected from the group consisting of hydrogen and optionally substituted $C_1$-$C_{10}$ alkyl;

each of $R_6$ and $R_7$ is independently selected from optionally substituted $C_1$-$C_4$ alkyl;

$R_8$ is selected from the group consisting of hydrogen, optionally substituted $C_1$-$C_{10}$ alkyl, optionally substituted $C_1$-$C_{10}$ alkenyl, halo, OR, $C(O)OR_c$, CN, $S(O)_nR_c$, and $S(O)_nNR_dR_d$;

each $R_9$ is independently selected from the group consisting of hydrogen and halo;

each $R_{10}$ is selected from the group consisting of hydrogen and optionally substituted $C_1$-$C_{10}$ alkyl;

Z is selected from the group consisting of $NR_bR_b$, optionally substituted 6-membered N-heteroaryl, and optionally substituted N-heterocyclic;

each $R_b$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; or two geminal $R_d$ groups are taken together with the nitrogen atom to which they are attached to form an optionally substituted heterocyclic or an optionally substituted heteroaryl; and each n is independently 0, 1 or 2.

In some embodiments, in compounds of Formula (IIa) or (IIIb), substituents of optionally substituted Z, $R_1$, $R_2$, $R_3$, $R_4$, $R_5$, $R_6$, $R_7$, $R_8$, $R_9$, and $R_{10}$ are each independently selected from the group consisting of $C_{1-4}$ alkyl optionally substituted with $OR_c$ or $NR_dR_d$; CN; halo; $C_{1-4}$ haloalkyl; $C_{2-4}$ alkynyl; $C_{4-6}$ cycloalkyl; 5-membered heterocyclyl optionally substituted with $C_{1-4}$ alkyl; $OR_c$; $COR_c$; $COOR_c$; $NR_dR_d$; $CONR_dR_d$; $OCONR_dR_d$; $S(O)_nR_c$; and $S(O)_n NR_dR_d$;

wherein each $R_c$ is independently selected from the group consisting of hydrogen, $C_{1-4}$ alkyl optionally substituted with phenyl or $CONR_dR_d$; $C_{1-4}$ haloalkyl; phenyl; and heteroaryl optionally substituted with —$CH_3$ or phenyl; and each $R_d$ is independently selected from the group consisting of hydrogen, $C_{1-4}$ alkyl, $COOC_{1-4}$ alkyl, $C_3$-$C_{12}$ cycloalkyl, and heteroaryl optionally substituted with —$OC_{1-4}$ alkyl;

or two $R_d$ together with nitrogen form a 3-6-membered heterocyclyl;

each n is independently 0, 1 or 2.

In some embodiments, the compound has the Formula (IIa) or (IIb), or is a pharmaceutically acceptable salt, solvate, clathrate or prodrug thereof, wherein $R_1$ and $R_2$ are each independently selected from hydrogen and optionally substituted $C_1$-$C_{10}$ alkyl.

In some embodiments, the compound has the Formula (IIa) or (IIb), or is a pharmaceutically acceptable salt, solvate, clathrate or prodrug thereof, wherein $R_1$ and $R_2$ are each hydrogen.

In some embodiments, the compound has the Formula (IIa) or (IIb), or is a pharmaceutically acceptable salt, solvate, clathrate or prodrug thereof, wherein $R_4$ is hydrogen or $C_1$-$C_4$ alkyl.

In some embodiments, the compound has the Formula (IIa) or (IIb), or is a pharmaceutically acceptable salt, solvate, clathrate or prodrug thereof, wherein $R_4$ is hydrogen or methyl.

In some embodiments, the compound has the Formula (IIa) or (IIb), or is a pharmaceutically acceptable salt, solvate, clathrate or prodrug thereof, wherein $R_6$ and $R_7$ are each independently selected from the group consisting of hydrogen, methyl, ethyl, methoxy, and cyclopropyl.

In some embodiments, the compound has the Formula (IIa) or (IIb), or is a pharmaceutically acceptable salt, solvate, clathrate or prodrug thereof, wherein $R_6$ and $R_7$ are each methyl.

In some embodiments, the compound has the Formula (IIa) or (IIb), or is a pharmaceutically acceptable salt, solvate, clathrate or prodrug thereof, wherein $R_4$, $R_6$, and $R_7$ are each hydrogen.

In some embodiments, the compound has the Formula (IIa) or (IIb), or is a pharmaceutically acceptable salt, solvate, clathrate or prodrug thereof, wherein $R_4$, $R_6$, and $R_7$ are each methyl.

In some embodiments, the compound has the Formula (IIa) or (IIb), or is a pharmaceutically acceptable salt, solvate, clathrate or prodrug thereof, wherein Z is optionally substituted N-heterocyclic.

In some embodiments, the compound has the Formula (IIa) or (IIb), or is a pharmaceutically acceptable salt, solvate, clathrate or prodrug thereof, wherein Z is an optionally substituted 5-membered N-heterocyclic, optionally having an additional heteroatom selected from the group consisting of O, S, and N.

In some embodiments, the compound has the Formula (IIa) or (IIb), or is a pharmaceutically acceptable salt, solvate, clathrate or prodrug thereof, wherein Z is an optionally substituted 6-membered N-heterocyclic, optionally having an additional heteroatom selected from the group consisting of O, S, and N.

In some embodiments, the compound has the Formula (IIa) or (IIb), or is a pharmaceutically acceptable salt, solvate, clathrate or prodrug thereof, wherein Z is 1-pyrrolidinyl or 1-piperidinyl, each optionally substituted.

In some embodiments, the compound has the Formula (IIa) or (IIb), or is a pharmaceutically acceptable salt, solvate, clathrate or prodrug thereof, wherein Z is selected from the group consisting of

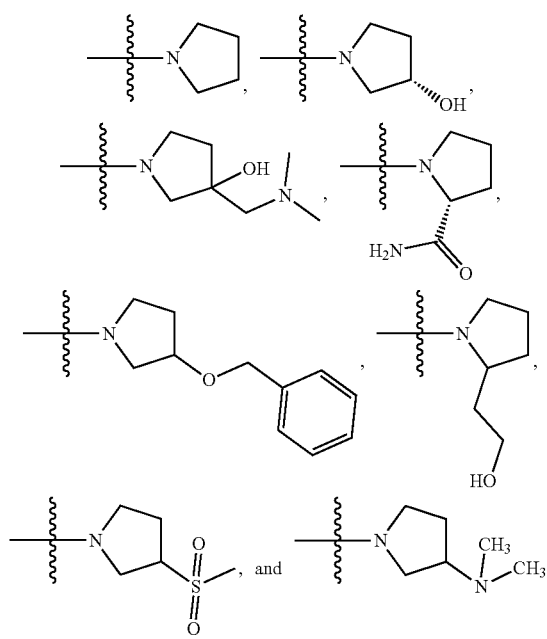

In some embodiments, the compound has the Formula (IIIa) or (IIIb), or is a pharmaceutically acceptable salt, solvate, clathrate or prodrug thereof, wherein Z is selected from the group consisting of

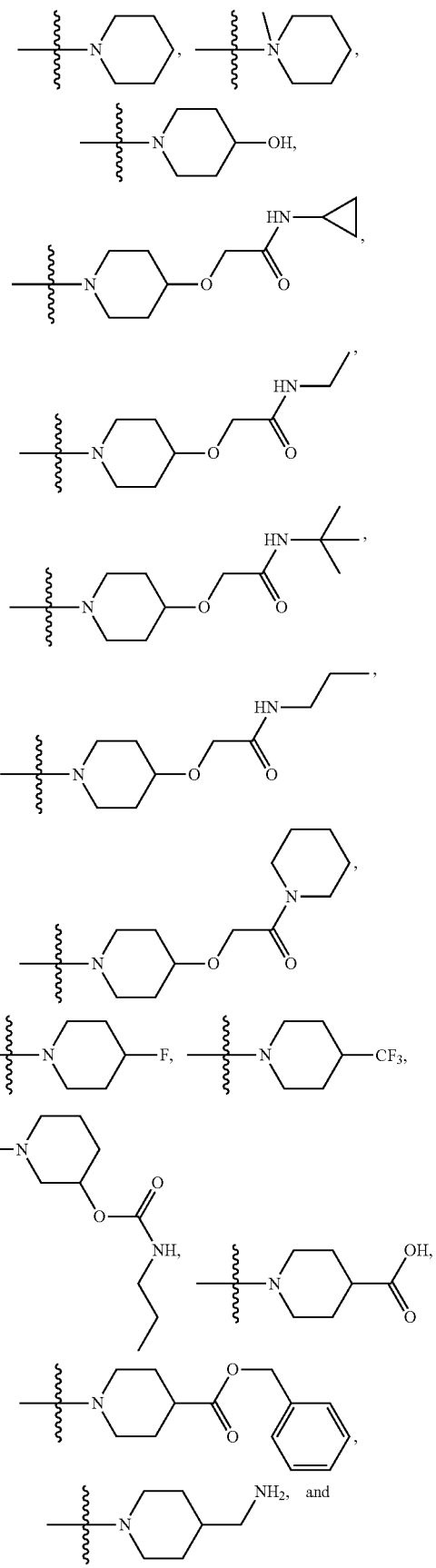

-continued

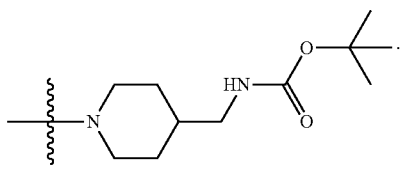

In some embodiments, the compound has the Formula (IIa) or (IIb), or is a pharmaceutically acceptable salt, solvate, clathrate or prodrug thereof, wherein Z is optionally substituted N-heteroaryl.

In some embodiments, the compound has the Formula (IIa) or (IIb), or is a pharmaceutically acceptable salt, solvate, clathrate or prodrug thereof, wherein Z is

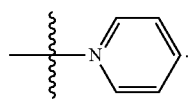

In some embodiments, the compound has the Formula (IIa) or (IIb), or is a pharmaceutically acceptable salt, solvate, clathrate or prodrug thereof, wherein Z is $NR_bR_b$.

In some embodiments, the compound has the Formula (IIa) or (IIb), or is a pharmaceutically acceptable salt, solvate, clathrate or prodrug thereof, wherein each $R_b$ is independently selected from the group consisting of hydrogen, optionally substituted $C_1$-$C_{10}$ alkyl, and optionally substituted $C_3$-$C_{12}$ cycloalkyl.

In some embodiments, the compound has the Formula (IIa) or (IIb), or is a pharmaceutically acceptable salt, solvate, clathrate or prodrug thereof, wherein each $R_b$ is independently selected from the group consisting of hydrogen, —$CH_3$, —$CH_2CH_2OH$, —$CH_2CHOHCH_2OH$, cyclopropyl, cycloheptyl,

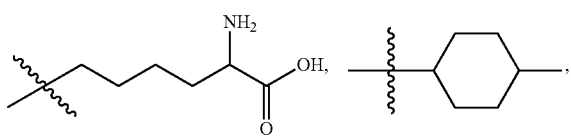

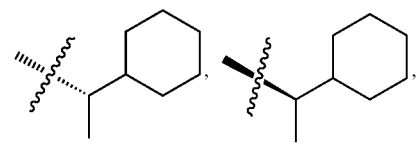

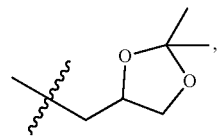

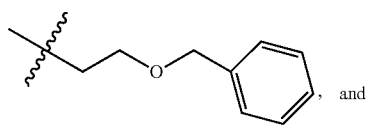, and

-continued

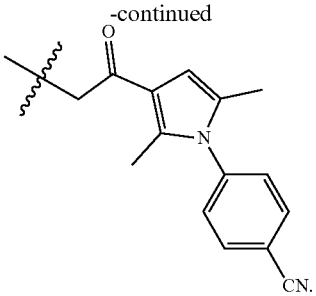

In some embodiments, the compound has the Formula (IIIa) or (IIIb), or is a pharmaceutically acceptable salt, solvate, clathrate or prodrug thereof, wherein each $R_9$ and $R_{10}$ are hydrogen.

In some embodiments, the compound has the Formula (IIIa) or (IIIb), or is a pharmaceutically acceptable salt, solvate, clathrate or prodrug thereof, wherein each $R_9$ is hydrogen and each $R_{10}$ is independently hydrogen, chloro, or fluoro.

In some embodiments, the compound has the Formula (IIIa) or (IIIb), or is a pharmaceutically acceptable salt, solvate, clathrate or prodrug thereof, wherein each $R_9$ is methyl and each $R_{10}$ is hydrogen.

In some embodiments, the compound has the Formula (IIIa) or (IIIb), or is a pharmaceutically acceptable salt, solvate, clathrate or prodrug thereof, wherein each $R_8$ is selected from the group consisting of hydrogen, hydroxyl, fluoro, chloro, bromo, —CN, —$OCH_3$, —$CF_3$, —$OCF_3$, —COOH, —$SO_2CH_3$,

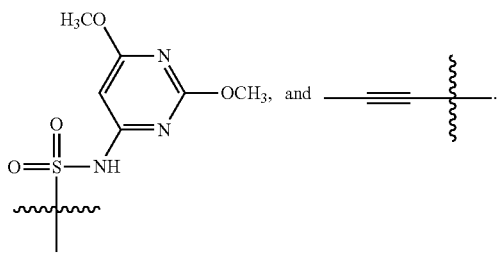

In some embodiments, the compound has the Formula (IIIc), Formula (IIId), Formula (IIIe), or Formula (IIIf):

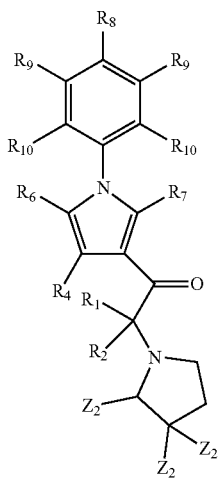

(IIIc)

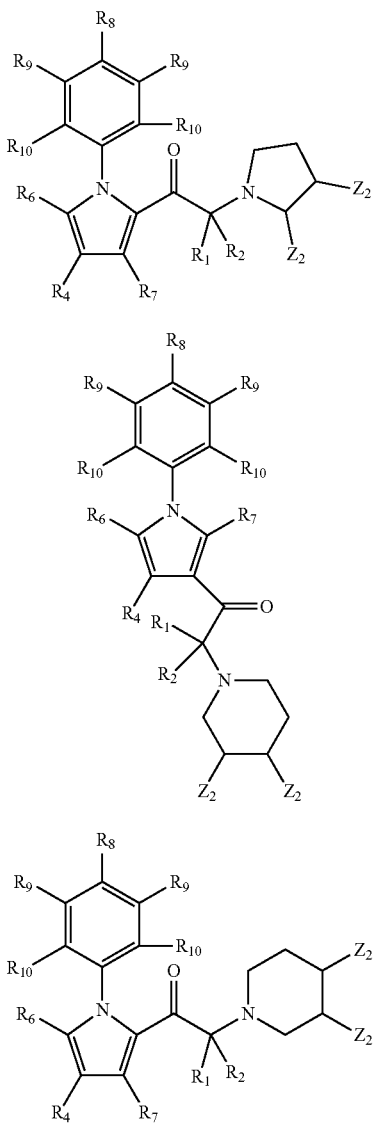

or is a pharmaceutically acceptable salt, solvate, clathrate or prodrug thereof;

wherein:

each of $R_1$ and $R_2$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, $CN$, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)R_c$, $OC(O)OR_c$, $(C=NR_d)R_c$, optionally substituted heterocyclic and optionally substituted heteroaryl;

$R_4$ is independently selected from the group consisting of hydrogen and optionally substituted $C_1$-$C_{10}$ alkyl;

each of $R_6$ and $R_7$ is independently selected from optionally substituted $C_1$-$C_4$ alkyl;

$R_8$ is selected from the group consisting of hydrogen, optionally substituted $C_1$-$C_{10}$ alkyl, optionally substituted $C_1$-$C_{10}$ alkenyl, halo, OR, $C(O)OR_c$, CN, $S(O)_nR_c$, and $S(O)_nNR_dR_d$;

each $R_9$ is independently selected from the group consisting of hydrogen and halo;

each $R_{10}$ is selected from the group consisting of hydrogen and optionally substituted $C_1$-$C_{10}$ alkyl;

each $Z_2$ is independently selected from the group consistent of hydrogen, hydroxy, —F, —$CH_3$, —$CF_3$, —$CH_2NH_2$, —$N(CH_3)_2$, —$CH_2N(CH_3)_2$, —$CH_2CH_2OH$, —COOH, —$CONH_2$, —$SO_2CH_3$, —$OCH_2CONHCH_2CH_3$, —$OCH_2CONHC(CH_3)_2$, —$OCH_2CONHCH_2CH_2CH_3$, —$CH_2NHCOOC(CH_3)_2$, —$N(CH_3)_2$,

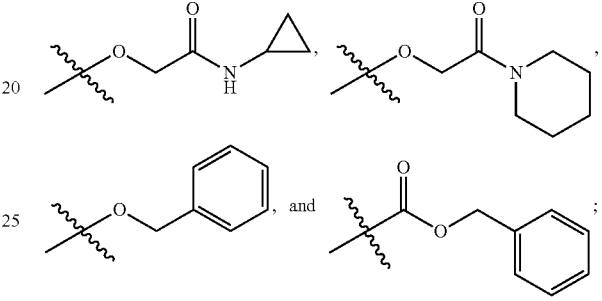

each $R_b$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; or two geminal $R_d$ groups are taken together with the nitrogen atom to which they are attached to form an optionally substituted heterocyclic or an optionally substituted heteroaryl; and each n is independently 0, 1 or 2.

In some embodiments, in compounds of Formula (IIIc), Formula (IIId), Formula (IIIe), or Formula (IIIf), substituents of optionally substituted $Z_2$, $R_1$, $R_2$, $R_4$, $R_5$, $R_6$, $R_7$, $R_8$, $R_9$, and $R_{10}$ are each independently selected from the group consisting of $C_{1-4}$ alkyl optionally substituted with $OR_c$ or $NR_dR_d$; CN; halo; $C_{1-4}$ haloalkyl; $C_{2-4}$ alkynyl; $C_{4-6}$ cycloalkyl; 5-membered heterocyclyl optionally substituted with $C_{1-4}$ alkyl; $OR_c$; $COR_c$; $COOR_c$; $NR_dR_d$; $CONR_dR_d$; $OCONR_dR_d$; $S(O)_nR_c$; and $S(O)_nNR_dR_d$;

wherein each $R_c$ is independently selected from the group consisting of hydrogen, $C_{1-4}$ alkyl optionally substituted with phenyl or CONR$_d$R$_d$; C$_{1-4}$ haloalkyl; phenyl; and heteroaryl optionally substituted with —CH$_3$ or phenyl; and each R$_d$ is independently selected from the group consisting of hydrogen, C$_{1-4}$ alkyl, COOC$_{1-4}$ alkyl, C$_3$-C$_{12}$ cycloalkyl, and heteroaryl optionally substituted with —OC$_{1-4}$ alkyl;

or two R$_d$ together with nitrogen form a 3-6-membered heterocyclyl;

each n is independently 0, 1 or 2.

In some embodiments, the compound has the Formula (IIIc), Formula (IIId), Formula (IIIe), or Formula (IIIf), or is a pharmaceutically acceptable salt, solvate, clathrate or prodrug thereof, wherein each Z$_2$ is independently hydrogen or hydroxyl; each of R$_1$, R$_2$, R$_4$, R$_6$, R$_7$, and R$_9$ are hydrogen; each R$_{10}$ are methyl; and R$_8$ is —COOH, chloro, or CN.

In some embodiments, the compound has the Formula (IIIc), Formula (IIId), Formula (IIIe), or Formula (IIIf), or is a pharmaceutically acceptable salt, solvate, clathrate or prodrug thereof, wherein each Z$_2$ is independently hydrogen or hydroxyl; each of R$_1$, R$_2$, R$_4$, R$_7$, R$_9$, and R$_{10}$ are hydrogen; R$_6$ is methyl or ethyl; and R$_8$ is —COOH, chloro, or CN.

In some embodiments, the compound has the Formula (IIIc), Formula (IIId), Formula (IIIe), or Formula (IIIf), or is a pharmaceutically acceptable salt, solvate, clathrate or prodrug thereof, wherein each Z$_2$ is independently hydrogen or hydroxyl; R$_4$ is hydrogen; R$_9$, and R$_{10}$ are hydrogen or halo, each of R$_6$ and R$_7$ are methyl, and R$_8$ is selected from the group consisting of hydrogen, hydroxyl, fluoro, chloro, bromo, —CN, —OCH$_3$, —CF$_3$, —OCF$_3$, —COOH, —SO$_2$CH$_3$,

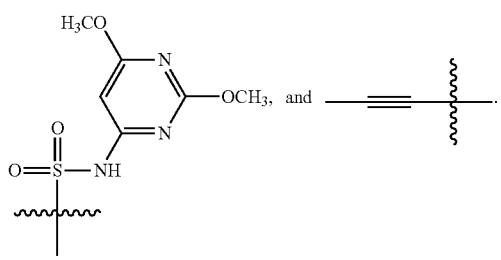

In some embodiments, the compound has the Formula (IIIg) or Formula (IIIh):

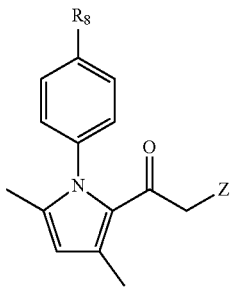

(IIIg)

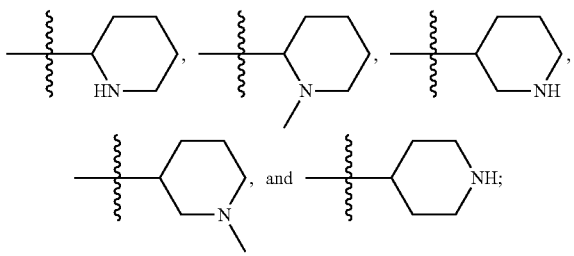

(IIIh)

or a pharmaceutically acceptable salt, solvate, clathrate or prodrug thereof;

wherein:

R$_8$ is selected from the group consisting of hydrogen, optionally substituted C$_1$-C$_{10}$ alkyl, optionally substituted C$_1$-C$_{10}$ alkenyl, halo, OR$_c$, C(O)OR$_c$, CN, S(O)$_n$R$_c$, and S(O)$_n$NR$_d$R$_d$;

wherein Z is selected from the group consisting of

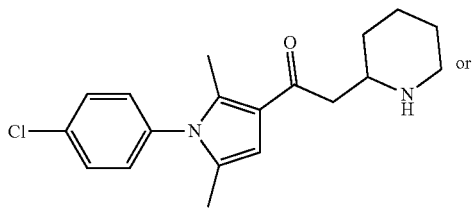

each R$_c$ is independently selected from the group consisting of hydrogen, optionally substituted C$_1$-C$_{10}$ alkyl, optionally substituted C$_2$-C$_{10}$ alkenyl, optionally substituted C$_2$-C$_{10}$ alkynyl, optionally substituted C$_3$-C$_{12}$ cycloalkyl, optionally substituted C$_3$-C$_{12}$ cycloalkenyl, optionally substituted heterocyclic, optionally substituted aryl and optionally substituted heteroaryl;

each R$_d$ is independently selected from the group consisting of hydrogen, optionally substituted C$_1$-C$_{10}$ alkyl, optionally substituted C$_2$-C$_{10}$ alkenyl, optionally substituted C$_2$-C$_{10}$ alkynyl, optionally substituted C$_1$-C$_{10}$ alkoxy, optionally substituted C$_3$-C$_{12}$ cycloalkyl, optionally substituted C$_3$-C$_{12}$ cycloalkenyl, optionally substituted heterocyclic, optionally substituted aryl and optionally substituted heteroaryl; or two geminal R$_d$ groups are taken together with the nitrogen atom to which they are attached to form an optionally substituted heterocyclic or an optionally substituted heteroaryl; and each n is independently 0, 1 or 2;

provided that the compound is not:

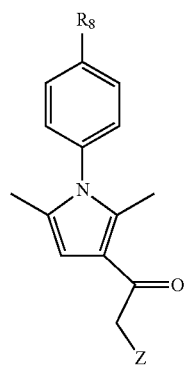

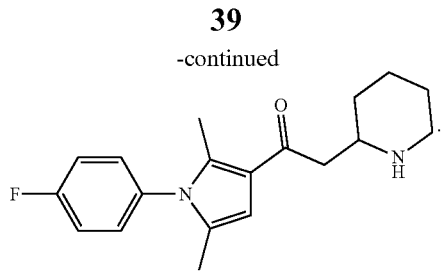

In some embodiments of a compound having the Formula (IIIg) or (IIIh), or a pharmaceutically acceptable salt, solvate, clathrate or prodrug thereof, $R_8$ is chloro, Compounds of Formula (IV)

In some embodiments, the compound has the Formula (IV):

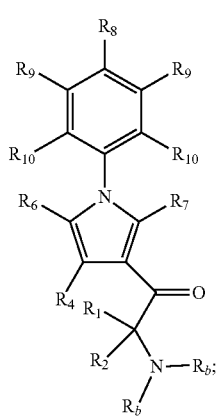

(IV)

or is a pharmaceutically acceptable salt, solvate, clathrate or prodrug thereof;

wherein:

each of $R_1$ and $R_2$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, $CN$, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)R_C$, $OC(O)OR_C$, $(C=NR_d)R_c$, optionally substituted heterocyclic and optionally substituted heteroaryl;

$R_4$ is independently selected from the group consisting of hydrogen and optionally substituted $C_1$-$C_{10}$ alkyl;

each of $R_6$ and $R_7$ is independently selected from optionally substituted $C_1$-$C_4$ alkyl;

$R_8$ is selected from the group consisting of hydrogen, optionally substituted $C_1$-$C_{10}$ alkyl, optionally substituted $C_1$-$C_{10}$ alkenyl, halo, OR, $C(O)OR_c$, CN, $S(O)_nR_c$, and $S(O)_nNR_dR_d$;

each $R_9$ is independently selected from the group consisting of hydrogen and halo;

each $R_{10}$ is selected from the group consisting of hydrogen and optionally substituted $C_1$-$C_{10}$ alkyl;

each $R_b$ is independently selected from the group consisting of hydrogen, —$CH_3$, —$CH_2CH_2OH$, —$CH_2CHOHCH_2OH$, cyclopropyl, cycloheptyl,

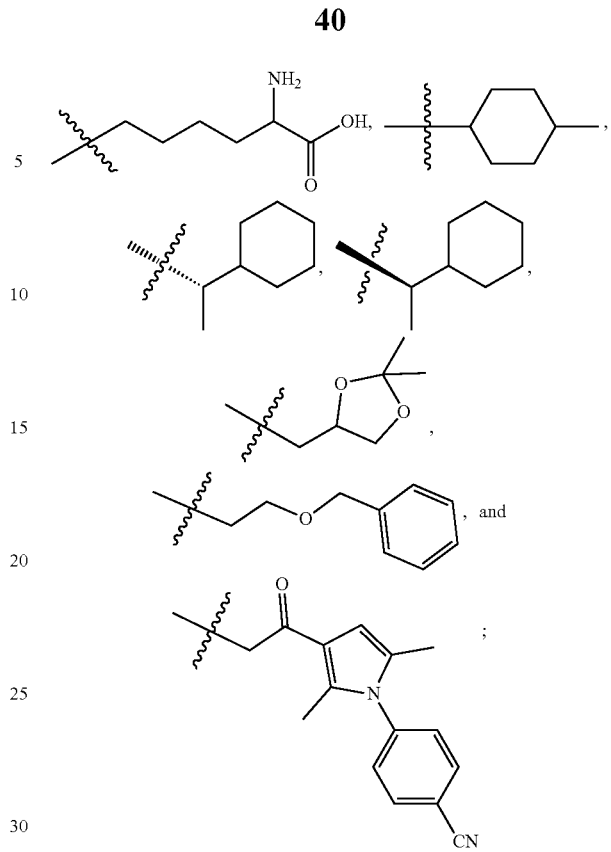

each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; or two geminal $R_d$ groups are taken together with the nitrogen atom to which they are attached to form an optionally substituted heterocyclic or an optionally substituted heteroaryl; and each n is independently 0, 1 or 2.

In some embodiments, in compounds of Formula (IV), substituents of optionally substituted $R_b$, $R_1$, $R_2$, $R_4$, $R_5$, $R_6$, $R_7$, $R_8$, $R_9$, and $R_{10}$ are each independently selected from the group consisting of $C_{1-4}$ alkyl optionally substituted with $OR_c$ or $NR_dR_d$; CN; halo; $C_{1-4}$ haloalkyl; $C_{2-4}$ alkynyl; $C_{4-6}$ cycloalkyl; 5-membered heterocyclyl optionally substituted with $C_{1-4}$ alkyl; $OR_c$; $COR_c$; $COOR_c$; $NR_dR_d$; $CONR_dR_d$; $OCONR_dR_d$; $S(O)_nR_c$; and $S(O)_nNR_dR_d$;

wherein each $R_c$ is independently selected from the group consisting of hydrogen, $C_{1-4}$ alkyl optionally substituted with phenyl or $CONR_dR_d$; $C_{1-4}$ haloalkyl; phenyl; and heteroaryl optionally substituted with —$CH_3$ or phenyl; and each $R_d$ is independently selected from the group consisting of hydrogen, $C_{1-4}$ alkyl, $COOC_{1-4}$ alkyl, $C_3$-$C_{12}$ cycloalkyl, and heteroaryl optionally substituted with —$OC_{1-4}$ alkyl;

or two $R_d$ together with nitrogen form a 3-6-membered heterocyclyl;

each n is independently 0, 1 or 2.

In some embodiments, the compound has the Formula (IV), or is a pharmaceutically acceptable salt, solvate, clathrate or prodrug thereof, wherein $R_4$ is hydrogen, each $R_6$ and $R_7$ is methyl; each $R_9$ and $R_{10}$ is hydrogen, and $R_8$ is CN.

Compounds of Formula (V)

In some embodiments, the compound has the Formula (V):

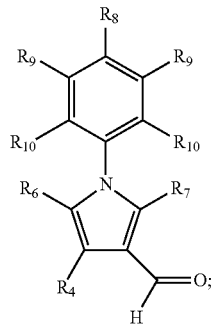

or is a pharmaceutically acceptable salt, solvate, clathrate or prodrug thereof, wherein $R_4$ is hydrogen or optionally substituted $C_1$-$C_4$ alkyl;

$R_6$ and $R_7$ are each independently selected from the group consisting of hydrogen, methyl, ethyl, methoxy, and cyclopropyl;

$R_8$ is selected from the group consisting of hydrogen, optionally substituted $C_1$-$C_{10}$ alkyl, optionally substituted $C_1$-$C_{10}$ alkenyl, halo, OR, C(O)OR$_c$, CN, S(O)$_n$R$_c$, and S(O)$_n$NR$_d$R$_d$;

each $R_9$ is independently selected from the group consisting of hydrogen and halo; and each $R_{10}$ is selected from the group consisting of hydrogen and optionally substituted $C_1$-$C_{10}$ alkyl.

In some embodiments, in compounds of Formula (V), substituents of optionally substituted $R_4$, $R_6$, $R_7$, $R_8$, $R_9$, and $R_{10}$ are each independently selected from the group consisting of $C_{1-4}$ alkyl optionally substituted with OR$_c$ or NR$_d$R$_d$; CN; halo; $C_{1-4}$ haloalkyl; $C_{2-4}$ alkynyl; $C_{4-6}$ cycloalkyl; 5-membered heterocyclyl optionally substituted with $C_{1-4}$ alkyl; OR$_c$; COR$_c$; COOR$_c$; NR$_d$R$_d$; CONR$_d$R$_d$; OCONR$_d$R$_d$; S(O)Re; and S(O)$_n$NR$_d$R$_d$;

wherein each $R_c$ is independently selected from the group consisting of hydrogen, $C_{1-4}$ alkyl optionally substituted with phenyl or CONR$_d$R$_d$; $C_{1-4}$ haloalkyl; phenyl; and heteroaryl optionally substituted with —CH$_3$ or phenyl; and each $R_d$ is independently selected from the group consisting of hydrogen, $C_{1-4}$ alkyl, COOC$_{1-4}$ alkyl, $C_3$-$C_{12}$ cycloalkyl, and heteroaryl optionally substituted with —OC$_{1-4}$ alkyl;

or two $R_d$ together with nitrogen form a 3-6-membered heterocyclyl;

each n is independently 0, 1 or 2.

In some embodiments, the compound has the Formula (V), or is a pharmaceutically acceptable salt, solvate, clathrate or prodrug thereof, wherein each of $R_4$, $R_9$, and $R_{10}$ are hydrogen; $R_6$ and $R_7$ are methyl; and $R_8$ is chloro or cyano.

In some embodiments, the compound has the Formula (V), or is a pharmaceutically acceptable salt, solvate, clathrate or prodrug thereof, wherein $R_4$ is methyl, optionally substituted; each of $R_9$, and $R_{10}$ are hydrogen; $R_6$ and $R_7$ are methyl; and $R_8$ is chloro or cyano.

In some embodiments, the compound has the Formula (V), or is a pharmaceutically acceptable salt, solvate, clathrate or prodrug thereof, wherein $R_4$ is

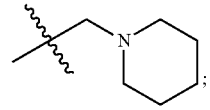

each of $R_9$, and $R_{10}$ are hydrogen; $R_6$ and $R_7$ are methyl; and $R_8$ is chloro or cyano.

Compounds of Formula (VI) and (VII)

In some embodiments, the compound has a structure of Formula (VI):

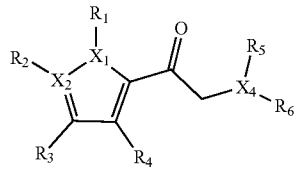

or a pharmaceutically acceptable salt, solvate, clathrate or prodrug thereof, wherein:

$X_1$ and $X_2$ are independently carbon or nitrogen, wherein one of $X_1$ or $X_2$ is nitrogen;

$X_4$ is N or C($R_7$);

$R_1$ is hydrogen or $C_{1-4}$ alkyl; and $R_2$ is selected from the group consisting of hydrogen, optionally substituted $C_{1-4}$ alkyl, and optionally substituted $C_{3-8}$ cycloalkyl;

each $R_3$ and $R_4$ is independently selected from the group consisting of hydrogen, $C_{1-4}$ alkyl, and $C_{3-8}$ cycloalkyl;

each $R_5$ and $R_6$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl;

or $R_5$ and $R_6$ combine with $X_4$ to form an optionally substituted 5-membered heterocycle, an optionally substituted 6-membered heterocycle, an optionally substituted 5-membered heteroaryl, or an optionally substituted 6-membered heteroaryl; and $R_7$ is hydrogen or $C_{1-4}$ alkyl;

wherein substituents of optionally substituted $R_2$, $R_5$, and $R_6$ are each independently selected from the group consisting of $C_{1-4}$ alkyl optionally substituted with OR$_c$ or NR$_d$R$_d$; CN; halo; $C_{1-4}$ haloalkyl; $C_{2-4}$ alkynyl; $C_{4-6}$ cycloalkyl; 5-membered heterocyclyl optionally substituted with $C_{1-4}$ alkyl; OR$_c$; COR$_c$; COOR$_c$; NR$_d$R$_d$; CONR$_d$R$_d$; OCONR$_d$R$_d$; S(O)$_n$R$_c$; and S(O)$_n$NR$_d$R$_d$;

wherein each $R_c$ is independently selected from the group consisting of hydrogen, $C_{1-4}$ alkyl optionally substituted with phenyl or CONR$_d$R$_d$; $C_{1-4}$ haloalkyl; phenyl; and heteroaryl optionally substituted with —CH$_3$ or phenyl; and each $R_d$ is independently selected from the group consisting of hydrogen, $C_{1-4}$ alkyl, $COOC_{1-4}$ alkyl, $C_3$-$C_{12}$ cycloalkyl, and heteroaryl optionally substituted with —$OC_{1-4}$ alkyl;
or two $R_d$ together with nitrogen form a 3-6-membered heterocyclyl;
each n is independently 0, 1 or 2.

In some embodiments, the compound has the Formula (VI), or is a pharmaceutically acceptable salt, solvate, clathrate or prodrug thereof, wherein $X_1$ is carbon, and $X_2$ and $X_4$ are each nitrogen.

In some embodiments, the compound has the Formula (VI), or is a pharmaceutically acceptable salt, solvate, clathrate or prodrug thereof, wherein $R_1$ is methyl.

In some embodiments, the compound has the Formula (VI), or is a pharmaceutically acceptable salt, solvate, clathrate or prodrug thereof, wherein $R_2$ is optionally substituted cyclobutyl.

In some embodiments, the compound has the Formula (VI), or is a pharmaceutically acceptable salt, solvate, clathrate or prodrug thereof, wherein optionally substituted cyclohexyl.

In some embodiments, the compound has the Formula (VI), or is a pharmaceutically acceptable salt, solvate, clathrate or prodrug thereof, wherein $R_5$ and $R_6$ combine with $X_4$ to form an optionally substituted 5-membered heterocycle or an optionally substituted 6-membered heterocycle.

In some embodiments, the compound has a structure of Formula (VII):

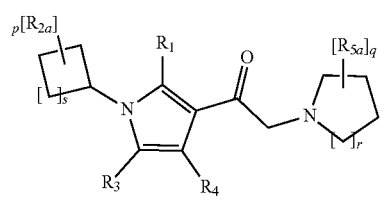

(VII)

or a pharmaceutically acceptable salt, solvate, clathrate or prodrug thereof, wherein:
each $R_1$, $R_3$, and $R_4$ is independently selected from the group consisting of hydrogen, $C_{1-4}$ alkyl, and $C_{3-8}$ cycloalkyl;
each of $R_{2a}$ is selected form the group consisting of hydrogen, $C_{1-4}$ alkyl, $C_{1-4}$ haloalkyl, halo, CN, $CONH_2$, COOH, and COO-benzyl;
each of $R_{5a}$ is selected form the group consisting of hydrogen and OH;
each n is independently 0, 1 or 2;
q is 0, 1 or 2;
r is 1 or 2; and
s is 1, 2, or 3.

In some embodiments, the compound has the Formula (VI) or (VII), or is a pharmaceutically acceptable salt, solvate, clathrate or prodrug thereof, wherein the compound is selected from the group consisting of:

32

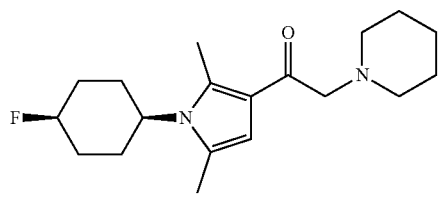

-continued

35

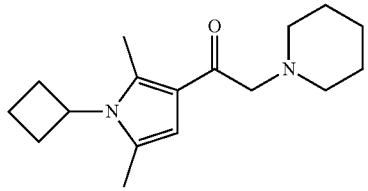

36

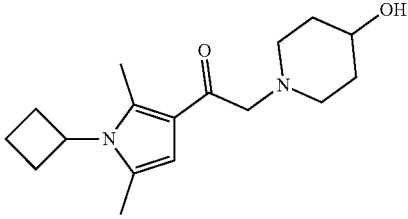

37

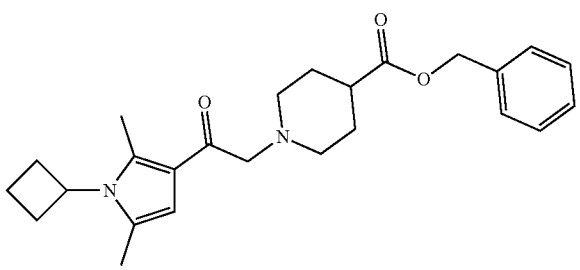

45

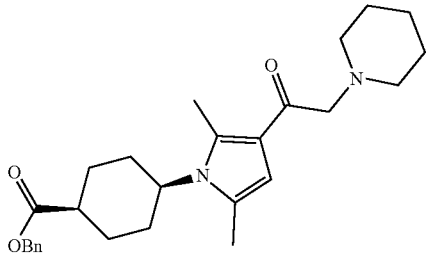

46

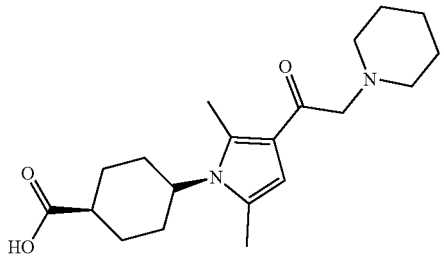

65

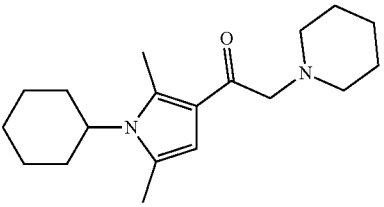

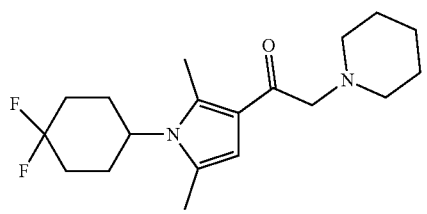

76

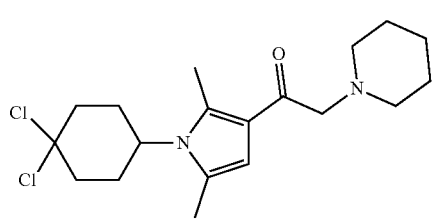

97

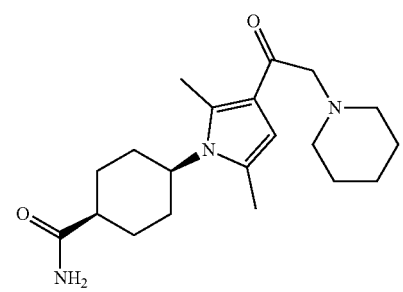

103

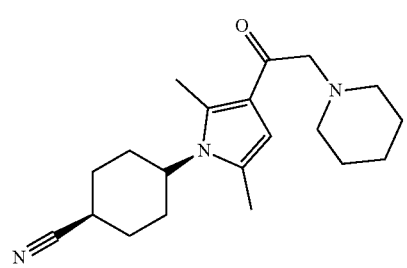

105

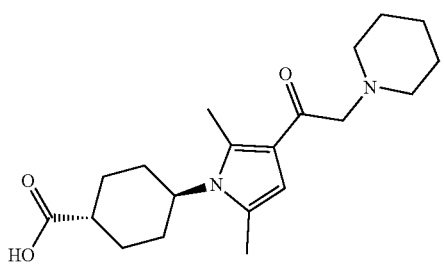

121

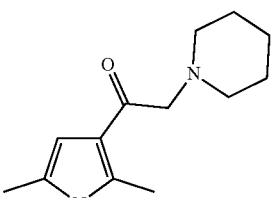

5

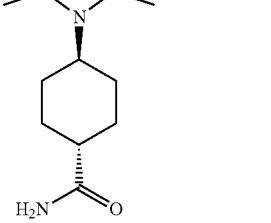

122

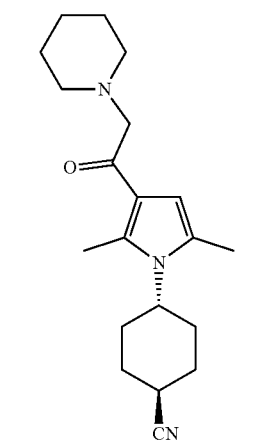

143

In some embodiments, the compound has a structure of Formula (VIII):

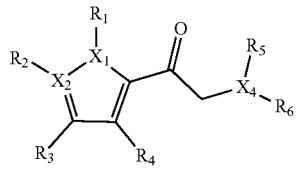

(VIII)

or a pharmaceutically acceptable salt, solvate, clathrate or prodrug thereof, wherein:

$X_1$ and $X_2$ are independently carbon or nitrogen, wherein one of $X_1$ or $X_2$ is nitrogen;

$X_4$ is N or $C(R_7)$;

$R_1$ is selected from the group consisting of optionally substituted $C_{1-4}$ alkyl, optionally substituted $C_{3-8}$ cycloalkyl, and optionally substituted $C_{5-6}$ aryl;

$R_2$ is hydrogen or $C_{1-4}$ alkyl;

each $R_3$ and $R_4$ is independently selected from the group consisting of hydrogen, $C_{1-4}$ alkyl, and $C_{3-8}$ cycloalkyl;

each $R_5$ and $R_6$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl;

or $R_5$ and $R_6$ combine with $X_4$ to form an optionally substituted 5-6-membered heterocycle, or an optionally substituted 5-6-membered heteroaryl; and $R_7$ is hydrogen or $C_{1-4}$ alkyl;

wherein substituents of optionally substituted $R_1$, $R_5$, and $R_6$ are each independently selected from the group consisting of $C_{1-4}$ alkyl optionally substituted with $OR_c$ or $NR_dR_d$; CN; halo; $C_{1-4}$ haloalkyl; $C_{2-4}$ alkynyl; $C_{4-6}$ cycloalkyl; 5-membered heterocyclyl optionally substituted with $C_{1-4}$ alkyl; $OR_c$; $COR_c$; $COOR_c$; $NR_dR_d$; $CONR_dR_d$; $OCONR_dR_d$; $S(O)_nR_c$ and $S(O)_nNR_dR_d$;

wherein each $R_c$ is independently selected from the group consisting of hydrogen, $C_{1-4}$ alkyl optionally substituted with phenyl or $CONR_dR_d$; $C_{1-4}$ haloalkyl; phenyl and heteroaryl optionally substituted with —$CH_3$ or phenyl; and each $R_d$ is independently selected from the group consisting of hydrogen, $C_{1-4}$ alkyl, $COOC_{1-4}$ alkyl, $C_3$-$C_{12}$ cycloalkyl, and heteroaryl optionally substituted with —$OC_{1-4}$ alkyl;

or two $R_d$ together with nitrogen form a 3-6-membered heterocyclyl;

each n is independently 0, 1 or 2.

In some embodiments, the compound has a structure of Formula (VIII), or is a pharmaceutically acceptable salt, solvate, clathrate or prodrug thereof, wherein $X_1$ and $X_4$ are each nitrogen, and $X_2$ is carbon.

In some embodiments, the compound has the Formula (VIII), or is a pharmaceutically acceptable salt, solvate, clathrate or prodrug thereof, wherein $R_1$ is optionally substituted phenyl.

In some embodiments, the compound has the Formula (VIII), or is a pharmaceutically acceptable salt, solvate, clathrate or prodrug thereof, wherein the phenyl is substituted with at least one $C_{1-4}$ alkyl and at least one halogen.

In some embodiments, the compound has the Formula (VIII), or is a pharmaceutically acceptable salt, solvate, clathrate or prodrug thereof, wherein $R_2$, $R_3$ and $R_4$ are each hydrogen.

In some embodiments, the compound has the Formula (VIII), or is a pharmaceutically acceptable salt, solvate, clathrate or prodrug thereof, wherein $R_5$ and $R_6$ combine with $X_4$ to form an optionally substituted 5-6-membered heterocycle, or an optionally substituted 5-6-membered heteroaryl.

In some embodiments, the compound has the Formula (VIII), or is a pharmaceutically acceptable salt, solvate, clathrate or prodrug thereof, wherein the compound is selected from the group consisting of:

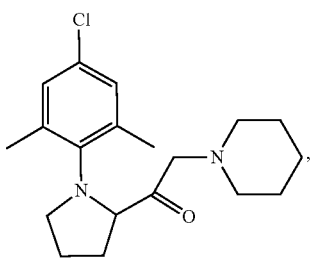

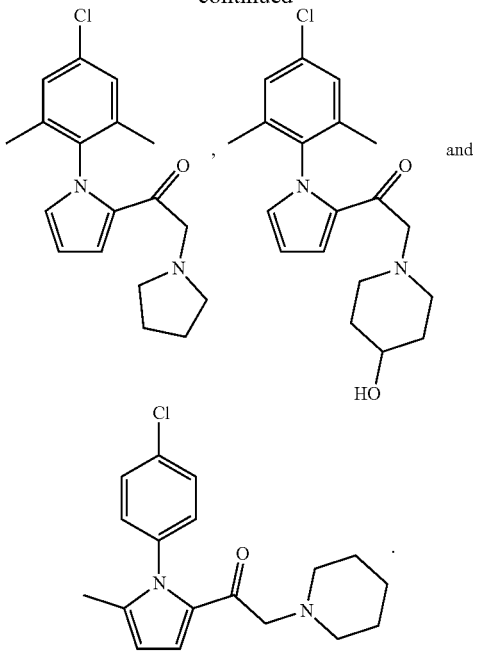

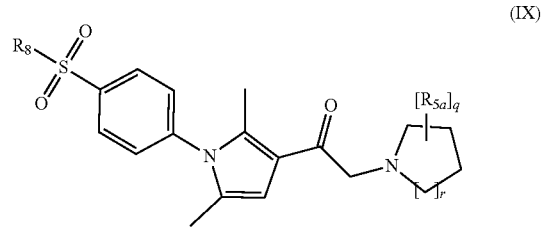

Compounds of Formula (IX)

In some embodiments, the compound has a structure of Formula (IX):

$$(IX)$$

or a pharmaceutically acceptable salt, solvate, clathrate or prodrug thereof, wherein:

$R_8$ is $C_{1-4}$alkyl or $NR_{8a}R_{8b}$, wherein $R_{8a}$ is selected from the group consisting of hydrogen, $C_{5-6}$ aryl and 5-6-membered heteroaryl, optionally substituted with —$OC_{1-4}$ alkyl.

each of $R_{5a}$ is selected form the group consisting of hydrogen, $C_{1-4}$ alkyl optionally substituted with $OR_c$ or $NR_dR_d$, halo, $C_{1-4}$ haloalkyl, $OR_c$, $COOR_c$, $NR_dR_d$, $CONR_dR_d$, $OCONR_dR_d$, and $S(O)_nR_c$;

each $R_c$ is independently selected from the group consisting of hydrogen, $C_{1-4}$ alkyl optionally substituted with phenyl or $CONR_dR_d$, $C_{1-4}$ haloalkyl, phenyl, and heteroaryl optionally substituted with —$CH_3$ or phenyl;

each $R_d$ is independently selected from the group consisting of hydrogen, $C_{1-4}$ alkyl, $COOC_{1-4}$ alkyl, $C_3$-$C_{12}$ cycloalkyl, and heteroaryl optionally substituted with —$OCH_3$; or two $R_d$ together form a heterocyclyl;

each n is independently 0, 1 or 2;

q is 0, 1 or 2; and r is 1 or 2.

In some embodiments, the compound has a structure of Formula (IX), or a pharmaceutically acceptable salt, solvate, clathrate or prodrug thereof, wherein $R_8$ is $C_{1-4}$ alkyl.

In some embodiments, the compound has a structure of Formula (IX), or a pharmaceutically acceptable salt, solvate, clathrate or prodrug thereof, wherein $R_8$ is methyl.

In some embodiments, the compound has a structure of Formula (IX), or a pharmaceutically acceptable salt, solvate, clathrate or prodrug thereof, wherein $R_8$ is $NR_{8a}R_{8b}$.

In some embodiments, the compound has a structure of Formula (IX), or a pharmaceutically acceptable salt, solvate, clathrate or prodrug thereof, wherein $R_{8a}$ is pyrimidinyl.

In some embodiments, the compound has a structure of Formula (IX), or a pharmaceutically acceptable salt, solvate, clathrate or prodrug thereof, wherein $R_{8a}$ is substituted with methoxy.

In some embodiments, the compound has a structure of Formula (IX), or a pharmaceutically acceptable salt, solvate, clathrate or prodrug thereof, wherein r is 2.

In some embodiments, the compound has the Formula (IX), or is a pharmaceutically acceptable salt, solvate, clathrate or prodrug thereof, wherein the compound is selected from the group consisting of:

1

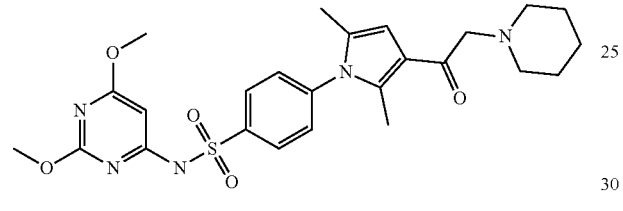

2

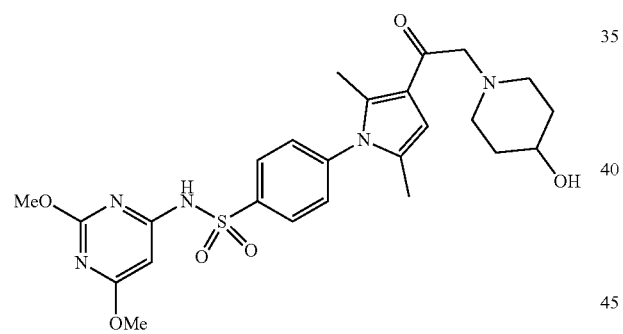

4

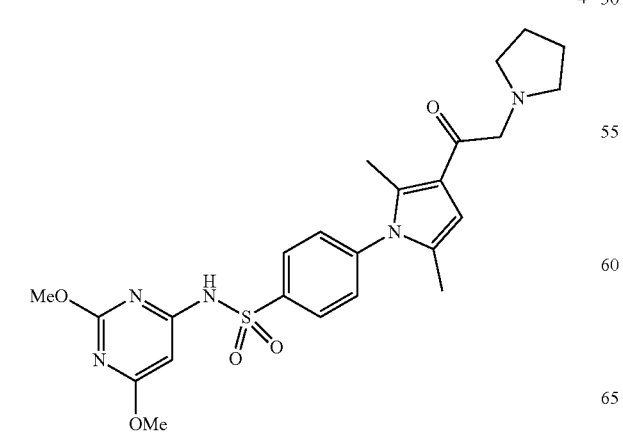

12

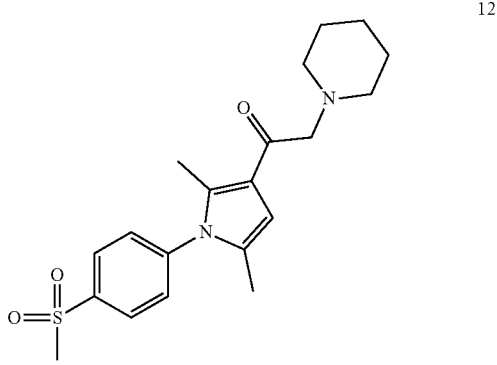

13

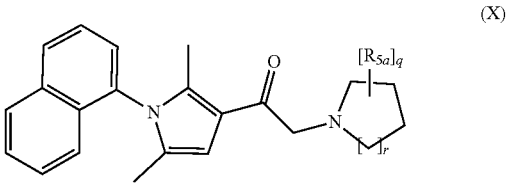

Compounds of Formula (X)

In some embodiments the compound has a structure of Formula (X):

(X)

or a pharmaceutically acceptable salt, solvate, clathrate or prodrug thereof, wherein:

each of $R_{5a}$ is selected form the group consisting of hydrogen, $C_{1-4}$ alkyl optionally substituted with $OR_c$ or $NR_dR_d$, halo, $C_{1-4}$ haloalkyl, $OR_c$, $COOR_c$, $NR_dR_d$, $CONR_dR_d$, $OCONR_dR_d$, and $S(O)_nR_c$;

each $R_c$ is independently selected from the group consisting of hydrogen, $C_{1-4}$ alkyl optionally substituted with phenyl or $CONR_dR_d$, $C_{1-4}$ haloalkyl, phenyl, and heteroaryl optionally substituted with —$CH_3$ or phenyl;

each $R_d$ is independently selected from the group consisting of hydrogen, $C_{1-4}$ alkyl, $COOC_{1-4}$ alkyl, $C_3$-$C_{12}$ cycloalkyl, and heteroaryl optionally substituted with —$OCH_3$;

or two $R_d$ together form a heterocyclyl;

each n is independently 0, 1 or 2;

q is 0, 1 or 2; and r is 1 or 2.

In some embodiments, the compound has the Formula (X), or is a pharmaceutically acceptable salt, solvate, clathrate or prodrug thereof, wherein the compound is selected from the group consisting of:
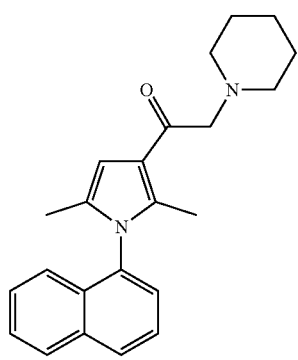
4
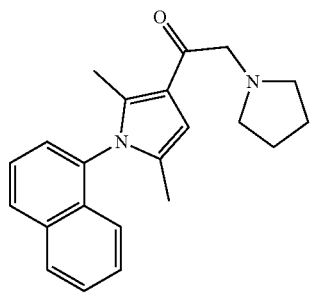
8
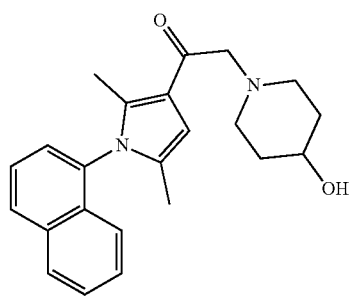
9
The present invention additionally encompasses the compounds shown below in Table 3:
TABLE 3
| Compound No. | Structure |
|---|---|
| 1 | 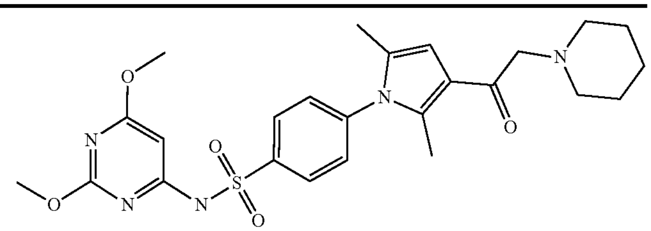 |
| 2 | 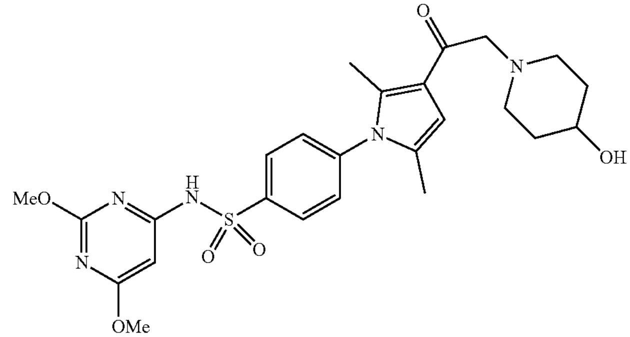 [SMILES: COc1cc(NS(=O)(=O)c2ccc(-n3c(C)cc(C(=O)CN4CCC(O)CC4)c3C)cc2)nc(OC)n1] |
| 3 | 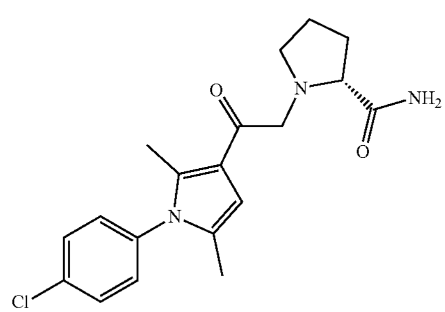 [SMILES: Cc1cc(C(=O)CN2CCC[C@@H]2C(N)=O)c(C)n1-c1ccc(Cl)cc1] |

TABLE 3-continued

| Compound No. | Structure |
| --- | --- |
| 4 | (2,5-dimethyl-1-{4-[(2,6-dimethoxypyrimidin-4-yl)sulfamoyl]phenyl}-1H-pyrrol-3-yl)(pyrrolidin-1-yl) ketone structure |
| 5 | 1-(2,5-dimethyl-1-(naphthalen-1-yl)-1H-pyrrol-3-yl)-2-(piperidin-1-yl)ethanone structure |
| 7 | 1-[2,5-dimethyl-1-(4-hydroxyphenyl)-1H-pyrrol-3-yl]-2-(piperidin-1-yl)ethanone structure |
| 8 | 1-[2,5-dimethyl-1-(naphthalen-1-yl)-1H-pyrrol-3-yl]-2-(pyrrolidin-1-yl)ethanone structure |

TABLE 3-continued
| Compound No. | Structure |
|---|---|
| 9 | 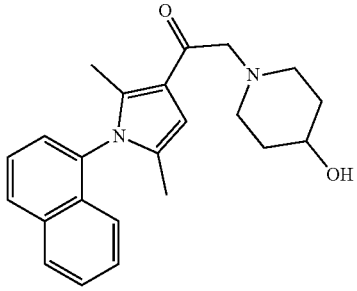 [SMILES: Cc1cc(C(=O)CN2CCC(O)CC2)c(C)n1-c1cccc2ccccc12] |
| 10 | 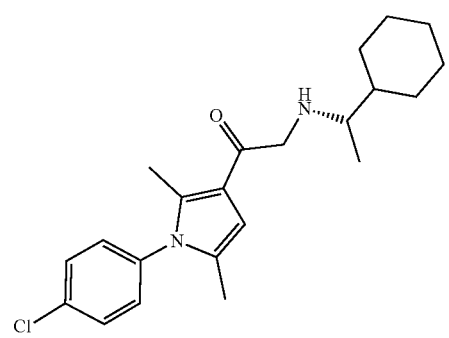 |
| 11 | 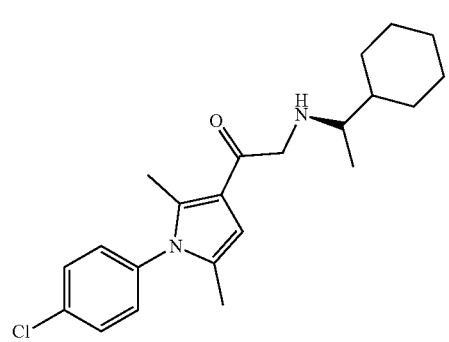 |
| 12 | 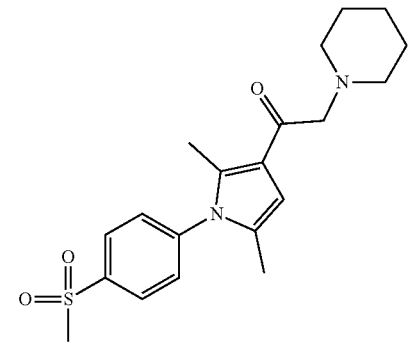 [SMILES: Cc1cc(C(=O)CN2CCCCC2)c(C)n1-c1ccc(S(C)(=O)=O)cc1] |

TABLE 3-continued
| Compound No. | Structure |
|---|---|
| 13 | 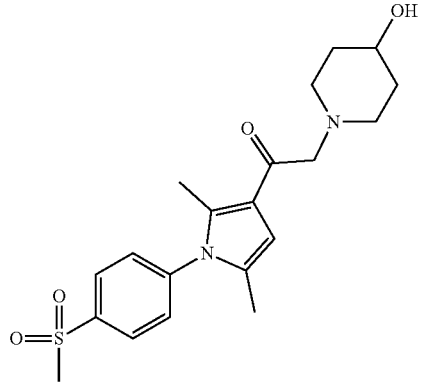 [SMILES: Cc1cc(C(=O)CN2CCC(O)CC2)c(C)n1-c1ccc(S(C)(=O)=O)cc1] |
| 14 | 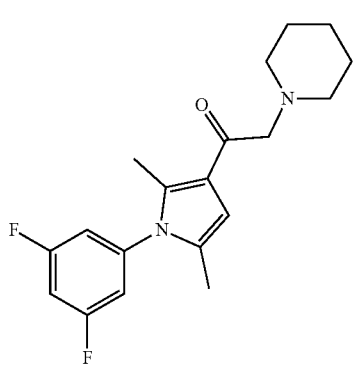 [SMILES: Cc1cc(C(=O)CN2CCCCC2)c(C)n1-c1cc(F)cc(F)c1] |
| 15 | 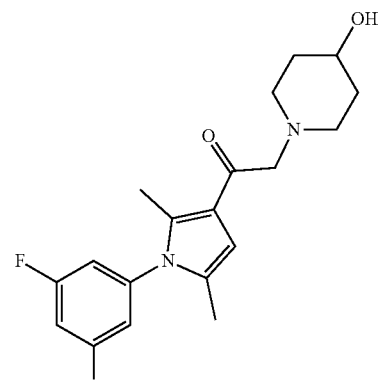 |
| 16 | 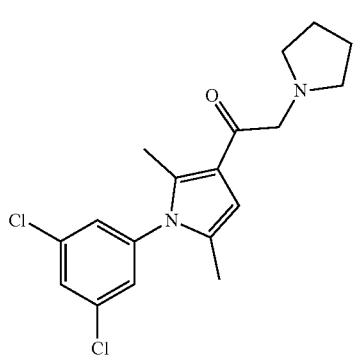 [SMILES: Cc1cc(C(=O)CN2CCCC2)c(C)n1-c1cc(Cl)cc(Cl)c1] |

TABLE 3-continued

| Compound No. | Structure |
| --- | --- |
| 17 | 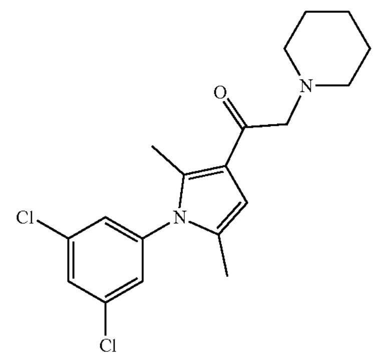 [SMILES: Cc1cc(C(=O)CN2CCCCC2)c(C)n1-c1cc(Cl)cc(Cl)c1] |
| 18 | 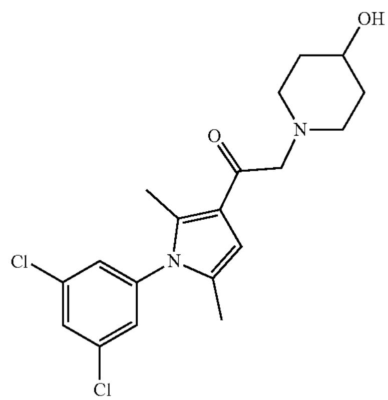 [SMILES: Cc1cc(C(=O)CN2CCC(O)CC2)c(C)n1-c1cc(Cl)cc(Cl)c1] |
| 19 | 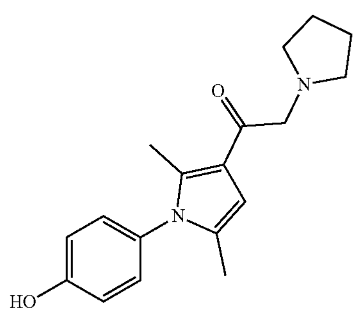 [SMILES: Cc1cc(C(=O)CN2CCCC2)c(C)n1-c1ccc(O)cc1] |
| 20 | 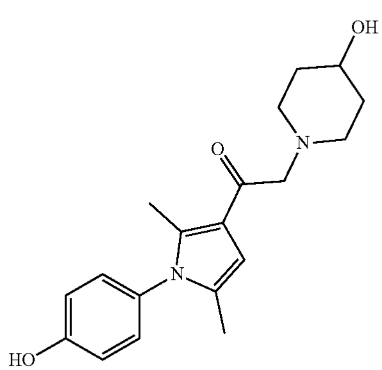 [SMILES: Cc1cc(C(=O)CN2CCC(O)CC2)c(C)n1-c1ccc(O)cc1] |

TABLE 3-continued
| Compound No. | Structure |
|---|---|
| 21 | 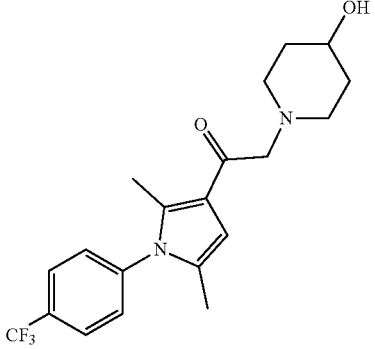 [SMILES: Cc1cc(C(=O)CN2CCC(O)CC2)c(C)n1-c1ccc(C(F)(F)F)cc1] |
| 22 | 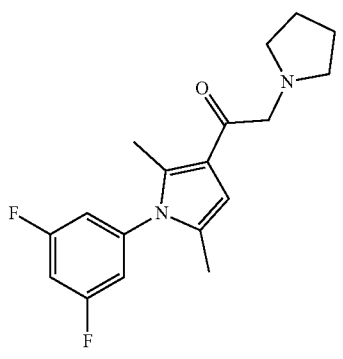 [SMILES: Cc1cc(C(=O)CN2CCCC2)c(C)n1-c1cc(F)cc(F)c1] |
| 23 | 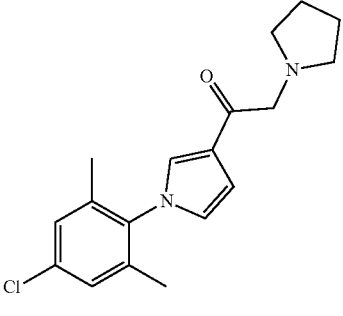 [SMILES: Cc1cc(Cl)cc(C)c1-n1ccc(C(=O)CN2CCCC2)c1] |
| 24 | 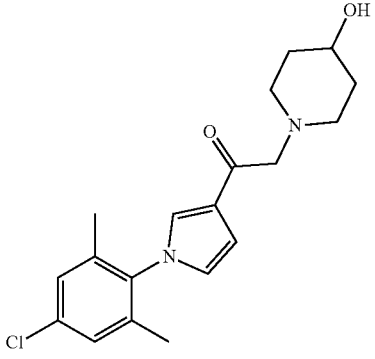 [SMILES: Cc1cc(Cl)cc(C)c1-n1ccc(C(=O)CN2CCC(O)CC2)c1] |

TABLE 3-continued

| Compound No. | Structure |
|---|---|
| 25 | *(1-(4-chlorophenyl)-2,5-dimethyl-1H-pyrrol-3-yl ketone linked via CH₂ to piperidine-4-carboxylic acid)* |
| 26 | *(1-(4-chloro-2,6-dimethylphenyl)-1H-pyrrol-3-yl ketone linked via CH₂ to piperidine)* |
| 27 | *(1-(4-chloro-2,6-dimethylphenyl)-1H-pyrrol-2-yl ketone linked via CH₂ to piperidine)* |
| 28 | *(1-(4-chloro-2,6-dimethylphenyl)-1H-pyrrol-2-yl ketone linked via CH₂ to pyrrolidine)* |
| 29 | *(1-(4-chloro-2,6-dimethylphenyl)-1H-pyrrol-2-yl ketone linked via CH₂ to 4-hydroxypiperidine)* |
| 32 | *(1-(4-fluorocyclohexyl)-2,5-dimethyl-1H-pyrrol-3-yl ketone linked via CH₂ to piperidine)* |

TABLE 3-continued

| Compound No. | Structure |
|---|---|
| 33 | 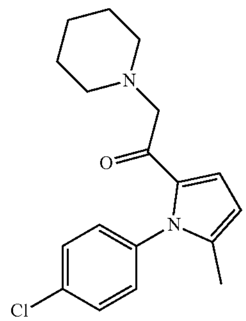 [SMILES: Cc1ccc(C(=O)CN2CCCCC2)n1-c1ccc(Cl)cc1] |
| 35 | 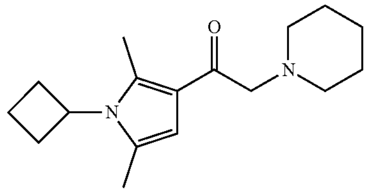 [SMILES: Cc1cc(C(=O)CN2CCCCC2)c(C)n1C1CCC1] |
| 36 | 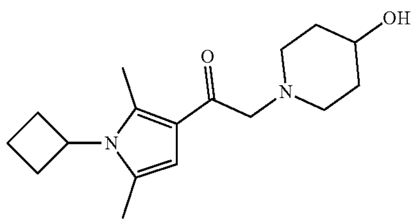 [SMILES: Cc1cc(C(=O)CN2CCC(O)CC2)c(C)n1C1CCC1] |
| 37 | 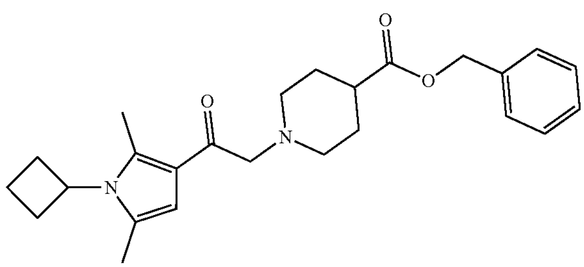 [SMILES: Cc1cc(C(=O)CN2CCC(C(=O)OCc3ccccc3)CC2)c(C)n1C1CCC1] |
| 38 | 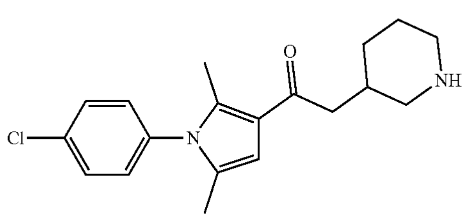 [SMILES: Cc1cc(C(=O)CC2CCCNC2)c(C)n1-c1ccc(Cl)cc1] |
| 39 | 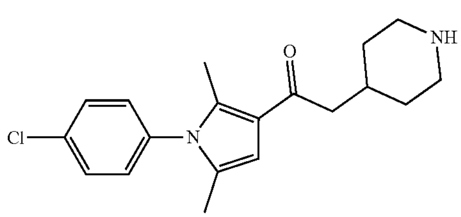 [SMILES: Cc1cc(C(=O)CC2CCNCC2)c(C)n1-c1ccc(Cl)cc1] |

TABLE 3-continued

| Compound No. | Structure |
|---|---|
| 40 | 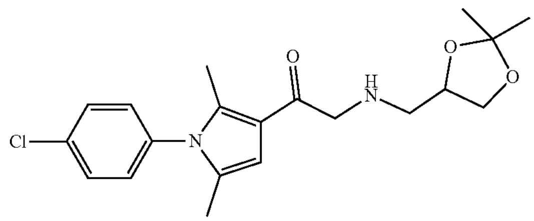 [SMILES: Cc1cc(C(=O)CNCC2COC(C)(C)O2)c(C)n1-c1ccc(Cl)cc1] |
| 41 | 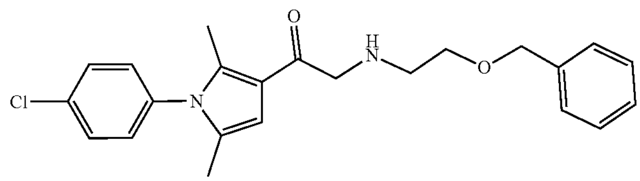 [SMILES: Cc1cc(C(=O)CNCCOCc2ccccc2)c(C)n1-c1ccc(Cl)cc1] |
| 42 | 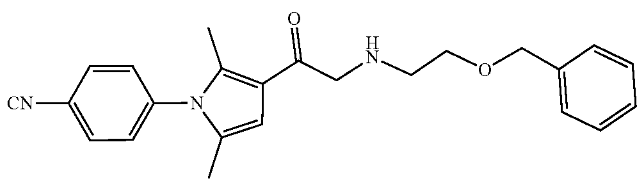 |
| 43 | 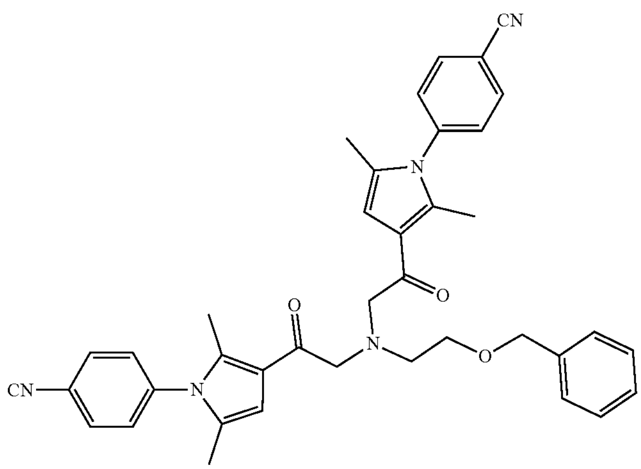 |
| 44 | 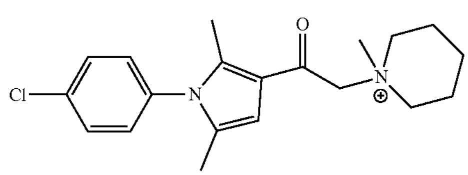 [SMILES: Cc1cc(C(=O)C[N+]2(C)CCCCC2)c(C)n1-c1ccc(Cl)cc1] |
| 45 | 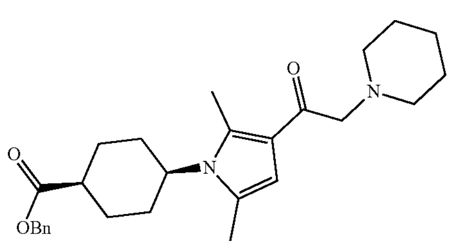 [SMILES: Cc1cc(C(=O)CN2CCCCC2)c(C)n1[C@H]1CC[C@@H](C(=O)OCc2ccccc2)CC1] |

TABLE 3-continued

| Compound No. | Structure |
| --- | --- |
| 46 | 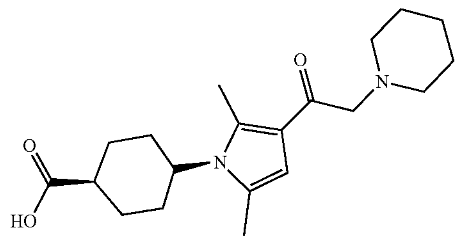 |
| 48 | 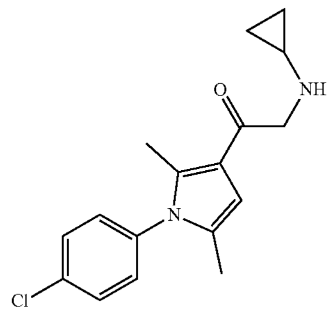 [SMILES: Cc1cc(C(=O)CNC2CC2)c(C)n1-c1ccc(Cl)cc1] |
| 49 | 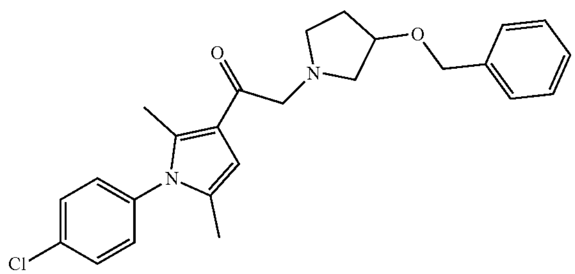 [SMILES: Cc1cc(C(=O)CN2CCC(OCc3ccccc3)C2)c(C)n1-c1ccc(Cl)cc1] |
| 50 | 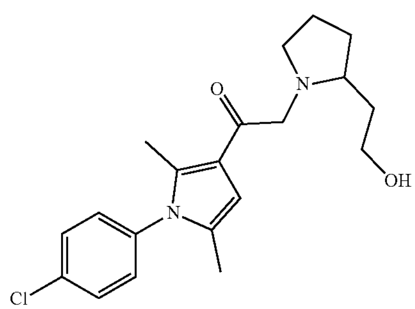 [SMILES: Cc1cc(C(=O)CN2CCCC2CCO)c(C)n1-c1ccc(Cl)cc1] |
| 51 | 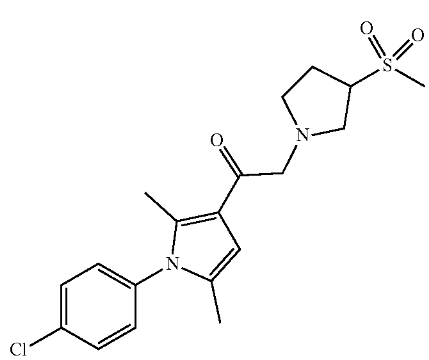 [SMILES: Cc1cc(C(=O)CN2CCC(S(C)(=O)=O)C2)c(C)n1-c1ccc(Cl)cc1] |

TABLE 3-continued

| Compound No. | Structure |
|---|---|
| 52 | 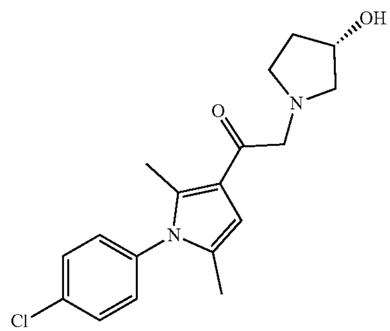 [SMILES: Cc1cc(C(=O)CN2CC[C@H](O)C2)c(C)n1-c1ccc(Cl)cc1] |
| 53 | 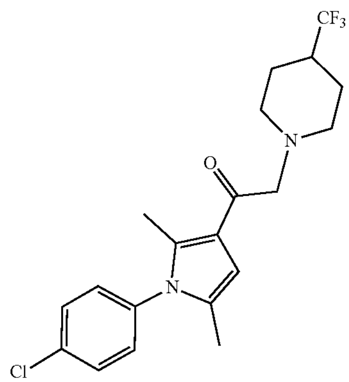 [SMILES: Cc1cc(C(=O)CN2CCC(C(F)(F)F)CC2)c(C)n1-c1ccc(Cl)cc1] |
| 54 | 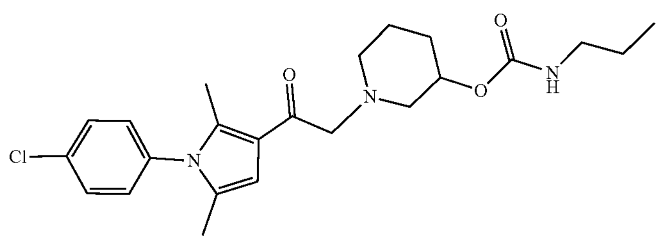 [SMILES: CCCNC(=O)OC1CCCN(CC(=O)c2cc(C)n(-c3ccc(Cl)cc3)c2C)C1] |
| 55 | 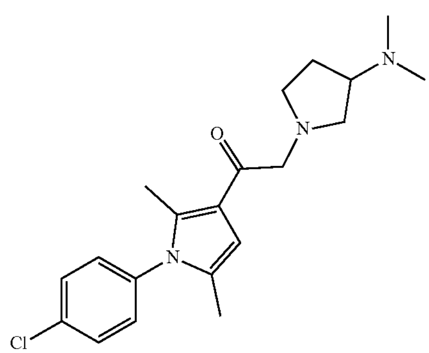 [SMILES: Cc1cc(C(=O)CN2CCC(N(C)C)C2)c(C)n1-c1ccc(Cl)cc1] |
| 56 | 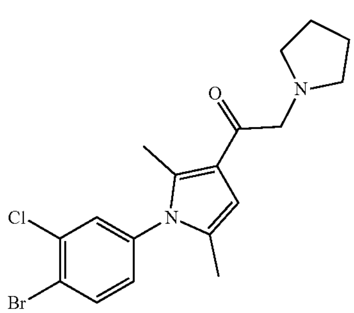 [SMILES: Cc1cc(C(=O)CN2CCCC2)c(C)n1-c1ccc(Br)c(Cl)c1] |

TABLE 3-continued
| Compound No. | Structure |
| --- | --- |
| 57 | 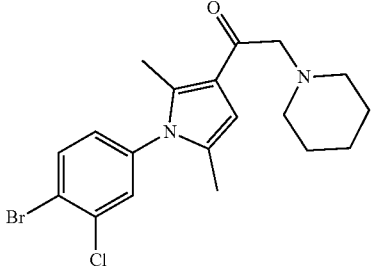 [SMILES: Cc1cc(C(=O)CN2CCCCC2)c(C)n1-c1ccc(Br)c(Cl)c1] |
| 58 | 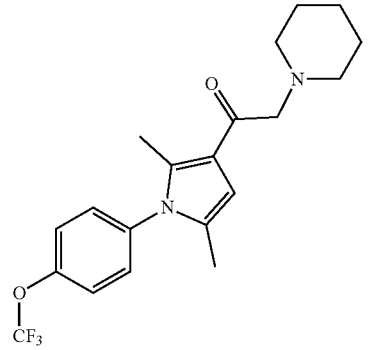 [SMILES: Cc1cc(C(=O)CN2CCCCC2)c(C)n1-c1ccc(OC(F)(F)F)cc1] |
| 59 | 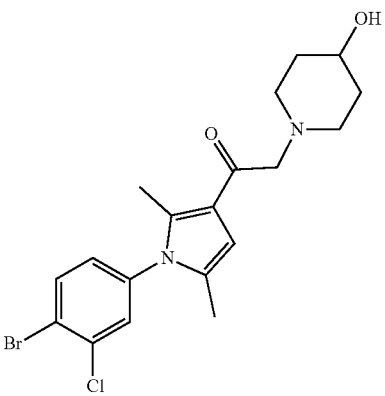 [SMILES: Cc1cc(C(=O)CN2CCC(O)CC2)c(C)n1-c1ccc(Br)c(Cl)c1] |
| 60 | 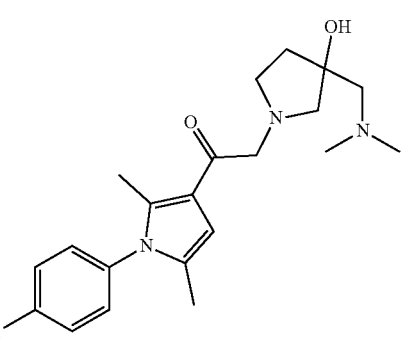 |

TABLE 3-continued
| Compound No. | Structure |
|---|---|
| 61 | 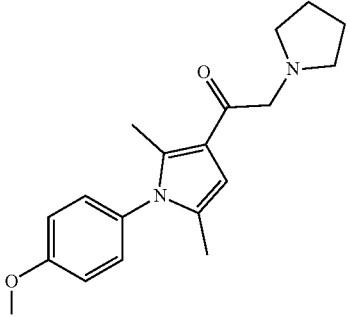 |
| 62 | 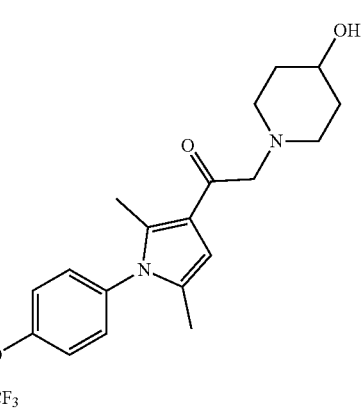 |
| 63 | 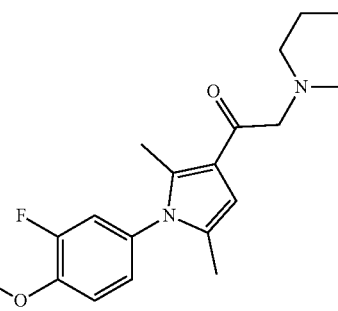 |
| 64 | 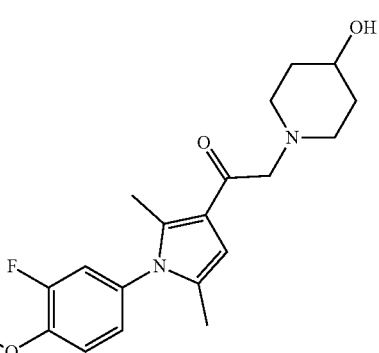 |
| 65 | 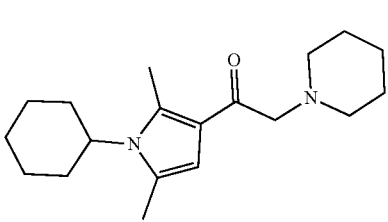 [SMILES: Cc1cc(C(=O)CN2CCCCC2)c(C)n1C1CCCCC1] |

TABLE 3-continued
| Compound No. | Structure |
|---|---|
| 66 | 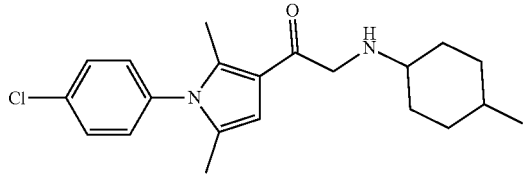 [SMILES: Cc1cc(C(=O)CNC2CCC(C)CC2)c(C)n1-c1ccc(Cl)cc1] |
| 67 | 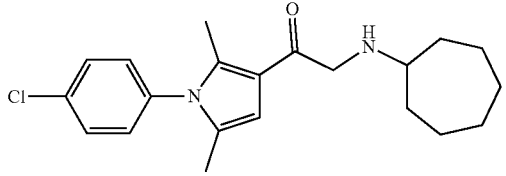 [SMILES: Cc1cc(C(=O)CNC2CCCCCC2)c(C)n1-c1ccc(Cl)cc1] |
| 68 | 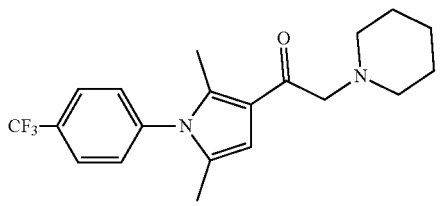 [SMILES: Cc1cc(C(=O)CN2CCCCC2)c(C)n1-c1ccc(C(F)(F)F)cc1] |
| 69 | 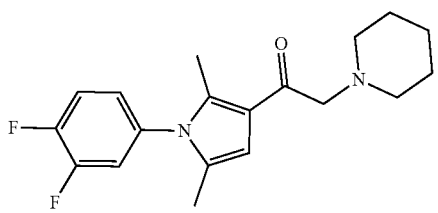 [SMILES: Cc1cc(C(=O)CN2CCCCC2)c(C)n1-c1ccc(F)c(F)c1] |
| 70 | 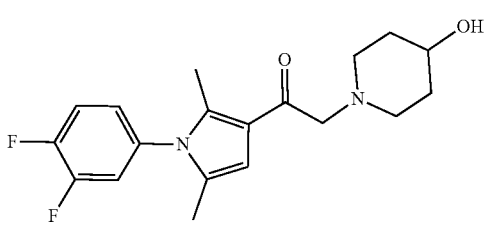 [SMILES: Cc1cc(C(=O)CN2CCC(O)CC2)c(C)n1-c1ccc(F)c(F)c1] |
| 71 | 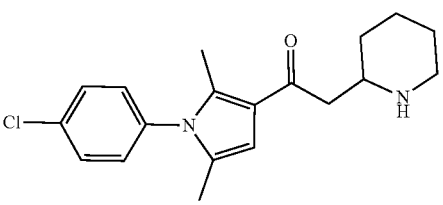 [SMILES: Cc1cc(C(=O)CC2CCCCN2)c(C)n1-c1ccc(Cl)cc1] |
| 72 | 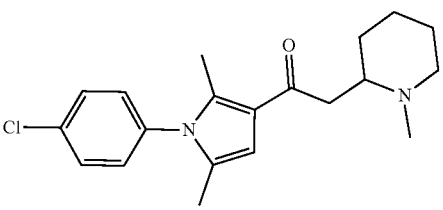 [SMILES: Cc1cc(C(=O)CC2CCCCN2C)c(C)n1-c1ccc(Cl)cc1] |

TABLE 3-continued

| Compound No. | Structure |
|---|---|
| 73 | 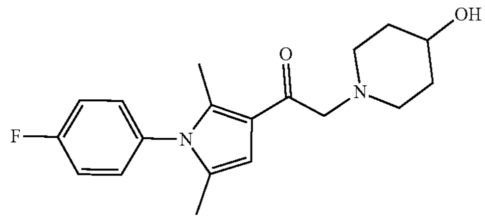 [SMILES: Cc1cc(C(=O)CN2CCC(O)CC2)c(C)n1-c1ccc(F)cc1] |
| 74 | 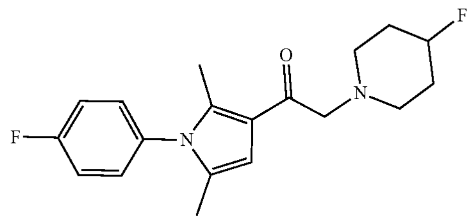 [SMILES: Cc1cc(C(=O)CN2CCC(F)CC2)c(C)n1-c1ccc(F)cc1] |
| 75 | 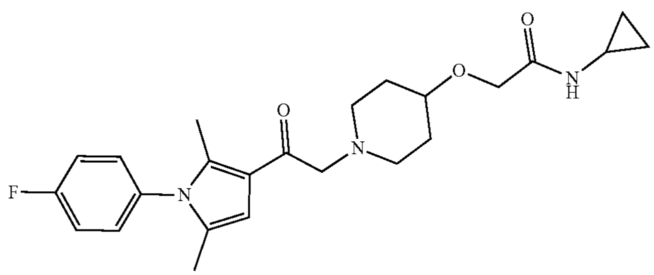 [SMILES: Cc1cc(C(=O)CN2CCC(OCC(=O)NC3CC3)CC2)c(C)n1-c1ccc(F)cc1] |
| 76 | 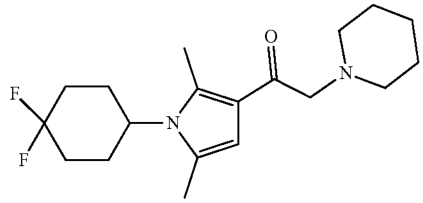 [SMILES: Cc1cc(C(=O)CN2CCCCC2)c(C)n1C1CCC(F)(F)CC1] |
| 77 | 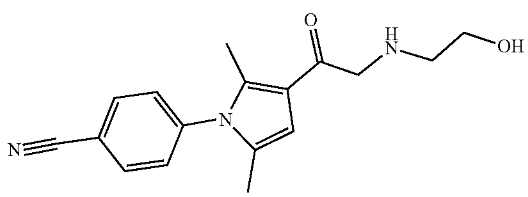 [SMILES: Cc1cc(C(=O)CNCCO)c(C)n1-c1ccc(C#N)cc1] |
| 79 | 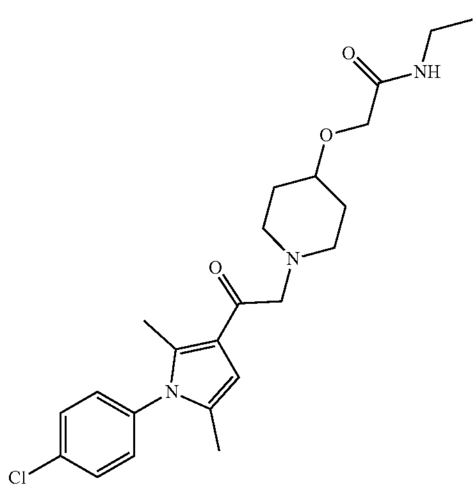 [SMILES: CCNC(=O)COC1CCN(CC(=O)c2cc(C)n(-c3ccc(Cl)cc3)c2C)CC1] |

TABLE 3-continued
| Compound No. | Structure |
|---|---|
| 80 | 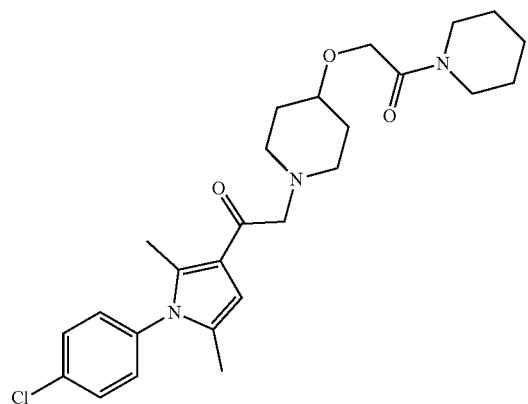 [SMILES: Cc1cc(C(=O)CN2CCC(OCC(=O)N3CCCCC3)CC2)c(C)n1-c1ccc(Cl)cc1] |
| 81 | 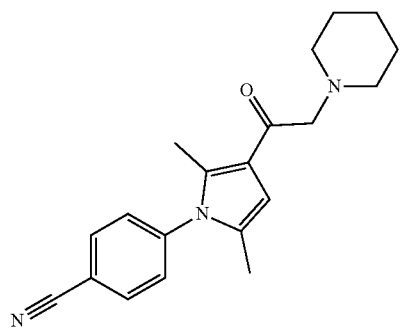 [SMILES: Cc1cc(C(=O)CN2CCCCC2)c(C)n1-c1ccc(C#N)cc1] |
| 82 | 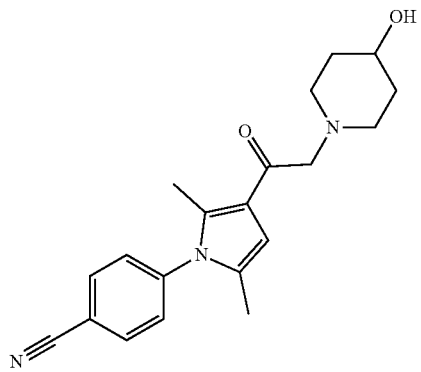 [SMILES: Cc1cc(C(=O)CN2CCC(O)CC2)c(C)n1-c1ccc(C#N)cc1] |
| 83 | 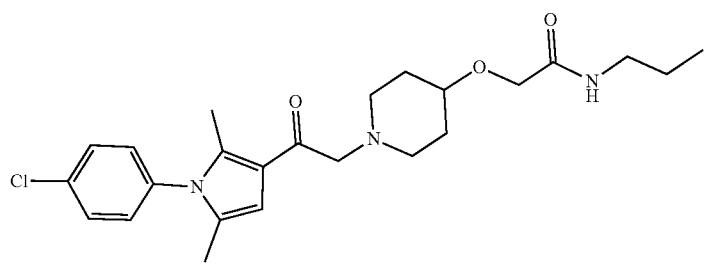 [SMILES: CCCNC(=O)COC1CCN(CC(=O)c2cc(C)n(-c3ccc(Cl)cc3)c2C)CC1] |

TABLE 3-continued
| Compound No. | Structure |
|---|---|
| 84 | 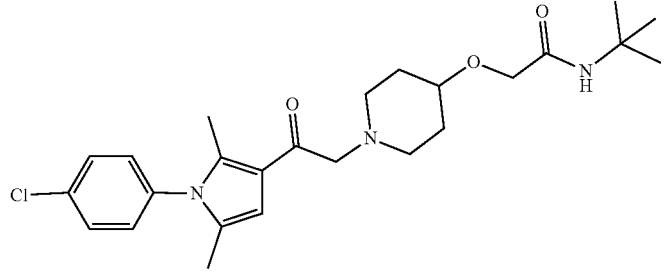 [SMILES: Cc1cc(C(=O)CN2CCC(OCC(=O)NC(C)(C)C)CC2)c(C)n1-c1ccc(Cl)cc1] |
| 85 | 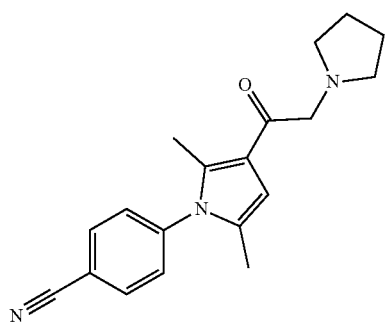 [SMILES: Cc1cc(C(=O)CN2CCCC2)c(C)n1-c1ccc(C#N)cc1] |
| 89A and 89B | 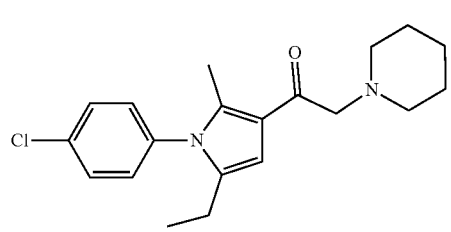 [SMILES: CCc1cc(C(=O)CN2CCCCC2)c(C)n1-c1ccc(Cl)cc1] |
| 90 | 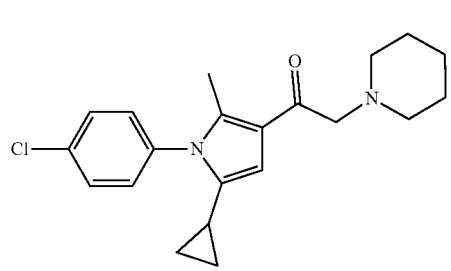 [SMILES: Cc1c(C(=O)CN2CCCCC2)cc(C2CC2)n1-c1ccc(Cl)cc1] |
| 91 | 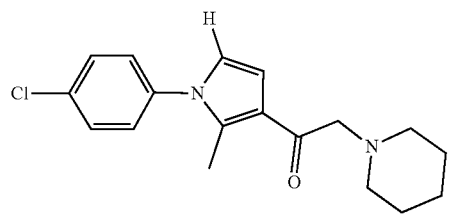 [SMILES: Cc1c(C(=O)CN2CCCCC2)ccn1-c1ccc(Cl)cc1] |

TABLE 3-continued

| Compound No. | Structure |
|---|---|
| 92 | 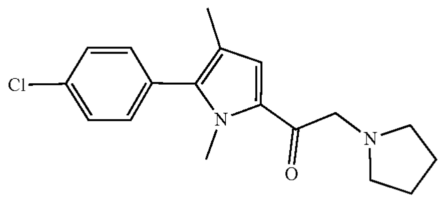 [SMILES: Cc1cc(C(=O)CN2CCCC2)n(C)c1-c1ccc(Cl)cc1] |
| 93 | 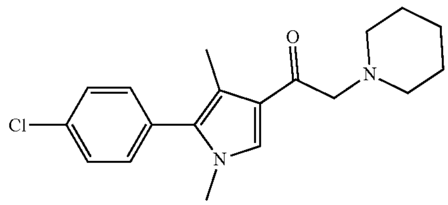 [SMILES: Cc1c(C(=O)CN2CCCCC2)cn(C)c1-c1ccc(Cl)cc1] |
| 94 | 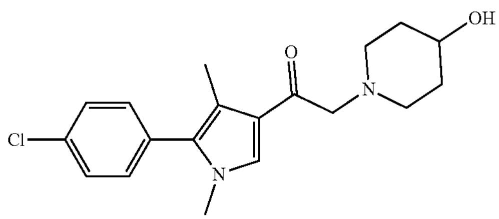 [SMILES: Cc1c(C(=O)CN2CCC(O)CC2)cn(C)c1-c1ccc(Cl)cc1] |
| 95 | 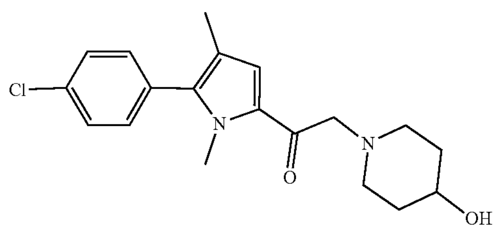 [SMILES: Cc1cc(C(=O)CN2CCC(O)CC2)n(C)c1-c1ccc(Cl)cc1] |
| 96 | 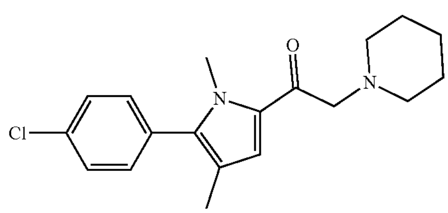 [SMILES: Cc1cc(C(=O)CN2CCCCC2)n(C)c1-c1ccc(Cl)cc1] |
| 97 | 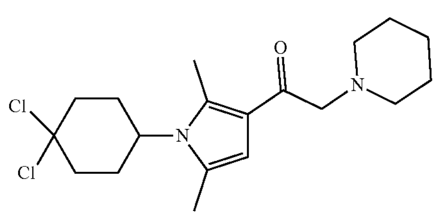 [SMILES: Cc1cc(C(=O)CN2CCCCC2)c(C)n1C1CCC(Cl)(Cl)CC1] |
| 99 | 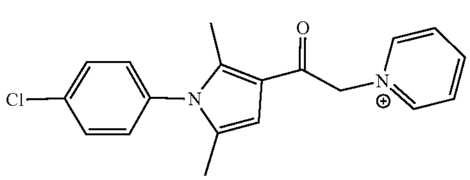 [SMILES: Cc1cc(C(=O)C[n+]2ccccc2)c(C)n1-c1ccc(Cl)cc1] |

TABLE 3-continued

| Compound No. | Structure |
|---|---|
| 100 | 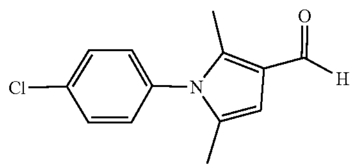 [SMILES: Cc1cc(C=O)c(C)n1-c1ccc(Cl)cc1] |
| 101 | 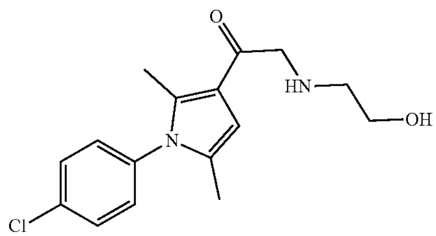 [SMILES: Cc1cc(C(=O)CNCCO)c(C)n1-c1ccc(Cl)cc1] |
| 102 | 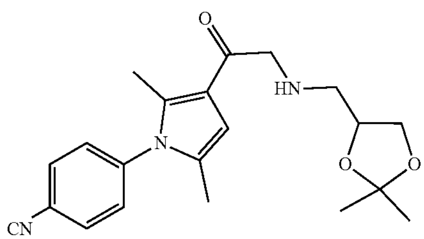 [SMILES: Cc1cc(C(=O)CNCC2COC(C)(C)O2)c(C)n1-c1ccc(C#N)cc1] |
| 103 | 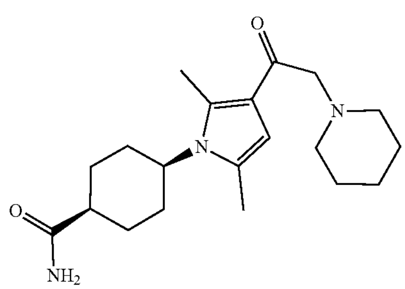 [SMILES: Cc1cc(C(=O)CN2CCCCC2)c(C)n1[C@H]1CC[C@@H](C(N)=O)CC1] |
| 105 | 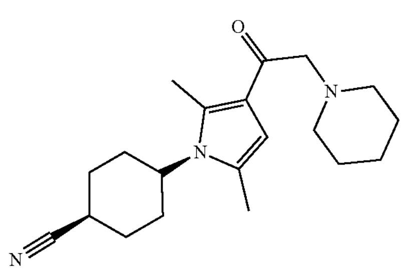 |
| 107 | 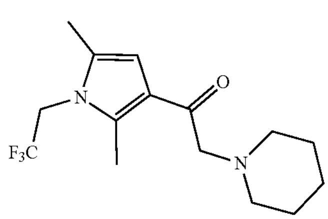 [SMILES: Cc1cc(C(=O)CN2CCCCC2)c(C)n1CC(F)(F)F] |

TABLE 3-continued
| Compound No. | Structure |
|---|---|
| 110 | 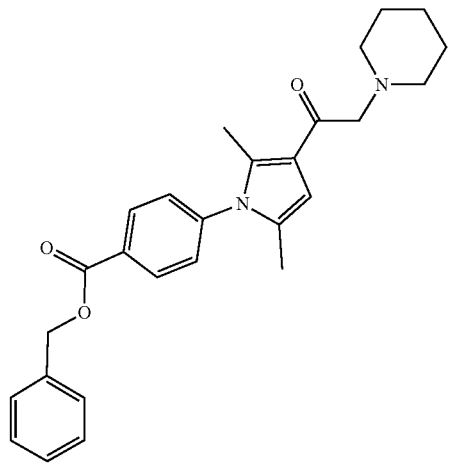 [SMILES: Cc1cc(C(=O)CN2CCCCC2)c(C)n1-c1ccc(C(=O)OCc2ccccc2)cc1] |
| 111 | 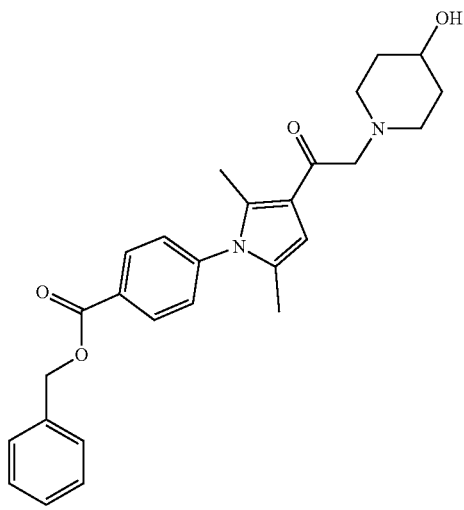 [SMILES: Cc1cc(C(=O)CN2CCC(O)CC2)c(C)n1-c1ccc(C(=O)OCc2ccccc2)cc1] |
| 112 | 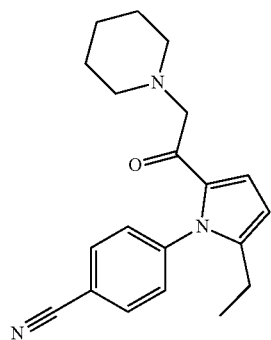 [SMILES: CCc1ccc(C(=O)CN2CCCCC2)n1-c1ccc(C#N)cc1] |

TABLE 3-continued
| Compound No. | Structure |
|---|---|
| 113 | 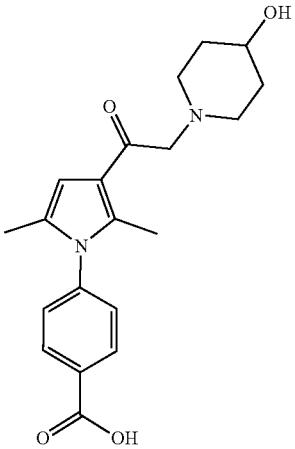 [SMILES: Cc1cc(C(=O)CN2CCC(O)CC2)c(C)n1-c1ccc(C(=O)O)cc1] |
| 114 | 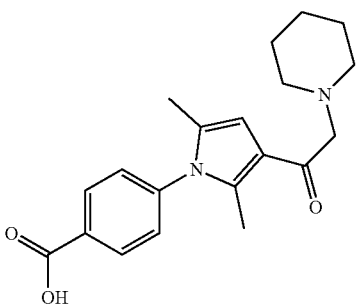 [SMILES: Cc1cc(C(=O)CN2CCCCC2)c(C)n1-c1ccc(C(=O)O)cc1] |
| 117 | 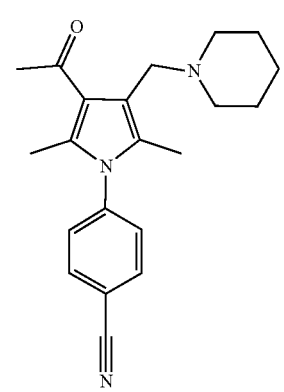 [SMILES: CC(=O)c1c(CN2CCCCC2)c(C)n(-c2ccc(C#N)cc2)c1C] |
| 120 | 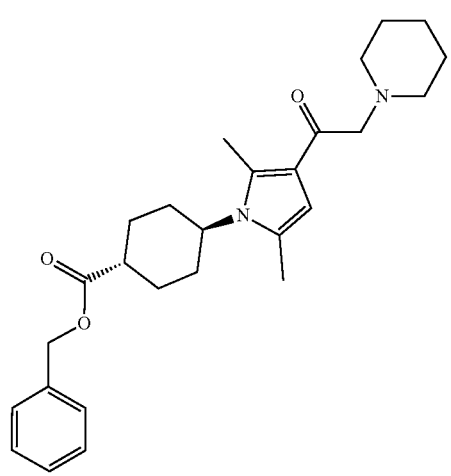 [SMILES: Cc1cc(C(=O)CN2CCCCC2)c(C)n1[C@H]1CC[C@H](C(=O)OCc2ccccc2)CC1] |

US 11,746,098 B2
93                                                                    94
TABLE 3-continued
| Compound No. | Structure |
|---|---|
| 121 | 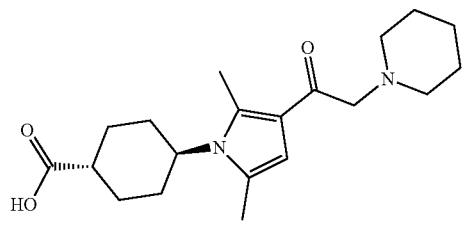 [SMILES: Cc1cc(C(=O)CN2CCCCC2)c(C)n1[C@H]1CC[C@H](C(=O)O)CC1] |
| 122 | 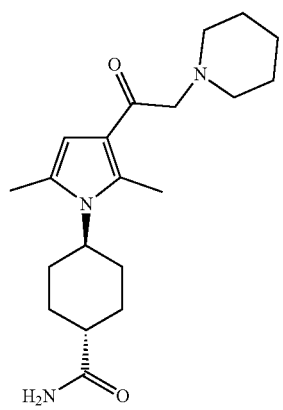 [SMILES: Cc1cc(C(=O)CN2CCCCC2)c(C)n1[C@H]1CC[C@H](C(N)=O)CC1] |
| 134 | 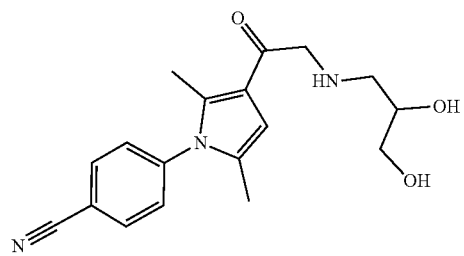 [SMILES: Cc1cc(C(=O)CNCC(O)CO)c(C)n1-c1ccc(C#N)cc1] |
| 135 | 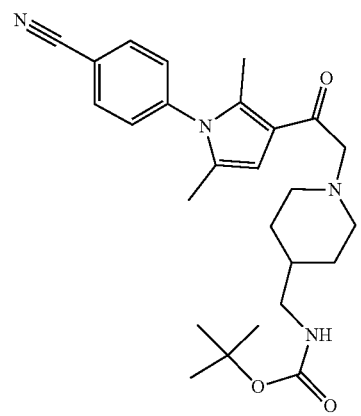 [SMILES: Cc1cc(C(=O)CN2CCC(CNC(=O)OC(C)(C)C)CC2)c(C)n1-c1ccc(C#N)cc1] |
| 136 | 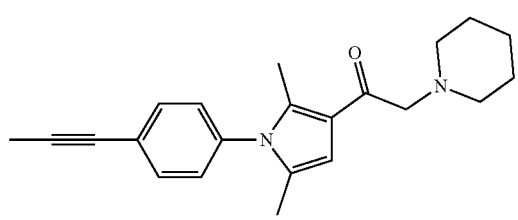 [SMILES: CC#Cc1ccc(-n2c(C)cc(C(=O)CN3CCCCC3)c2C)cc1] |

TABLE 3-continued

| Compound No. | Structure |
| --- | --- |
| 137 | 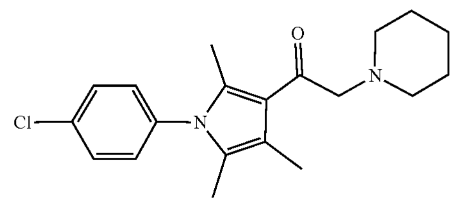 [SMILES: Cc1c(C(=O)CN2CCCCC2)c(C)n(-c2ccc(Cl)cc2)c1C] |
| 138 | 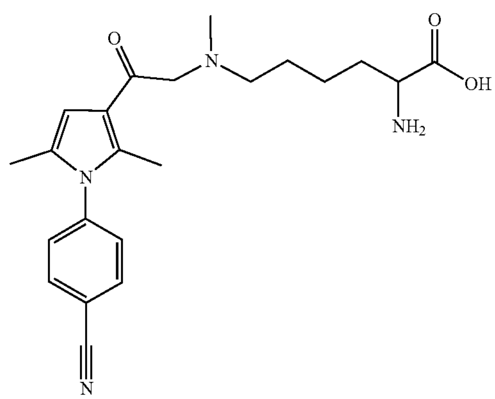 [SMILES: Cc1cc(C(=O)CN(C)CCCCC(N)C(=O)O)c(C)n1-c1ccc(C#N)cc1] |
| 139 | 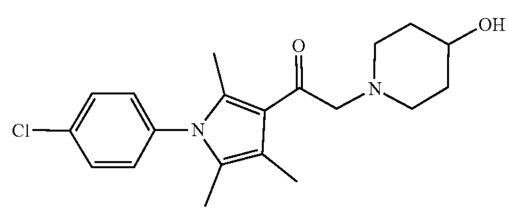 [SMILES: Cc1c(C(=O)CN2CCC(O)CC2)c(C)n(-c2ccc(Cl)cc2)c1C] |
| 140 | 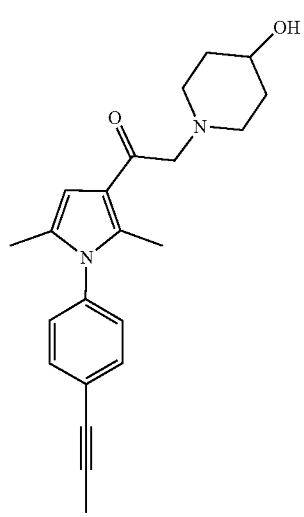 [SMILES: CC#Cc1ccc(-n2c(C)cc(C(=O)CN3CCC(O)CC3)c2C)cc1] |

TABLE 3-continued

| Compound No. | Structure |
|---|---|
| 143 | 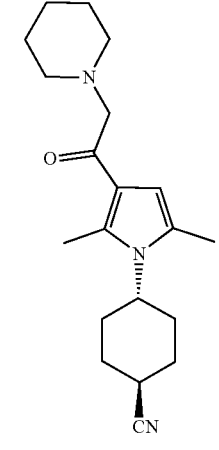 [SMILES: Cc1cc(C(=O)CN2CCCCC2)c(C)n1[C@H]1CC[C@H](C#N)CC1] |
| 157 | 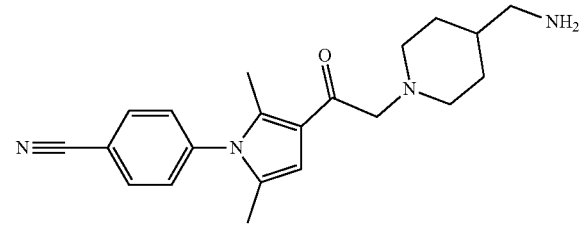 [SMILES: Cc1cc(C(=O)CN2CCC(CN)CC2)c(C)n1-c1ccc(C#N)cc1] |
| 158 | 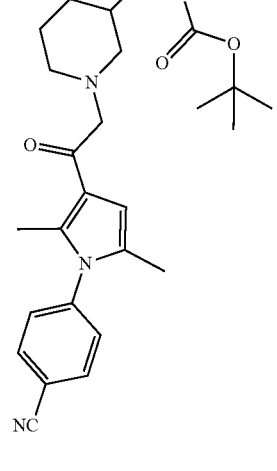 |
| 159 | 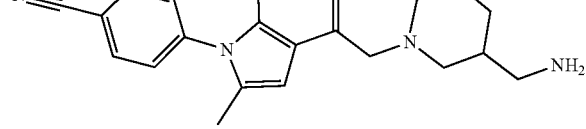 |

In some embodiments, the invention is directed to a compound shown above in Table 1, wherein the compound is not Compound 93 or Compound 96. In some embodiments, the invention is directed to a compound shown above in Table 1, wherein the compound is not Compound 71.

Definitions

The term "alkyl", as used herein, unless otherwise indicated, refers to both branched and straight-chain saturated aliphatic hydrocarbon groups having the specified number of carbon atoms; for example, "$C_1$-$C_{10}$ alkyl" denotes alkyl having 1 to 10 carbon atoms. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

The term, "alkenyl", as used herein, refers to both straight and branched-chain moieties having the specified number of carbon atoms and having at least one carbon-carbon double bond.

The term, "alkynyl", as used herein, refers to both straight and branched-chain moieties having the specified number or carbon atoms and having at least one carbon-carbon triple bond.

The term "cycloalkyl," as used herein, refers to cyclic alkyl moieties having 3 or more carbon atoms. Examples of cycloalkyl include, but are not limited to, cyclopropyl, cyclobutyl, cyclopentyl, cyclohexyl, cycloheptyl and adamantyl.

The term "cycloalkenyl," as used herein, refers to cyclic alkenyl moieties having 3 or more carbon atoms.

The term "cycloalkynyl," as used herein, refers to cyclic alkynyl moieties having 5 or more carbon atoms.

The term "heterocyclic" encompasses heterocycloalkyl, heterocycloalkenyl, heterobicycloalkyl, heterobicycloalkenyl, heteropolycycloalkyl, heteropolycycloalkenyl, and the like. Heterocycloalkyl refers to cycloalkyl groups containing one or more heteroatoms (O, S, or N) within the ring. Heterocycloalkenyl as used herein refers to cycloalkenyl groups containing one or more heteroatoms (O, S or N) within the ring. Heterobicycloalkyl refers to bicycloalkyl groups containing one or more heteroatoms (O, S or N) within a ring. Heterobicycloalkenyl as used herein refers to bicycloalkenyl groups containing one or more heteroatoms (O, S or N) within a ring. The foregoing heterocyclic groups may be C-attached or heteroatom-attached (where such is possible). As used herein, the term N-heterocyclic denotes that the heterocyclic group is N-attached. For example, when Z is N-heterocyclic, it is N-attached to the carbon to which $R_1$ and $R_2$ are attached. In some embodiments, heterocyclic encompasses an optionally substituted 5-membered N-heterocyclic, optionally having an additional heteroatom selected from the group consisting of O, S, and N. In some embodiments, heterocyclic encompasses an optionally substituted 6-membered N-heterocyclic, optionally having an additional heteroatom selected from the group consisting of O, S, and N. In some embodiments, the maximum number of heteroatoms is three, or two. In some embodiments, the heterocyclic comprises a single heteroatom. Representative examples of N-heterocyclic include, but are not limited to, pyrrolind-1-yl (1-pyrrolidinyl), piperidin-1-yl (1-piperidinyl), piperazin-1-yl (1-piperazinyl) and morpholin-1-yl (1-morpholinyl).

Cycloalkyl, cycloalkenyl, heterocyclic, groups also include groups similar to those described above for each of these respective categories, but which are substituted with one or more oxo moieties.

The term "aryl", as used herein, refers to mono- or polycyclic aromatic carbocyclic ring systems. A polycyclic aryl is a polycyclic ring system that comprises at least one aromatic ring. Polycyclic aryls can comprise fused rings, covalently attached rings or a combination thereof. The term "aryl" embraces aromatic radicals, such as, phenyl, naphthyl, indenyl, tetrahydronaphthyl, and indanyl. An aryl group may be substituted or unsubstituted. In some embodiments, the aryl is a $C_4$-$C_{10}$ aryl.

The term "heteroaryl", as used herein, refers to aromatic carbocyclic groups containing one or more heteroatoms (O, S, or N) within a ring. A heteroaryl group can be monocyclic or polycyclic. A heteroaryl group may additionally be substituted or unsubstituted. The heteroaryl groups of this invention can also include ring systems substituted with one or more oxo moieties. A polycyclic heteroaryl can comprise fused rings, covalently attached rings or a combination thereof. A polycyclic heteroaryl is a polycyclic ring system that comprises at least one aromatic ring containing one or more heteroatoms within a ring. Polycyclic aryls can comprise fused rings, covalently attached rings or a combination thereof. Examples of heteroaryl groups include, but are not limited to, pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, triazinyl, isoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, thiazolopyridinyl, oxazolopyridinyl and azaindolyl. The foregoing heteroaryl groups may be C-attached or heteroatom-attached (where such is possible). For instance, a group derived from pyrrole may be pyrrol-1-yl (N-attached) or pyrrol-3-yl (C-attached). In some embodiments, the heteroaryl is 4- to 10-membered heteroaryl.

The term "substituted" refers to substitution by independent replacement of one, two, or three or more of the hydrogen atoms with substituents including, but not limited to, —$C_1$-$C_{12}$ alkyl, —$C_2$-$C_{12}$ alkenyl, —$C_2$-$C_{12}$ alkynyl, —$C_3$-$C_{12}$ cycloalkyl, —$C_3$-$C_{12}$ cycloalkenyl, $C_3$-$C_{12}$ cycloalkynyl, -heterocyclic, —F, —Cl, —Br, —I, —OH, —$NO_2$, —$N_3$, —CN, —$NH_2$, oxo, thioxo, —$NHR_x$, —$NR_xR_x$, dialkylamino, -diarylamino, -diheteroarylamino, —$OR_x$, —C(O)$R_y$, —C(O)C(O)$R_y$, —$OCO_2R_y$, —OC(O) $R_y$, OC(O)C(O)$R_y$, —NHC(O)$R_y$, —$NHCO_2R_y$, —NHC(O) C(O)$R_y$, NHC(S)$NH_2$, —NHC(S)$NHR_x$, —NHC(NH)$NH_2$, —NHC(NH)$NHR_x$, —NHC(NH)$R_x$, —C(NH)$NHR_x$, and (C=$NR_x$)$R_x$; —$NR_xC(O)R_x$, —$NR_xC(O)N(R_x)_2$, —$NR_xCO_2R_y$, —$NR_xC(O)C(O)R_y$, —$NR_xC(S)NH_2$, —$NR_xC(S)NHR_x$, —$NR_xC(NH)NH_2$, —$NR_xC(NH)NHR_x$, —$NR_xC(NH)R_x$, —C(NR$_x$)$NHR_x$—S(O)$R_y$, —$NHSO_2R_x$, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, -polyalkoxyalkyl, -polyalkoxy, -methoxymethoxy, -methoxyethoxy, —SH, —S—$R_x$, or -methylthiomethyl, wherein $R_x$ is selected from the group consisting of hydrogen, —$C_1$-$C_{12}$ alkyl, —$C_2$-$C_{12}$ alkenyl, —$C_2$-$C_{12}$ alkynyl, —$C_3$-$C_{12}$ cycloalkyl, -aryl, -heteroaryl and -heterocyclic and —$R_y$ is selected from the group consisting of hydrogen, —$C_1$-$C_{12}$ alkyl, —$C_2$-$C_{12}$ alkenyl, —$C_2$-$C_{12}$ alkynyl, —$C_3$-$C_{12}$ cycloalkyl, -aryl, -heteroaryl, -heterocyclic, —$NH_2$, —NH—$C_1$-$C_{12}$ alkyl, —NH—$C_2$-$C_{12}$ alkenyl, —NH—$C_2$-$C_{12}$-alkynyl, —NH—$C_3$-$C_{12}$ cycloalkyl, —NH-aryl, —NH-heteroaryl and —NH-heterocyclic. It is understood that the aryls, heteroaryls, alkyls, and the like can be further substituted.

The term "haloalkyl" as used herein refers to an alkyl group having 1 to (2n+1) substituent(s) independently selected from F, Cl, Br or I, where n is the maximum number of carbon atoms in the alkyl group.

As will be understood by the skilled artisan, "H" is the symbol for hydrogen, "N" is the symbol for nitrogen, "S" is the symbol for sulfur, and "O" is the symbol for oxygen. "Me" is an abbreviation for methyl.

Non-limiting examples of optionally substituted aryl are phenyl, substituted phenyl, napthyl and substituted naphthyl.

Certain of the compounds described herein contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. "Isomers" are different compounds that have the same molecular formula. "Stereoisomers" are isomers that differ only in the way the atoms are arranged in space. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. When the compounds described herein contain olefinic double bonds or other centers of geometric asymmetry, and unless specified otherwise, it is intended that the compounds include both E and Z geometric isomers. Likewise, all tautomeric forms are also intended to be included.

The term "enantiomerically pure" means a stereomerically pure composition of a compound. For example, a stereochemically pure composition is a composition that is free or substantially free of other stereoisomers of that compound. In another example, for a compound having one chiral center, an enantiomerically pure composition of the compound is free or substantially free of the other enantiomer. In yet another example, for a compound having two chiral centers, an enantiomerically pure composition is free or substantially free of the other diastereomers.

Where a particular stereochemistry is described or depicted it is intended to mean that a particular enantiomer is present in excess relative to the other enantiomer. A compound has an R-configuration at a specific position when it is present in excess compared to the compound having an S-configuration at that position. A compound has an S-configuration at a specific position when it is present in excess compared to the compound having an R-configuration at that position.

Likewise, all tautomeric forms are also intended to be included. Where a particular compound is described or depicted, it is intended to encompass that chemical structure as well as tautomers of that structure.

It is to be understood that atoms making up the compounds of the present invention are intended to include isotopic forms of such atoms. Isotopes, as used herein, include those atoms having the same atomic number but different mass numbers. Isotopes of hydrogen include, for example, tritium and deuterium, and isotopes of carbon include, for example, $^{13}C$ and $^{14}C$. The invention therefore encompasses embodiments in which one or more of the hydrogen atoms in a compound of Formula (I), (Ia), (Ib), (IIa), (IIb), (IIIa), (IIIb), (IIIc), (IIId), (IIIe), (IIIf), (IIIg), (IIIh), (IV), (V), (VI), (VII), (VIII), (IX) or (X), or a compound described herein, are replaced with deuterium. The invention also encompasses embodiments wherein one or more of the carbon atoms in a compound of Formula (I), (Ia), (Ib), (IIa), (IIb), (IIIa), (IIIb), (IIIc), (IIId), (IIIe), (IIIf), (IIIg), (IIIh), (IV), (V), (VI), (VII), (VIII), (IX) or (X), or a compound described herein, are replaced with silicon atoms. The invention additionally encompasses embodiment wherein one or more of the nitrogen atoms in a compound of Formula (I), (Ia), (Ib), (IIa), (IIb), (IIIa), (IIIb), (IIIc), (IIId), (IIIe), (IIIf), (IIIg), (IIIh), (IV), (V), (VI), (VII), (VIII), (IX) or (X), or a compound described herein, are oxidized to N-oxide.

Methods of Synthesis

Methods for the synthesis of the compounds of Formula (I), (Ia), (Ib), (IIa), (IIb), (IIIa), (IIIb), (IIIc), (IIId), (IIIe), (IIIf), (IIIg), (IIIh), (IV), (V), (VI), (VII), (VIII), (IX) or (X), or a compound as described herein have been described in the literature, for example in: 1) Banik, B. et al. "Simple Synthesis of Substituted Pyrroles" J. Org. Chem, 2004, 69, 213; 2) Sawada, Y. et al. "Eight-Membered Oxygen Heterocycles by Brook Rearrangement-mediated [3+4] Annulation" Org. Lett. 2004, 6, 2277; 3) Aube, J. et al. "Synthetic Aspects of an Asymmetric Nitrogen-Insertion Process: Preparation of Chiral, Non-Racemic Caprolactams and Valerolactams. Total Synthesis of (−)-Alloyohimbane" J. Am. Chem. Soc. 1990, 112, 4879; 4) Ookawa, A. et al. "Asymmetric Synthesis of Optically Active threo- and erythro-Pyrrolidinylbenzyl Alcohol by the Highly Stereospecific Arylation of (S)-Proline and the Subsequent Highly Diastereoselective Reduction of the α-Amineo Ketone" J. Chem. Soc. Perkin Trans. I, 1987, 7, 1465.

Exemplary synthetic routes for the preparation of compounds the compounds of Formula (I), (Ia), (Ib), (IIa), (IIb), (IIIa), (IIb), (IIIc), (IIId), (IIIe), (IIIf), (IIIg), (IIIh), (IV), (V), (VI), (VII), (VIII), (IX) or (X) are shown in the Schemes I to II below. As will be understood by the skilled artisan, diastereomers can be separated from the reaction mixture using column chromatography.

Scheme I

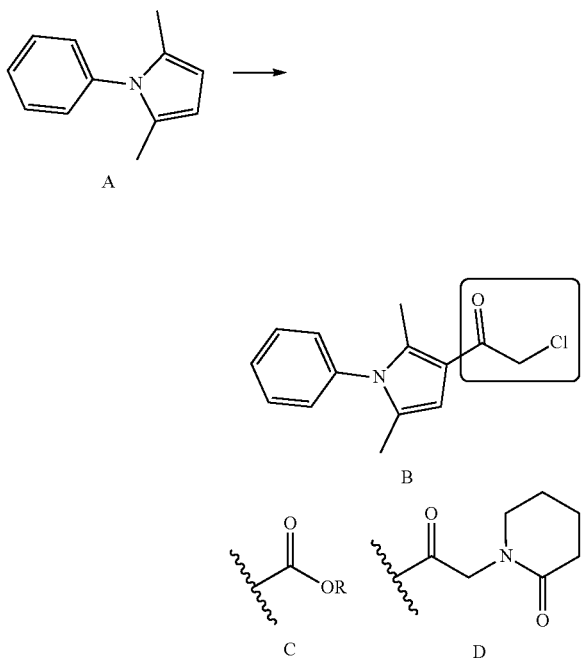

A Paal-Knorr pyrrole synthesis using aniline and an appropriate diketone affords pyrrole $A^1$. A Friedel-Crafts acylation with chloroacetyl chloride and $AlCl_3$ provides intermediate B. The chloride can be easily displaced with a variety of $O^2$, $N^3$, S and C based nucleophiles to provide the desired compounds.

Scheme II

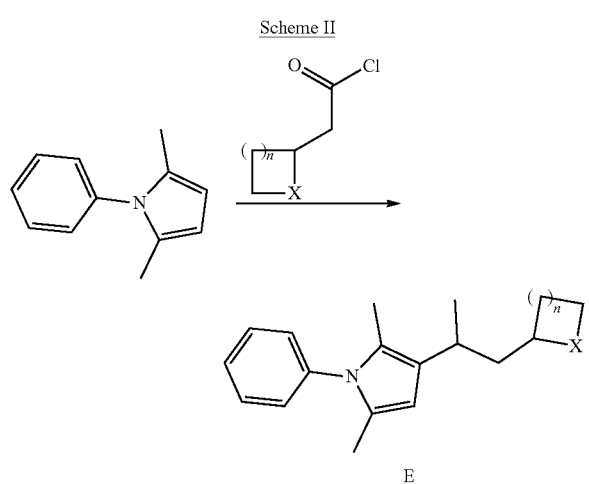

E

A Friedel-Crafts acylation using an appropriately substituted acetylchloride and pyrrole A will afford the desired acyl pyrroles E where X can be optionally substituted N, S, C, O.[4]

Formulations

The invention encompasses pharmaceutically acceptable salts of the compounds described herein. Thus, in certain aspects, the invention is directed to pharmaceutically acceptable salts of compounds of the invention and pharmaceutical compositions thereof. A "pharmaceutically acceptable salt" includes an ionic bond-containing product of the reaction between the disclosed compound with either an acid or a base, suitable for administering to a subject. Pharmaceutically acceptable salts are well known in the art and are described, for example, in Berge et al. (1977), Pharmaceutical Salts. Journal of Pharmaceutical Sciences, 69(1): 1-19, the contents of which are herein incorporated by reference. A non-limiting example of a pharmaceutically acceptable salt is an acid salt of a compound containing an amine or other basic group which can be obtained by reacting the compound with a suitable organic or inorganic acid. Examples of pharmaceutically acceptable salts also can be metallic salts including, but not limited to, sodium, magnesium, calcium, lithium and aluminum salts. Further examples of pharmaceutically acceptable salts include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures), succinates, trifluoroacetates, benzoates and salts with amino acids such as glutamic acid. Salts can also be formed with suitable organic bases when the compound comprises an acid functional group such as —C(O)OH or —SO$_3$H. Such bases suitable for the formation of a pharmaceutically acceptable base addition salts with compounds of the present invention include organic bases that are nontoxic and strong enough to react with the acid functional group. Such organic bases are well known in the art and include amino acids such as arginine and lysine, mono-, di-, and triethanolamine, choline, mono-, di-, and trialkylamine, such as methylamine, dimethylamine, and trimethylamine, guanidine, N-benzylphenethylamine, N-methylglucosamine, N-methylpiperazine, morpholine, ethylendiamine, tris(hydroxymethyl)aminomethane, and the like.

The activity of the compound described herein to inhibit USP14 can be measured using previously described methodology [B. H. Lee et al. Nature 2010, 467 (9), 179, the contents of which are expressly incorporated by reference herein].

The invention also includes hydrates of the compounds described herein, including, for example, solvates of the compounds described herein, pharmaceutical compositions comprising the solvates and methods of use of the solvates. In some embodiments, the invention is a solvate of a compound of Formula (I), (Ia), (Ib), (IIa), (IIb), (IIIa), (IIIb), (IIIc), (IIId), (IIIe), (IIIf), (IIIg), (IIIh), (IV), (V), (VI), (VII), (VIII), (IX) or (X), or any compound described herein, or a pharmaceutical composition thereof.

Also included in the present invention are prodrugs of the compounds described herein, for example, prodrugs of a compound of Formula (I), (Ia), (Ib), (IIa), (IIb), (IIIa), (IIIb), (IIIc), (IIId), (IIIe), (IIIf), (IIIg), (IIIh), (IV), (V), (VI), (VII), (VIII), (IX) or (X), or any compound described herein, or a pharmaceutical composition of any of thereof or method of use of the prodrug.

The invention additionally includes clathrates of the compounds described herein, pharmaceutical compositions comprising the clathrates, and methods of use of the clathrates. In some embodiments, the invention is directed to clathrates of a compound of Formula (I), (Ia), (Ib), (IIa), (Ib), (IIIa), (IIIb), (IIIc), (IIId), (IIIe), (IIIf), (IIIg), (IIIh), (IV), (V), (VI), (VII), (VIII), (IX) or (X), or any compound described herein, or a pharmaceutical composition thereof.

Methods of Treating

The invention encompasses a method of inhibiting deubiquitination activity of a Usp14 protein comprising contacting the Usp14 protein with a compound described herein, or a pharmaceutically acceptable salt, solvate, clathrate or prodrug thereof, in an amount sufficient to inhibit deubiquitination activity of the Usp14 protein. In certain embodiments, a cell is contacted with the compound described herein or a pharmaceutically acceptable salt, solvate, clathrate or prodrug thereof, in an amount sufficient to inhibit deubiquitination activity of the Usp14 protein.

The invention also encompasses a method of enhancing protein degradation by a proteasome in a cell comprising contacting the cell with a compound of a compound described herein, or a pharmaceutically acceptable salt, solvate, clathrate or prodrug thereof, in an amount sufficient to enhance protein degradation by the proteasome.

In some embodiments, the invention includes pharmaceutical compositions comprising a pharmaceutically acceptable carrier or excipient and a compound described herein. The compounds described herein, or a pharmaceutically acceptable salt, solvate, clathrate or prodrug, thereof can be administered in pharmaceutical compositions comprising a pharmaceutically acceptable carrier or excipient. The excipient can be chosen based on the expected route of administration of the composition in therapeutic applications. The route of administration of the composition depends on the condition to be treated. For example, intravenous injection may be preferred for treatment of a systemic disorder and oral administration may be preferred to treat a gastrointestinal disorder. The route of administration and the dosage of the composition to be administered can be determined by the skilled artisan without undue experimentation in conjunction with standard dose-response studies. Relevant circumstances to be considered in making those determinations include the condition or conditions to be treated, the choice of composition to be administered, the age, weight, and response of the individual patient, and the severity of the patient's symptoms.

Pharmaceutical compositions comprising the compounds described herein, or a pharmaceutically acceptable salt, solvate, clathrate or prodrug, or a compound described herein, can be administered by a variety of routes including, but not limited to, parenteral, oral, pulmonary, ophthalmic, nasal, rectal, vaginal, aural, topical, buccal, transdermal, intravenous, intramuscular, subcutaneous, intradermal, intraocular, intracerebral, intralymphatic, intraarticular, intrathecal and intraperitoneal.

The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the pharmacologic agent or composition. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like. Pharmaceutical compositions can also include large, slowly metabolized macromolecules such as proteins, polysaccharides such as chitosan, polylactic acids, polyglycolic acids and copolymers (such as latex functionalized SEPHAROSE™, agarose, cellulose, and the like), polymeric amino acids, amino acid copolymers, and lipid aggregates (such as oil droplets or liposomes).

The compositions can be administered parenterally such as, for example, by intravenous, intramuscular, intrathecal or subcutaneous injection. Parenteral administration can be accomplished by incorporating a composition into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as, for example, benzyl alcohol or methyl parabens, antioxidants such as, for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

Injectable formulations can be prepared either as liquid solutions or suspensions; solid forms suitable for solution in, or suspension in, liquid vehicles prior to injection can also be prepared. The preparation also can also be emulsified or encapsulated in liposomes or micro particles such as polylactide, polyglycolide, or copolymer for enhanced adjuvant effect [Langer, *Science* 249: 1527, 1990 and Hanes, *Advanced Drug Delivery Reviews* 28: 97-119, 1997]. The compositions and pharmacologic agents described herein can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, transdermal applications and ocular delivery. For suppositories, binders and carriers include, for example, polyalkylene glycols or triglycerides; such suppositories can be formed from mixtures containing the active ingredient in the range of about 0.5% to about 10%, preferably about 1% to about 2%. Oral formulations include excipients, such as pharmaceutical grades of mannitol, lactose, starch, magnesium stearate, sodium saccharine, cellulose, and magnesium carbonate. Topical application can result in transdermal or intradermal delivery. Transdermal delivery can be achieved using a skin patch or using transferosomes. [Paul et al., Eur. J. Immunol. 25: 3521-24, 1995; Cevc et al., *Biochem. Biophys. Acta* 1368: 201-15, 1998].

For the purpose of oral therapeutic administration, the pharmaceutical compositions can be incorporated with excipients and used in the form of tablets, troches, capsules, elixirs, suspensions, syrups, wafers, chewing gums and the like. Tablets, pills, capsules, troches and the like may also contain binders, excipients, disintegrating agent, lubricants, glidants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and non-toxic in the amounts used. In another embodiment, the composition is administered as a tablet or a capsule.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor, and the like. For vaginal administration, a pharmaceutical composition may be presented as pessaries, tampons, creams, gels, pastes, foams or spray.

The pharmaceutical composition can also be administered by nasal administration. As used herein, nasally administering or nasal administration includes administering the composition to the mucus membranes of the nasal passage or nasal cavity of the patient. As used herein, pharmaceutical compositions for nasal administration of a composition include therapeutically effective amounts of the compounds prepared by well-known methods to be administered, for example, as a nasal spray, nasal drop, suspension, gel, ointment, cream or powder. Administration of the composition may also take place using a nasal tampon or nasal sponge.

For topical administration, suitable formulations may include biocompatible oil, wax, gel, powder, polymer, or other liquid or solid carriers. Such formulations may be administered by applying directly to affected tissues, for example, a liquid formulation to treat infection of conjunctival tissue can be administered dropwise to the subject's eye, or a cream formulation can be administered to the skin.

Rectal administration includes administering the pharmaceutical compositions into the rectum or large intestine. This can be accomplished using suppositories or enemas. Suppository formulations can easily be made by methods known in the art. For example, suppository formulations can be prepared by heating glycerin to about 120° C., dissolving the pharmaceutical composition in the glycerin, mixing the heated glycerin after which purified water may be added, and pouring the hot mixture into a suppository mold.

Transdermal administration includes percutaneous absorption of the composition through the skin. Transdermal formulations include patches, ointments, creams, gels, salves and the like.

In addition to the usual meaning of administering the formulations described herein to any part, tissue or organ whose primary function is gas exchange with the external environment, for purposes of the present invention, "pulmonary" will also mean to include a tissue or cavity that is contingent to the respiratory tract, in particular, the sinuses. For pulmonary administration, an aerosol formulation containing the active agent, a manual pump spray, nebulizer or pressurized metered-dose inhaler as well as dry powder formulations are contemplated. Suitable formulations of this type can also include other agents, such as antistatic agents, to maintain the disclosed compounds as effective aerosols.

A drug delivery device for delivering aerosols comprises a suitable aerosol canister with a metering valve containing a pharmaceutical aerosol formulation as described and an actuator housing adapted to hold the canister and allow for drug delivery. The canister in the drug delivery device has a head space representing greater than about 15% of the total volume of the canister. Often, the compound intended for pulmonary administration is dissolved, suspended or emulsified in a mixture of a solvent, surfactant and propellant. The mixture is maintained under pressure in a canister that has been sealed with a metering valve.

The invention also encompasses a method of treating a patient suffering from a condition associated with a dysfunction in protein homeostasis comprising administering to said patient a therapeutically effective amount of a compound described herein.

"Treating" or "treatment" includes preventing or delaying the onset of the symptoms, complications, or biochemical indicia of a disease, alleviating or ameliorating the symptoms or arresting or inhibiting further development of the disease, condition, or disorder. A "subject" is an animal to be treated or in need of treatment. A "patient" is a human subject in need of treatment.

An "effective amount" refers to that amount of an agent that is sufficient to achieve a desired and/or recited effect. In the context of a therapeutic agent, an "effective amount" of the therapeutic agent that is sufficient to ameliorate of one or more symptoms of a disorder and/or prevent advancement of a disorder, cause regression of the disorder and/or to achieve a desired effect.

As used herein, the term "inhibiting" or "decreasing" encompasses causing a net decrease by either direct or indirect means. The term "increasing" or "enhancing" means to cause a net gain by either direct or indirect means.

The invention encompasses the treatment of a condition associated with a dysfunction in proteostasis. Proteostasis refers to protein homeostasis. Dysfunction in protein homeostasis is a result of protein misfolding, protein aggregation, defective protein trafficking or protein degradation. Exemplary proteins of which there can be a dysfunction in proteostasis, for example that can exist in a misfolded state, include, but are not limited to, glucocerebrosidase, hexosamine A, cystic fibrosis transmembrane conductance regulator, aspartylglucsaminidase, α-galactosidase A, cysteine transporter, acid ceramidase, acid α-L-fucosidase, protective protein, cathepsin A, acid β-glucosidase, acid β-galactosidase, iduronate 2-sulfatase, α-L-iduronidase, galactocerebrosidase, acid α-mannosidase, acid β-mannosidase, arylsulfatase B, arylsulfatase A, N-acetylgalactosamine-6-sulfate sulfatase, acid β-galactosidase, N-acetylglucosamine-1-phosphotransferase, acid sphingmyelinase, NPC-1, acid α-glucosidase, β-hexosamine B, heparin N-sulfatase, α-N-acetylglucosaminidase, islet amyloid polypeptide (IAPP or amylin), α-glucosaminide N-acetyltransferase, N-acetylglucosamine-6-sulfate sulfatase, α-N-acetylgalactosaminidase, α-neuramidase, β-glucuronidase, β-hexosamine A and acid lipase, polyglutamine, α-synuclein, Aβ peptide, tau protein, transthyretin, insulin, TAR DNA-binding protein 43 (TDP-43), ataxin-3, superoxide dismutase (SOD), and rhodopsin.

In certain embodiments, the protein is selected from the group consisting of huntingtin, tau, alpha-synuclein, al antitrypsin and superoxide dismutase.

Protein conformational diseases encompass gain of function disorders and loss of function disorders. In one embodiment, the protein conformational disease is a gain of function disorder. The terms "gain of function disorder," "gain of function disease," "gain of toxic function disorder" and "gain of toxic function disease" are used interchangeably herein. A gain of function disorder is a disease characterized by increased aggregation-associated proteotoxicity. In these diseases, aggregation exceeds clearance inside and/or outside of the cell. Gain of function diseases include, but are not limited to neurodegenerative diseases associated with aggregation of polyglutamine, Lewy body diseases, amyotrophic lateral sclerosis, transthyretin-associated aggregation diseases, Alzheimer's disease, Machado-Joseph disease, cerebral B-amyloid angiopathy, retinal ganglion cell degeneration, tautopathies (progressive supranuclear palsy, corticobasal degeration, frontotemporal lobar degeneration), cerebral hemorrhage with amyloidosis, Alexander disease, Serpinopathies, familial amyloidotic neuropathy, senile systemic amyloidosis, ApoAI amyloidosis, ApoAII amyloidosis, ApoAIV amyloidosis, familial amyloidosis of the Finnish type, lysoyzme amyloidosis, fibrinogen amyloidosis, dialysis amyloidosis, inclusion body myositis/myopathy, cataracts, medullary thyroid carcinoma, cardiac atrial amyloidosis, pituitary prolactinoma, hereditary lattice corneal dystrophy, cutaneous lichen amyloidosis, corneal lactoferrin amyloidosis, corneal lactoferrin amyloidosis, pulmonary alveolar proteinosis, odontogenic tumor amyloid, seminal vesical amyloid, sickle cell disease, critical illness myopathy, von Hippel-Lindau disease, spinocerebellar ataxia 1, Angelman syndrome, giant axon neuropathy, inclusion body myopathy with Paget disease of bone, frontotemporal dementia (IBMPFD) and prion diseases. Neurodegenerative diseases associated with aggregation of polyglutamine include, but are not limited to, Huntington's disease, dentatorubral and pallidoluysian atrophy, several forms of spino-cerebellar ataxia, and spinal and bulbarmuscular atrophy. Alzheimer's disease is characterized by the formation of two types of aggregates: extracellular aggregates of A☐ peptide and intracellular aggregates of the microtubule associated protein tau. Transthyretin-associated aggregation diseases include, for example, senile systemic amyloidoses and familial amyloidotic neuropathy. Lewy body diseases are characterized by an aggregation of D-synuclein protein and include, for example, Parkinson's disease. Prion diseases (also known as transmissible spongiform encephalopathies or TSEs) are characterized by aggregation of prion proteins. Exemplary human prion diseases are Creutzfeldt-Jakob Disease (CJD), Variant Creutzfeldt-Jakob Disease, Gerstmann-Straussler-Scheinker Syndrome, Fatal Familial Insomnia and Kuru. Additional neurodegenerative diseases include tauopathies, Frontal Lobe Dementia (FLD), Dementias (including, but not limited to, Dementia with Lewy bodies (DLB), familial dementia, Serpinopathies, Down's Syndrome dementia), Multiple Sclerosis, and Neuropathic pain.

In a further embodiment, the protein conformation disease is a loss of function disorder. The terms "loss of function disease" and "loss of function disorder" are used interchangeably herein. Loss of function diseases are a group of diseases characterized by inefficient folding of a protein resulting in excessive degradation of the protein. Loss of function diseases include, for example, lysosomal storage diseases. Lysosomal storage diseases are a group of diseases characterized by a specific lysosomal enzyme deficiency which may occur in a variety of tissues, resulting in the build-up of molecules normally degraded by the deficient enzyme. The lysosomal enzyme deficiency can be in a lysosomal hydrolase or a protein involved in the lysosomal trafficking. Lysosomal storage diseases include, but are not limited to, aspartylglucosaminuria, Fabry's disease, Batten disease, Cystinosis, Farber, Fucosidosis, Galactasidosialidosis, Gaucher's disease (including Types 1, 2 and 3), Gm1 gangliosidosis, Hunter's disease, Hurler-Scheie's disease, Krabbe's disease, α-Mannosidosis, β-Mannosidosis, Maroteaux-Lamy's disease, Metachromatic Leukodystrophy, Morquio A syndrome, Morquio B syndrome, Mucolipidosis II, Mucolipidosis III, Neimann-Pick Disease (including Types A, B and C), Pompe's disease, Sandhoff disease, Sanfilippo syndrome (including Types A, B, C and D), Schindler disease, Schindler-Kanzaki disease, Sialidosis, Sly syndrome, Tay-Sach's disease and Wolman disease.

In yet an additional embodiment, the disease associated with a dysfunction in proteostasis is a myopathy. In some embodiments, the myopathy is selected from the group consisting of Duchenne muscular dystrophy (DMD), Becker's muscular dystrophy (BMD), Spinal muscular atrophy (SMA), Spinal-Bulbar Muscular Atrophy (SBMA), Inclusion body myositis, Freidreich's Ataxia, multiple systems atrophy, spinocerebellar ataxias and seipinopathies.

In another embodiment, the disease associated with a dysfunction in proteostasis is a cardiovascular disease. Cardiovascular diseases include, but are not limited to, coronary artery disease, myocardial infarction, stroke, restenosis and arteriosclerosis. Conditions associated with a dysfunction of proteostasis also include ischemic conditions, such as, ischemia/reperfusion injury, myocardial ischemia, stable angina, unstable angina, stroke, ischemic heart disease and cerebral ischemia.

In yet another embodiment, the disease associated with a dysfunction in proteostasis is diabetes and/or complications of diabetes, including, but not limited to, diabetic retinopathy, cardiomyopathy, neuropathy, nephropathy, and impaired wound healing.

In a further embodiment, the disease associated with a dysfunction in proteostasis is an ocular disease including, but not limited to, age-related macular degeneration (AMD), diabetic macular edema (DME), diabetic retinopathy, glaucoma, cataracts, retinitis pigmentosa (RP) and dry macular degeneration.

In some embodiments, the condition associated with a dysfunction in proteostasis is selected from the group consisting of Huntington's disease, Alzheimer's disease, Parkinson's disease, amyotrophic lateral sclerosis, diabetes and complications thereof, ocular diseases and cancer or tumor.

Additional conditions associated with a dysfunction of proteostasis include hemoglobinopathies, inflammatory diseases, intermediate filament diseases, drug-induced lung damage and hearing loss. The invention also encompasses methods for the treatment of hemoglobinopathies (such as sickle cell anemia), an inflammatory disease (such as inflammatory bowel disease, colitis, ankylosing spondylitis), intermediate filament diseases (such as non-alcoholic and alcoholic fatty liver disease) and drug induced lung damage (such as methotrexate-induced lung damage). The invention additionally encompasses methods for treating hearing loss, such as noise-induced hearing loss, aminoglycoside-induced hearing loss, and cisplatin-induced hearing loss.

In addition to conditions associated with a dysfunction in proteostasis, the compound of the present invention can be used to treat a disease or condition characterized by deficient proteasome activity or deficient activity of other components of the ubiquitin-proteasome pathway. Such conditions include, for example, Hippel-Lindau disease, spino-cerebellar ataxia 1, Angelman syndrome, giant axon neuropathy, inclusion body myopathy with Paget disease, and frontotemporal dementia.

In certain embodiments, the invention encompasses a method for the treatment of a condition selected from the group consisting of Parkinson's disease, Alzheimer's disease, Frontotemporal lobar dementia (FTLD), Progressive Supranuclear Palsy (PSP), Amyotrophic lateral sclerosis (ALS), Spinocerebellar ataxia (SCA), Retinitis pigmentosum, prion diseases and autism.

In certain embodiments, the invention includes methods for the treatment of a condition associated with a dysfunction in proteostasis comprising administering to a patient in need thereof an effective amount of a compound of Formula (I), (Ia), (Ib), (IIa), (IIb), (IIIa), (IIIb), (IIIc), (IIId), (IIIe), (IIIf), (IIIg), (IIIh), (IV), (V), (VI), (VII), (VIII), (IX) or (X), or a pharmaceutically acceptable salt, solvate, clathrate or prodrug, of any of thereof, and a second agent (e.g., a second therapeutic agent). Co-administered agents, compounds, or therapeutics need not be administered at exactly the same time. In certain embodiments, however, Formula (I), (Ia), (Ib), (IIa), (IIb), (IIa), (IIb), (IIIc), (IIId), (IIIe), (IIIf), (IIIg), (IIIh), (IV), (V), (VI), (VII), (VIII), (IX) or (X), or a pharmaceutically acceptable salt, solvate, clathrate or prodrug, or a compound described herein, is administered substantially simultaneously as the second agent.

By "substantially simultaneously," it is meant that the compound of Formula (I), (Ia), (Ib), (IIa), (IIb), (IIIa), (IIIb), (IIIc), (IIId), (IIIe), (IIIf), (IIIg), (IIIh), (IV), (V), (VI), (VII), (VIII), (IX) or (X), or a pharmaceutically acceptable salt, solvate, clathrate or prodrug of any of thereof, is administered before, at the same time, and/or after the administration of the second agent, and encompasses, for example, administration within the same treatment session or as part of the same treatment regimen. Exemplary second agents include pharmacologic chaperones and proteostasis regulators (such as, those described below).

In yet additional aspects, the invention encompasses a method for treating a condition characterized by deficient proteasome activity or deficiency of other components of the ubiquitin-proteasome pathway in a subject comprising administering to said subject an effective amount of a compound of the invention, or a pharmaceutically acceptable salt, solvate, clathrate or prodrug thereof.

In an additional embodiment, the invention is directed to a pharmaceutical composition comprising a compound of Formula (I), (Ia), (Ib), (IIa), (IIb), (IIIa), (IIIb), (IIIc), (IIId), (IIIe), (IIIf), (IIIg), (IIIh), (IV), (V), (VI), (VII), (VIII), (IX) or (X), or a pharmaceutically azcceptable salt, solvate, clathrate or prodrug of any of thereof, and a second agent, wherein the second agent is selected from the group consisting of a pharmacologic chaperone and a proteostasis regulator. The invention also encompasses a method of treating a patient suffering from a condition associated with a dysfunction in proteostasis comprising administering a therapeutically effective amount of a compound of the invention and a second agent, wherein the second agent is a pharmacologic chaperone. Pharmacologic chaperones or kinetic stabilizers refer to compounds that bind an existing steady state level of the folded mutant protein and chemically enhance the folding equilibrium by stabilizing the fold [Bouvier, Chem Biol 14: 241-242, 2007; Fan et al., Nat Med 5: 112-115, 1999; Sawkar et al., Proc Natl Acad Sci USA 99:15428-15433, 2002; Johnson and Kelly, Accounts of Chemical Research 38: 911-921, 2005]. The pharmacologic chaperone is administered in an amount that, in combination with a compound described herein, is sufficient to treat a patient suffering from a condition associated with a dysfunction in proteostasis. Exemplary pharmacologic chaperones are described in U.S. Patent Application Publication No's. 20080056994, 20080009516, 20070281975, 20050130972, 20050137223, 20050203019, 20060264467 and 20060287358, the contents of each of which are incorporated by reference herein.

In another embodiment, the invention is a method of treating a patient suffering from a condition associated with a dysfunction in proteostasis comprising administering to said patient an effective amount of a compound described herein, or a pharmaceutically acceptable salt, solvate, clathrate or prodrug, of any of thereof, and a second agent, wherein the second agent is a proteostasis regulator. The term "proteostasis regulator" refers to small molecules, siRNA and biologicals (including, for example, proteins) that enhance cellular protein homeostasis. For example, proteostasis regulators can be agents that influence protein synthesis, folding, trafficking and degradation pathways. Proteostasis regulators encompass pharmacologic agents that stimulate the heat shock response (HSR) signaling activity. Proteostasis regulators function by manipulating signaling pathways, including, but not limited to, the heat shock response or the unfolded protein response, or both, resulting in transcription and translation of proteostasis network components. Proteostasis regulators can enhance the folding, trafficking and function of proteins (for example, mutated proteins). Proteostasis regulators can also regulate protein chaperones by upregulating transcription or translation of the protein chaperone, or inhibiting degradation of the protein chaperone. Proteostasis regulators can influence the biology of folding, often by the coordinated increase in chaperone and folding enzyme levels and macromolecules that bind to partially folded conformational ensembles, thus enabling their progression to intermediates with more native structure and ultimately increasing the concentration of folded mutant protein for export. In one aspect, the proteostasis regulator is distinct from a chaperone in that the proteostasis regulator can enhance the homeostasis of a mutated protein but does not bind the mutated protein. In addition, proteostasis regulators can upregulate an aggregation pathway or a disaggregase activity. Exemplary proteostasis regulators are the celastrols, MG-132 and L-type $Ca^{2+}$ channel blockers (e.g., dilitiazem and verapamil). The term "celastrols" refers to celastrol and derivatives or analogs thereof, including, but not limited to, those celastrol derivatives described in Westerheide et al., J Biol Chem, 2004. 279(53): p. 56053-60, the contents of which are expressly incorporated by reference herein. Celastrol derivatives include, for example, celastrol methyl ester, dihydrocelastrol diacetate, celastrol butyl ether, dihydrocelastrol, celastrol benzyl ester, primesterol, primesterol diacetate and triacetate of celastrol. In certain aspects, the proteostasis regulator is a heat shock response activator. A heat shock response activator is an agent that indirectly or directly activates the heat shock response, for example, by directly or indirectly activating heat shock transcription factor 1 (HSF1), inhibiting Hsp90, and/or activating chaperone expression (Westerheide et al., J Biol Chem, 2004. 279(53): p. 56053-60, the contents of which are expressly incorporated by reference herein). The terms "heat shock response activator," "heat shock activator," "heat shock response inducer," and "heat shock inducer" are used interchangeably herein. Non-limiting examples of heat shock response activators are celastrols, non-steroidal anti-inflammatory drugs, ansamycin, geldenamycin, radiciol, glucuronic acid, and tributylin. Heat shock response activators have also been described, for example, in U.S. Patent Application Publication No's. 20070259820, 20070207992, 20070179087, 20060148767, the contents of each of which are expressly incorporated by reference herein. In some embodiments, the heat shock response activator is a small molecule heat shock response activator.

The invention also encompasses a method of treating cancer or a tumor in a patient in need thereof comprising administering to said patient an effective amount of a compound of Formula (I), (Ia), (Ib), (IIa), (IIb), (IIIa), (IIIb), (IIIc), (IIId), (IIIe), (IIIf), (IIIg), (IIIh), (IV), (V), (VI), (VII), (VIII), (IX) or (X), or a pharmaceutically acceptable salt, solvate, clathrate or prodrug, of any of thereof, The invention additionally encompasses a method of treating cancer or a tumor in a patient in need thereof comprising administering to said patient an effective amount of a compound described herein. Cancers that can be treated according to methods of the present invention include, but are not limited to, breast cancer, colon cancer, pancreatic cancer, prostate cancer, lung cancer, ovarian cancer, cervical cancer, multiple myeloma, basal cell carcinoma, neuroblastoma, hematologic cancer, rhabdomyosarcoma, liver cancer, skin cancer, leukemia, basal cell carcinoma, bladder cancer, endometrial cancer, glioma, lymphoma, and gastrointestinal cancer.

In another embodiment, the invention is a method of treating cancer or a tumor comprising administering a compound of Formula (I), (Ia), (Ib), (IIa), (IIb), (IIIa), (IIIb), (IIIc), (IIId), (IIIe), (IIIf), (IIIg), (IIIh), (IV), (V), (VI), (VII), (VIII), (IX) or (X), or a pharmaceutically acceptable salt, solvate, clathrate or prodrug, of any of thereof, in combination with the administration of a chemotherapeutic agent. Chemotherapeutic agents that can be utilized include, but are not limited to, alkylating agents such as cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2''-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL®, Bristol-Myers Squibb Oncology, Princeton, N.J.) and docetaxel (TAXOTERE®; Aventis Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; and pharmaceutically acceptable salts, acids or derivatives of any of the above.

In a further embodiment, the invention is a method of treating cancer or a tumor comprising administering to a patient in need thereof an effective amount of a compound of Formula (I), (Ia), (Ib), (IIa), (IIb), (IIIa), (IIIb), (IIIc), (IIId), (IIIe), (IIIf), (IIIg), (IIIh), (IV), (V), (VI), (VII), (VIII), (IX) or (X), or a pharmaceutically acceptable salt, solvate, clathrate or prodrug, of any of thereof, in combination with radiation therapy.

In yet an additional embodiment, the invention is a method of treating a viral infection comprising administering to a subject in need thereof an effective amount of a compound of Formula (I), (Ia), (Ib), (IIa), (IIb), (IIIa), (IIIb), (IIIc), (IIId), (IIIe), (IIIf), (IIIg), (IIIh), (IV), (V), (VI), (VII), (VIII), (IX) or (X), or a pharmaceutically acceptable salt, solvate, clathrate or prodrug, of any of thereof, In certain embodiments, the viral infection is an infection from a virus of the flavivirus family. Examples of viruses in the flavivirus family include, for example, Dengue virus, West Nile virus, Japanese encephalitis virus, yellow fever virus and tick-borne encephalitis viruses. In an additional embodiment, the virus is the La Crosse virus. In another embodiment, the virus is Dengue virus or West Nile virus.

Embodiments of the Invention

Further embodiments are provided herein.

Embodiment 1: A compound having the Formula (I):

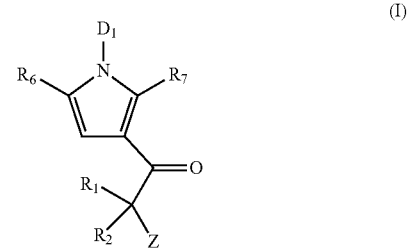

or a pharmaceutically acceptable salt, solvate, clathrate or prodrug thereof, wherein:

$D_1$ is selected from the group consisting of optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl and optionally substituted naphthyl;

each of $R_1$ and $R_2$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, $N_3$, halo, $OR_c$, $NR_dR_d$, $C(O)OR_c$, $NO_2$, $CN$, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $OC(O)R_c$, $(C=NR_d)R_c$, optionally substituted heterocyclic and optionally substituted heteroaryl;

each of $R_6$ and $R_7$ is independently selected from optionally substituted $C_1$-$C_4$ alkyl;

Z is selected from the group consisting of $NR_bR_b$, optionally substituted N-heterocyclic, and optionally substituted N-heteroaryl;

each $R_b$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; or two geminal $R_d$ groups are taken together with the nitrogen atom to which they are attached to form an optionally substituted heterocyclic or an optionally substituted heteroaryl; and each n is independently 0, 1 or 2.

Embodiment 2: The compound of Embodiment 1, or a pharmaceutically acceptable salt, solvate, clathrate or prodrug thereof, wherein $D_1$ is optionally substituted $C_1$-$C_{10}$ alkyl.

Embodiment 3: The compound of Embodiment 1, or a pharmaceutically acceptable salt, solvate, clathrate or prodrug thereof, wherein $D_1$ is optionally substituted methyl or optionally substituted ethyl.

Embodiment 4: The compound of Embodiment 1, or a pharmaceutically acceptable salt, solvate, clathrate or prodrug thereof, wherein $D_1$ is —$CH_2CF_3$.

Embodiment 5: The compound of Embodiment 1, or a pharmaceutically acceptable salt, solvate, clathrate or prodrug thereof, wherein $D_1$ is optionally substituted $C_3$-$C_2$ cycloalkyl.

Embodiment 6: The compound of Embodiment 1, or a pharmaceutically acceptable salt, solvate, clathrate or prodrug thereof, wherein $D_1$ is optionally substituted $C_3$-$C_6$ cycloalkyl.

Embodiment 7: The compound of Embodiment 1, or a pharmaceutically acceptable salt, solvate, clathrate or prodrug thereof, wherein $D_1$ is selected from the group consisting of optionally substituted cyclobutyl, optionally substituted cyclopentyl and optionally substituted cyclohexyl.

Embodiment 8: The compound of Embodiment 1, or a pharmaceutically acceptable salt, solvate, clathrate or prodrug thereof, wherein $D_1$ is optionally substituted naphthyl.

Embodiment 9: The compound of Embodiment 1, or a pharmaceutically acceptable salt, solvate, clathrate or prodrug thereof, wherein $D_1$ is optionally substituted cyclohexyl.

Embodiment 10: The compound of Embodiment 1, wherein $D_1$ is selected from the group consisting of:

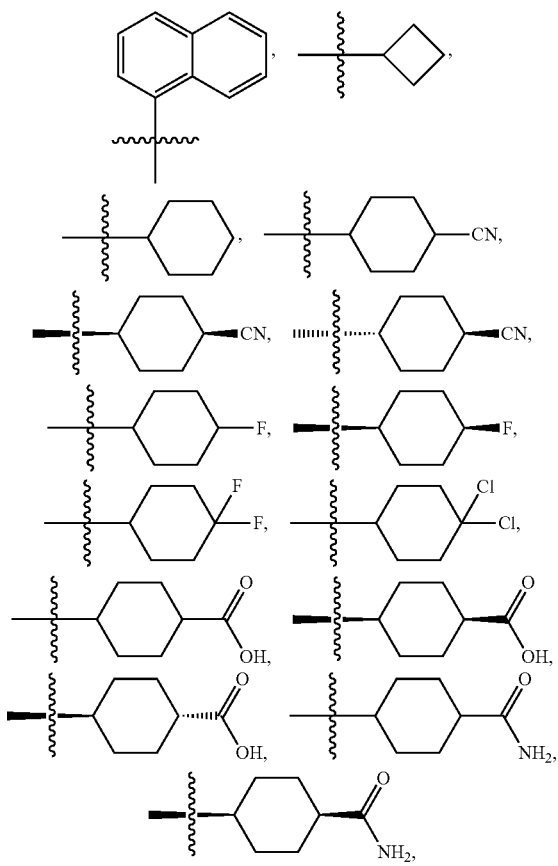

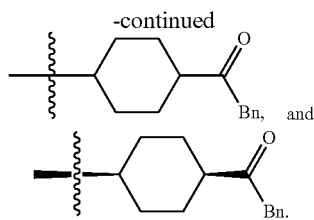

Embodiment 11: The compound of Embodiment 1, or a pharmaceutically acceptable salt, solvate, clathrate or prodrug thereof, having Formula (Ia) or Formula (Ib):

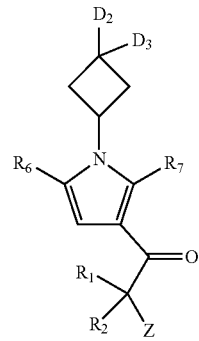

(Ia)

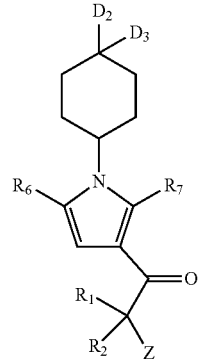

(Ib)

wherein $D_2$ and $D_3$ are each independently selected from the group consisting of hydrogen, CN, fluoro, chloro, —COOH, —$CONH_2$, and

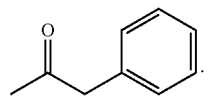

Embodiment 12: The compound of any one of embodiments 1 to 11, or a pharmaceutically acceptable salt, solvate, clathrate or prodrug thereof, wherein $R_6$ and $R_7$ are each independently selected from methyl and ethyl.

Embodiment 13: The compound of any one of embodiments 1 to 11, or a pharmaceutically acceptable salt, solvate, clathrate or prodrug thereof, wherein $R_6$ and $R_7$ are each methyl.

Embodiment 14: The compound of any one of embodiments 1 to 13, or a pharmaceutically acceptable salt, solvate, clathrate or prodrug thereof, wherein $R_1$ and $R_2$ are each independently selected from hydrogen and optionally substituted $C_1$-$C_{10}$ alkyl.

Embodiment 15: The compound of any one of embodiments 1 to 13, or a pharmaceutically acceptable salt, solvate, clathrate or prodrug thereof, wherein $R_1$ and $R_2$ are each hydrogen.

Embodiment 16: The compound of any one of embodiments 1 to 15, or a pharmaceutically acceptable salt, solvate, clathrate or prodrug thereof, wherein Z is $NR_bR_b$.

Embodiment 17: The compound of any one of embodiments 6, or a pharmaceutically acceptable salt, solvate, clathrate or prodrug thereof, wherein each $R_b$ is independently selected from the group consisting of hydrogen, optionally substituted $C_1$-$C_{10}$ alkyl, and optionally substituted $C_3$-$C_{12}$ cycloalkyl.

Embodiment 18: The compound of any one of embodiments 1 to 15, or a pharmaceutically acceptable salt, solvate, clathrate or prodrug thereof, wherein Z is optionally substituted N-heterocyclic.

Embodiment 19: The compound of embodiment 18, or a pharmaceutically acceptable salt, solvate, clathrate or prodrug thereof, wherein Z is an optionally substituted 5-membered N-heterocyclic, optionally having an additional heteroatom selected from the group consisting of O, S, and N.

Embodiment 20: The compound of embodiment 18, or a pharmaceutically acceptable salt, solvate, clathrate or prodrug thereof, wherein Z is an optionally substituted 6-membered N-heterocyclic, optionally having an additional heteroatom selected from the group consisting of O, S, and N.

Embodiment 21: The compound of embodiment 18, or a pharmaceutically acceptable salt, solvate, clathrate or prodrug thereof, wherein Z is 1-pyrrolidinyl or 1-piperidinyl, each optionally substituted.

Embodiment 22: The compound of embodiment 18, or a pharmaceutically acceptable salt, solvate, clathrate or prodrug thereof, wherein Z is selected from the group consisting of

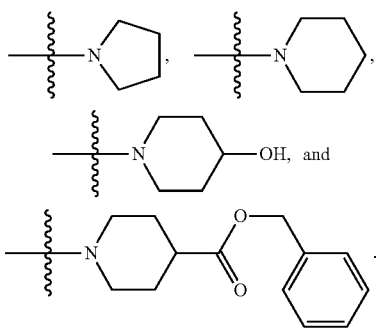

Embodiment 23: The compound of embodiments 21 or 22, or a pharmaceutically acceptable salt, solvate, clathrate or prodrug thereof, wherein $R_6$ and $R_7$ are each methyl, and wherein $R_1$ and $R_2$ are hydrogen.

Embodiment 24: The compound of embodiment 1, or a pharmaceutically acceptable salt, solvate, clathrate or prodrug thereof, selected from the group consisting of: Compound Nos. 5, 8, 9, 32, 35, 36, 37, 45, 46, 65, 76, 97, 103, 105, 107, 120, 121, 122, and 143.

Embodiment 25: A compound having the Formula (IIa) or (IIb):

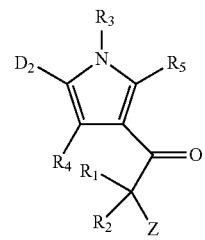

(IIa)

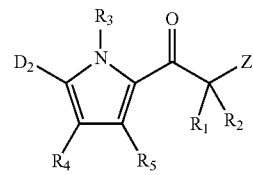

(IIb)

or a pharmaceutically acceptable salt, solvate, clathrate or prodrug thereof, wherein:

$D_2$ is selected from the group consisting of optionally substituted aryl and optionally substituted heteroaryl;

each of $R_1$ and $R_2$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, C(O)$OR_c$, $NO_2$, CN, C(O)$R_c$, C(O)C(O)$R_c$, C(O)$NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, OC(O)$R_c$, OC(O)$OR_c$, (C=$NR_d$)$R_c$, optionally substituted heterocyclic and optionally substituted heteroaryl;

each of $R_3$, $R_4$ and $R_5$ is independently selected from the group consisting of hydrogen and optionally substituted $C_1$-$C_{10}$ alkyl;

Z is selected from the group consisting of $NR_bR_b$, optionally substituted N-heterocyclic, and optionally substituted N-heteroaryl;

each $R_b$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; or two geminal $R_d$ groups are taken together with the nitrogen atom to which they are attached to form an optionally substituted heterocyclic or an optionally substituted heteroaryl; and each n is independently 0, 1 or 2;
provided that the compound is not:

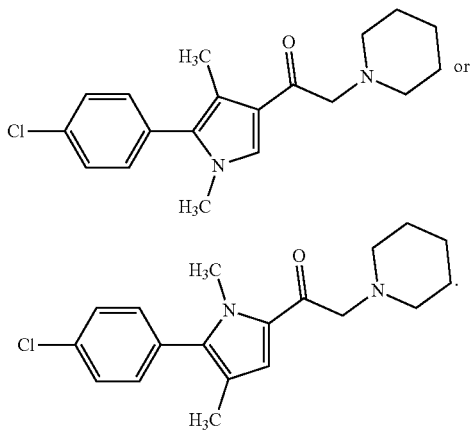

Embodiment 26: The compound of embodiment 25, or a pharmaceutically acceptable salt, solvate, clathrate or prodrug thereof, wherein $D_2$ is an optionally substituted phenyl.

Embodiment 27: The compound of embodiment 25, or a pharmaceutically acceptable salt, solvate, clathrate or prodrug thereof, wherein $D_2$ is

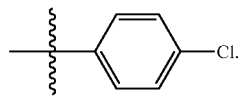 [SMILES: *c1ccc(Cl)cc1]

Embodiment 28: The compound of any one of embodiments 25 to 27, or a pharmaceutically acceptable salt, solvate, clathrate or prodrug thereof, wherein $R_1$ and $R_2$ are each independently selected from hydrogen and optionally substituted $C_1$-$C_{10}$ alkyl.

Embodiment 29: The compound of any one of embodiments 25 to 27, or a pharmaceutically acceptable salt, solvate, clathrate or prodrug thereof, wherein $R_1$ and $R_2$ are each hydrogen.

Embodiment 30: The compound of any one of embodiments 25 to 29, or a pharmaceutically acceptable salt, solvate, clathrate or prodrug thereof, wherein $R_5$ is hydrogen.

Embodiment 31: The compound of any one of embodiments 25 to 30, or a pharmaceutically acceptable salt, solvate, clathrate or prodrug thereof, wherein $R_3$ and $R_4$ are each independently optionally substituted $C_1$-$C_4$ alkyl.

Embodiment 32: The compound of any one of embodiments 25 to 30, or a pharmaceutically acceptable salt, solvate, clathrate or prodrug thereof, wherein $R_3$ and $R_4$ are each methyl.

Embodiment 33: The compound of any one of embodiments 25 to 32, or a pharmaceutically acceptable salt, solvate, clathrate or prodrug thereof, wherein Z is $NR_bR_b$.

Embodiment 34: The compound of embodiment 33, or a pharmaceutically acceptable salt, solvate, clathrate or prodrug thereof, wherein each $R_b$ is independently selected from the group consisting of hydrogen, optionally substituted $C_1$-$C_{10}$ alkyl, and optionally substituted $C_3$-$C_{12}$ cycloalkyl.

Embodiment 35: The compound of any one of embodiments 25 to 32, or a pharmaceutically acceptable salt, solvate, clathrate or prodrug thereof, wherein Z is optionally substituted N-heterocyclic.

Embodiment 36: The compound of embodiment 35, or a pharmaceutically acceptable salt, solvate, clathrate or prodrug thereof, wherein Z is an optionally substituted 5-membered N-heterocyclic, optionally having an additional heteroatom selected from the group consisting of O, S, and N.

Embodiment 37: The compound of embodiment 35, or a pharmaceutically acceptable salt, solvate, clathrate or prodrug thereof, wherein Z is an optionally substituted 6-membered N-heterocyclic, optionally having an additional heteroatom selected from the group consisting of O, S, and N.

Embodiment 38: The compound of embodiment 35, or a pharmaceutically acceptable salt, solvate, clathrate or prodrug thereof, wherein Z is 1-pyrrolidinyl or 1-piperidinyl, each optionally substituted.

Embodiment 39: The compound of embodiment 35, or a pharmaceutically acceptable salt, solvate, clathrate or prodrug thereof, wherein Z is optionally substituted 1-pyrrolindinyl.

Embodiment 40: The compound of embodiment 35, or a pharmaceutically acceptable salt, solvate, clathrate or prodrug thereof, wherein Z is optionally substituted 1-piperidinyl.

Embodiment 41: The compound of embodiment 35, or a pharmaceutically acceptable salt, solvate, clathrate or prodrug thereof, wherein Z is selected from the group consisting of

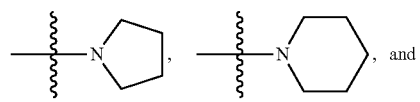, and

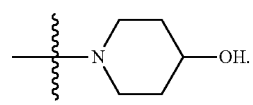

Embodiment 42: The compound of embodiment 25, or a pharmaceutically acceptable salt, solvate, clathrate or prodrug thereof, selected from the group consisting of: Compound Nos. 92, 94, and 95.

Embodiment 43: A compound having the Formula (IIIa) or (IIIb):

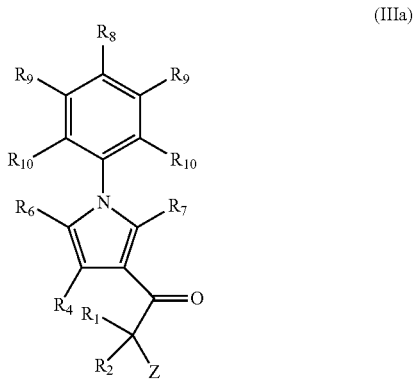

(IIIa)

-continued

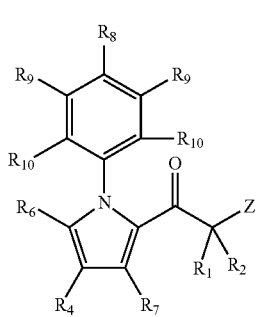

(IIIb)

or a pharmaceutically acceptable salt, solvate, clathrate or prodrug thereof, wherein:

each of $R_1$ and $R_2$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, $CN$, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)R_c$, $OC(O)OR_c$, $(C=NR_d)R_c$, optionally substituted heterocyclic and optionally substituted heteroaryl;

$R_4$ is independently selected from the group consisting of hydrogen and optionally substituted $C_1$-$C_{10}$ alkyl;

each of $R_6$ and $R_7$ is independently selected from optionally substituted $C_1$-$C_4$ alkyl;

$R_8$ is selected from the group consisting of hydrogen, optionally substituted $C_1$-$C_{10}$ alkyl, optionally substituted $C_1$-$C_{10}$ alkenyl, halo, $OR$, $C(O)OR_c$, $CN$, $S(O)_nR_c$, and $S(O)_nNR_dR_d$;

each $R_9$ is independently selected from the group consisting of hydrogen and halo;

each $R_{10}$ is selected from the group consisting of hydrogen and optionally substituted $C_1$-$C_{10}$ alkyl;

Z is selected from the group consisting of $NR_bR_b$, optionally substituted 6-membered N-heteroaryl, and optionally substituted N-heterocyclic;

each $R_b$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; or two geminal $R_d$ groups are taken together with the nitrogen atom to which they are attached to form an optionally substituted heterocyclic or an optionally substituted heteroaryl; and each n is independently 0, 1 or 2.

Embodiment 44: The compound of embodiment 43, or a pharmaceutically acceptable salt, solvate, clathrate or prodrug thereof, wherein $R_1$ and $R_2$ are each independently selected from hydrogen and optionally substituted $C_1$-$C_{10}$ alkyl.

Embodiment 45: The compound of embodiment 43, or a pharmaceutically acceptable salt, solvate, clathrate or prodrug thereof, wherein $R_1$ and $R_2$ are each hydrogen.

Embodiment 46: The compound of any one of embodiments 43 to 45, or a pharmaceutically acceptable salt, solvate, clathrate or prodrug thereof, wherein $R_4$ is hydrogen or $C_1$-$C_4$ alkyl.

Embodiment 47: The compound of any one of embodiments 43 to 45, or a pharmaceutically acceptable salt, solvate, clathrate or prodrug thereof, wherein $R_4$ is hydrogen or methyl.

Embodiment 48: The compound of any one of embodiments 43 to 47, or a pharmaceutically acceptable salt, solvate, clathrate or prodrug thereof, wherein $R_6$ and $R_7$ are each independently selected from the group consisting of hydrogen, methyl, ethyl, methoxy, and cyclopropyl.

Embodiment 49: The compound of of any one of embodiments 43 to 47, or a pharmaceutically acceptable salt, solvate, clathrate or prodrug thereof, wherein $R_6$ and $R_7$ are each methyl.

Embodiment 50: The compound of any one of embodiments 43 to 45, or a pharmaceutically acceptable salt, solvate, clathrate or prodrug thereof, wherein $R_4$, $R_6$, and $R_7$ are each hydrogen.

Embodiment 51: The compound of any one of embodiments 43 to 45, or a pharmaceutically acceptable salt, solvate, clathrate or prodrug thereof, wherein $R_4$, $R_6$, and $R_7$ are each methyl.

Embodiment 52: The compound of any one of embodiments 43 to 51, or a pharmaceutically acceptable salt, solvate, clathrate or prodrug thereof, wherein Z is optionally substituted N-heterocyclic.

Embodiment 53: The compound of embodiment 52, or a pharmaceutically acceptable salt, solvate, clathrate or prodrug thereof, wherein Z is an optionally substituted 5-membered N-heterocyclic, optionally having an additional heteroatom selected from the group consisting of O, S, and N.

Embodiment 54: The compound of embodiment 52, or a pharmaceutically acceptable salt, solvate, clathrate or prodrug thereof, wherein Z is an optionally substituted 6-membered N-heterocyclic, optionally having an additional heteroatom selected from the group consisting of O, S, and N.

Embodiment 55: The compound of embodiment 52, or a pharmaceutically acceptable salt, solvate, clathrate or prodrug thereof, wherein Z is 1-pyrrolidinyl or 1-piperidinyl, each optionally substituted.

Embodiment 56: The compound of embodiment 55, or a pharmaceutically acceptable salt, solvate, clathrate or prodrug thereof, having Formula (IIIc), Formula (IIId), Formula (IIIe), or Formula (IIIf):

(IIIc)

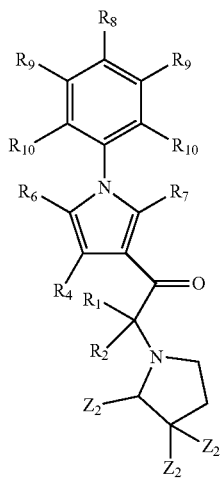

(IIId)

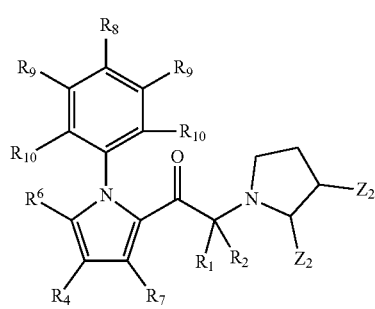

(IIIe)

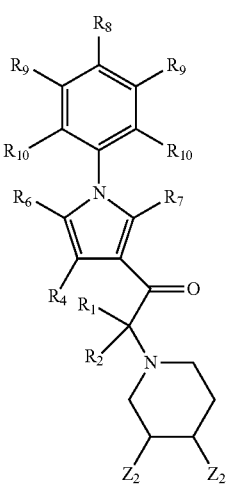

(IIIf)

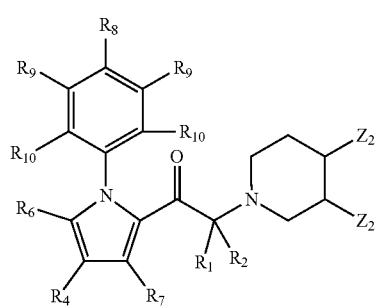

wherein each $Z_2$ is independently selected from the group consistent of hydrogen, hydroxy, —F, —CH$_3$, —CF$_3$, —CH$_2$NH$_2$, —N(CH$_3$)$_2$, —CH$_2$N(CH$_3$)$_2$, —CH$_2$CH$_2$OH, —COOH, —CONH$_2$, —SO$_2$CH$_3$, —OCH$_2$CONHCH$_2$CH$_3$, —OCH$_2$CONHC(CH$_3$)$_2$, —OCH$_2$CONHCH$_2$CH$_2$CH$_3$, —CH$_2$NHCOOC(CH$_3$)$_2$, —N(CH$_3$)$_2$,

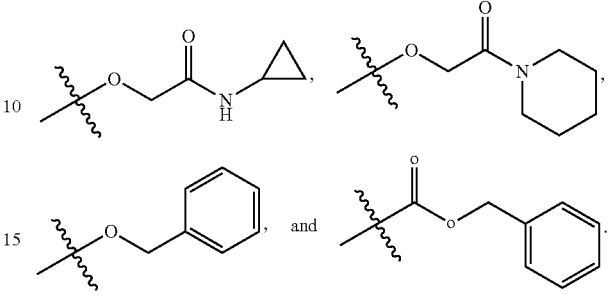

Embodiment 57: The compound of embodiment 52, or a pharmaceutically acceptable salt, solvate, clathrate or prodrug thereof, wherein Z is selected from the group consisting of

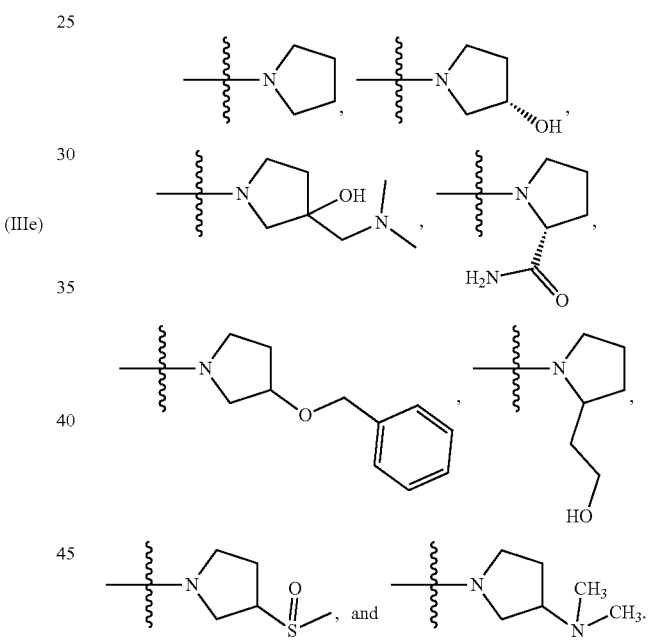

Embodiment 58: The compound of embodiment 52, or a pharmaceutically acceptable salt, solvate, clathrate or prodrug thereof, wherein Z is selected from the group consisting of

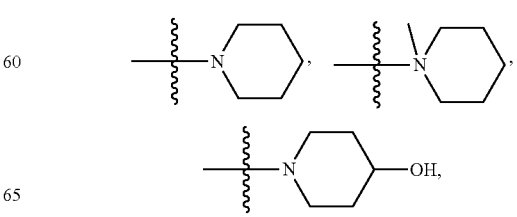

-continued

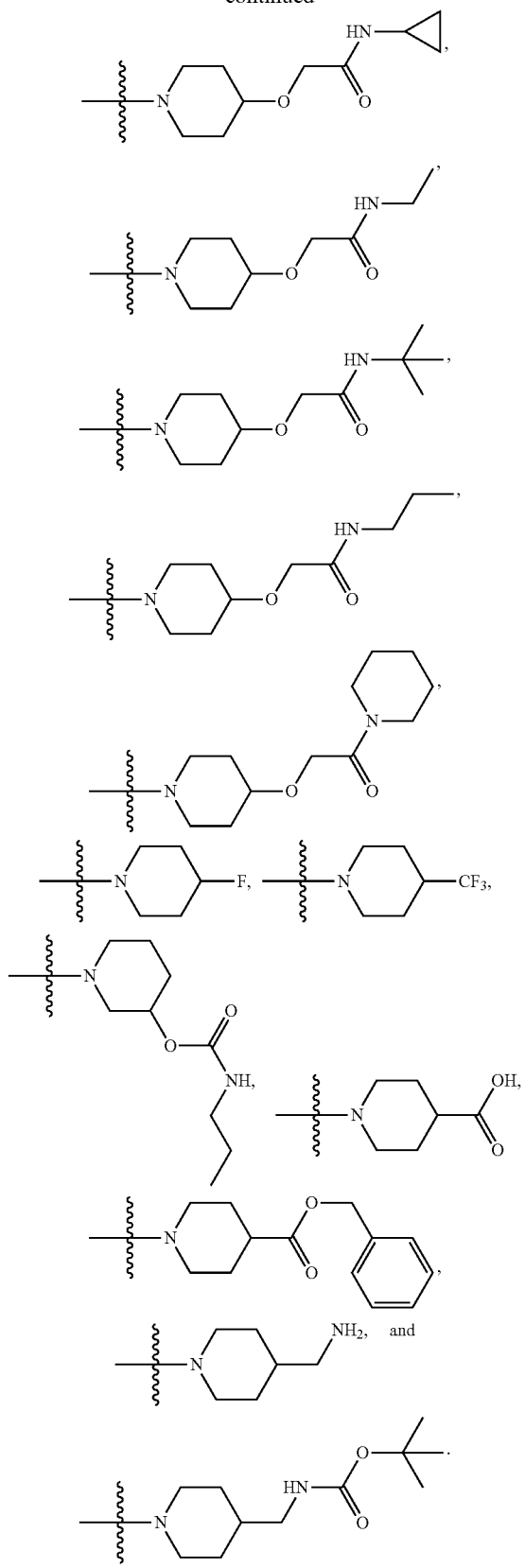

Embodiment 59: The compound of any one of embodiments 43 to 51, or a pharmaceutically acceptable salt, solvate, clathrate or prodrug thereof, wherein Z is optionally substituted 6-membered N-heteroaryl.

Embodiment 60: The compound of embodiment 59, or a pharmaceutically acceptable salt, solvate, clathrate or prodrug thereof, wherein Z is

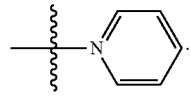

Embodiment 61: The compound of any one of embodiments 43 to 51, or a pharmaceutically acceptable salt, solvate, clathrate or prodrug thereof, wherein Z is $NR_bR_b$.

Embodiment 62: The compound of embodiment 61, or a pharmaceutically acceptable salt, solvate, clathrate or prodrug thereof, wherein each $R_b$ is independently selected from the group consisting of hydrogen, optionally substituted $C_1$-$C_{10}$ alkyl, and optionally substituted $C_3$-$C_{12}$ cycloalkyl.

Embodiment 63: The compound of embodiment 61, or a pharmaceutically acceptable salt, solvate, clathrate or prodrug thereof, wherein each $R_b$ is independently selected from the group consisting of hydrogen, —$CH_3$, —$CH_2CH_2OH$, —$CH_2CHOHCH_2OH$, cyclopropyl, cycloheptyl,

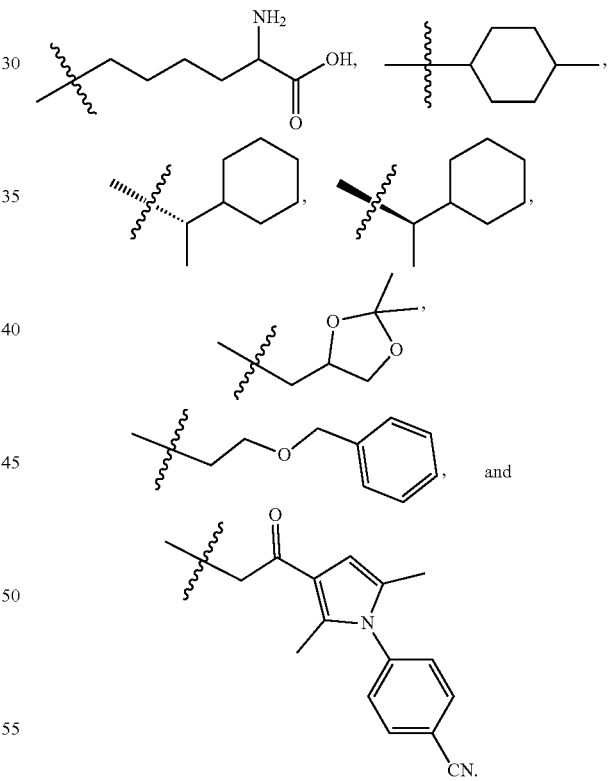

and

Embodiment 64: The compound of any one of embodiments 43 to 63, or a pharmaceutically acceptable salt, solvate, clathrate or prodrug thereof, wherein each $R_9$ and $R_{10}$ are hydrogen.

Embodiment 65: The compound of any one of embodiments 43 to 63, or a pharmaceutically acceptable salt, solvate, clathrate or prodrug thereof, wherein each $R_9$ is hydrogen and each $R_{10}$ is independently hydrogen, chloro, or fluoro.

Embodiment 66: The compound of any one of embodiments 43 to 63, or a pharmaceutically acceptable salt, solvate, clathrate or prodrug thereof, wherein each $R_9$ is methyl and each $R_{10}$ is hydrogen.

Embodiment 67: The compound of any one of embodiments 42 to 66, or a pharmaceutically acceptable salt, solvate, clathrate or prodrug thereof, wherein each $R_8$ is selected from the group consisting of hydrogen, hydroxyl, fluoro, chloro, bromo, —CN, —OCH$_3$, —CF$_3$, —OCF$_3$, —COOH, —SO$_2$CH$_3$,

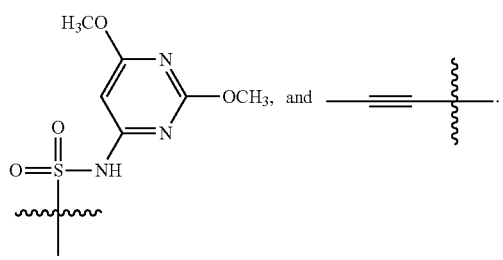

Embodiment 68: A compound having the Formula (IIIg) or (IIIh):

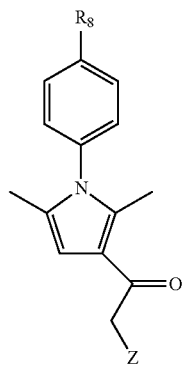

(IIIg)

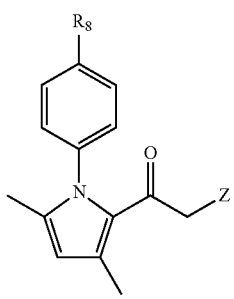

(IIIh)

or a pharmaceutically acceptable salt, solvate, clathrate or prodrug thereof;

wherein:

$R_8$ is selected from the group consisting of hydrogen, optionally substituted $C_1$-$C_{10}$ alkyl, optionally substituted $C_1$-$C_{10}$ alkenyl, halo, OR, C(O)OR$_c$, CN, S(O)$_n$R$_c$, and S(O)$_n$NR$_d$R$_d$;

wherein Z is selected from the group consisting of

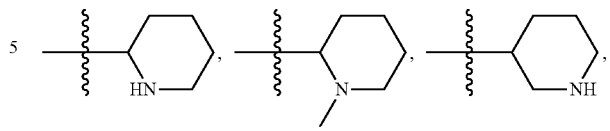

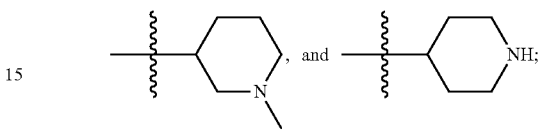

each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; or two geminal $R_d$ groups are taken together with the nitrogen atom to which they are attached to form an optionally substituted heterocyclic or an optionally substituted heteroaryl; and each n is independently 0, 1 or 2;

provided that the compound is not:

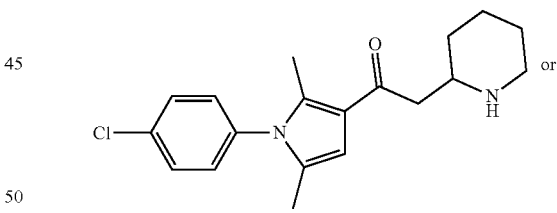

or

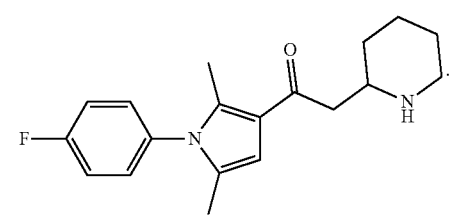

Embodiment 69: The embodiment of claim 68, or a pharmaceutically acceptable salt, solvate, clathrate or prodrug thereof, wherein $R_8$ is chloro.

Embodiment 70: A compound having the Formula (IV):

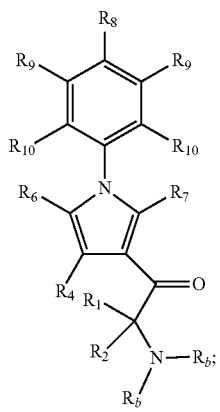

or is a pharmaceutically acceptable salt, solvate, clathrate or prodrug thereof;
wherein:
each of $R_1$ and $R_2$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, $CN$, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)R_c$, $OC(O)OR_c$, $(C{=}NR_d)R_c$, optionally substituted heterocyclic and optionally substituted heteroaryl;
$R_4$ is independently selected from the group consisting of hydrogen and optionally substituted $C_1$-$C_{10}$ alkyl;
each of $R_6$ and $R_7$ is independently selected from optionally substituted $C_1$-$C_4$ alkyl;
$R_8$ is selected from the group consisting of hydrogen, optionally substituted $C_1$-$C_{10}$ alkyl, optionally substituted $C_1$-$C_{10}$ alkenyl, halo, OR, $C(O)OR_c$, CN, $S(O)_nR_c$, and $S(O)_nNR_dR_d$;
each $R_9$ is independently selected from the group consisting of hydrogen and halo;
each $R_{10}$ is selected from the group consisting of hydrogen and optionally substituted $C_1$-$C_{10}$ alkyl;
each $R_b$ is independently selected from the group consisting of hydrogen, —CH$_3$, —CH$_2$CH$_2$OH, —CH$_2$CHOHCH$_2$OH, cyclopropyl, cycloheptyl,

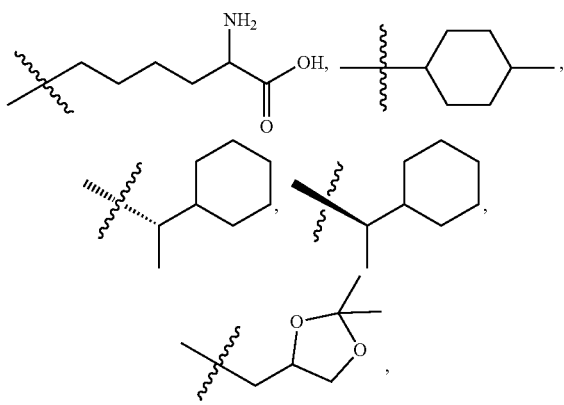

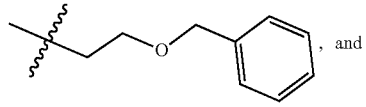, and

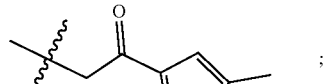;

each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;
each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; or two geminal $R_d$ groups are taken together with the nitrogen atom to which they are attached to form an optionally substituted heterocyclic or an optionally substituted heteroaryl; and
each n is independently 0, 1 or 2.

Embodiment 71: The compound of embodiment 70, or a pharmaceutically acceptable salt, solvate, clathrate or prodrug thereof, wherein $R_4$ is hydrogen, each $R_6$ and $R_7$ is methyl; each $R_9$ and $R_{10}$ is hydrogen, and $R_8$ is CN.

Embodiment 72: A compound having the Formula (V):

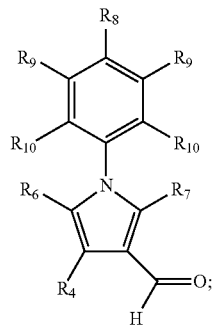

or is a pharmaceutically acceptable salt, solvate, clathrate or prodrug thereof;
wherein $R_4$ is hydrogen or optionally substituted $C_1$-$C_4$ alkyl;
$R_6$ and $R_7$ are each independently selected from the group consisting of hydrogen, methyl, ethyl, methoxy, and cyclopropyl;
$R_8$ is selected from the group consisting of hydrogen, optionally substituted $C_1$-$C_{10}$ alkyl, optionally substituted $C_1$-$C_{10}$ alkenyl, halo, OR, $C(O)OR_c$, CN, $S(O)_nR_c$, and $S(O)_nNR_dR_d$;

each $R_9$ is independently selected from the group consisting of hydrogen and halo; and each $R_{10}$ is selected from the group consisting of hydrogen and optionally substituted $C_1$-$C_{10}$ alkyl.

Embodiment 73: The compound of embodiment 72, or a pharmaceutically acceptable salt, solvate, clathrate or prodrug thereof, wherein each of $R_4$, $R_9$, and $R_{10}$ are hydrogen; $R_6$ and $R_7$ are methyl; and $R_8$ is chloro or cyano.

Embodiment 74: The compound of embodiment 72, or a pharmaceutically acceptable salt, solvate, clathrate or prodrug thereof, wherein $R_4$ is methyl, optionally substituted; each of $R_9$, and $R_{10}$ are hydrogen; $R_6$ and $R_7$ are methyl; and $R_8$ is chloro or cyano.

Embodiment 75: The compound of embodiment 72, or a pharmaceutically acceptable salt, solvate, clathrate or prodrug thereof, wherein $R_4$ is

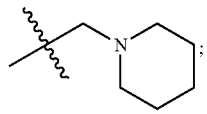

each of $R_9$, and $R_{10}$ are hydrogen; $R_6$ and $R_7$ are methyl; and $R_8$ is chloro or cyano.

Embodiment 76: A compound or a pharmaceutically acceptable salt, solvate, clathrate or prodrug thereof, selected from the group consisting of: Compound Nos. 1, 2, 3, 4, 5, 7, 8, 9, 10, 11, 12, 13, 14, 15, 16, 17, 18, 19, 20, 21, 22, 23, 24, 25, 26, 27, 28, 29, 32, 33, 35, 36, 37, 38, 39, 40, 41, 42, 43, 44, 45, 46, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 79, 80, 81, 82, 83, 84, 85, 89A, 89B, 90, 91, 92, 93, 94, 95, 96, 97, 99, 100, 101, 102, 103, 105, 107, 110, 111, 112, 113, 114, 117, 120, 121, 122, 134, 135, 136, 137, 138, 139, 140, 143, 157, 158, and 159.

Embodiment 77: A pharmaceutical composition comprising a pharmaceutically acceptable carrier or excipient and a compound of any one of embodiments 1 to 76, or a pharmaceutically acceptable salt, solvate, clathrate or prodrug thereof.

Embodiment 78: A method of inhibiting deubiquitination activity of a Usp14 protein comprising contacting the Usp14 protein with an effective amount of a compound of any one of embodiments 1 to 76, or a pharmaceutically acceptable salt, solvate, clathrate or prodrug thereof, in an amount sufficient to inhibit deubiquitination activity of the Usp14 protein.

Embodiment 79: A method of enhancing protein degradation by a proteasome in a cell comprising contacting the cell with an effective amount of a compound of any one of embodiments 1 to 76, or a pharmaceutically acceptable salt, solvate, clathrate or prodrug thereof, in an amount sufficient to enhance protein degradation by the proteasome.

Embodiment 80: A method of treating a patient suffering from a condition associated with a dysfunction in proteostasis comprising administering to said patient an effective amount of a compound of any one of embodiments 1 to 76.

Embodiment 81: The method of embodiment 78, wherein the condition associated with a dysfunction of proteostasis is a gain of function condition.

Embodiment 82: The method of embodiment 78, wherein the condition associated with a dysfunction of protein homeostasis is a loss of function condition.

Embodiment 83: The method of embodiment 78, wherein the condition is associated with a dysfunction in the proteostasis of a protein selected from the group consisting of hexosamine A, cystic fibrosis transmembrane conductance regulator, aspartylglucsaminidase, α-galactosidase A, cysteine transporter, acid ceremidase, acid α-L-fucosidase, protective protein, cathepsin A, acid β-glucosidase, acid β-galactosidase, iduronate 2-sulfatase, α-L-iduronidase, galactocerebrosidase, acid α-mannosidase, acid β-mannosidase, arylsulfatase B, arylsulfatase A, N-acetylgalactosamine-6-sulfate sulfatase, acid β-galactosidase, N-acetylglucosamine-1-phosphotransferase, acid sphingmyelinase, NPC-1, acid α-glucosidase, β-hexosamine B, heparin N-sulfatase, α-N-acetylglucosaminidase, islet amyloid polypeptide (IAPP or amylin), α-glucosaminide N-acetyltransferase, N-acetylglucosamine-6-sulfate sulfatase, a1 anti-trypsin, α-N-acetylgalactosaminidase, α-neuramidase, β-glucuronidase, β-hexosamine A and acid lipase, polyglutamine, α-synuclein, Aβ peptide, tau protein, hERG potassium channel, islet amyloid polypeptide, transthyretin, Huntingtin, superoxide dismutase, TAR DNA-binding protein 43 (TDP-43), ataxin-3, superoxide dismutase (SOD), and rhodopsin.

Embodiment 84: The method of embodiment 83, wherein the protein is selected from the group consisting of Huntingtin, tau, alpha-synuclein, a1 anti-trypsin and superoxide dismutase.

Embodiment 85: The method of embodiment 78, wherein the condition is selected from the group consisting of Huntington's disease, Alzheimer's disease, Parkinson's disease, amyotrophic lateral sclerosis, diabetes and complications of diabetes.

Embodiment 86: The method of embodiment 78, wherein the condition is selected from the group consisting of Parkinson's disease, Alzheimer's disease, Frontotemporal lobar dementia (FTLD), Progressive Supranuclear Palsy (PSP), Amyotrophic lateral sclerosis (ALS), Spinocerebellar ataxia (SCA), Retinitis pigmentosum, Prion diseases and autism.

Embodiment 87: The method of embodiment 78, further comprising administering a second agent selected from the group consisting of a proteostasis regulator and a pharmacologic chaperone.

Embodiment 88: A method of enhancing proteasome function in a subject comprising administering to said subject an effective amount of a compound of any one of embodiments 1 to 76, or a pharmaceutically acceptable salt, solvate, clathrate or prodrug thereof.

Embodiment 89: A method for treating a condition characterized by deficient proteasome activity or deficiency of other components of the ubiquitin-proteasome pathway in a subject comprising administering to said subject an effective amount of a compound of any one of embodiments 1 to 76, or a pharmaceutically acceptable salt, solvate, clathrate or prodrug thereof.

Embodiment 90: A method of treating cancer or a tumor in a subject in need thereof comprising administering to said subject an effective amount of a compound of any one embodiments 1 to 76, or a pharmaceutically acceptable salt, solvate, clathrate or prodrug thereof.

Embodiment 91: A pharmaceutical composition comprising:
  a pharmaceutically acceptable carrier or excipient;
  an agent selected from the group consisting of a proteostasis regulator and a pharmacologic chaperone; and
  a compound of any one of embodiments 1 to 76, or a pharmaceutically acceptable salt, solvate, clathrate or prodrug thereof.

Exemplary Embodiments

The invention is illustrated by the following examples which are not meant to be limiting in any way.

EXEMPLIFICATION

Examples 1-4: Benzyl trans-4-[2,5-Dimethyl-3-(2-piperidin-1-yl-acetyl)-1H-pyrrol-1-yl]-cyclohexanecarboxylate (Compound 120), trans-4-(2,5-Dimethyl-3-(2-(piperidin-1-yl)acetyl)-1H-pyrrol-1-yl)cyclohexane-1-carboxylic acid (Compound 121), trans-4-(2,5-Dimethyl-3-(2-(piperidin-1-yl)acetyl)-1H-pyrrol-1-yl)cyclohexane-1-carboxamide (Compound 122), trans-4-(2,5-Dimethyl-3-(2-(piperidin-1-yl)acetyl)-1H-pyrrol-1-yl)cyclohexane-1-carbonitrile (Compound 143)

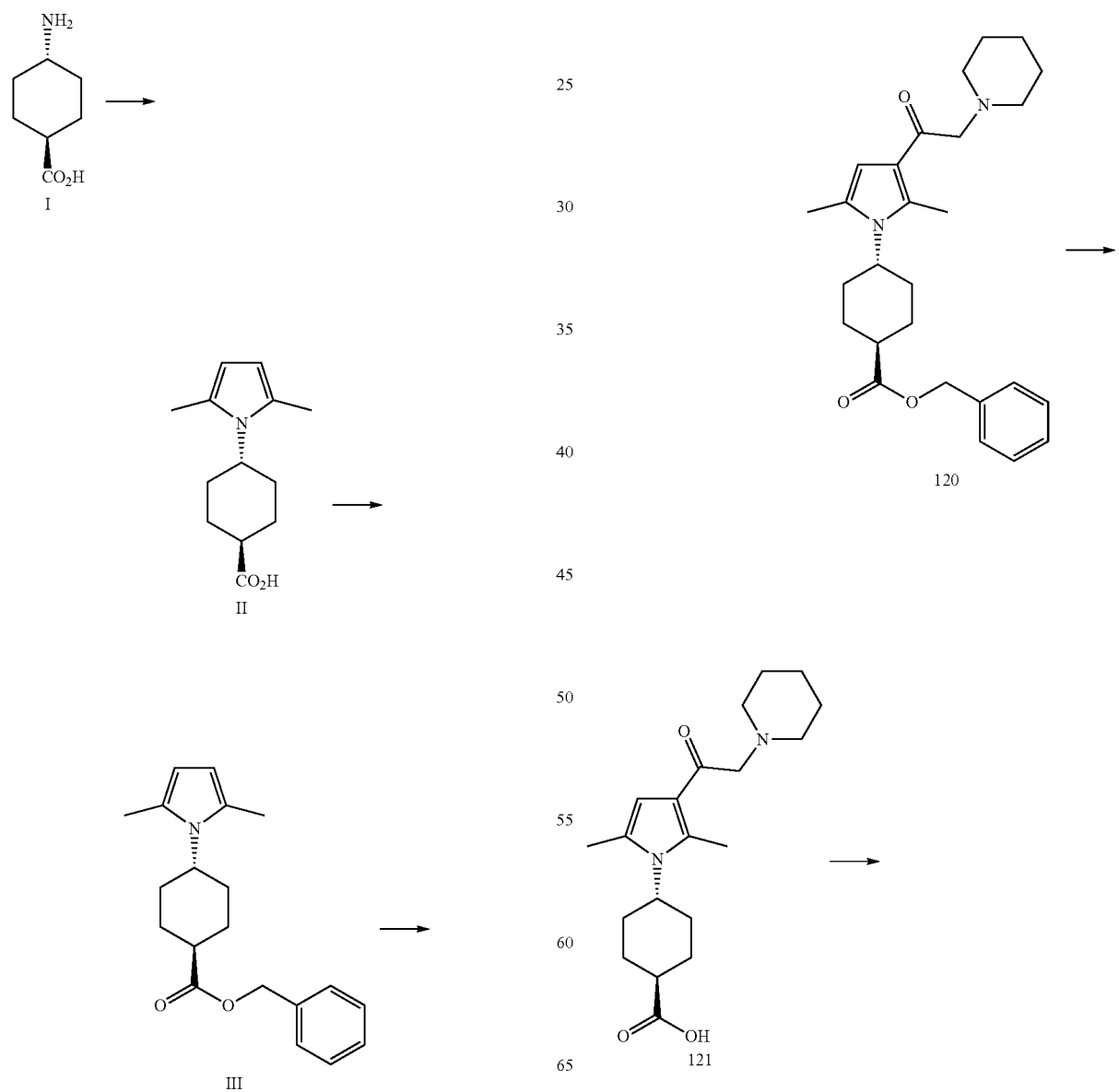

-continued

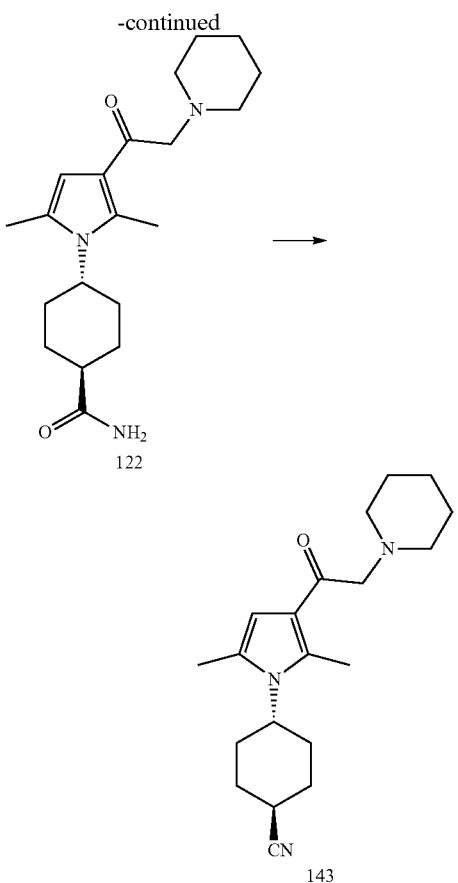

Synthesis of trans-4-(2,5-Dimethyl-1H-pyrrol-1-yl)-cyclohexanecarboxylic Acid (II): To a mixture of trans-4-amino-cyclohexanecarboxylic acid (5.00 g, 0.035 mol) in methanol (50 mL), was added 2,5-hexanedione (4.90 mL, 0.042 mol). The reaction mixture was heated at reflux for 3 h and then allowed to cool to room temperature. The reaction mixture was concentrated under vacuum and the remaining residue was diluted with water (50 mL). The mixture was extracted with dichloromethane (2×25 mL) and then the combined organic extracts were washed with water (20 mL) and brine (20 mL). Organic layer was dried over sodium sulfate and then concentrated. The crude product mixture was purified by the column chromatography on (100-200 mesh) silica gel using 25% ethyl acetate in hexanes as the eluant to afford compound II (5.10 g, 65%) as an off white solid. $^1$HNMR (400 MHz, CDCl$_3$) δ 11.22 (bs, 1H), 5.73 (s, 2H), 3.97-3.89 (m, 1H), 2.42-2.35 (m, 1H), 2.27 (bs, 6H), 2.23-2.20 (m, 1H), 2.20-2.17 (m, 1H), 2.07-1.90 (m, 4H), 1.66-1.56 (m, 2H); MS (ESI, negative mode) m/z 220 (M$^-$-H).

Synthesis of Benzyl trans-4-(2,5-Dimethyl-1H-pyrrol-1-yl)-cyclohexanecarboxylate (III): To a stirred solution of compound II (4.40 g, 0.020 mol), in dry tetrahydrofuran (50 mL), being maintained under a nitrogen atmosphere at room temperature, was added cesium carbonate (12.94 g, 0.0398 mol) and then bromomethyl benzene (7.20 mL, 0.060 mol). The resulting mixture was then heated at reflux for 3 h before being allowed to cool to room temperature. The reaction mixture was diluted with water (100 mL) and then extracted with dichloromethane (2×20 mL). The combined organic extracts were washed with water and brine, before the organic layer was dried over sodium sulfate and concentrated. The crude product mixture was purified by the column chromatography on (100-200 mesh) silica gel using 3% ethyl acetate in hexanes as the eluant to afford compound III (2.80 g, 46%) as a brown sticky gum. $^1$HNMR (400 MHz, CDCl$_3$) δ 7.39-7.31 (m, 5H), 7.26-7.22 (m, 1H), 7.17-7.13 (m, 1H), 5.13 (s, 2H), 3.95-3.88 (m, 1H), 2.42-2.36 (m, 1H), 2.27 (brs, 6H), 2.19-2.14 (m, 2H), 2.02-1.94 (m, 4H), 1.67-1.53 (m, 2H); MS (ESI, positive mode) m/z 312 (MH$^+$).

Synthesis of Benzyl trans-4-[3-(2-Chloro-acetyl)-2,5-dimethyl-1H-pyrrol-1-yl]-cyclohexanecarboxylate (IV): To a cold (0° C.) solution of aluminum chloride (1.44 g, 0.011 mol) in dichloromethane (20 mL) was added chloroacetyl chloride (0.85 mL, 0.011 mol) in a dropwise manner. The resulting mixture was allowed to stir at the reduced temperature for 0.5 h. Then a solution of compound III (2.80 g, 0.009 mol) in dichloromethane (5 mL) was added to the reaction mixture in single portion. The resulting mixture was allowed to stir at room temperature for 2 h and was then poured over crushed ice (200 mL). The mixture was basified with an aqueous saturated sodium bicarbonate solution (100 mL) and then extracted with dichloromethane (2×30 mL). The combined organic extracts were washed with water (50 mL), dried over sodium sulfate, and then concentrated under vacuum. The crude product mixture was purified by column chromatography on (100-200-mesh) silica gel using 8% ethyl acetate in hexanes as the eluant to afford compound IV (0.950 g, 28%) as a brown oil. $^1$H-NMR (400 MHz, CDCl$_3$): δ 7.39-7.30 (m, 5H), 6.15 (s, 1H), 5.12 (s, 2H), 4.40 (s, 2H), 4.04-3.99 (m, 1H), 2.62 (s, 3H), 2.38-2.41 (m, 1H), 2.26-2.18 (m, 5H), 2.06-1.99 (q, 2H), 1.62 (dq, J=12.9, 3.4 Hz, 2H), 1.64-1.60 (m, 2H); MS (ESI, positive mode) m/z 388 (MH$^+$).

Synthesis of Benzyl trans-4-[2,5-Dimethyl-3-(2-piperidin-1-yl-acetyl)-1H-pyrrol-1-yl]-cyclohexanecarboxylate (Compound 120): To a solution of compound IV (0.070 g, 0.180 mmol) in N,N-dimethylformamide (1.5 mL) was added potassium carbonate (0.062 g, 0.452 mmol) and piperdine (0.023 g, 0.452 mmol). The resultant mixture was allowed to stir at room temperature for 3 h and was then poured over crushed ice. The mixture was extracted with dichloromethane (2×10 mL) and the combined organic extracts were washed with water (2×10 mL) and then saturated brine solution (1×10 mL). The organic layer was then dried over sodium sulfate and concentrated under vacuum. The crude product mixture was purified by column chromatography on (100-200 mesh) silica gel using 5% methanol in dichloromethane as the eluant to afford Compound 120 (0.030 g, 38%) as a brown, sticky mass. $^1$H-NMR (400 MHz, CDCl$_3$): δ 7.38-7.30 (m, 5H), 6.20 (s, 1H), 5.12 (s, 2H), 4.03-3.97 (m, 1H), 3.61 (brs, 2H), 2.64 (brs, 3H), 2.60 (brs, 3H), 2.44-2.36 (m, 1H), 2.25 (brs, 2H), 2.18 (d, J=12.2 Hz, 2H), 2.04-1.99 (m, 2H), 1.92-1.90 (m, 2H), 1.68-1.62 (m, 4H), 1.60-1.56 (m, 2H), 1.46 (brs, 2H), 1.24 (s, 2H); MS (ESI, positive mode) m/z 437 (MH$^+$).

Synthesis of trans-4-[2,5-Dimethyl-3-(2-piperidin-1-yl-acetyl)-pyrrol-1-yl]-cyclohexanecarboxylic Acid (Compound 121). To a solution of Compound 120 (0.900 g, 2.06 mmol) in ethyl acetate (50 mL) was added 10% palladium on carbon (200 mg, 20% weight of Benzyl trans-4-[2,5-Dimethyl-3-(2-piperidin-1-yl-acetyl)-1H-pyrrol-1-yl]-cyclohexanecarboxylate). The resulting mixture was placed under 1 atm of hydrogen gas and allowed to stir at room temperature for 16 h. The reaction mixture was then filtered through a pad of celite (5.00 g) and the filter pad was washed with methanol (~50 mL). The filtrate was then concentrated under vacuum and remaining solids were washed with diethyl ether (~10 mL) to afford compound 121 (0.300 g, 42%) as an off-white solid. $^1$H-NMR (400 MHz, DMSO-$d_6$): δ 12.11 (brs, 1H), 6.26 (s, 1H), 4.04 (brt, J=12.5 Hz, 1H), 3.35 (s, 2H), 2.53 (s, 3H), 2.50-2.48 (m, 2H), 2.39 (bs, 3H), 2.33-2.29 (m, 1H), 2.24 (brs, 3H), 2.03-1.96 (m, 4H), 1.78-1.75 (m, 2H), 1.53-1.46 (m, 5H), 1.37-1.33 (m, 2H); MS (ESI, positive mode) m/z 347 (MH$^+$).

Synthesis of trans-4-[2,5-Dimethyl-3-(2-piperidin-1-yl-acetyl)-pyrrol-1-yl]-cyclohexanecarboxamide (Compound 122): To a cold solution (0° C.) of compound 121 (0.100 g, 0.289 mmol) in acetonitrile (2 mL) was added triethylamine (0.120 mL, 0.867 mmol) and 0-(benzotriazol-1-yl)-N,N,N',N'-tetramethyluronium hexafluorophosphate (0.120 g, 0.317 mmol). The resulting mixture was treated with solid ammonium chloride (0.017 g, 0.317 mmol) and then allowed to warm to room temperature and stir for 2 h. The reaction mixture was filtered and the filtered solids were washed with n-pentane (2×10 mL) to afford compound 122 (0.015 g, 19%) as an off white solid. $^1$HNMR (400 MHz, DMSO-$d_6$) δ 7.71-767 (d, 1H), 7.22 (s, 1H), 6.75 (s, 1H), 6.26 (s, 1H), 4.14-4.12 (m, 1H), 4.03 (bs, 2H), 3.01-2.99 (m, 1H), 2.58-2.51 (m, 3H), 2.25 (brs, 3H), 2.19-2.13 (m, 1H), 2.01-1.77 (m, 6H), 1.63-1.52 (m, 5H), 1.38-1.31 (m, 2H), 1.28-1.23 (m, 2H), 0.89-0.87 (m, 1H); MS (ESI, negative mode) m/z 346 (M$^-$-H).

Synthesis of trans-4-[2,5-Dimethyl-3-(2-piperidin-1-yl-acetyl)-pyrrol-1-yl]-cyclohexanecarbonitrile (Compound 143): To a solution of compound 122 (0.200 g, 0.579 mmol) in dry ethylene dichloride (10 mL) was added 1-propylphosphonic acid cyclic anhydride (0.85 mL, 1.44 mmol). The reaction mixture was then heated at reflux for 4 h before being allowed to cool to room temperature. The reaction mixture was concentrated under vacuum and the crude product mixture was purified by column chromatography on neutral alumina using 70% ethyl acetate in hexanes as the eluant to afford compound 143 (0.040 g, 21%) as a brown solid; $^1$H-NMR (400 MHz, CDCl$_3$): δ 6.24 (s, 1H), 4.00 (brt, J=11.8 Hz, 1H), 3.47 (s, 2H), 2.60 (s, 3H), 2.48-2.45 (m, 4H), 2.33 (brs, 1H) 2.30 (brs, 1H), 2.25 (s, 3H), 2.07-1.93 (m, 4H), 1.80-1.69 (m, 2H), 1.63-1.62 (m, 6H), 1.43-1.42 (m, 2H); MS (ESI, positive mode) m/z 328 (MH$^+$).

Example 5: 4-(2,5-Dimethyl-3-(2-(piperidin-1-yl) acetyl)-1H-pyrrol-1-yl)benzonitrile (Compound 81)

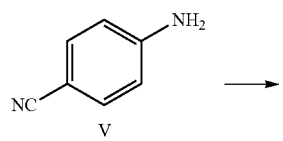

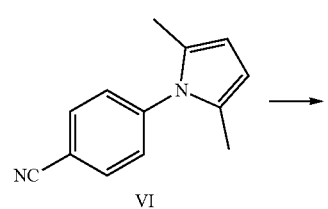

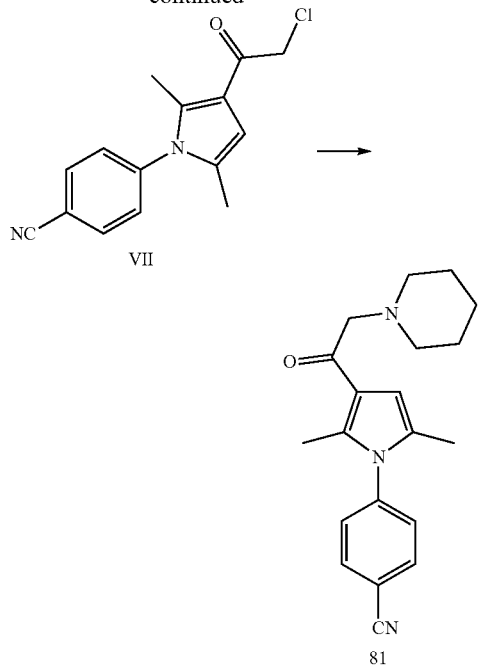

Synthesis of 4-(2,5-Dimethyl-1H-pyrrol-1-yl)benzonitrile (VI): A mixture of p-aminobenzonitrile (V, 2.00 g, 0.010 mol) and hexane-2,5-dione (5.70 g, 0.050 mol) in acetic acid (30 mL) was heated at reflux for 2 h. After cooling to room temperature, the excess acetic acid was removed under vacuum and the remaining material was then diluted with water. The mixture was extracted with ethyl acetate (3×100 mL) and the combined organic extracts were washed with water and brine. The organic layer was dried over anhydrous sodium sulfate and then concentrated to obtain the crude product mixture. The crude product was purified by column chromatography on (100-200 mesh) silica gel using 2% ethyl acetate in hexanes as the eluant to afford product VI (3.00 g, 97%) as a white solid. $^1$H NMR (400 MHz, CDCl$_3$): δ 7.76 (d, J=8.4 Hz, 2H), 7.34 (d, J=8.4 Hz, 2H), 5.93 (s, 2H), 2.03 (s, 6H).

Synthesis of 4-(3-(2-Chloroacetyl)-2,5-Dimethyl-1H-pyrrol-1-yl)benzonitrile (VII): To a cold (0° C.) suspension of anhydrous aluminum chloride (2.60 g, 0.019 mol) in dry dichloromethane (50 mL) was added chloro-acetyl chloride (2.20 g, 0.019 mol). The resulting mixture was allowed to stir at the reduced temperature for 0.5 h and then a solution of compound VI (3.30 g, 0.018 mol) in dichloromethane (30 mL) was added in single portion. The reaction mixture was allowed to warm to room temperature and stir 2 h before being poured into ice water. The mixture was extracted with dichloromethane (3×100 mL) and the combined organic extracts were dried over sodium sulfate. After condensing the organic layer, the remaining crude product mixture was purified by column chromatography on (100-200 mesh) silica gel using 30% ethyl acetate in hexanes to obtain compound VII (1.40 g, 31%) as a black solid. $^1$H NMR (400 MHz, CDCl$_3$): δ 7.76 (d, J=8.5 Hz, 1H), 7.31 (d, J=2.3 Hz, 1H), 6.97 (dd, J=8.5, 2.4 Hz, 1H), 6.30 (s, 1H), 4.45 (s, 2H), 2.33 (s, 3H), 2.00 (s, 3H).

Synthesis of 4-(2,5-Dimethyl-3-(2-(piperidin-1-yl) acetyl)-1H-pyrrol-1-yl)benzonitrile (Compound 81): To a cold (0° C.) suspension of compound VII (0.300 g, 1.00 mmol) in acetonitrile (25 ml) was added piperidine (0.180 g, 2.00 mmol) and triethylamine (0.330 g, 3.00 mmol). The mixture was allowed to warm to room temperature and for 2 h. The reaction mixture was poured onto ice (10 g) and then extracted with ethyl acetate (3×20 mL). The combined organic extracts were washed with water (40 mL) and brine, then dried over anhydrous sodium sulfate. The organic layer was then concentrated under reduced pressure and the crude product mixture was triturated with n-pentane to afford compound 81 (0.035 g, 10%) as a light brown solid. $^1$H NMR (400 MHz, CDCl$_3$): δ 7.81 (d, J=8.4 Hz, 2H), 7.31 (d, J=8.4 Hz, 2H), 6.43 (s, 1H), 3.55 (s, 2H), 2.52 (brs, 4H), 2.31 (s, 3H), 1.98 (s, 3H), 1.68-1.60 (m, 4H), 1.45 (brs, 2H); MS (ESI, positive mode) m/z 322 (MH$^+$).

The compounds shown below in Table 4 were prepared using the procedures similar to those described in Examples 1 to 5 above.

TABLE 4

| Compound No. | Chemical Name | Structure | HPLC-MS [M + H]$^+$ m/z |
|---|---|---|---|
| 1 | N-(2,6-Dimethoxy-pyrimidin-4-yl)-4-(2,5-dimethyl-3-(2-(piperidin-1-yl)acetyl)-1H-pyrrol-1-yl)benzenesulfonamide | 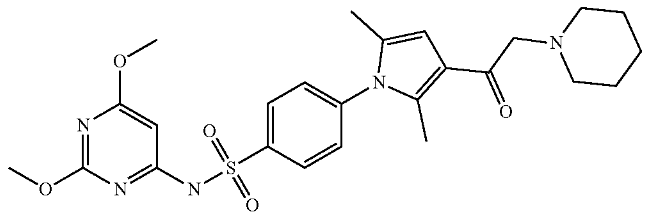 [SMILES: COc1cc(NS(=O)(=O)c2ccc(-n3c(C)cc(C(=O)CN4CCCCC4)c3C)cc2)nc(OC)n1] | 514.3 |
| 2 | N-(2,6-Dimethoxy-pyrimidin-4-yl)-4-(3-(2-(4-hydroxypiperdin-1-yl)acetyl)-2,5-dimethyl-1H-pyrrol-1-yl)benzenesulfonamide | 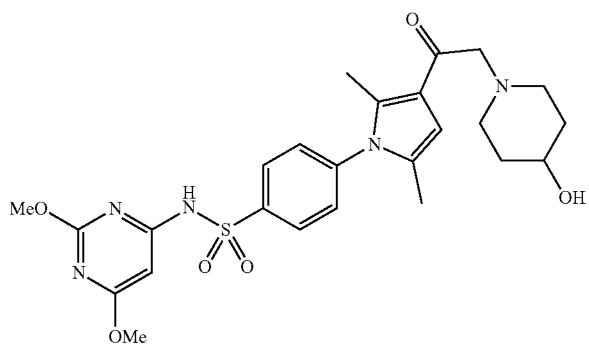 [SMILES: COc1cc(NS(=O)(=O)c2ccc(-n3c(C)cc(C(=O)CN4CCC(O)CC4)c3C)cc2)nc(OC)n1] | 530.0 |
| 3 | (R)-1-(2-(1-(4-Chlorophenyl)-2,5-dimethyl-1H-pyrrol-3-yl)-2-oxoethyl)pyrrolidine-2-carboxamide | 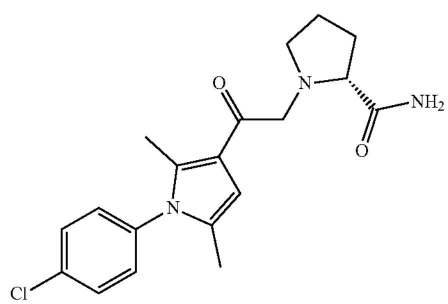 [SMILES: Cc1cc(C(=O)CN2CCC[C@@H]2C(N)=O)c(C)n1-c1ccc(Cl)cc1] | 360.0 |
| 4 | N-(2,6-Dimethoxy-pyrimidin-4-yl)-4-(2,5-dimethyl-3-(2-(pyrrolidin-1-yl)acetyl)-1H-pyrrol-1-yl)benzenesulfonamide | 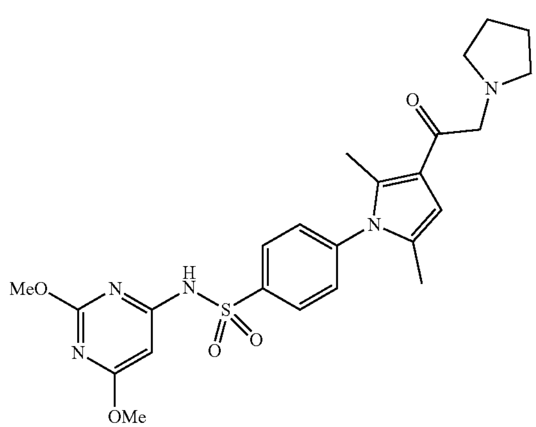 [SMILES: COc1cc(NS(=O)(=O)c2ccc(-n3c(C)cc(C(=O)CN4CCCC4)c3C)cc2)nc(OC)n1] | 500.1 |

TABLE 4-continued

| Compound No. | Chemical Name | Structure | HPLC-MS [M + H]+ m/z |
|---|---|---|---|
| 5 | 1-(2,5-Dimethyl-1-(naphthalen-1-yl)-1H-pyrrol-3-yl)-2-(piperidin-1-yl)ethanone | 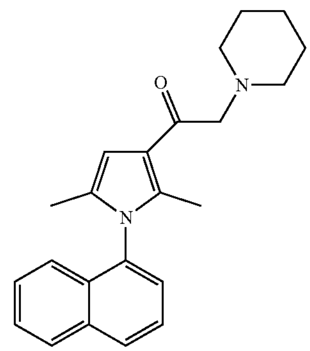 [SMILES: Cc1cc(C(=O)CN2CCCCC2)c(C)n1-c1cccc2ccccc12] | 347.2 |
| 7 | 1-(1-(4-Hydroxyphenyl)-2,5-dimethyl-1H-pyrrol-3-yl)-2-(piperidin-1-yl)ethanone | 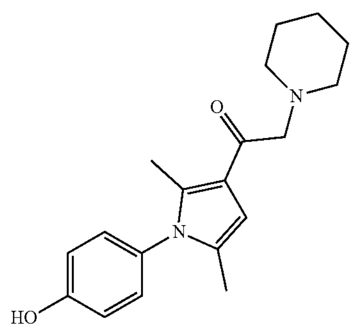 [SMILES: Cc1cc(C(=O)CN2CCCCC2)c(C)n1-c1ccc(O)cc1] | 313.1 |
| 8 | 1-(2,5-Dimethyl-1-(naphthalen-1-yl)-1H-pyrrol-3-yl)-2-(pyrrolidin-1-yl)ethanone | 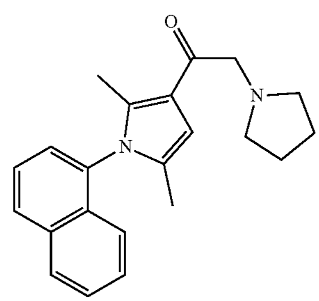 [SMILES: Cc1cc(C(=O)CN2CCCC2)c(C)n1-c1cccc2ccccc12] | 333.2 |
| 9 | 1-(2,5-Dimethyl-1-(naphthalen-1-yl)-1H-pyrrol-3-yl)-2-(4-hydroxypiperidin-1-yl)ethanone | 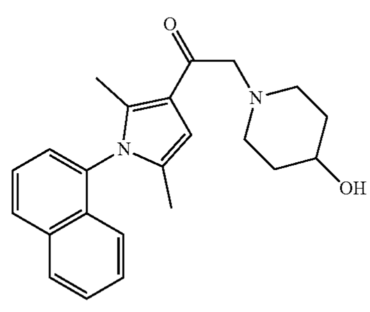 [SMILES: Cc1cc(C(=O)CN2CCC(O)CC2)c(C)n1-c1cccc2ccccc12] | 363.3 |

TABLE 4-continued
| Compound No. | Chemical Name | Structure | HPLC-MS [M + H]+ m/z |
|---|---|---|---|
| 10 | (S)-1-(1-(4-Chlorophenyl)-2,5-dimethyl-1H-pyrrol-3-yl)-2-((1-cyclohexylethyl)amino)ethanone | 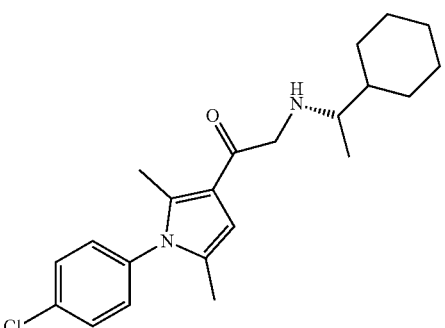 | 372.8 |
| 11 | (R)-1-(1-(4-Chlorophenyl)-2,5-dimethyl-1H-pyrrol-3-yl)-2-((1-cyclohexylethyl)amino)ethan-one | 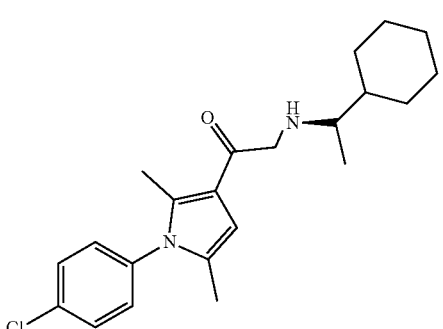 | 372.8 |
| 12 | 1-(2,5-Dimethyl-1-(4-(methylsulfonyl)phenyl)-1H-pyrrol-3-yl)-2-(piperidin-1-yl)ethanone | 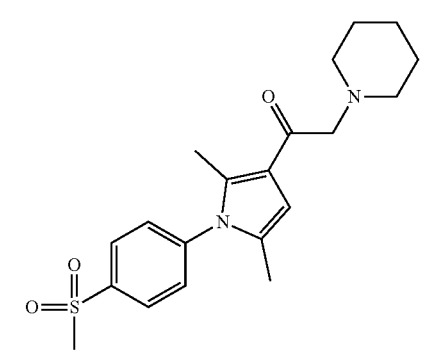 [SMILES: Cc1cc(C(=O)CN2CCCCC2)c(C)n1-c1ccc(S(C)(=O)=O)cc1] | 375.1 |
| 13 | 1-(2,5-Dimethyl-1-(4-(methylsulfonyl)phenyl)-1H-pyrrol-3-yl)-2-(4-hydroxypiperidin-1-yl)ethanone | 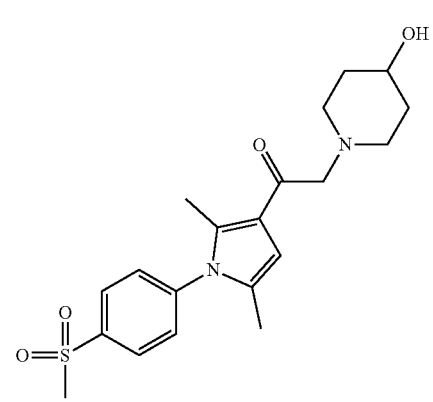 [SMILES: Cc1cc(C(=O)CN2CCC(O)CC2)c(C)n1-c1ccc(S(C)(=O)=O)cc1] | 391.1 |

TABLE 4-continued

| Compound No. | Chemical Name | Structure | HPLC-MS [M + H]+ m/z |
|---|---|---|---|
| 14 | 1-(1-(3,5-Difluorophenyl)-2,5-dimethyl-1H-pyrrol-3-yl)-2-(piperidin-1-yl)ethanone | 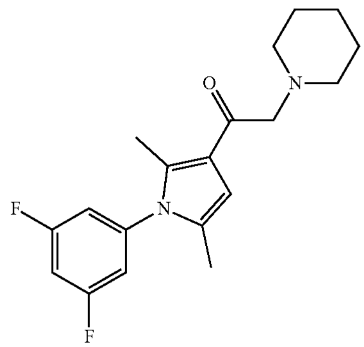 [SMILES: Cc1cc(C(=O)CN2CCCCC2)c(C)n1-c1cc(F)cc(F)c1] | 333.2 |
| 15 | 1-(1-(3,5-Difluorophenyl)-2,5-dimethyl-1H-pyrrol-3-yl)-2-(4-hydroxy-piperidin-1-yl)ethanone | 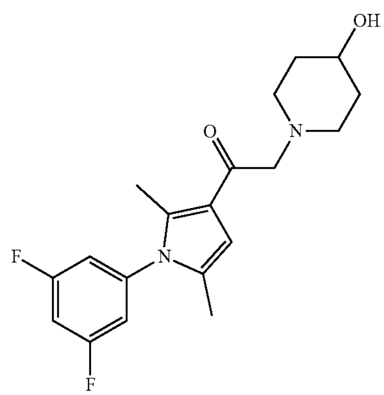 [SMILES: Cc1cc(C(=O)CN2CCC(O)CC2)c(C)n1-c1cc(F)cc(F)c1] | 349.3 |
| 16 | 1-(1-(3,5-Dichlorophenyl)-2,5-dimethyl-1H-pyrrol-3-yl)-2-(pyrrolidin-1-yl)ethanone | 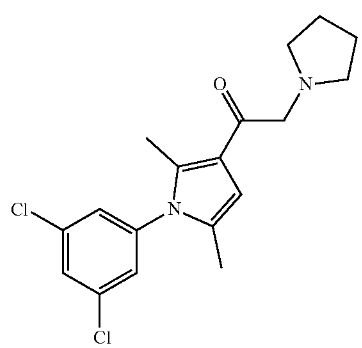 [SMILES: Cc1cc(C(=O)CN2CCCC2)c(C)n1-c1cc(Cl)cc(Cl)c1] | 351.0 |
| 17 | 1-(1-(3,5-Dichlorophenyl)-2,5-dimethyl-1H-pyrrol-3-yl)-2-(piperidin-1-yl)ethanone | 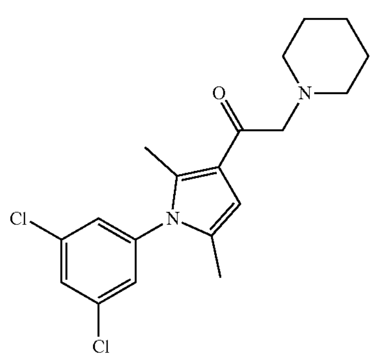 [SMILES: Cc1cc(C(=O)CN2CCCCC2)c(C)n1-c1cc(Cl)cc(Cl)c1] | 365.1 |

TABLE 4-continued
| Compound No. | Chemical Name | Structure | HPLC-MS [M + H]+ m/z |
|---|---|---|---|
| 18 | 1-(1-(3,5-Dichlorophenyl)-2,5-dimethyl-1H-pyrrol-3-yl)-2-(4-hydroxy-piperidin-1-yl)ethanone | 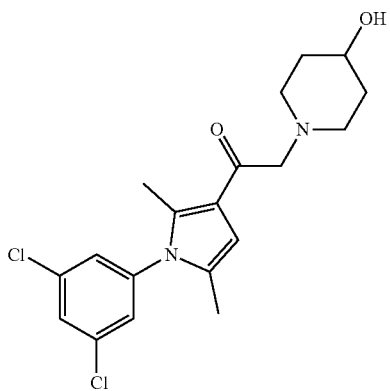 [SMILES: Cc1cc(C(=O)CN2CCC(O)CC2)c(C)n1-c1cc(Cl)cc(Cl)c1] | 381.1 |
| 19 | 1-(1-(4-Hydroxyphenyl)-2,5-dimethyl-1H-pyrrol-3-yl)-2-(pyrrolidin-1-yl)ethanone | 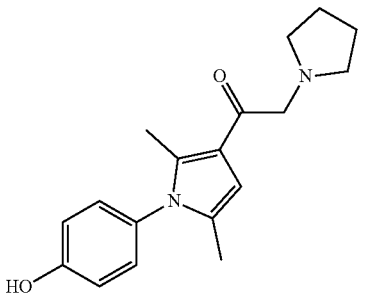 [SMILES: Cc1cc(C(=O)CN2CCCC2)c(C)n1-c1ccc(O)cc1] | 299.0 |
| 20 | 1-(1-(4-Hydroxyphenyl)-2,5-dimethyl-1H-pyrrol-3-yl)-2-(4-hydroxy-piperidin-1-yl)ethanone | 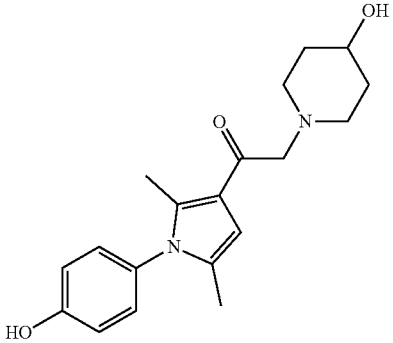 [SMILES: Cc1cc(C(=O)CN2CCC(O)CC2)c(C)n1-c1ccc(O)cc1] | 329.3 |
| 21 | 1-(2,5-Dimethyl-1-(4-(trifluoromethyl)phenyl)-1H-pyrrol-3-yl)-2-(4-hydroxy-piperidin-1-yl)ethanone | 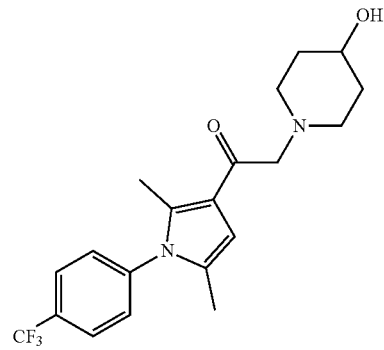 [SMILES: Cc1cc(C(=O)CN2CCC(O)CC2)c(C)n1-c1ccc(C(F)(F)F)cc1] | 381.0 |

TABLE 4-continued

| Compound No. | Chemical Name | Structure | HPLC-MS [M + H]+ m/z |
|---|---|---|---|
| 22 | 1-(1-(3,5-Difluorophenyl)-2,5-dimethyl-1H-pyrrol-3-yl)-2-(pyrrolidin-1-yl)ethanone | 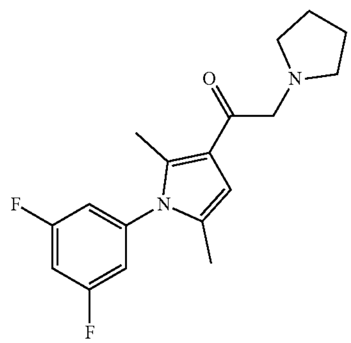 [SMILES: Cc1cc(C(=O)CN2CCCC2)c(C)n1-c1cc(F)cc(F)c1] | 319.1 |
| 23 | 1-(1-(4-Chloro-2,6-dimethylphenyl)-1H-pyrrol-3-yl)-2-(pyrrolidin-1-yl)ethanone | 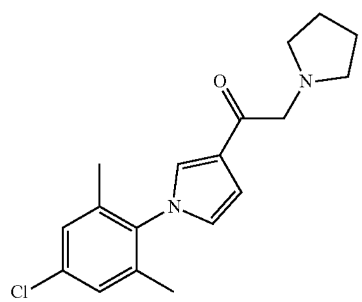 [SMILES: Cc1cc(Cl)cc(C)c1-n1ccc(C(=O)CN2CCCC2)c1] | 316.8 |
| 24 | 1-(1-(4-Chloro-2,6-dimethylphenyl)-1H-pyrrol-3-yl)-2-(4-hydroxy-piperidin-1-yl)ethanone | 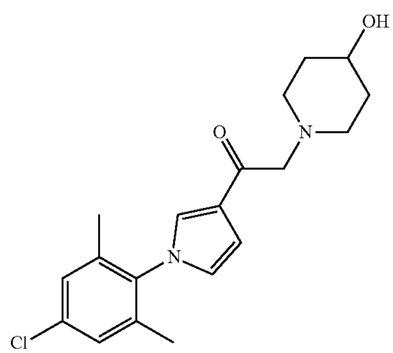 [SMILES: Cc1cc(Cl)cc(C)c1-n1ccc(C(=O)CN2CCC(O)CC2)c1] | 347.1 |
| 25 | 1-(2-(1-(4-Chlorophenyl)-2,5-dimethyl-1H-pyrrol-3-yl)-2-oxoethyl) piperidine-4-carboxylic acid | 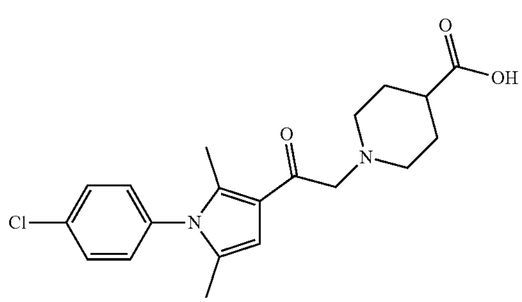 [SMILES: Cc1cc(C(=O)CN2CCC(C(=O)O)CC2)c(C)n1-c1ccc(Cl)cc1] | 375.1 |
| 26 | 1-(1-(4-Chloro-2,6-dimethylphenyl)-1H-pyrrol-3-yl)-2-(piperidin-1-yl)ethanone | 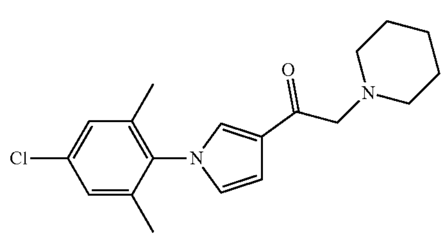 [SMILES: Cc1cc(Cl)cc(C)c1-n1ccc(C(=O)CN2CCCCC2)c1] | 330.8 |

TABLE 4-continued

| Compound No. | Chemical Name | Structure | HPLC-MS [M + H]+ m/z |
|---|---|---|---|
| 27 | 1-(1-(4-Chloro-2,6-dimethylphenyl)-1H-pyrrol-2-yl)-2-(piperidin-1-yl)ethanone | 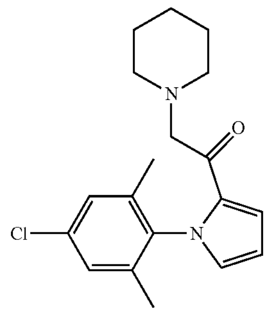 [SMILES: Cc1cc(Cl)cc(C)c1-n1cccc1C(=O)CN1CCCCC1] | 330.8 & 333.0 |
| 28 | 1-(1-(4-Chloro-2,6-dimethylphenyl)-1H-pyrrol-2-yl)-2-(pyrrolidin-1-yl)ethanone | 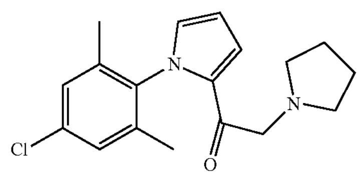 [SMILES: Cc1cc(Cl)cc(C)c1-n1cccc1C(=O)CN1CCCC1] | 317.0 & 319.1 |
| 29 | 1-(1-(4-Chloro-2,6-dimethylphenyl)-1H-pyrrol-2-yl)-2-(4-hydroxypiperidin-1-yl)ethanone | 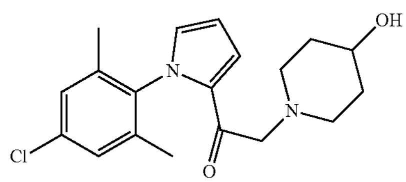 [SMILES: Cc1cc(Cl)cc(C)c1-n1cccc1C(=O)CN1CCC(O)CC1] | 346.9 & 349.0 |
| 32 | 1-(1-(cis-4-Fluorocyclohexyl)-2,5-dimethyl-1H-pyrrol-3-yl)-2-(piperidin-1-yl)ethanone | 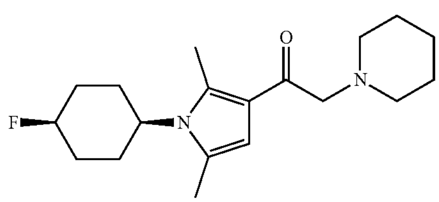 [SMILES: Cc1cc(C(=O)CN2CCCCC2)c(C)n1[C@H]1CC[C@@H](F)CC1] | [M − F]+ = 301.2 |
| 33 | 1-(1-(4-Chlorophenyl)-5-methyl-1H-pyrrol-2-yl)-2-(piperidin-1-yl)ethanone | 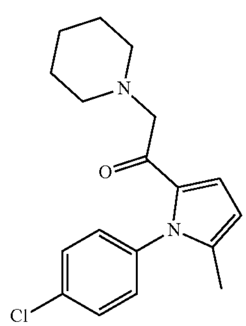 [SMILES: Cc1ccc(C(=O)CN2CCCCC2)n1-c1ccc(Cl)cc1] | 317.3 |
| 35 | 1-(1-Cyclobutyl-2,5-dimethyl-1H-pyrrol-3-yl)-2-(piperidin-1-yl)ethanone | 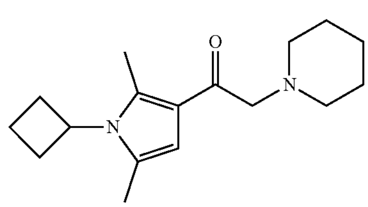 [SMILES: Cc1cc(C(=O)CN2CCCCC2)c(C)n1C1CCC1] | 275.2 |

TABLE 4-continued

| Compound No. | Chemical Name | Structure | HPLC-MS [M + H]+ m/z |
|---|---|---|---|
| 36 | 1-(1-Cyclobutyl-2,5-dimethyl-1H-pyrrol-3-yl)-2-(4-hydroxy-piperidin-1-yl)ethanone | 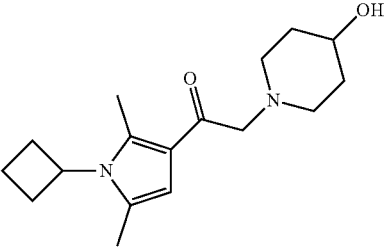 [SMILES: Cc1cc(C(=O)CN2CCC(O)CC2)c(C)n1C1CCC1] | 291.2 |
| 37 | Benzyl 1-(2-(1-cyclobutyl-2,5-dimethyl-1H-pyrrol-3-yl)-2-oxoethyl)piperidine-4-carboxylate | 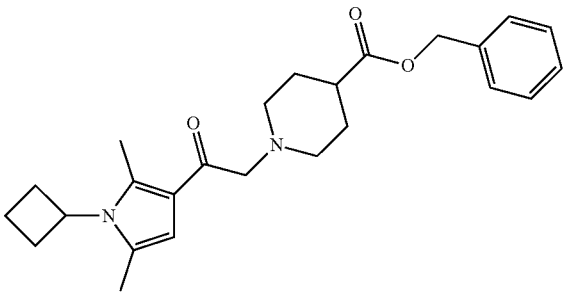 [SMILES: Cc1cc(C(=O)CN2CCC(C(=O)OCc3ccccc3)CC2)c(C)n1C1CCC1] | 409.2 |
| 38 | 1-(1-(4-Chlorophenyl)-2,5-dimethyl-1H-pyrrol-3-yl)-2-(piperidin-3-yl)ethanone | 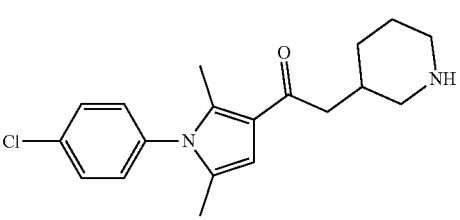 [SMILES: Cc1cc(C(=O)CC2CCCNC2)c(C)n1-c1ccc(Cl)cc1] | 331.2 |
| 39 | 1-(1-(4-Chlorophenyl)-2,5-dimethyl-1H-pyrrol-3-yl)-2-(piperidin-4-yl)ethanone | 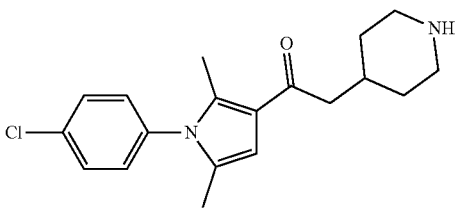 [SMILES: Cc1cc(C(=O)CC2CCNCC2)c(C)n1-c1ccc(Cl)cc1] | 331.2 |
| 40 | 1-(1-(4-Chlorophenyl)-2,5-dimethyl-1H-pyrrol-3-yl)-2-(((2,2-dimethyl-1,3-dioxolan-4-yl)methyl)amino)ethanone | 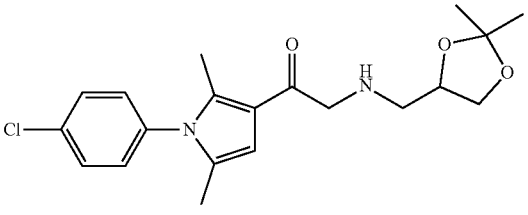 [SMILES: Cc1cc(C(=O)CNCC2COC(C)(C)O2)c(C)n1-c1ccc(Cl)cc1] | 377.2 |
| 41 | 2-((2-(Benzyloxy)ethyl)amino)-1-(1-(4-chlorophenyl)-2,5-dimethyl-1H-pyrrol-3-yl)ethanone | 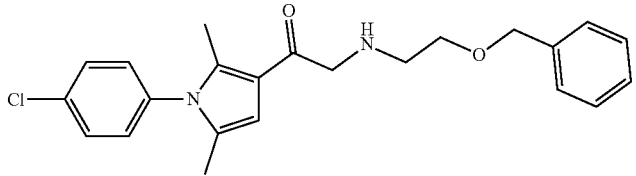 [SMILES: Cc1cc(C(=O)CNCCOCc2ccccc2)c(C)n1-c1ccc(Cl)cc1] | 397.1 |

TABLE 4-continued

| Compound No. | Chemical Name | Structure | HPLC-MS [M + H]+ m/z |
|---|---|---|---|
| 42 | 4-(3-(2-((2-(Benzyloxy)ethyl)amino)acetyl)-2,5-dimethyl-1H-pyrrol-1-yl)benzonitrile | 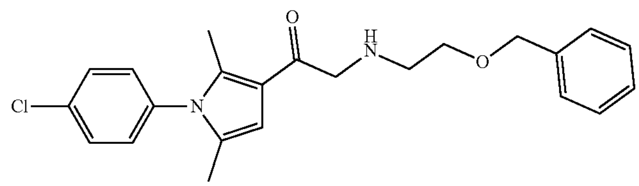 [SMILES: Cc1cc(C(=O)CNCCOCc2ccccc2)c(C)n1-c1ccc(Cl)cc1] | 387.9 |
| 43 | 4,4'-(3,3'-(2,2'-((2-(Benzyloxy)ethyl)azanediyl)bis(acetyl))bis(2,5-dimethyl-1H-pyrrole-3,1-diyl))dibenzonitrile | 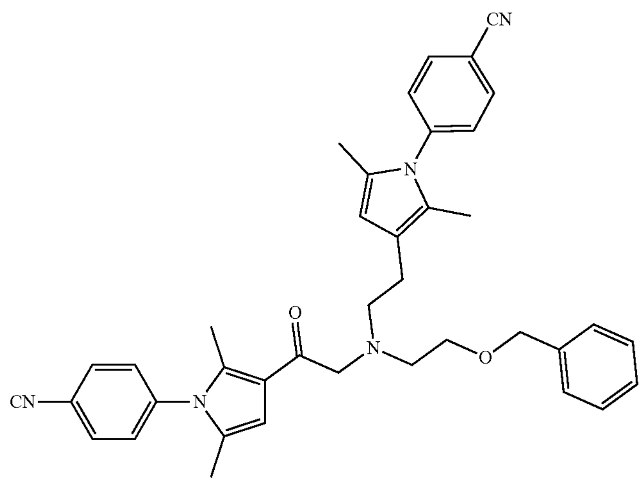 | 623.9 |
| 44 | 1-(2-(1-(4-Chlorophenyl)-2,5-dimethyl-1H-pyrrol-3-yl)-2-oxoethyl)-1-methylpiperidin-1-ium Iodide | 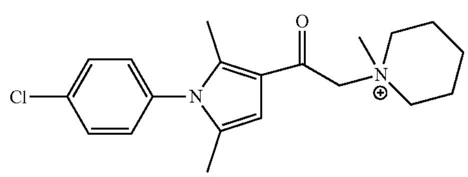 [SMILES: Cc1cc(C(=O)C[N+]2(C)CCCCC2)c(C)n1-c1ccc(Cl)cc1] | 345.1 |
| 45 | cis-Benzyl 4-(2,5-dimethyl-3-(2-(piperidin-1-yl)acetyl)-1H-pyrrol-1-yl)cyclohexanecarboxylate | 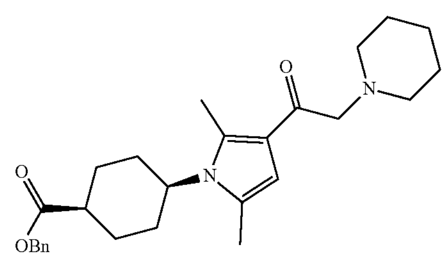 [SMILES: Cc1cc(C(=O)CN2CCCCC2)c(C)n1[C@H]1CC[C@@H](C(=O)OCc2ccccc2)CC1] | 437.3 |
| 46 | cis-4-(2,5-Dimethyl-3-(2-(piperidin-1-yl)acetyl)-1H-pyrrol-1-yl)cyclohexanecarboxylic acid | 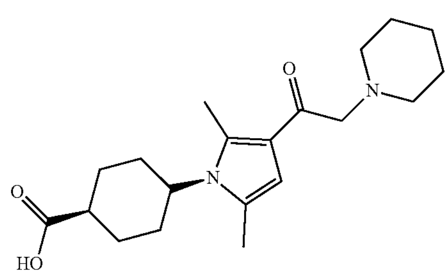 | 347.2 |

TABLE 4-continued

| Compound No. | Chemical Name | Structure | HPLC-MS [M + H]+ m/z |
|---|---|---|---|
| 48 | 1-(1-(4-Chlorophenyl)-2,5-dimethyl-1H-pyrrol-3-yl)-2-(cyclopropylamino)ethanone | 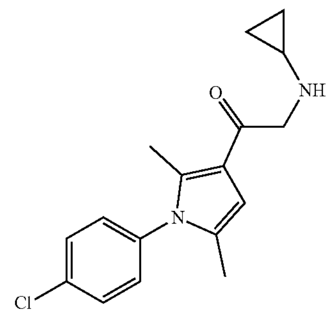 [SMILES: Cc1cc(C(=O)CNC2CC2)c(C)n1-c1ccc(Cl)cc1] | 303.0 |
| 49 | 2-(3-(Benzyloxy)pyrrolidin-1-yl)-1-(1-(4-chlorophenyl)-2,5-dimethyl-1H-pyrrol-3-yl)ethanone | 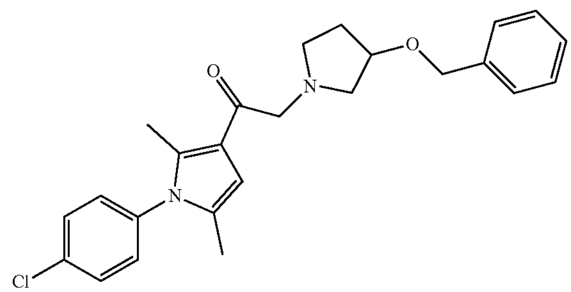 [SMILES: Cc1cc(C(=O)CN2CCC(OCc3ccccc3)C2)c(C)n1-c1ccc(Cl)cc1] | 423.0 |
| 50 | 1-(1-(4-Chlorophenyl)-2,5-dimethyl-1H-pyrrol-3-yl)-2-(2-(2-hydroxyethyl)pyrrolidin-1-yl)ethanone | 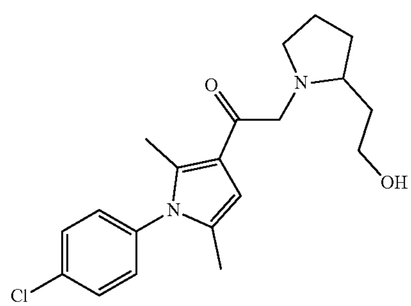 [SMILES: Cc1cc(C(=O)CN2CCCC2CCO)c(C)n1-c1ccc(Cl)cc1] | 361.1 |
| 51 | 1-(1-(4-Chlorophenyl)-2,5-dimethyl-1H-pyrrol-3-yl)-2-(3-(methylsulfonyl)pyrrolidin-1-yl)ethanone | 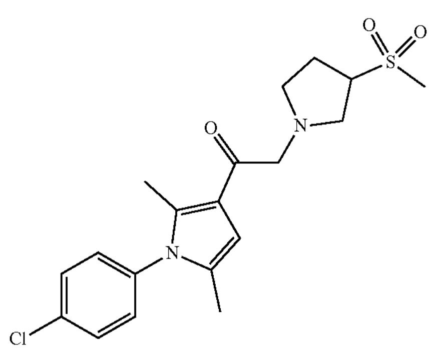 [SMILES: Cc1cc(C(=O)CN2CCC(S(C)(=O)=O)C2)c(C)n1-c1ccc(Cl)cc1] | 395.1 |

TABLE 4-continued

| Compound No. | Chemical Name | Structure | HPLC-MS [M + H]+ m/z |
|---|---|---|---|
| 52 | (S)-1-(1-(4-Chlorophenyl)-2,5-dimethyl-1H-pyrrol-3-yl)-2-(3-hydroxypyrrolidin-1-yl)ethanone | 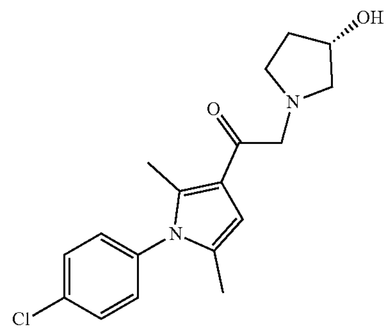 [SMILES: Cc1cc(C(=O)CN2CC[C@H](O)C2)c(C)n1-c1ccc(Cl)cc1] | 333.02 & 335.00 |
| 53 | 1-(1-(4-Chlorophenyl)-2,5-dimethyl-1H-pyrrol-3-yl)-2-(4-(trifluoromethyl)piperidin-1-yl)ethanone | 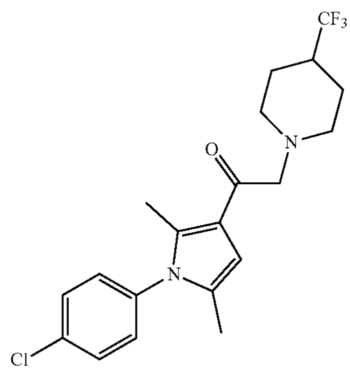 [SMILES: Cc1cc(C(=O)CN2CCC(C(F)(F)F)CC2)c(C)n1-c1ccc(Cl)cc1] | 399.0 & 401.0 |
| 54 | 1-(2-(1-(4-Chlorophenyl)-2,5-dimethyl-1H-pyrrol-3-yl)-2-oxoethyl)piperidin-3-yl propylcarbamate | 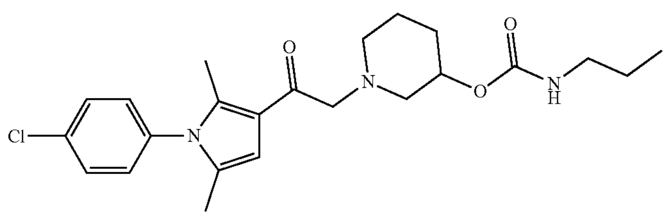 [SMILES: CCCNC(=O)OC1CCCN(CC(=O)c2cc(C)n(-c3ccc(Cl)cc3)c2C)C1] | 446.1 & 448.0 |
| 55 | 1-(1-(4-Chlorophenyl)-2,5-dimethyl-1H-pyrrol-3-yl)-2-(3-(dimethylamino)pyrrolidin-1-yl)ethanone | 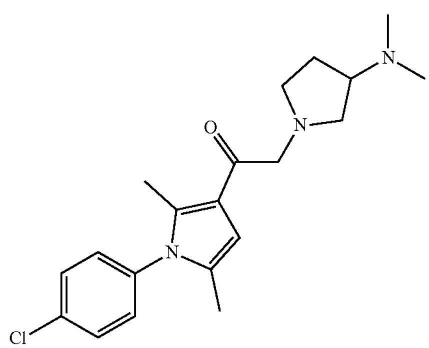 [SMILES: Cc1cc(C(=O)CN2CCC(N(C)C)C2)c(C)n1-c1ccc(Cl)cc1] | 360.0 |
| 56 | 1-(1-(4-Bromo-3-chlorophenyl)-2,5-dimethyl-1H-pyrrol-3-yl)-2-(pyrrolidin-1-yl)ethanone | 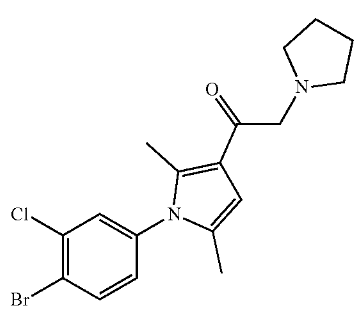 [SMILES: Cc1cc(C(=O)CN2CCCC2)c(C)n1-c1ccc(Br)c(Cl)c1] | 394.8 |

TABLE 4-continued

| Compound No. | Chemical Name | Structure | HPLC-MS [M + H]+ m/z |
|---|---|---|---|
| 57 | 1-(1-(4-Bromo-3-chlorophenyl)-2,5-dimethyl-1H-pyrrol-3-yl)-2-(piperidin-1-yl)ethanone | 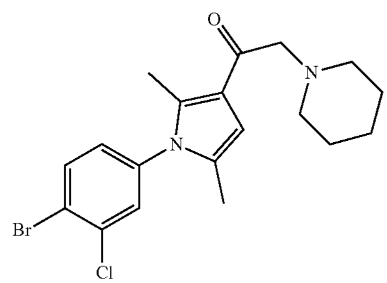 [SMILES: Cc1cc(C(=O)CN2CCCCC2)c(C)n1-c1ccc(Br)c(Cl)c1] | 411.2 |
| 58 | 1-(2,5-Dimethyl-1-(4-(trifluoromethoxy)phenyl)-1H-pyrrol-3-yl)-2-(piperidin-1-yl)ethanone | 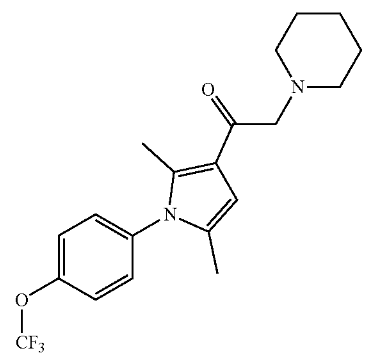 [SMILES: Cc1cc(C(=O)CN2CCCCC2)c(C)n1-c1ccc(OC(F)(F)F)cc1] | 381.1 |
| 59 | 1-(1-(4-Bromo-3-chlorophenyl)-2,5-dimethyl-1H-pyrrol-3-yl)-2-(4-hydroxy-piperidin-1-yl)ethanone | 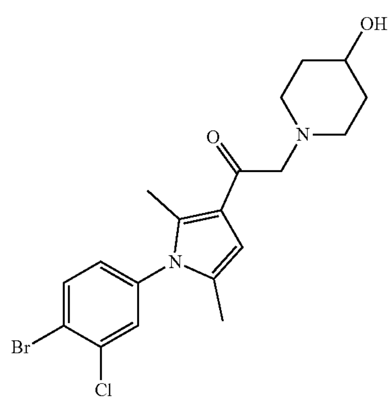 [SMILES: Cc1cc(C(=O)CN2CCC(O)CC2)c(C)n1-c1ccc(Br)c(Cl)c1] | 425.2 |
| 60 | 1-(1-(4-Chlorophenyl)-2,5-dimethyl-1H-pyrrol-3-yl)-2-(3-((dimethylamino)methyl)-3-hydroxy-pyrrolidin-1-yl)ethanone | 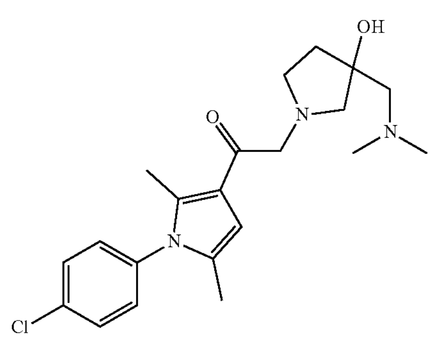 [SMILES: Cc1cc(C(=O)CN2CCC(O)(CN(C)C)C2)c(C)n1-c1ccc(Cl)cc1] | 390.1 |

TABLE 4-continued

| Compound No. | Chemical Name | Structure | HPLC-MS [M + H]+ m/z |
|---|---|---|---|
| 61 | 1-(2,5-Dimethyl-1-(4-(trifluoromethoxy)phenyl)-1H-pyrrol-3-yl)-2-(pyrrolidin-1-yl)ethanone | 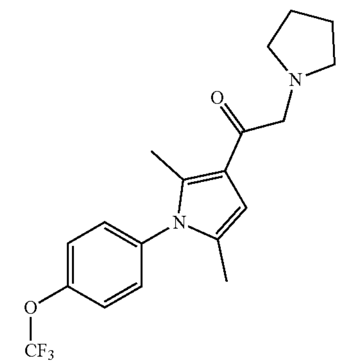 [SMILES: Cc1cc(C(=O)CN2CCCC2)c(C)n1-c1ccc(OC(F)(F)F)cc1] | 366.8 |
| 62 | 1-(2,5-dimethyl-1-(4-(trifluoromethoxy)phenyl)-1H-pyrrol-3-yl)-2-(4-hydroxypiperidin-1-yl)ethanone | 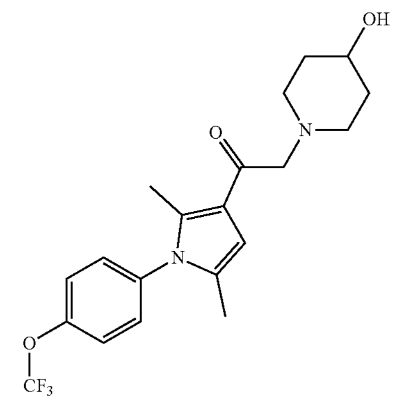 [SMILES: Cc1cc(C(=O)CN2CCC(O)CC2)c(C)n1-c1ccc(OC(F)(F)F)cc1] | 396.9 |
| 63 | 1-(1-(3-Fluoro-4-methoxyphenyl)-2,5-dimethyl-1H-pyrrol-3-yl)-2-(piperidin-1-yl)ethanone | 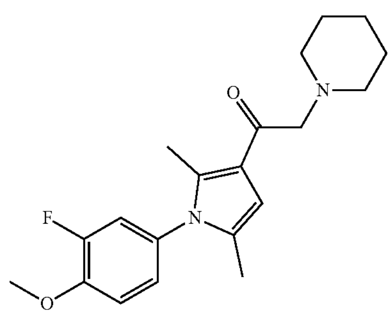 [SMILES: COc1ccc(-n2c(C)cc(C(=O)CN3CCCCC3)c2C)cc1F] | 345.5 |
| 64 | 1-(1-(3-Fluoro-4-methoxyphenyl)-2,5-dimethyl-1H-pyrrol-3-yl)-2-(4-hydroxypiperidin-1-yl)ethanone | 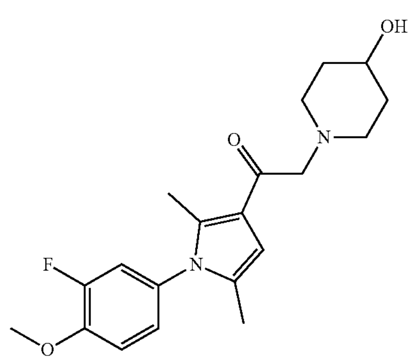 [SMILES: COc1ccc(-n2c(C)cc(C(=O)CN3CCC(O)CC3)c2C)cc1F] | 361.3 |

TABLE 4-continued

| Compound No. | Chemical Name | Structure | HPLC-MS [M + H]+ m/z |
|---|---|---|---|
| 65 | 1-(1-Cyclohexyl-2,5-dimethyl-1H-pyrrol-3-yl)-2-(piperidin-1-yl)ethanone | 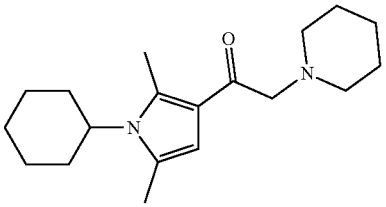 [SMILES: Cc1cc(C(=O)CN2CCCCC2)c(C)n1C1CCCCC1] | 303.19 |
| 66 | 1-(1-(4-Chlorophenyl)-2,5-dimethyl-1H-pyrrol-3-yl)-2-((4-methylcyclohexyl)amino)ethanone | 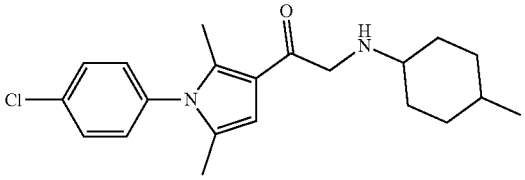 [SMILES: Cc1cc(C(=O)CNC2CCC(C)CC2)c(C)n1-c1ccc(Cl)cc1] | 359.0 |
| 67 | 1-(1-(4-Chlorophenyl)-2,5-dimethyl-1H-pyrrol-3-yl)-2-(cycloheptylamino)ethanone | 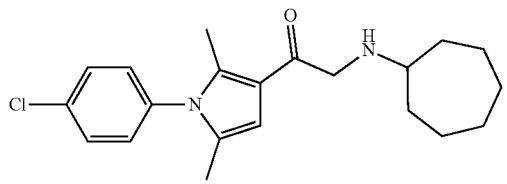 [SMILES: Cc1cc(C(=O)CNC2CCCCCC2)c(C)n1-c1ccc(Cl)cc1] | 359.3 |
| 68 | 1-(2,5-Dimethyl-1-(4-(trifluoromethyl)phenyl)-1H-pyrrol-3-yl)-2-(piperidin-1-yl)ethanone | 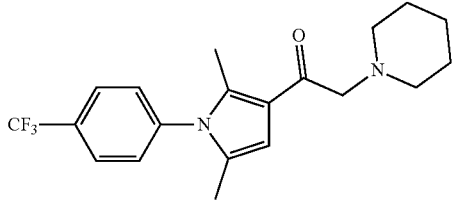 [SMILES: Cc1cc(C(=O)CN2CCCCC2)c(C)n1-c1ccc(C(F)(F)F)cc1] | 365.1 |
| 69 | 1-(1-(3,4-Difluorophenyl)-2,5-dimethyl-1H-pyrrol-3-yl)-2-(piperidin-1-yl)ethanone | 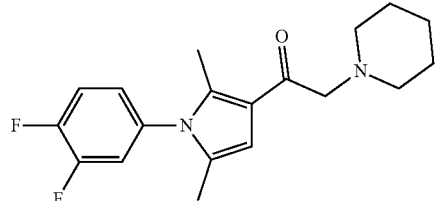 | 333.0 |
| 70 | 1-(1-(3,4-Difluorophenyl)-2,5-dimethyl-1H-pyrrol-3-yl)-2-(4-hydroxypiperidin-1-yl)ethanone | 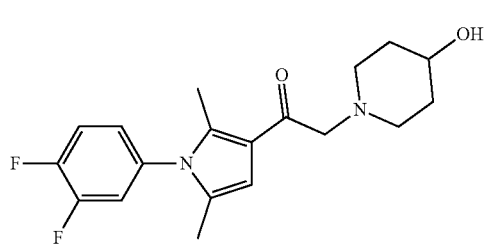 [SMILES: Cc1cc(C(=O)CN2CCC(O)CC2)c(C)n1-c1ccc(F)c(F)c1] | 349.1 |
| 71 | 1-(1-(4-Chlorophenyl)-2,5-dimethyl-1H-pyrrol-3-yl)-2-(piperidin-2-yl)ethanone | 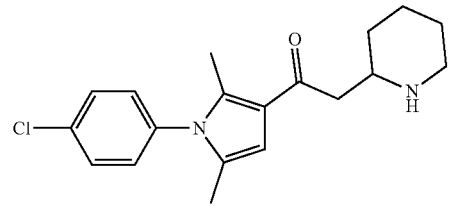 [SMILES: Cc1cc(C(=O)CC2CCCCN2)c(C)n1-c1ccc(Cl)cc1] | 331.2 |

TABLE 4-continued

| Compound No. | Chemical Name | Structure | HPLC-MS [M + H]+ m/z |
|---|---|---|---|
| 72 | 1-(1-(4-Chlorophenyl)-2,5-dimethyl-1H-pyrrol-3-yl)-2-(1-methyl-piperidin-2-yl)ethanone | 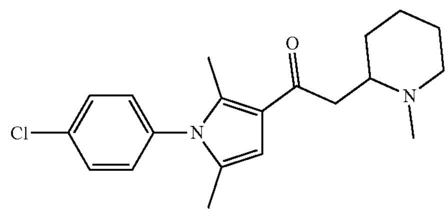 [SMILES: Cc1cc(C(=O)CC2CCCCN2C)c(C)n1-c1ccc(Cl)cc1] | 345.1 |
| 73 | 1-(1-(4-Fluorophenyl)-2,5-dimethyl-1H-pyrrol-3-yl)-2-(4-hydroxypiperidin-1-yl)ethanone | 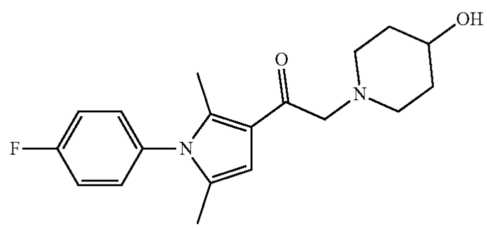 [SMILES: Cc1cc(C(=O)CN2CCC(O)CC2)c(C)n1-c1ccc(F)cc1] | 331.0 |
| 74 | 1-(1-(4-Fluorophenyl)-2,5-dimethyl-1H-pyrrol-3-yl)-2-(4-fluoropiperidin-1-yl)ethanone | 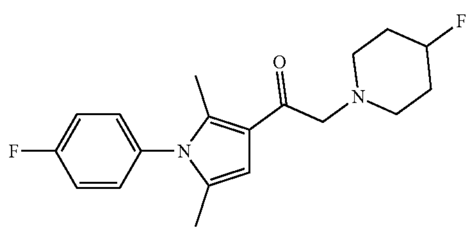 [SMILES: Cc1cc(C(=O)CN2CCC(F)CC2)c(C)n1-c1ccc(F)cc1] | 333.1 |
| 75 | N-Cyclopropyl-2-((1-(2-(1-(4-fluorophenyl)-2,5-dimethyl-1H-pyrrol-3-yl)-2-oxoethyl)piperidin-4-yl)oxy)acetamide | 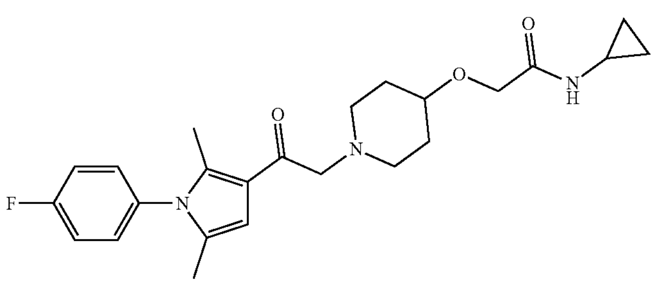 [SMILES: Cc1cc(C(=O)CN2CCC(OCC(=O)NC3CC3)CC2)c(C)n1-c1ccc(F)cc1] | 427.8 |
| 76 | 1-(1-(4,4-Difluoro-cyclohexyl)-2,5-dimethyl-1H-pyrrol-3-yl)-2-(piperidin-1-yl)ethanone | 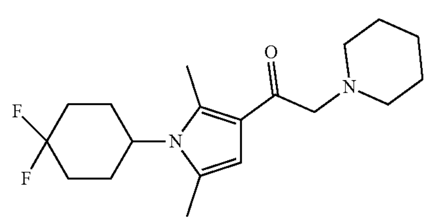 [SMILES: Cc1cc(C(=O)CN2CCCCC2)c(C)n1C1CCC(F)(F)CC1] | 339.2 |
| 77 | 4-(3-(2-((2-Hydroxyethyl)amino)acetyl)-2,5-dimethyl-1H-pyrrol-1-yl)benzonitrile | 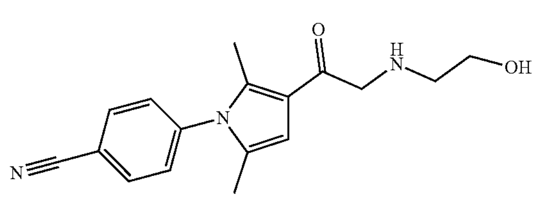 [SMILES: Cc1cc(C(=O)CNCCO)c(C)n1-c1ccc(C#N)cc1] | 298.3 |

TABLE 4-continued
| Compound No. | Chemical Name | Structure | HPLC-MS [M + H]+ m/z |
|---|---|---|---|
| 79 | 2-((1-(2-(1-(4-Chlorophenyl)-2,5-dimethyl-1H-pyrrol-3-yl)-2-oxoethyl)piperidin-4-yl)oxy)-N-ethylacetamide | 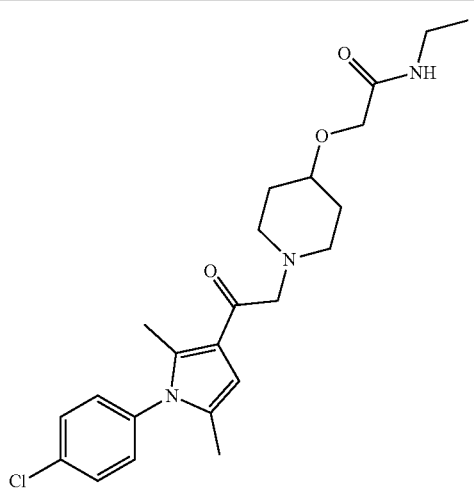 [SMILES: CCNC(=O)COC1CCN(CC(=O)c2cc(C)n(-c3ccc(Cl)cc3)c2C)CC1] | 432.05 |
| 80 | 1-(1-(4-Chlorophenyl)-2,5-dimethyl-1H-pyrrol-3-yl)-2-(4-(2-oxo-2-(piperidin-1-yl)ethoxy)piperidin-1-yl)ethanone | 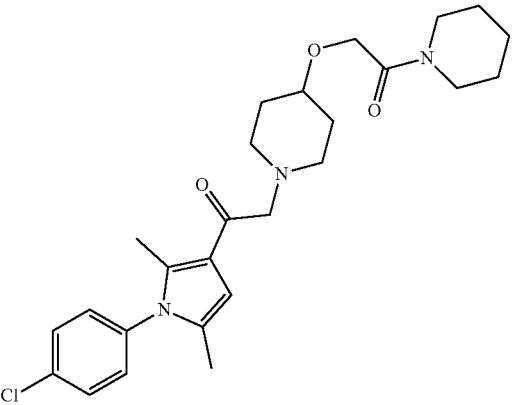 [SMILES: Cc1cc(C(=O)CN2CCC(OCC(=O)N3CCCCC3)CC2)c(C)n1-c1ccc(Cl)cc1] | 472.1 & 474.1 |
| 81 | 4-(2,5-Dimethyl-3-(2-(piperidin-1-yl)acetyl)-1H-pyrrol-1-yl)benzonitrile | 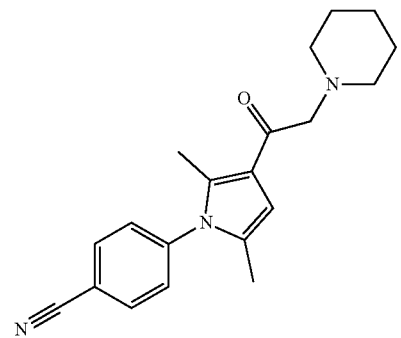 [SMILES: Cc1cc(C(=O)CN2CCCCC2)c(C)n1-c1ccc(C#N)cc1] | 321.9 |

TABLE 4-continued

| Compound No. | Chemical Name | Structure | HPLC-MS [M + H]+ m/z |
|---|---|---|---|
| 82 | 4-(3-(2-(4-Hydroxy-piperidin-1-yl)acetyl)-2,5-dimethyl-1H-pyrrol-1-yl)benzonitrile | 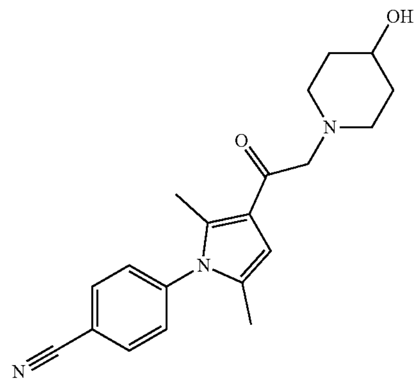 [SMILES: Cc1cc(C(=O)CN2CCC(O)CC2)c(C)n1-c1ccc(C#N)cc1] | 337.8 |
| 83 | 2-((1-(2-(1-(4-Chlorophenyl)-2,5-dimethyl-1H-pyrrol-3-yl)-2-oxoethyl)piperidin-4-yl)oxy)-N-propylacetamide | 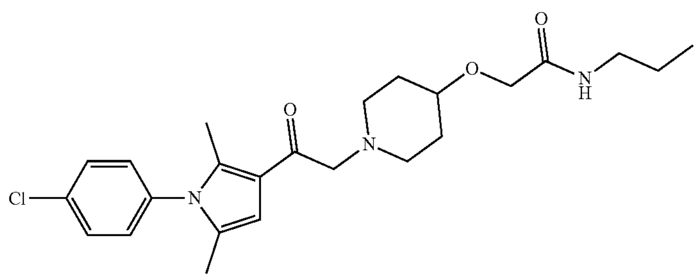 [SMILES: CCCNC(=O)COC1CCN(CC(=O)c2cc(C)n(-c3ccc(Cl)cc3)c2C)CC1] | 446.1 & 448.1 |
| 84 | N-(tert-Butyl)-2-((1-(2-(1-(4-chlorophenyl)-2,5-dimethyl-1H-pyrrol-3-yl)-2-oxoethyl)piperidin-4-yl)oxy)acetamide | 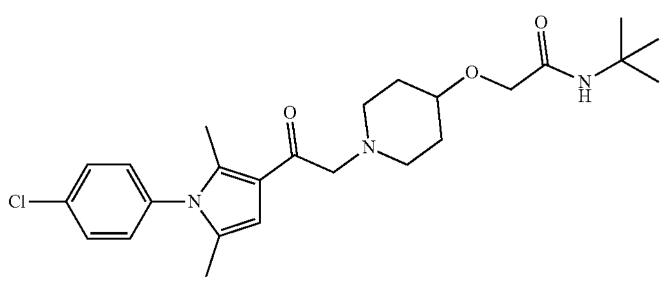 [SMILES: Cc1cc(C(=O)CN2CCC(OCC(=O)NC(C)(C)C)CC2)c(C)n1-c1ccc(Cl)cc1] | 460.1 & 462.1 |
| 85 | 4-(2,5-Dimethyl-3-(2-(pyrrolidin-1-yl)acetyl)-1H-pyrrol-1-yl)benzonitrile | 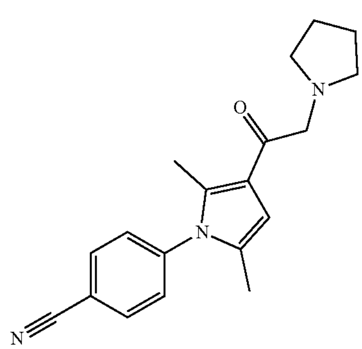 [SMILES: Cc1cc(C(=O)CN2CCCC2)c(C)n1-c1ccc(C#N)cc1] | 307.8 |
| 89A and 89B | 1-(1-(4-Chlorophenyl)-2-ethyl-5-methyl-1H-pyrrol-3-yl)-2-(piperidin-1-yl)ethanone compound with 1-(1-(4-chlorophenyl)-5-ethyl-2- | 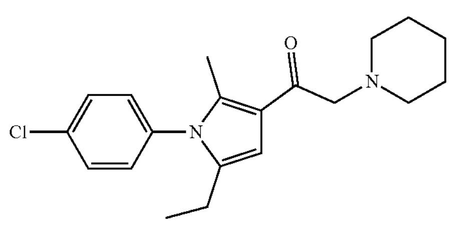 [SMILES: CCc1cc(C(=O)CN2CCCCC2)c(C)n1-c1ccc(Cl)cc1] | 345.3 |

TABLE 4-continued

| Compound No. | Chemical Name | Structure | HPLC-MS [M + H]+ m/z |
|---|---|---|---|
|  | methyl-1H-pyrrol-3-yl)-2-(piperidin-1-yl)ethanone (1:1) |  |  |
| 90 | 1-(1-(4-Chlorophenyl)-5-cyclopropyl-2-methyl-1H-pyrrol-3-yl)-2-(piperidin-1-yl)ethanone | 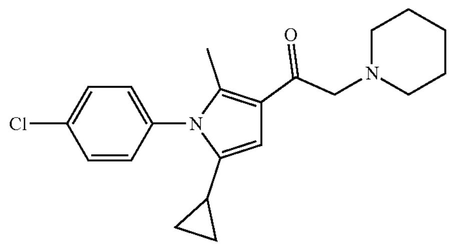 [SMILES: Cc1c(C(=O)CN2CCCCC2)cc(C2CC2)n1-c1ccc(Cl)cc1] | 357.1 |
| 91 | 1-(1-(4-Chlorophenyl)-2-methyl-1H-pyrrol-3-yl)-2-(piperidin-1-yl)ethanone | 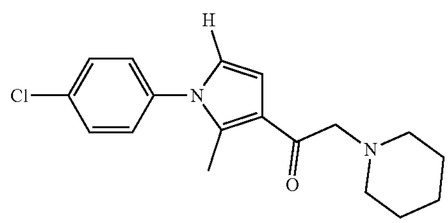 [SMILES: Cc1c(C(=O)CN2CCCCC2)ccn1-c1ccc(Cl)cc1] | 317.2 |
| 92 | 1-(5-(4-Chlorophenyl)-1,4-dimethyl-1H-pyrrol-2-yl)-2-(pyrrolidin-1-yl)ethanone | 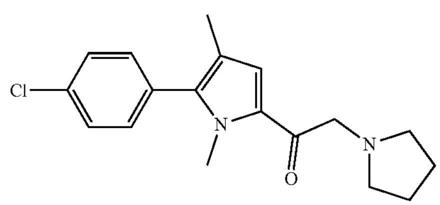 [SMILES: Cc1cc(C(=O)CN2CCCC2)n(C)c1-c1ccc(Cl)cc1] | 316.8 |
| 93 | 1-(5-(4-Chlorophenyl)-1,4-dimethyl-1H-pyrrol-3-yl)-2-(piperidin-1-yl)ethanone | 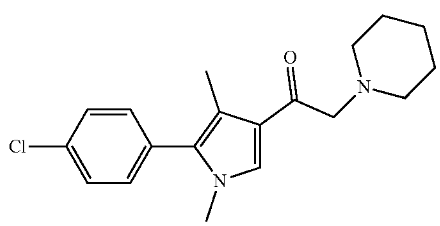 [SMILES: Cc1c(C(=O)CN2CCCCC2)cn(C)c1-c1ccc(Cl)cc1] | 330.8 |
| 94 | 1-(5-(4-Chlorophenyl)-1,4-dimethyl-1H-pyrrol-3-yl)-2-(4-hydroxypiperidin-1-yl)ethanone | 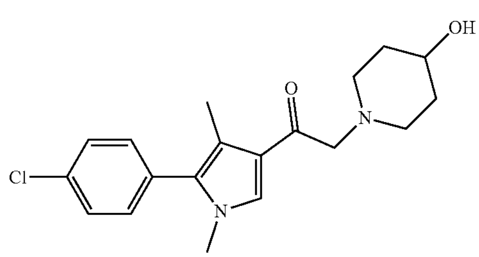 [SMILES: Cc1c(C(=O)CN2CCC(O)CC2)cn(C)c1-c1ccc(Cl)cc1] | 346.8 |

TABLE 4-continued

| Compound No. | Chemical Name | Structure | HPLC-MS [M + H]+ m/z |
|---|---|---|---|
| 95 | 1-(5-(4-Chlorophenyl)-1,4-dimethyl-1H-pyrrol-2-yl)-2-(4-hydroxy-piperidin-1-yl)ethanone | 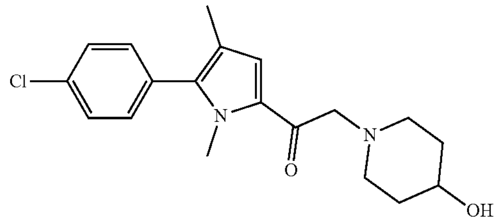 [SMILES: Cc1cc(C(=O)CN2CCC(O)CC2)n(C)c1-c1ccc(Cl)cc1] | 346.8 |
| 96 | 1-(5-(4-Chlorophenyl)-1,4-dimethyl-1H-pyrrol-2-yl)-2-(piperidin-1-yl)ethanone | 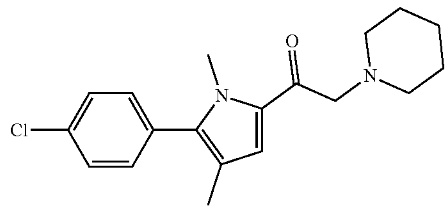 [SMILES: Cc1cc(C(=O)CN2CCCCC2)n(C)c1-c1ccc(Cl)cc1] | 330.9 |
| 97 | 1-(1-(4,4-Dichlorocyclohexyl)-2,5-dimethyl-1H-pyrrol-3-yl)-2-(piperidin-1-yl)ethanone | 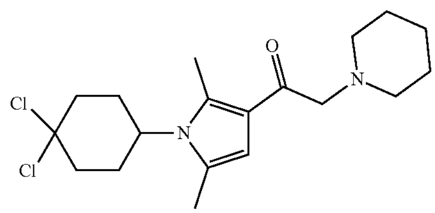 [SMILES: Cc1cc(C(=O)CN2CCCCC2)c(C)n1C1CCC(Cl)(Cl)CC1] | 371.1 & 373.1 |
| 99 | 1-(2-(1-(4-Chlorophenyl)-2,5-dimethyl-1H-pyrrol-3-yl)-2-oxoethyl)pyridin-1-ium Chloride | 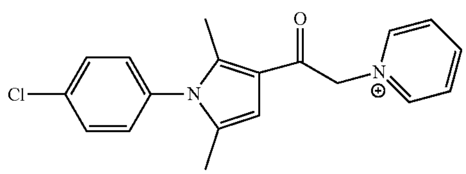 [SMILES: Cc1cc(C(=O)C[n+]2ccccc2)c(C)n1-c1ccc(Cl)cc1] | 325.1 & 327.1 |
| 100 | 1-(4-Chlorophenyl)-2,5-dimethyl-1H-pyrrole-3-carbaldehyde | 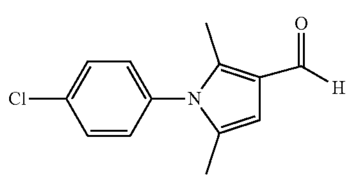 [SMILES: Cc1cc(C=O)c(C)n1-c1ccc(Cl)cc1] | 234.0 & 236.0 |
| 101 | 1-(1-(4-Chlorophenyl)-2,5-dimethyl-1H-pyrrol-3-yl)-2-((2-hydroxyethyl)amino)ethan-one | 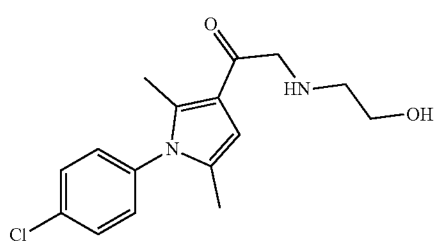 [SMILES: Cc1cc(C(=O)CNCCO)c(C)n1-c1ccc(Cl)cc1] | 306.9 |
| 102 | 4-(3-(2-(((2,2-Dimethyl-1,3-dioxolan-4-yl)methyl)amino)acetyl)-2,5-dimethyl-1H-pyrrol-1-yl)benzonitrile | 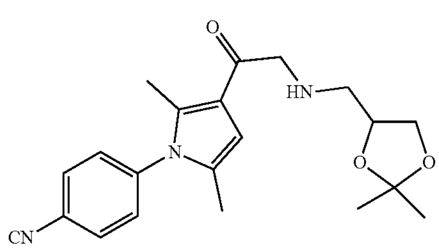 | 368.1 |

TABLE 4-continued

| Compound No. | Chemical Name | Structure | HPLC-MS [M + H]+ m/z |
|---|---|---|---|
| 103 | cis-4-(2,5-Dimethyl-3-(2-(piperidin-1-yl)acetyl)-1H-pyrrol-1-yl)cyclohexane-carboxamide | 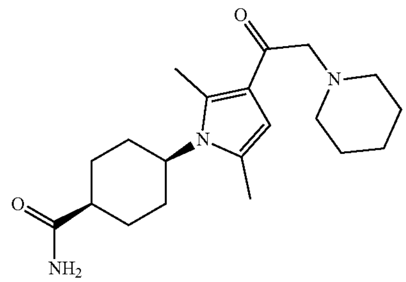 [SMILES: Cc1cc(C(=O)CN2CCCCC2)c(C)n1[C@H]1CC[C@@H](C(N)=O)CC1] | 346.2 |
| 105 | cis-(2,5-Dimethyl-3-(2-(piperidin-1-yl)acetyl)-1H-pyrrol-1-yl)cyclohexane-carbonitrile | 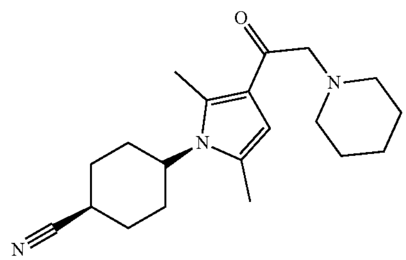 | 328.3 |
| 107 | 1-(2,5-Dimethyl-1-(2,2,2-trifluoroethyl)-1H-pyrrol-3-yl)-2-(piperidin-1-yl)ethanone | 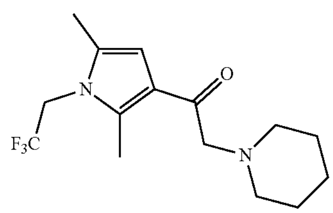 [SMILES: Cc1cc(C(=O)CN2CCCCC2)c(C)n1CC(F)(F)F] | 303.05 |
| 110 | trans-Benzyl 4-(2,5-dimethyl-3-(2-(piperidin-1-yl)acetyl)-1H-pyrrol-1-yl)benzoate | 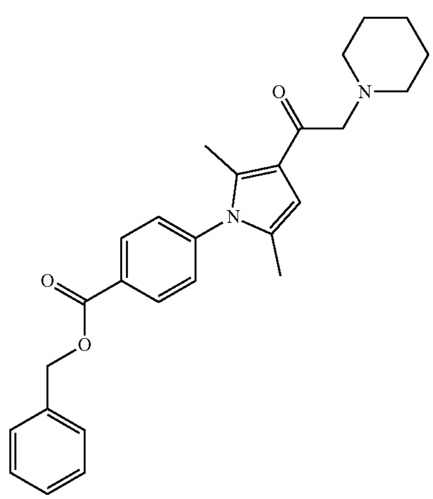 [SMILES: Cc1cc(C(=O)CN2CCCCC2)c(C)n1-c1ccc(C(=O)OCc2ccccc2)cc1] | 431.1 |

TABLE 4-continued

| Compound No. | Chemical Name | Structure | HPLC-MS [M + H]+ m/z |
|---|---|---|---|
| 111 | trans-Benzyl 4-(3-(2-(4-hydroxy-piperidin-1-yl)acetyl)-2,5-dimethyl-1H-pyrrol-1-yl)benzoate | 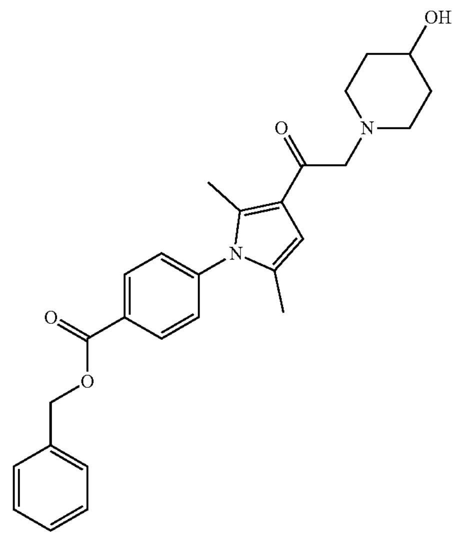 [SMILES: Cc1cc(C(=O)CN2CCC(O)CC2)c(C)n1-c1ccc(C(=O)OCc2ccccc2)cc1] | 446.8 |
| 112 | 4-(2-Ethyl-5-(2-(piperidin-1-yl)acetyl)-1H-pyrrol-1-yl)benzonitrile | 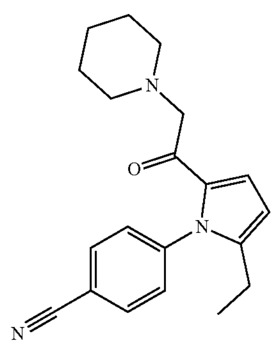 [SMILES: CCc1ccc(C(=O)CN2CCCCC2)n1-c1ccc(C#N)cc1] | 322.0 |
| 113 | 4-(3-(2-(4-Hydroxy-piperidin-1-yl)acetyl)-2,5-dimethyl-1H-pyrrol-1-yl)benzoic acid | 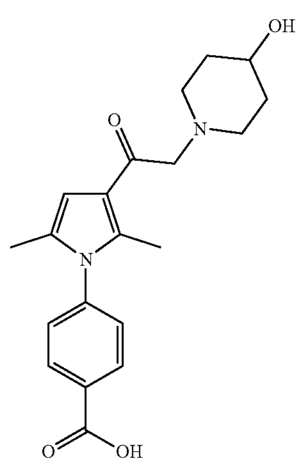 [SMILES: Cc1cc(C(=O)CN2CCC(O)CC2)c(C)n1-c1ccc(C(=O)O)cc1] | 357.2 |

TABLE 4-continued

| Compound No. | Chemical Name | Structure | HPLC-MS [M + H]+ m/z |
|---|---|---|---|
| 114 | 4-(2,5-Dimethyl-3-(2-(piperidin-1-yl)acetyl)-1H-pyrrol-1-yl)benzoic acid | 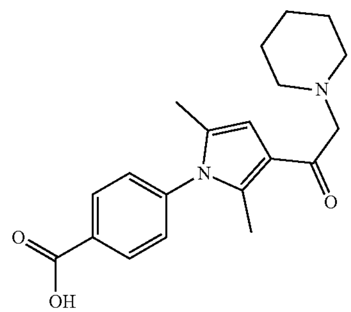 [SMILES: Cc1cc(C(=O)CN2CCCCC2)c(C)n1-c1ccc(C(=O)O)cc1] | 341.2 |
| 117 | 4-(3-Acetyl-2,5-dimethyl-4-(piperidin-1-ylmethyl)-1H-pyrrol-1-yl)benzonitrile | 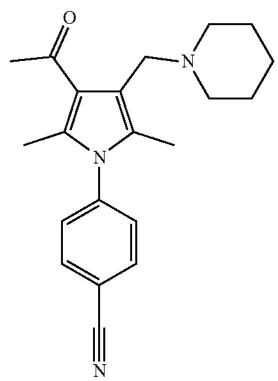 [SMILES: CC(=O)c1c(CN2CCCCC2)c(C)n(-c2ccc(C#N)cc2)c1C] | 335.9 |
| 120 | Benzyl trans-4-[2,5-Dimethyl-3-(2-piperidin-1-yl-acetyl)-1H-pyrrol-1-yl]-cyclohexane-carboxylate | 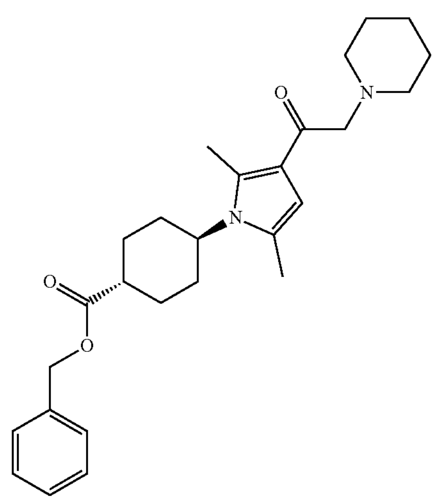 [SMILES: Cc1cc(C(=O)CN2CCCCC2)c(C)n1[C@H]1CC[C@H](C(=O)OCc2ccccc2)CC1] | |
| 121 | trans-4-(2,5-Dimethyl-3-(2-(piperidin-1-yl)acetyl)-1H-pyrrol-1-yl)cyclohexane-carboxylic acid | 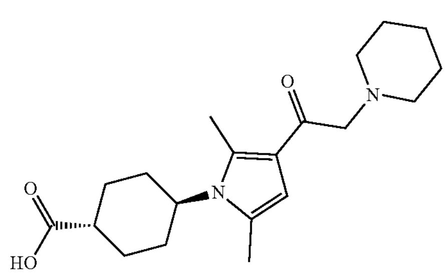 [SMILES: Cc1cc(C(=O)CN2CCCCC2)c(C)n1[C@H]1CC[C@H](C(=O)O)CC1] | 347.4 |

TABLE 4-continued

| Compound No. | Chemical Name | Structure | HPLC-MS [M + H]+ m/z |
|---|---|---|---|
| 122 | trans-4-(2,5-Dimethyl-3-(2-(piperidin-1-yl)acetyl)-1H-pyrrol-1-yl)cyclohexane-carboxamide | 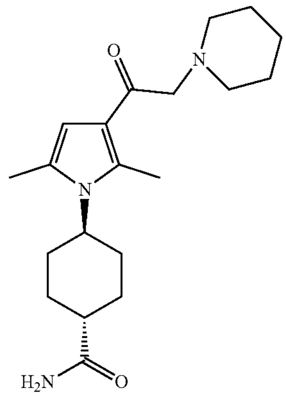 [SMILES: Cc1cc(C(=O)CN2CCCCC2)c(C)n1[C@H]1CC[C@H](C(N)=O)CC1] | 346.1 |
| 134 | 4-(3-(2-((2,3-Dihydroxypropyl)amino)acetyl)-2,5-dimethyl-1H-pyrrol-1-yl)benzonitrile | 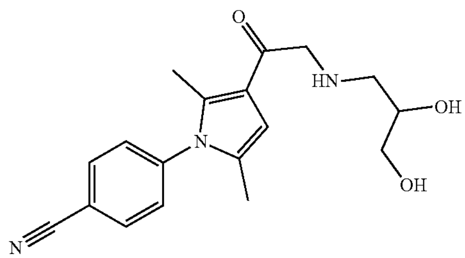 [SMILES: Cc1cc(C(=O)CNCC(O)CO)c(C)n1-c1ccc(C#N)cc1] | 328.3 |
| 135 | tert-butyl ((1-(2-(1-(4-Cyanophenyl)-2,5-dimethyl-1H-pyrrol-3-yl)-2-oxoethyl)piperidin-4-yl)methyl)carbamate | 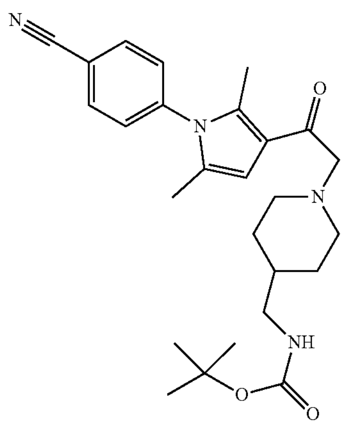 [SMILES: Cc1cc(C(=O)CN2CCC(CNC(=O)OC(C)(C)C)CC2)c(C)n1-c1ccc(C#N)cc1] | 451.1 |
| 136 | 1-(2,5-Dimethyl-1-(4-(prop-1-yn-1-yl)phenyl)-1H-pyrrol-3-yl)-2-(piperidin-1-yl)ethanone | 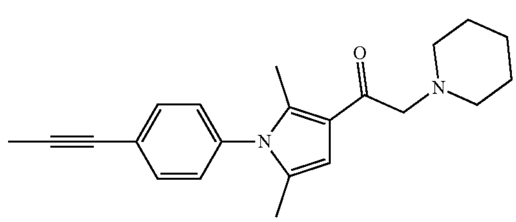 [SMILES: CC#Cc1ccc(-n2c(C)cc(C(=O)CN3CCCCC3)c2C)cc1] | 335.1 |
| 137 | 1-(1-(4-Chlorophenyl)-2,4,5-trimethyl-1H-pyrrol-3-yl)-2-(piperidin-1-yl)ethanone | 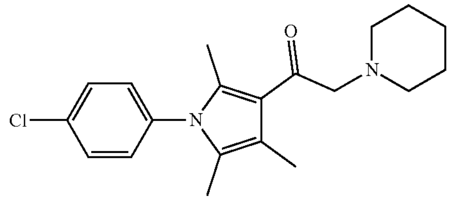 [SMILES: Cc1c(C(=O)CN2CCCCC2)c(C)n(-c2ccc(Cl)cc2)c1C] | 345.0 |

TABLE 4-continued

| Compound No. | Chemical Name | Structure | HPLC-MS [M + H]+ m/z |
|---|---|---|---|
| 138 | 2-Amino-6-((2-(1-(4-cyanophenyl)-2,5-dimethyl-1H-pyrrol-3-yl)-2-oxoethyl)(methyl)amino)hexa-noic acid | 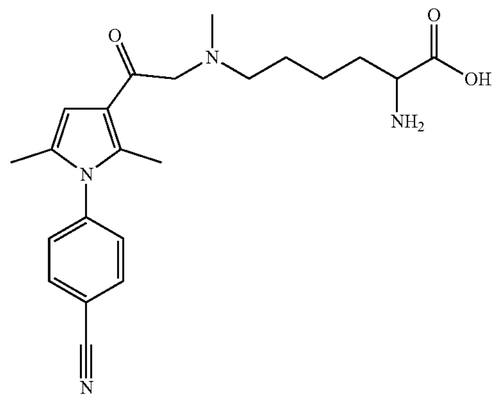 [SMILES: Cc1cc(C(=O)CN(C)CCCCC(N)C(=O)O)c(C)n1-c1ccc(C#N)cc1] | 396.9 |
| 139 | 1-(1-(4-Chlorophenyl)-2,4,5-trimethyl-1H-pyrrol-3-yl)-2-(4-hydroxypiperidin-1-yl)ethanone | 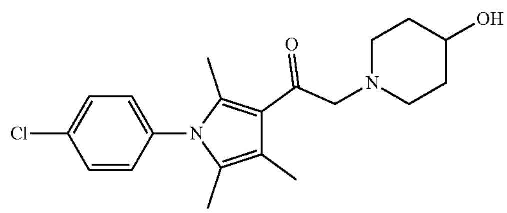 [SMILES: Cc1c(C(=O)CN2CCC(O)CC2)c(C)n(-c2ccc(Cl)cc2)c1C] | 361.1 |
| 140 | 1-(2,5-Dimethyl-1-(4-(prop-1-yn-1-yl)phenyl)-1H-pyrrol-3-yl)-2-(4-hydroxypiperidin-1-yl)ethanone | 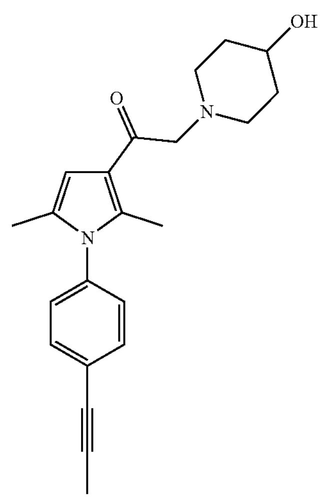 [SMILES: CC#Cc1ccc(-n2c(C)cc(C(=O)CN3CCC(O)CC3)c2C)cc1] | 351.0 |
| 143 | trans-4-(2,5-Dimethyl-3-(2-(piperidin-1-yl)acetyl)-1H-pyrrol-1-yl)cyclohexanecarbonitrile | 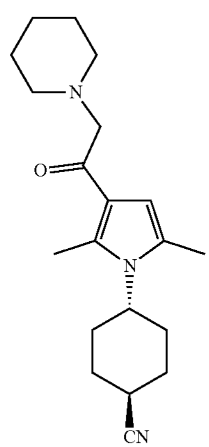 [SMILES: Cc1cc(C(=O)CN2CCCCC2)c(C)n1[C@H]1CC[C@H](C#N)CC1] | 328.3 |

TABLE 4-continued

| Compound No. | Chemical Name | Structure | HPLC-MS [M + H]+ m/z |
|---|---|---|---|
| 157 | 4-(3-(2-(4-(Aminomethyl)piperidin-1-yl)acetyl)-2,5-dimethyl-1H-pyrrol-1-yl)benzonitrile | 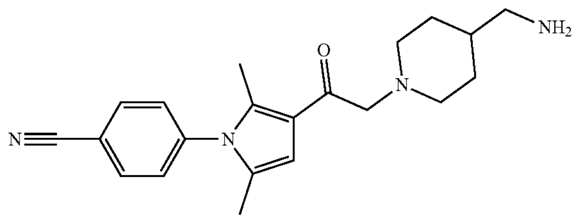 [SMILES: Cc1cc(C(=O)CN2CCC(CN)CC2)c(C)n1-c1ccc(C#N)cc1] | 351.0 |
| 158 | tert-butyl ((1-(2-(1-(4-cyanophenyl)-2,5-dimethyl-1H-pyrrol-3-yl)-2-oxoethyl)piperidin-3-yl)methyl)carbamate | 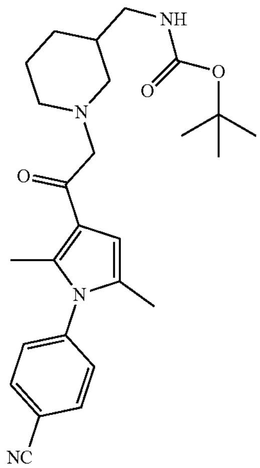 [SMILES: Cc1cc(C(=O)CN2CCCC(CNC(=O)OC(C)(C)C)C2)c(C)n1-c1ccc(C#N)cc1] | 451.3 |
| 159 | 4-(3-(2-(3-(Aminomethyl)piperidin-1-yl)acetyl)-2,5-dimethyl-1H-pyrrol-1-yl)benzonitrile | 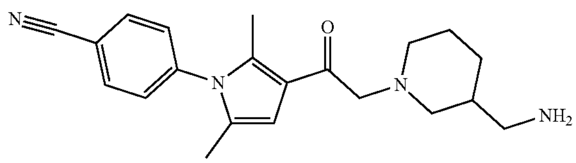 [SMILES: Cc1cc(C(=O)CN2CCCC(CN)C2)c(C)n1-c1ccc(C#N)cc1] | 351.0 |

Example 6: USP14 Inhibition Assay

Using previously described methodology [B. H. Lee et al. Nature 2010, 467 (9), 179, the contents of which are expressly incorporated by reference herein], select compounds described herein were found to inhibit USP14 as delineated in Table 5. "I" in the Table below designates an $IC_{50}$ of >5 µM, "II" in the Table below designates and $IC_{50}$ between 0.5 and 5 µM, and "III" designates an $IC_{50}$<0.5 µM. The $IC_{50}$ values in the Table below represent the average value from a minimum of two experimental determinations.

TABLE 5

| Compound No. | Chemical Structure | $IC_{50}$ Category |
|---|---|---|
| 1 | 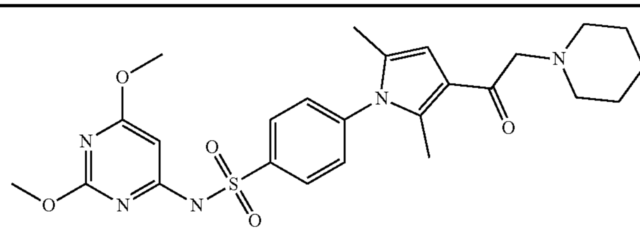 | I |

TABLE 5-continued

| Compound No. | Chemical Structure | IC$_{50}$ Category |
|---|---|---|
| 2 | 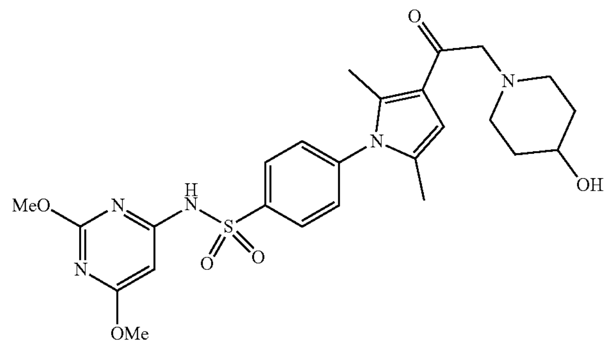 [SMILES: COc1cc(NS(=O)(=O)c2ccc(-n3c(C)cc(C(=O)CN4CCC(O)CC4)c3C)cc2)nc(OC)n1] | I |
| 3 | 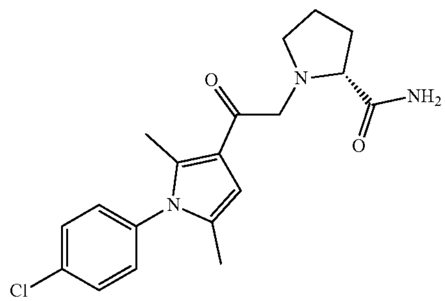 [SMILES: Cc1cc(C(=O)CN2CCC[C@@H]2C(N)=O)c(C)n1-c1ccc(Cl)cc1] | I |
| 4 | 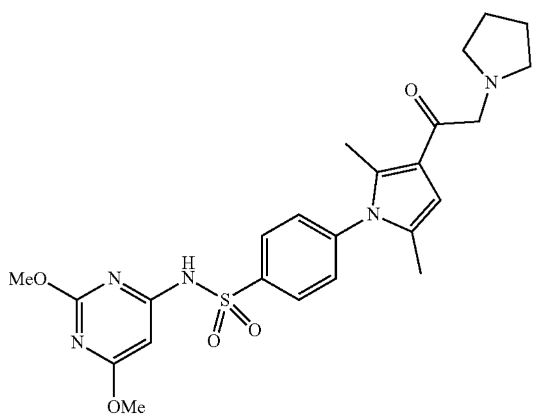 [SMILES: COc1cc(NS(=O)(=O)c2ccc(-n3c(C)cc(C(=O)CN4CCCC4)c3C)cc2)nc(OC)n1] | I |
| 5 | 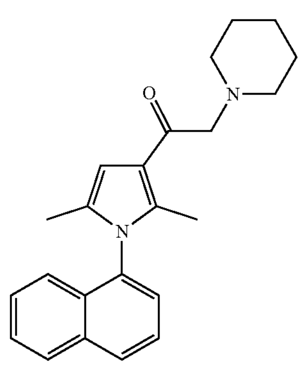 [SMILES: Cc1cc(C(=O)CN2CCCCC2)c(C)n1-c1cccc2ccccc12] | I |

TABLE 5-continued

| Compound No. | Chemical Structure | IC$_{50}$ Category |
|---|---|---|
| 7 | 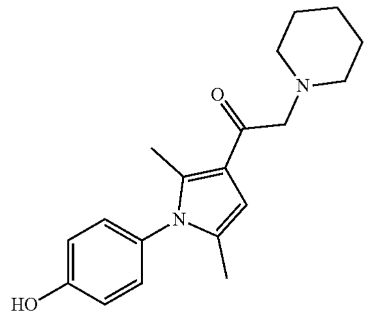 [SMILES: Cc1cc(C(=O)CN2CCCCC2)c(C)n1-c1ccc(O)cc1] | I |
| 8 | 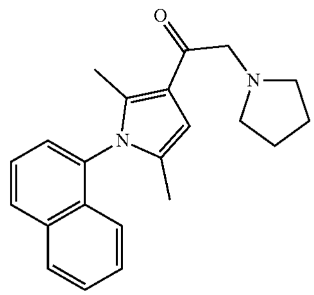 [SMILES: Cc1cc(C(=O)CN2CCCC2)c(C)n1-c1cccc2ccccc12] | I |
| 9 | 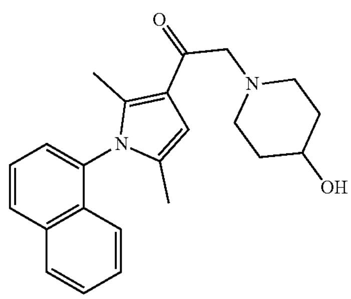 [SMILES: Cc1cc(C(=O)CN2CCC(O)CC2)c(C)n1-c1cccc2ccccc12] | I |
| 10 | 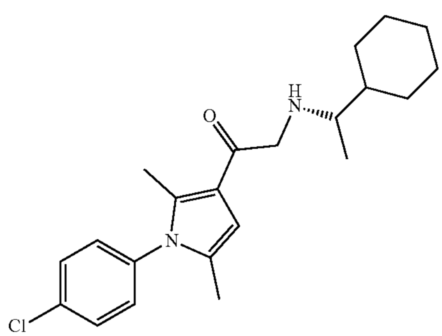 | I |
| 11 | 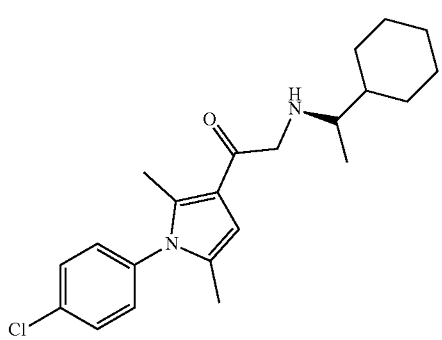 | I |

TABLE 5-continued

| Compound No. | Chemical Structure | IC$_{50}$ Category |
| --- | --- | --- |
| 12 | 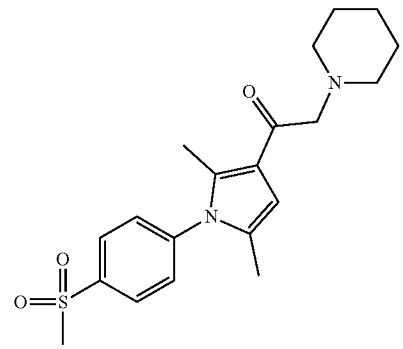 [SMILES: Cc1cc(C(=O)CN2CCCCC2)c(C)n1-c1ccc(S(C)(=O)=O)cc1] | I |
| 13 | 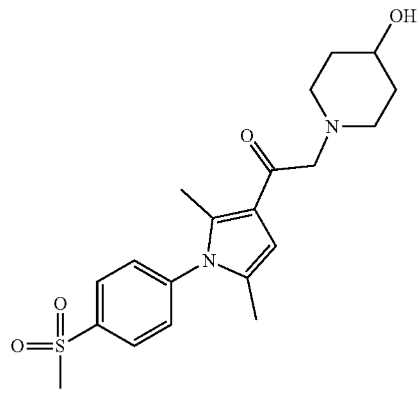 [SMILES: Cc1cc(C(=O)CN2CCC(O)CC2)c(C)n1-c1ccc(S(C)(=O)=O)cc1] | I |
| 14 | 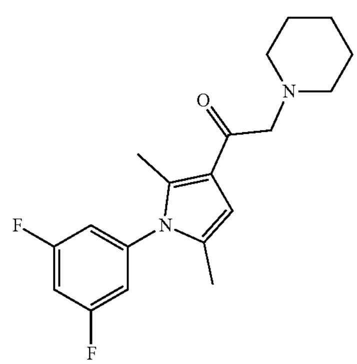 [SMILES: Cc1cc(C(=O)CN2CCCCC2)c(C)n1-c1cc(F)cc(F)c1] | I |
| 15 | 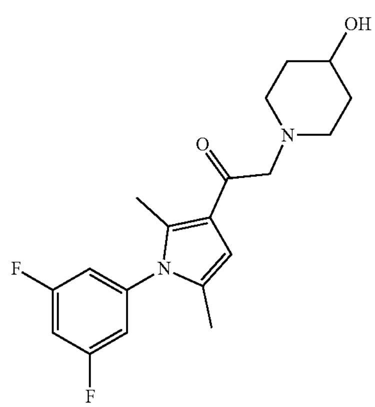 [SMILES: Cc1cc(C(=O)CN2CCC(O)CC2)c(C)n1-c1cc(F)cc(F)c1] | I |

TABLE 5-continued

| Compound No. | Chemical Structure | IC$_{50}$ Category |
|---|---|---|
| 16 | 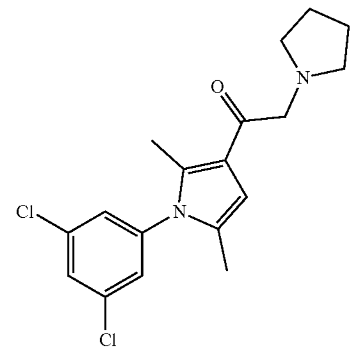 [SMILES: Cc1cc(C(=O)CN2CCCC2)c(C)n1-c1cc(Cl)cc(Cl)c1] | I |
| 17 | 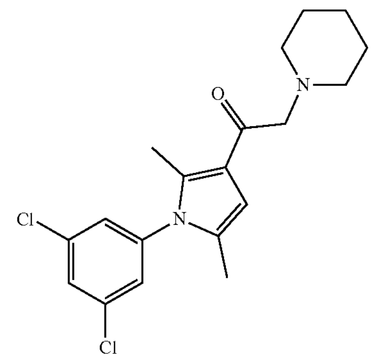 [SMILES: Cc1cc(C(=O)CN2CCCCC2)c(C)n1-c1cc(Cl)cc(Cl)c1] | I |
| 18 | 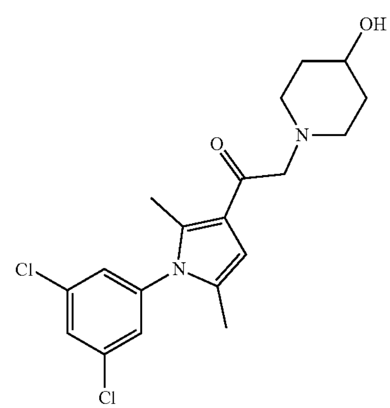 [SMILES: Cc1cc(C(=O)CN2CCC(O)CC2)c(C)n1-c1cc(Cl)cc(Cl)c1] | I |
| 19 | 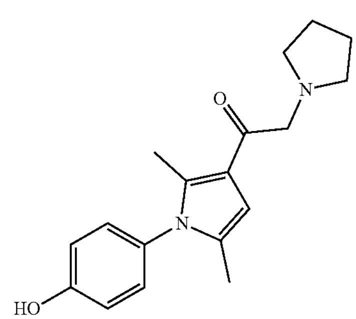 [SMILES: Cc1cc(C(=O)CN2CCCC2)c(C)n1-c1ccc(O)cc1] | I |

TABLE 5-continued

| Compound No. | Chemical Structure | IC$_{50}$ Category |
|---|---|---|
| 20 | 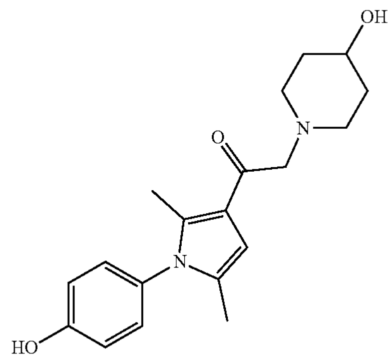 [SMILES: Cc1cc(C(=O)CN2CCC(O)CC2)c(C)n1-c1ccc(O)cc1] | I |
| 21 | 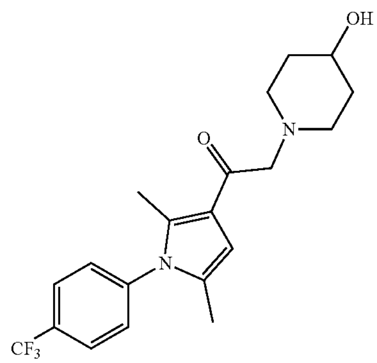 [SMILES: Cc1cc(C(=O)CN2CCC(O)CC2)c(C)n1-c1ccc(C(F)(F)F)cc1] | I |
| 22 | 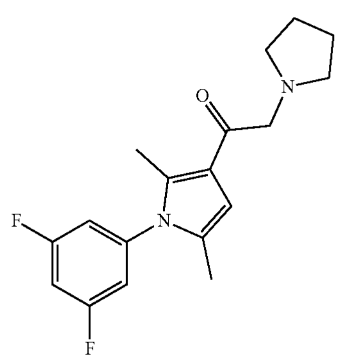 [SMILES: Cc1cc(C(=O)CN2CCCC2)c(C)n1-c1cc(F)cc(F)c1] | I |
| 23 | 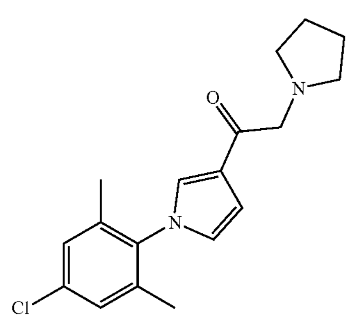 [SMILES: Cc1cc(Cl)cc(C)c1-n1ccc(C(=O)CN2CCCC2)c1] | I |

TABLE 5-continued
| Compound No. | Chemical Structure | IC$_{50}$ Category |
|---|---|---|
| 24 | 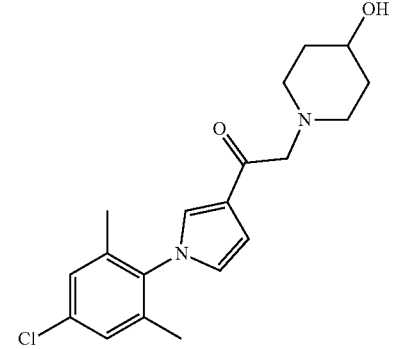 [SMILES: Cc1cc(Cl)cc(C)c1-n1ccc(C(=O)CN2CCC(O)CC2)c1] | I |
| 25 | 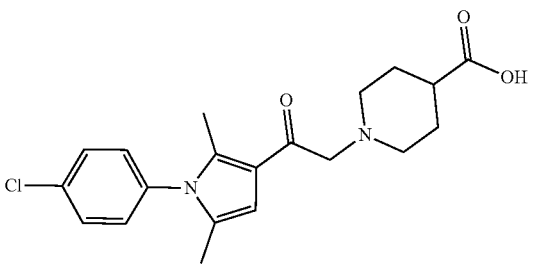 [SMILES: Cc1cc(C(=O)CN2CCC(C(=O)O)CC2)c(C)n1-c1ccc(Cl)cc1] | I |
| 26 | 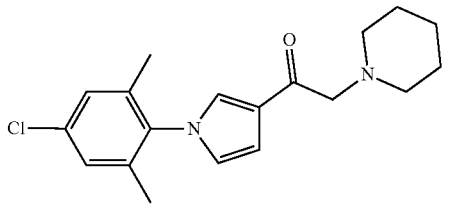 [SMILES: Cc1cc(Cl)cc(C)c1-n1ccc(C(=O)CN2CCCCC2)c1] | I |
| 27 | 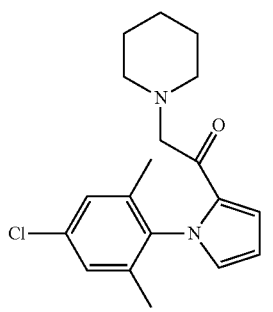 [SMILES: Cc1cc(Cl)cc(C)c1-n1cccc1C(=O)CN1CCCCC1] | I |
| 28 | 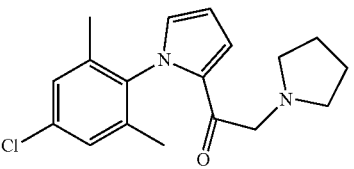 [SMILES: Cc1cc(Cl)cc(C)c1-n1cccc1C(=O)CN1CCCC1] | I |
| 29 | 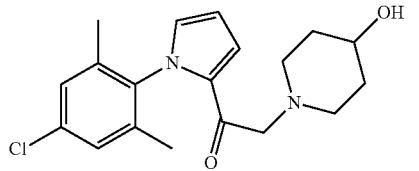 [SMILES: Cc1cc(Cl)cc(C)c1-n1cccc1C(=O)CN1CCC(O)CC1] | I |

TABLE 5-continued

| Compound No. | Chemical Structure | IC$_{50}$ Category |
|---|---|---|
| 32 | 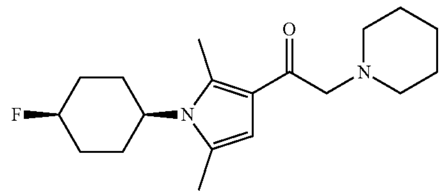 [SMILES: Cc1cc(C(=O)CN2CCCCC2)c(C)n1[C@H]1CC[C@@H](F)CC1] | I |
| 33 | 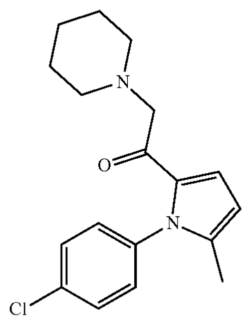 [SMILES: Cc1ccc(C(=O)CN2CCCCC2)n1-c1ccc(Cl)cc1] | I |
| 35 | 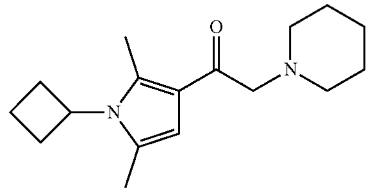 [SMILES: Cc1cc(C(=O)CN2CCCCC2)c(C)n1C1CCC1] | I |
| 36 | 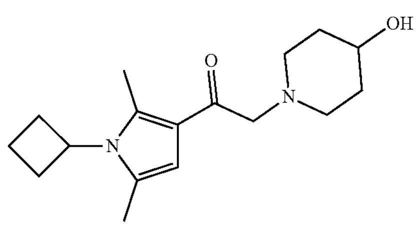 [SMILES: Cc1cc(C(=O)CN2CCC(O)CC2)c(C)n1C1CCC1] | I |
| 37 | 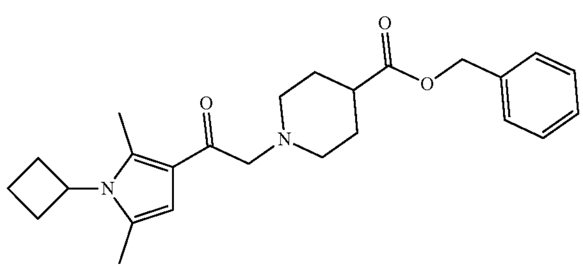 [SMILES: Cc1cc(C(=O)CN2CCC(C(=O)OCc3ccccc3)CC2)c(C)n1C1CCC1] | I |
| 38 | 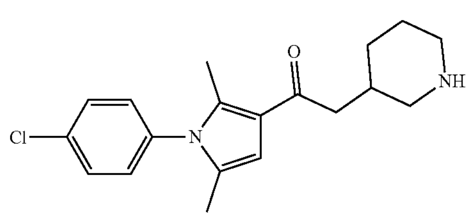 [SMILES: Cc1cc(C(=O)CC2CCCNC2)c(C)n1-c1ccc(Cl)cc1] | I |

TABLE 5-continued

| Compound No. | Chemical Structure | IC$_{50}$ Category |
|---|---|---|
| 39 | 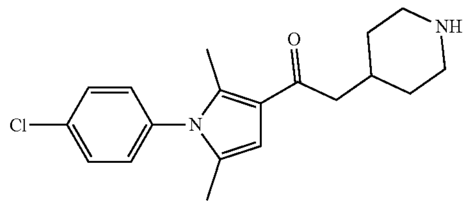 [SMILES: Cc1cc(C(=O)CC2CCNCC2)c(C)n1-c1ccc(Cl)cc1] | I |
| 40 | 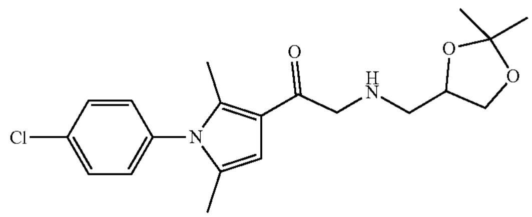 [SMILES: Cc1cc(C(=O)CNCC2COC(C)(C)O2)c(C)n1-c1ccc(Cl)cc1] | I |
| 41 | 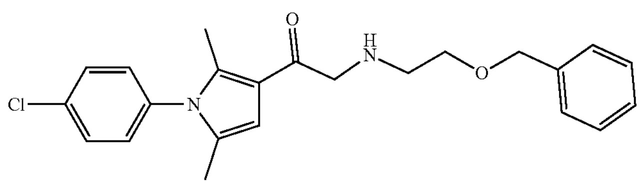 [SMILES: Cc1cc(C(=O)CNCCOCc2ccccc2)c(C)n1-c1ccc(Cl)cc1] | I |
| 42 | 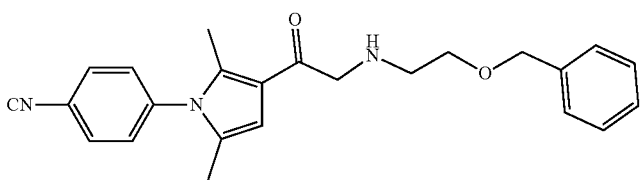 | I |
| 43 | 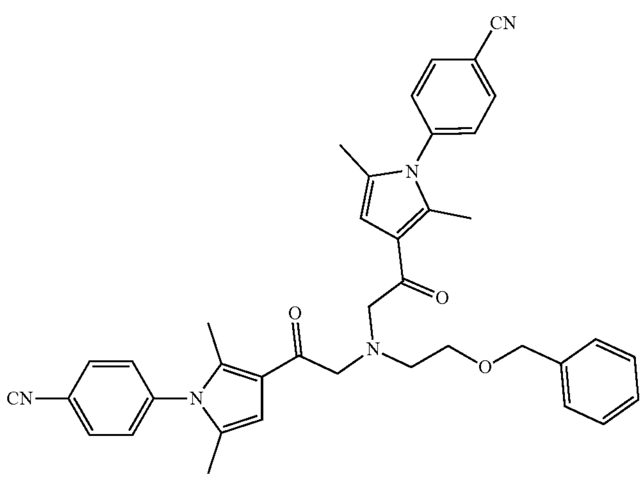 | I |
| 44 | 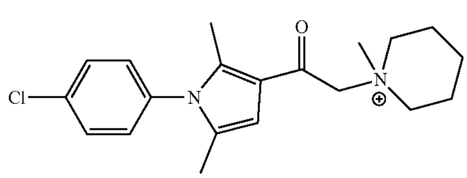 [SMILES: Cc1cc(C(=O)C[N+]2(C)CCCCC2)c(C)n1-c1ccc(Cl)cc1] | I |

TABLE 5-continued
| Compound No. | Chemical Structure | IC$_{50}$ Category |
| --- | --- | --- |
| 45 | 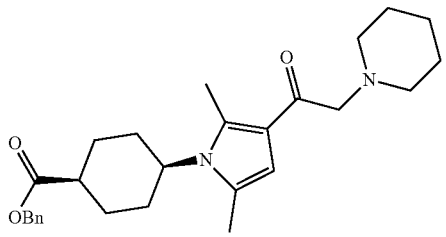 [SMILES: Cc1cc(C(=O)CN2CCCCC2)c(C)n1[C@H]1CC[C@@H](C(=O)OCc2ccccc2)CC1] | I |
| 46 | 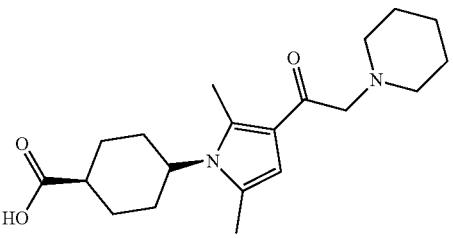 | I |
| 48 | 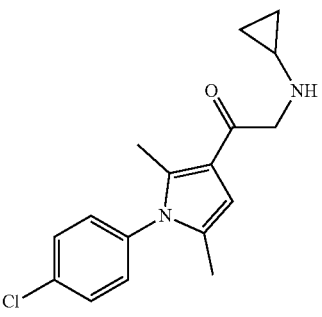 [SMILES: Cc1cc(C(=O)CNC2CC2)c(C)n1-c1ccc(Cl)cc1] | II |
| 49 | 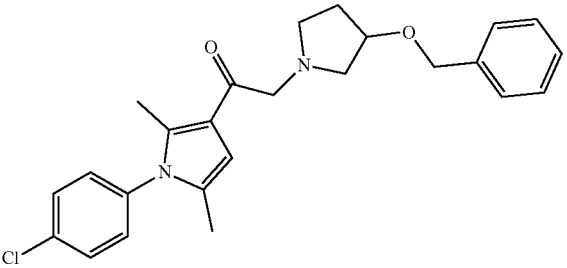 [SMILES: Cc1cc(C(=O)CN2CCC(OCc3ccccc3)C2)c(C)n1-c1ccc(Cl)cc1] | II |
| 50 | 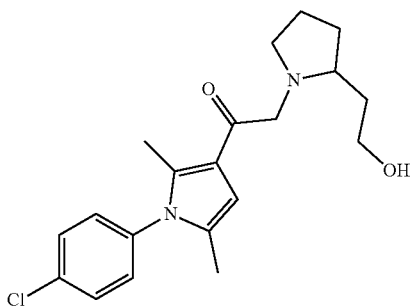 [SMILES: Cc1cc(C(=O)CN2CCCC2CCO)c(C)n1-c1ccc(Cl)cc1] | II |

TABLE 5-continued

| Compound No. | Chemical Structure | IC$_{50}$ Category |
|---|---|---|
| 51 | 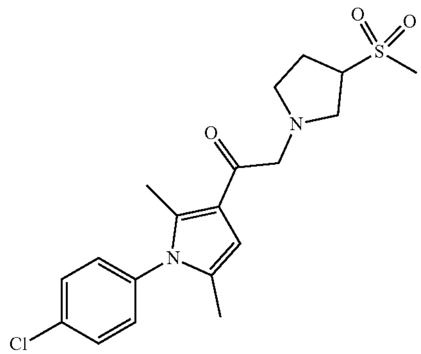 [SMILES: Cc1cc(C(=O)CN2CCC(S(C)(=O)=O)C2)c(C)n1-c1ccc(Cl)cc1] | II |
| 52 | 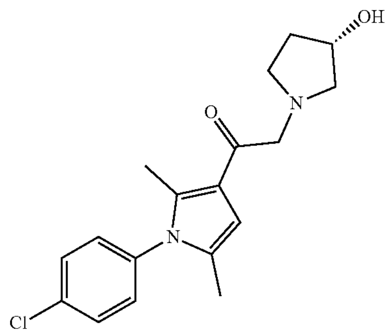 [SMILES: Cc1cc(C(=O)CN2CC[C@H](O)C2)c(C)n1-c1ccc(Cl)cc1] | II |
| 53 | 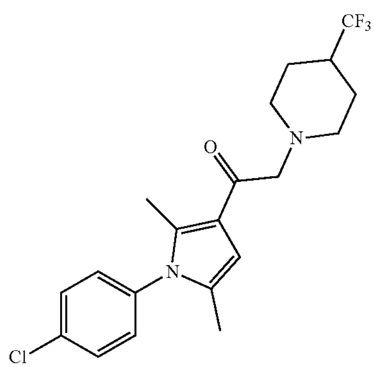 [SMILES: Cc1cc(C(=O)CN2CCC(C(F)(F)F)CC2)c(C)n1-c1ccc(Cl)cc1] | II |
| 54 | | II | ns
TABLE 5-continued

| Compound No. | Chemical Structure | IC$_{50}$ Category |
|---|---|---|
| 55 | 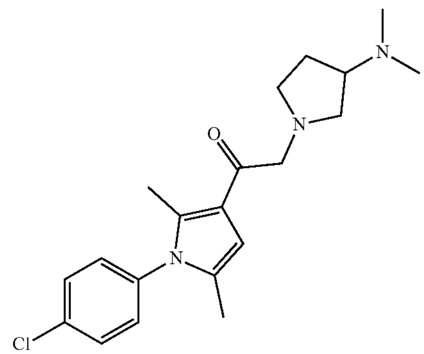 [SMILES: Cc1cc(C(=O)CN2CCC(N(C)C)C2)c(C)n1-c1ccc(Cl)cc1] | II |
| 56 | 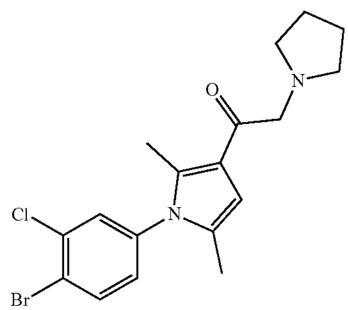 [SMILES: Cc1cc(C(=O)CN2CCCC2)c(C)n1-c1ccc(Br)c(Cl)c1] | II |
| 57 | 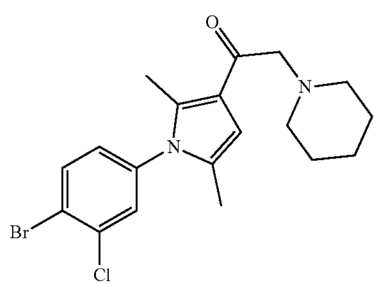 [SMILES: Cc1cc(C(=O)CN2CCCCC2)c(C)n1-c1ccc(Br)c(Cl)c1] | II |
| 58 | 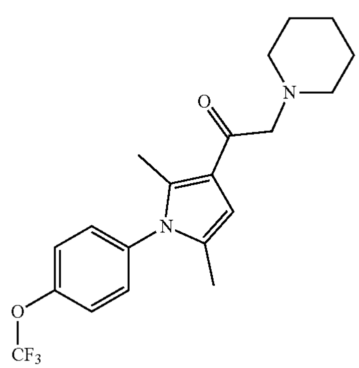 [SMILES: Cc1cc(C(=O)CN2CCCCC2)c(C)n1-c1ccc(OC(F)(F)F)cc1] | II |

TABLE 5-continued

| Compound No. | Chemical Structure | IC$_{50}$ Category |
|---|---|---|
| 59 | 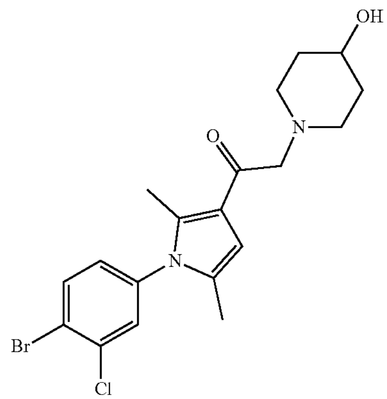 [SMILES: Cc1cc(C(=O)CN2CCC(O)CC2)c(C)n1-c1ccc(Br)c(Cl)c1] | II |
| 60 | 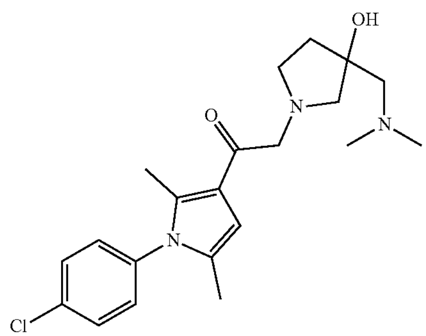 [SMILES: Cc1cc(C(=O)CN2CCC(O)(CN(C)C)C2)c(C)n1-c1ccc(Cl)cc1] | II |
| 61 | 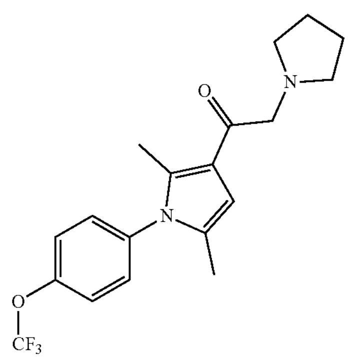 [SMILES: Cc1cc(C(=O)CN2CCCC2)c(C)n1-c1ccc(OC(F)(F)F)cc1] | II |
| 62 | 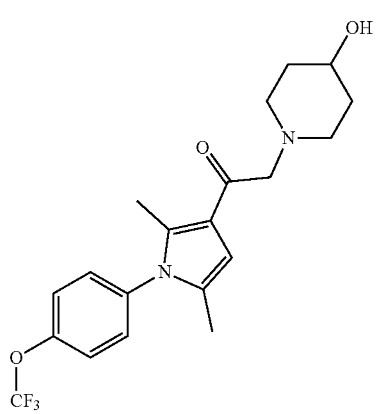 [SMILES: Cc1cc(C(=O)CN2CCC(O)CC2)c(C)n1-c1ccc(OC(F)(F)F)cc1] | II |

TABLE 5-continued

| Compound No. | Chemical Structure | IC$_{50}$ Category |
|---|---|---|
| 63 | 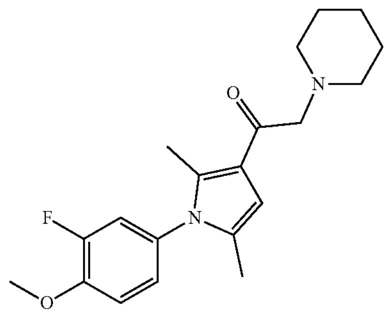 [SMILES: COc1ccc(-n2c(C)cc(C(=O)CN3CCCCC3)c2C)cc1F] | II |
| 64 | 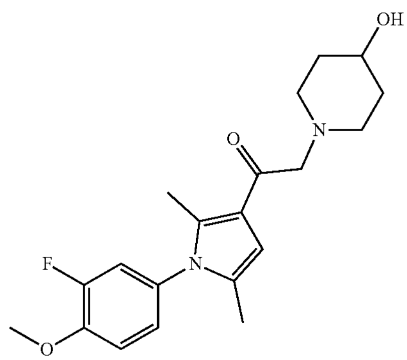 [SMILES: COc1ccc(-n2c(C)cc(C(=O)CN3CCC(O)CC3)c2C)cc1F] | II |
| 65 | 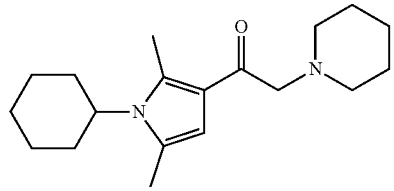 [SMILES: Cc1cc(C(=O)CN2CCCCC2)c(C)n1C1CCCCC1] | II |
| 66 | 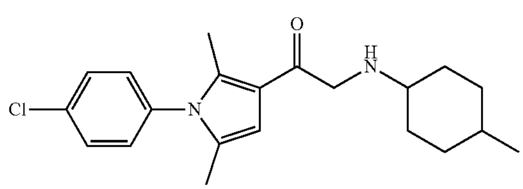 [SMILES: Cc1cc(C(=O)CNC2CCC(C)CC2)c(C)n1-c1ccc(Cl)cc1] | II |
| 67 | 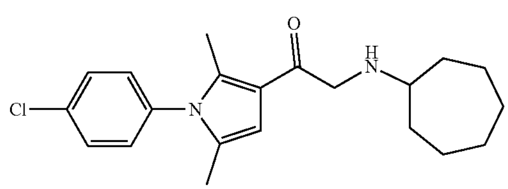 [SMILES: Cc1cc(C(=O)CNC2CCCCCC2)c(C)n1-c1ccc(Cl)cc1] | II |
| 68 | 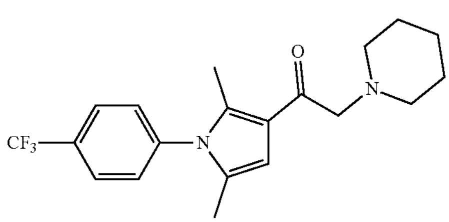 [SMILES: Cc1cc(C(=O)CN2CCCCC2)c(C)n1-c1ccc(C(F)(F)F)cc1] | II |

TABLE 5-continued
| Compound No. | Chemical Structure | IC$_{50}$ Category |
|---|---|---|
| 69 | 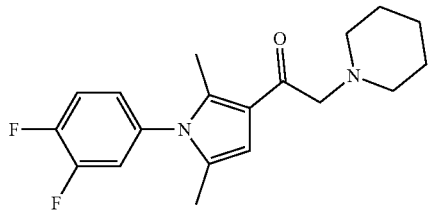 [SMILES: Cc1cc(C(=O)CN2CCCCC2)c(C)n1-c1ccc(F)c(F)c1] | II |
| 70 | 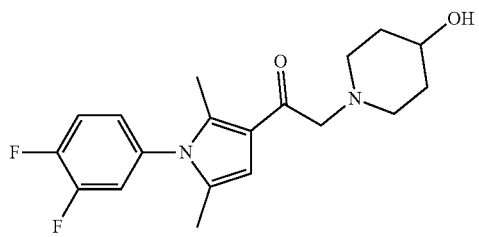 [SMILES: Cc1cc(C(=O)CN2CCC(O)CC2)c(C)n1-c1ccc(F)c(F)c1] | II |
| 71 | 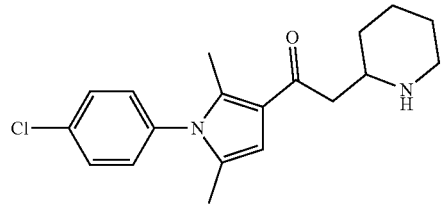 [SMILES: Cc1cc(C(=O)CC2CCCCN2)c(C)n1-c1ccc(Cl)cc1] | II |
| 72 | 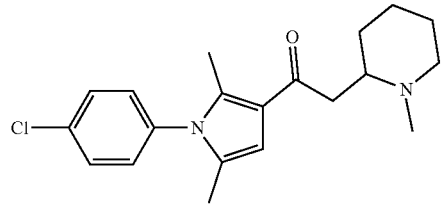 [SMILES: Cc1cc(C(=O)CC2CCCCN2C)c(C)n1-c1ccc(Cl)cc1] | II |
| 73 | 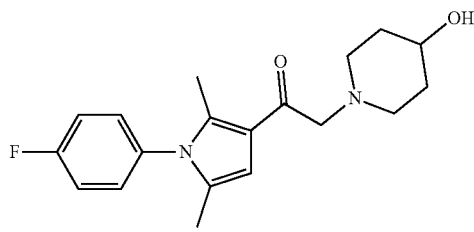 [SMILES: Cc1cc(C(=O)CN2CCC(O)CC2)c(C)n1-c1ccc(F)cc1] | II |
| 74 | 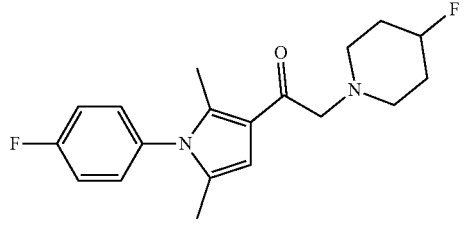 [SMILES: Cc1cc(C(=O)CN2CCC(F)CC2)c(C)n1-c1ccc(F)cc1] | II |

TABLE 5-continued

| Compound No. | Chemical Structure | IC$_{50}$ Category |
|---|---|---|
| 75 | 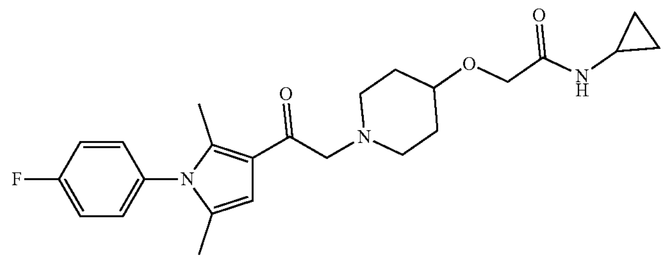 [SMILES: Cc1cc(C(=O)CN2CCC(OCC(=O)NC3CC3)CC2)c(C)n1-c1ccc(F)cc1] | II |
| 76 | 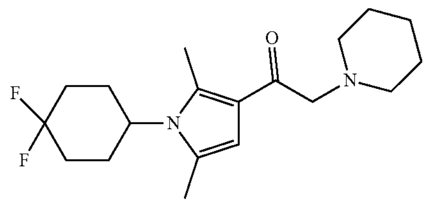 [SMILES: Cc1cc(C(=O)CN2CCCCC2)c(C)n1C1CCC(F)(F)CC1] | II |
| 77 | 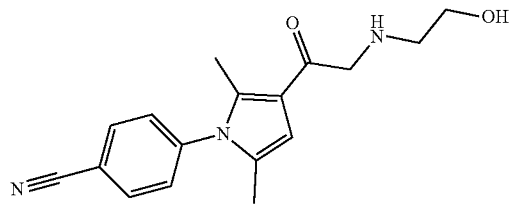 [SMILES: Cc1cc(C(=O)CNCCO)c(C)n1-c1ccc(C#N)cc1] | II |
| 79 | 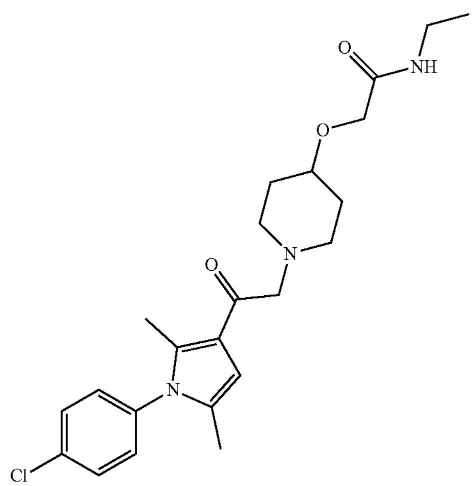 [SMILES: CCNC(=O)COC1CCN(CC(=O)c2cc(C)n(-c3ccc(Cl)cc3)c2C)CC1] | III |
| 80 | 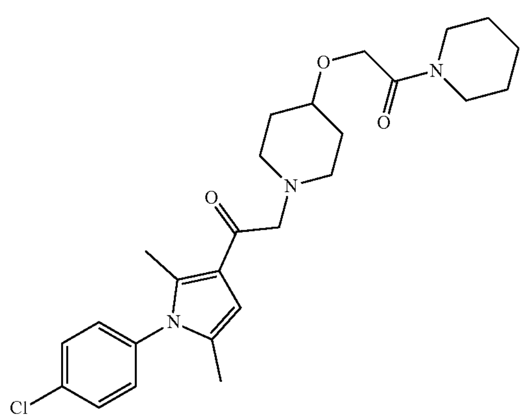 [SMILES: Cc1cc(C(=O)CN2CCC(OCC(=O)N3CCCCC3)CC2)c(C)n1-c1ccc(Cl)cc1] | III |

TABLE 5-continued
| Compound No. | Chemical Structure | IC$_{50}$ Category |
|---|---|---|
| 81 | 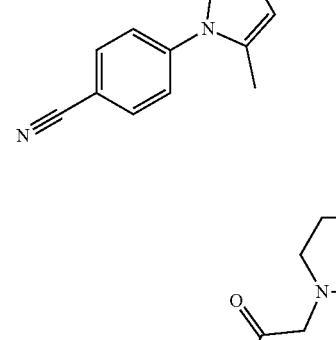 | III |
| 82 | 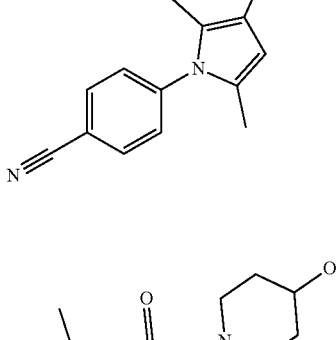 | III |
| 83 | 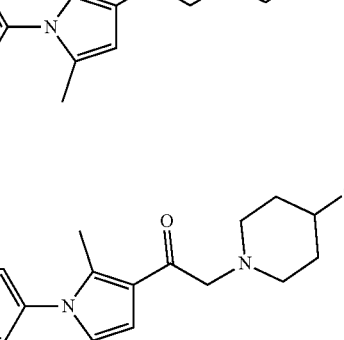 | III |
| 84 | 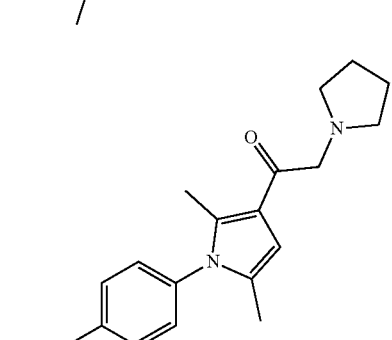 | III |
| 85 | 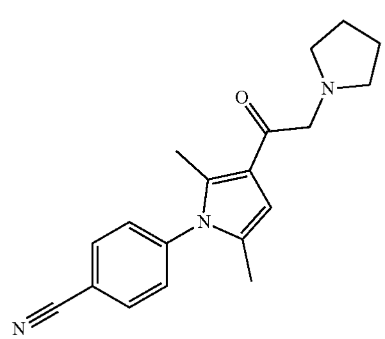 [SMILES: Cc1cc(C(=O)CN2CCCC2)c(C)n1-c1ccc(C#N)cc1] | III |

TABLE 5-continued

| Compound No. | Chemical Structure | IC$_{50}$ Category |
|---|---|---|
| 89A and 89B | | III, III |
| 90 | 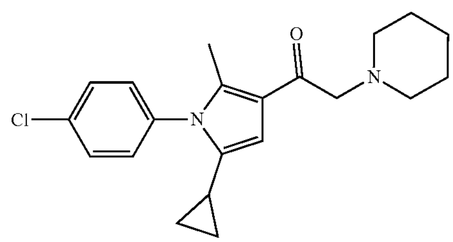 [SMILES: Cc1c(C(=O)CN2CCCCC2)cc(C2CC2)n1-c1ccc(Cl)cc1] | III |
| 91 | 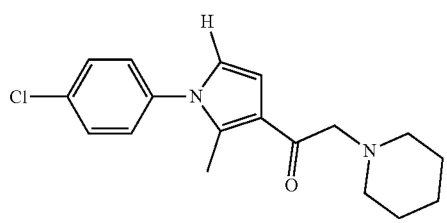 [SMILES: Cc1c(C(=O)CN2CCCCC2)ccn1-c1ccc(Cl)cc1] | III |
| 92 | 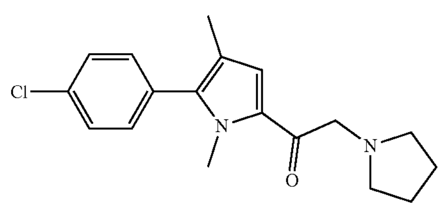 [SMILES: Cc1cc(C(=O)CN2CCCC2)n(C)c1-c1ccc(Cl)cc1] | III |
| 93 | 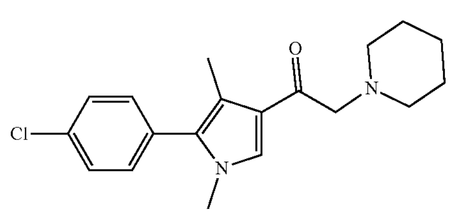 [SMILES: Cc1c(C(=O)CN2CCCCC2)cn(C)c1-c1ccc(Cl)cc1] | III |
| 94 | 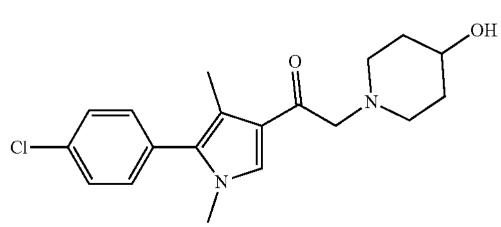 [SMILES: Cc1c(C(=O)CN2CCC(O)CC2)cn(C)c1-c1ccc(Cl)cc1] | III |

TABLE 5-continued

| Compound No. | Chemical Structure | IC$_{50}$ Category |
|---|---|---|
| 95 | 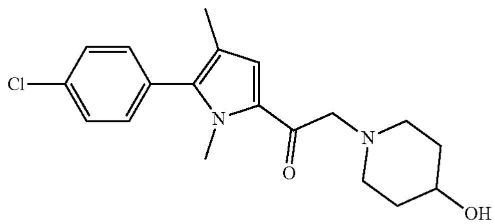 [SMILES: Cc1cc(C(=O)CN2CCC(O)CC2)n(C)c1-c1ccc(Cl)cc1] | III |
| 96 | 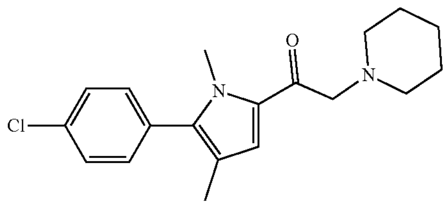 [SMILES: Cc1cc(C(=O)CN2CCCCC2)n(C)c1-c1ccc(Cl)cc1] | III |
| 97 | 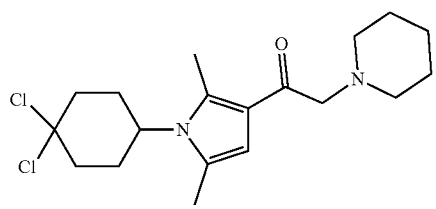 [SMILES: Cc1cc(C(=O)CN2CCCCC2)c(C)n1C1CCC(Cl)(Cl)CC1] | III |
| 99 | 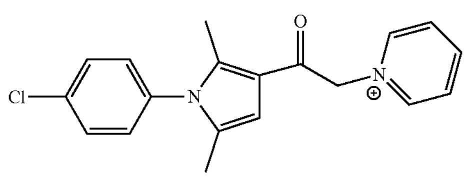 [SMILES: Cc1cc(C(=O)C[n+]2ccccc2)c(C)n1-c1ccc(Cl)cc1] | III |
| 100 | 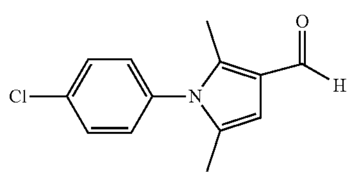 [SMILES: Cc1cc(C=O)c(C)n1-c1ccc(Cl)cc1] | I |
| 101 | 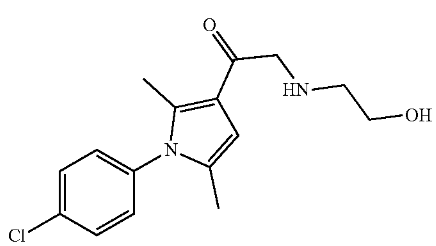 [SMILES: Cc1cc(C(=O)CNCCO)c(C)n1-c1ccc(Cl)cc1] | I |
| 102 | 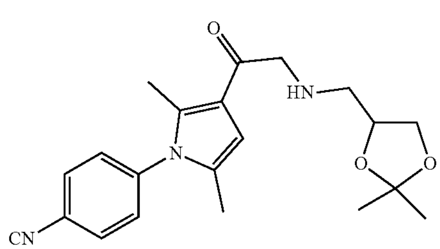 | I |

TABLE 5-continued

| Compound No. | Chemical Structure | IC$_{50}$ Category |
|---|---|---|
| 103 | 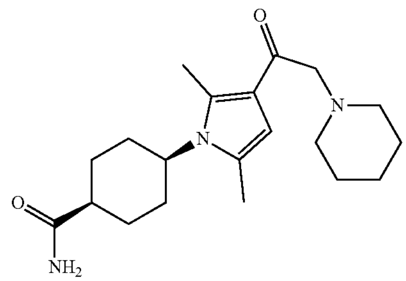 [SMILES: Cc1cc(C(=O)CN2CCCCC2)c(C)n1[C@H]1CC[C@@H](C(N)=O)CC1] | I |
| 105 | 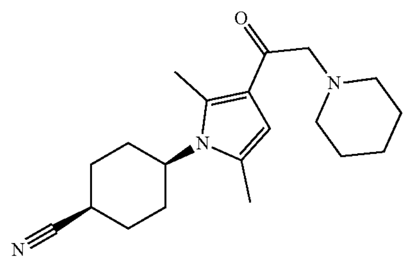 [SMILES: Cc1cc(C(=O)CN2CCCCC2)c(C)n1[C@H]1CC[C@@H](C#N)CC1] | I |
| 107 | 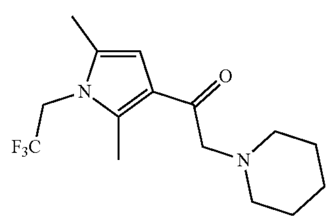 [SMILES: Cc1cc(C(=O)CN2CCCCC2)c(C)n1CC(F)(F)F] | I |
| 110 | 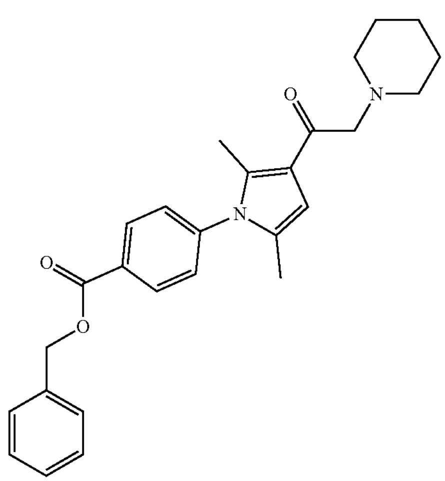 [SMILES: Cc1cc(C(=O)CN2CCCCC2)c(C)n1-c1ccc(C(=O)OCc2ccccc2)cc1] | I |

TABLE 5-continued

| Compound No. | Chemical Structure | IC$_{50}$ Category |
|---|---|---|
| 111 | 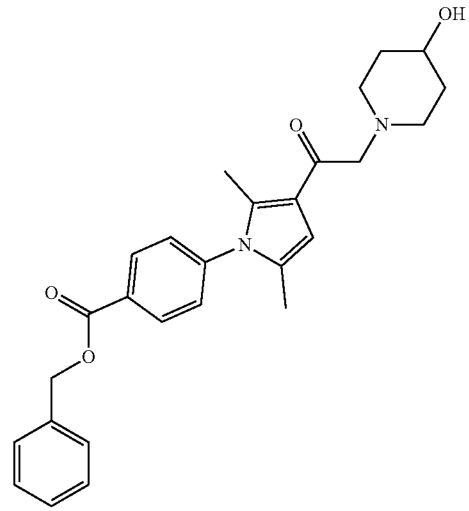 [SMILES: Cc1cc(C(=O)CN2CCC(O)CC2)c(C)n1-c1ccc(C(=O)OCc2ccccc2)cc1] | I |
| 112 | 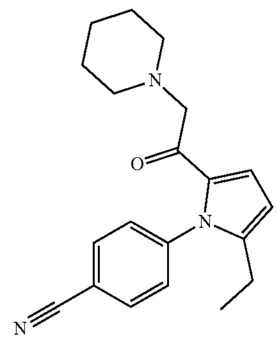 [SMILES: CCc1ccc(C(=O)CN2CCCCC2)n1-c1ccc(C#N)cc1] | I |
| 113 | 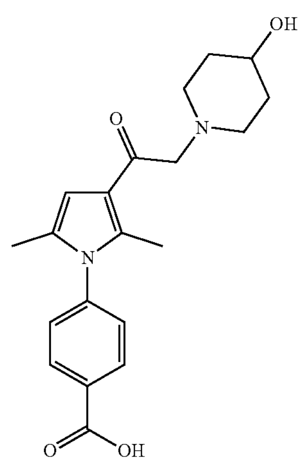 [SMILES: Cc1cc(C(=O)CN2CCC(O)CC2)c(C)n1-c1ccc(C(=O)O)cc1] | I |
| 114 | 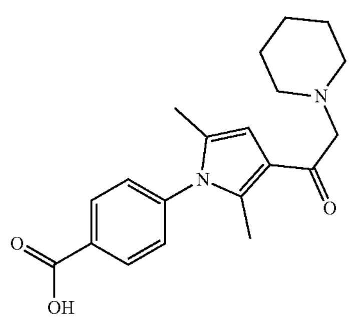 [SMILES: Cc1cc(C(=O)CN2CCCCC2)c(C)n1-c1ccc(C(=O)O)cc1] | I |

TABLE 5-continued
| Compound No. | Chemical Structure | IC$_{50}$ Category |
|---|---|---|
| 117 | 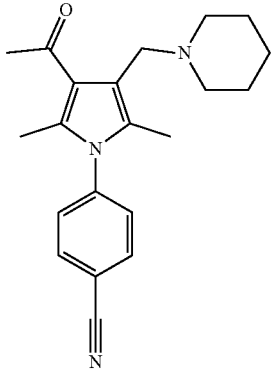 [SMILES: CC(=O)c1c(CN2CCCCC2)c(C)n(-c2ccc(C#N)cc2)c1C] | I |
| 120 | 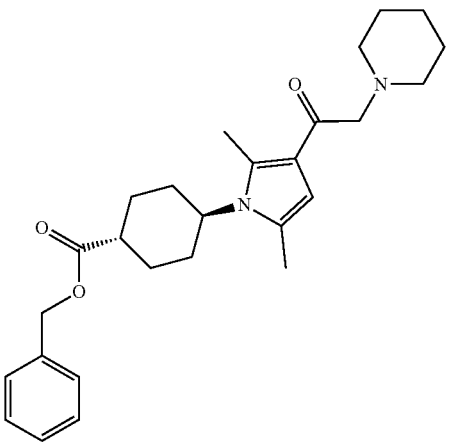 [SMILES: Cc1cc(C(=O)CN2CCCCC2)c(C)n1[C@H]1CC[C@H](C(=O)OCc2ccccc2)CC1] | |
| 121 | 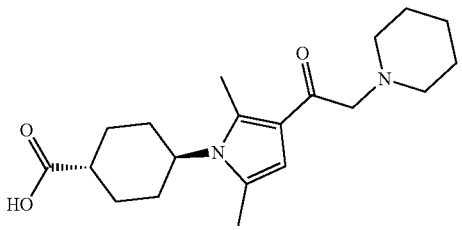 [SMILES: Cc1cc(C(=O)CN2CCCCC2)c(C)n1[C@H]1CC[C@H](C(=O)O)CC1] | I |
| 122 | 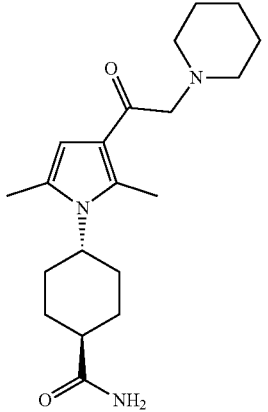 [SMILES: Cc1cc(C(=O)CN2CCCCC2)c(C)n1[C@H]1CC[C@H](C(N)=O)CC1] | I |

TABLE 5-continued

| Compound No. | Chemical Structure | IC$_{50}$ Category |
| --- | --- | --- |
| 134 | 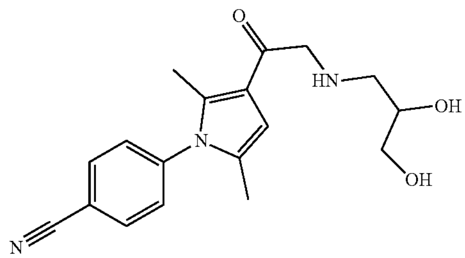 [SMILES: Cc1cc(C(=O)CNCC(O)CO)c(C)n1-c1ccc(C#N)cc1] | II |
| 135 | 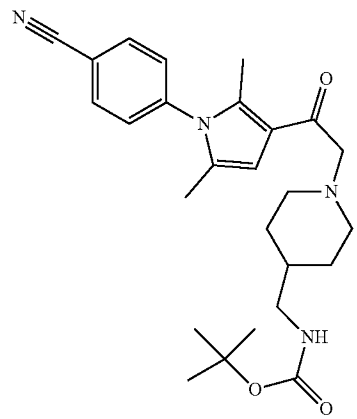 [SMILES: Cc1cc(C(=O)CN2CCC(CNC(=O)OC(C)(C)C)CC2)c(C)n1-c1ccc(C#N)cc1] | II |
| 136 | 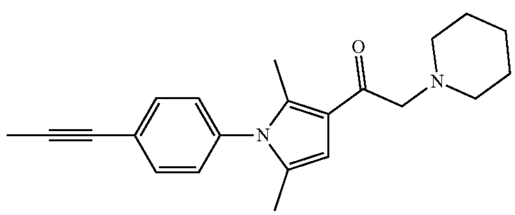 [SMILES: CC#Cc1ccc(-n2c(C)cc(C(=O)CN3CCCCC3)c2C)cc1] | II |
| 137 | 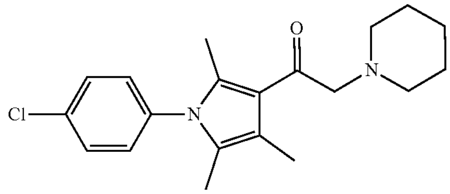 [SMILES: Cc1c(C(=O)CN2CCCCC2)c(C)n(-c2ccc(Cl)cc2)c1C] | II |
| 138 | 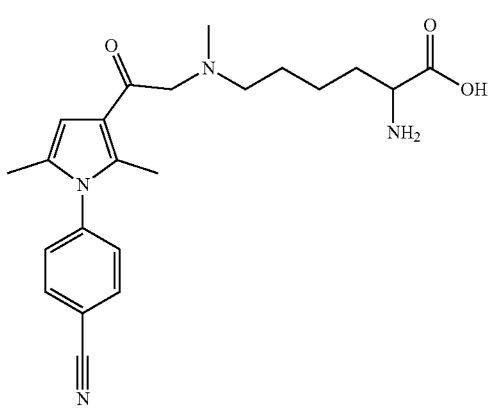 [SMILES: Cc1cc(C(=O)CN(C)CCCCC(N)C(=O)O)c(C)n1-c1ccc(C#N)cc1] | II |

TABLE 5-continued

| Compound No. | Chemical Structure | IC$_{50}$ Category |
| --- | --- | --- |
| 139 | 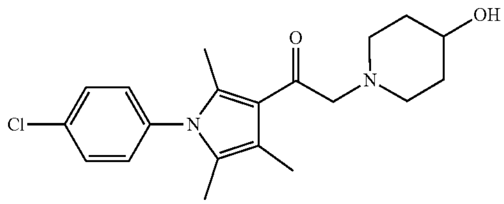 [SMILES: Cc1c(C(=O)CN2CCC(O)CC2)c(C)n(-c2ccc(Cl)cc2)c1C] | II |
| 140 | 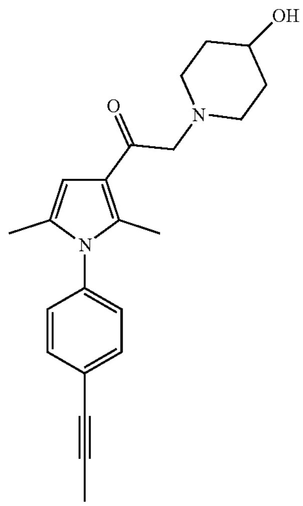 [SMILES: CC#Cc1ccc(-n2c(C)cc(C(=O)CN3CCC(O)CC3)c2C)cc1] | II |
| 143 | 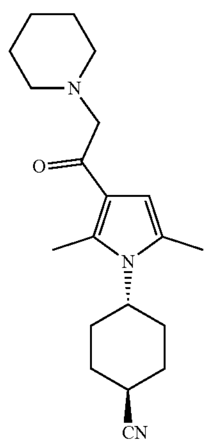 [SMILES: Cc1cc(C(=O)CN2CCCCC2)c(C)n1[C@H]1CC[C@H](C#N)CC1] | II |
| 157 | 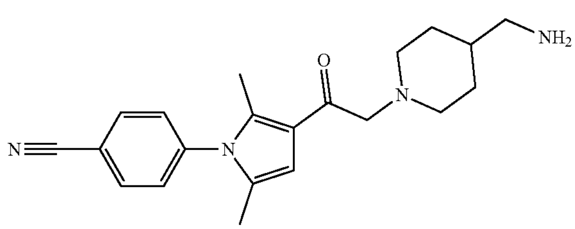 [SMILES: Cc1cc(C(=O)CN2CCC(CN)CC2)c(C)n1-c1ccc(C#N)cc1] | III |

TABLE 5-continued

| Compound No. | Chemical Structure | IC$_{50}$ Category |
|---|---|---|
| 158 | 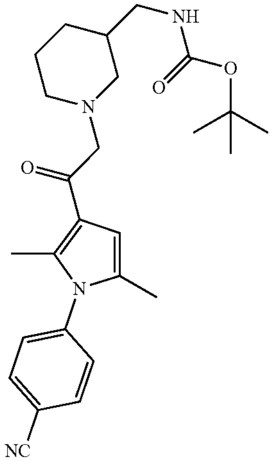 [SMILES: Cc1cc(C(=O)CN2CCCC(CNC(=O)OC(C)(C)C)C2)c(C)n1-c1ccc(C#N)cc1] | III |
| 159 | 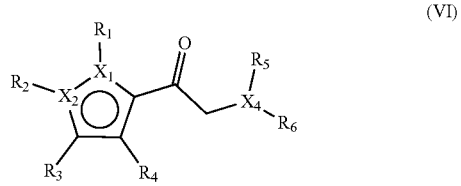 | III |

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound having a structure of Formula (VI):

(VI)

or a pharmaceutically acceptable salt or solvate thereof;
wherein:
$X_1$ and $X_2$ are independently carbon or nitrogen, wherein one of $X_1$ and $X_2$ is nitrogen;
$X_4$ is N;
$R_1$ is hydrogen or $C_{1-4}$ alkyl;
$R_2$ is selected from the group consisting of optionally substituted cyclobutyl and substituted cyclohexyl;
$R_3$ and $R_4$ are each independently selected from the group consisting of hydrogen, $C_{1-4}$ alkyl, and $C_{3-8}$ cycloalkyl; and
$R_5$ and $R_6$ are each independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl;
or $R_5$ and $R_6$ combine with $X_4$ to form an optionally substituted 5-membered heterocyclic, an optionally substituted 6-membered heterocycle, an optionally substituted 5-membered heteroaryl, or an optionally substituted 6-membered heteroaryl;
wherein substituents of optionally substituted $R_2$, $R_5$, and $R_6$ are each independently selected from the group consisting of $C_{1-4}$ alkyl optionally substituted with $OR_c$ or $NR_dR_d$; CN; halo; $C_{1-4}$ haloalkyl; $C_{2-4}$ alkynyl; $C_{4-6}$ cycloalkyl; 5-membered heterocyclic optionally substituted with $C_{1-4}$ alkyl; $OR_c$; $COR_c$; $COOR_c$; $NR_dR_d$; $CONR_dR_d$; $OCONR_dR_d$; $S(O)_nR_c$; and $S(O)_nNR_dR_d$;
wherein each $R_c$ is independently selected from the group consisting of hydrogen, $C_{1-4}$ alkyl optionally substituted with phenyl or $CONR_dR_d$; $C_{1-4}$ haloalkyl; phenyl; and heteroaryl optionally substituted with —$CH_3$ or phenyl; and
each $R_d$ is independently selected from the group consisting of hydrogen, $C_{1-4}$ alkyl, $COOC_{1-4}$ alkyl, $C_3$-$C_{12}$ cycloalkyl, and heteroaryl optionally substituted with —$OC_{1-4}$ alkyl;
or two $R_d$ together with the nitrogen atom to which they are attached form a 3-6-membered heterocyclic; and
each n is independently 0, 1 or 2.

2. The compound of claim 1, or a pharmaceutically acceptable salt or solvate thereof, wherein $X_1$ is carbon, and $X_2$ and $X_4$ are each nitrogen.

3. The compound of claim 1, or a pharmaceutically acceptable salt or solvate thereof, wherein $R_2$ is optionally substituted cyclobutyl.

4. The compound of claim 1, or a pharmaceutically acceptable salt or solvate thereof, wherein $R_2$ is substituted cyclohexyl.

5. The compound of claim 1, or a pharmaceutically acceptable salt or solvate thereof, wherein $R_5$ and $R_6$ combine with $X_4$ to form an optionally substituted 5-membered heterocyclic or an optionally substituted 6-membered heterocyclic.

6. The compound of claim 1, wherein said compound has a structure of Formula (VII):

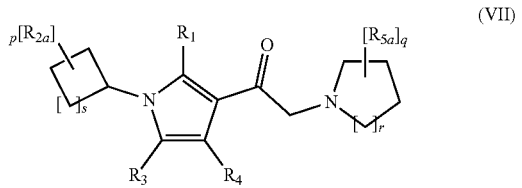

or a pharmaceutically acceptable salt or solvate thereof; wherein:

$R_3$ and $R_4$ are each independently selected from the group consisting of hydrogen, $C_{1-4}$ alkyl, and $C_{3-8}$ cycloalkyl;

each $R_{2a}$ is independently selected from the group consisting of hydrogen, $C_{1-4}$ alkyl, $C_{1-4}$ haloalkyl, halo, CN, $CONH_2$, COOH, and COO-benzyl;

each $R_{5a}$ is independently selected from the group consisting of hydrogen and OH;

each p is independently 0, 1 or 2;

q is 0, 1 or 2;

r is 1 or 2; and s is 1 or 3;

wherein when s is 3, then p is 1 or 2, and each $R_{2a}$ is independently selected from the group consisting of $C_{1-4}$ alkyl, $C_{1-4}$ haloalkyl, halo, CN, $CONH_2$, COOH, and COO-benzyl.

7. The compound of claim 1, or a pharmaceutically acceptable salt or solvate thereof, selected from the group consisting of:

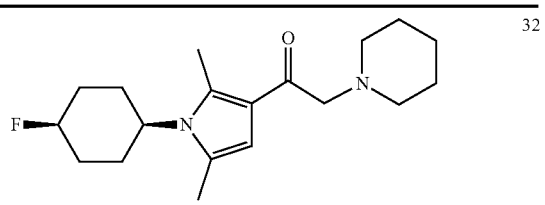

32

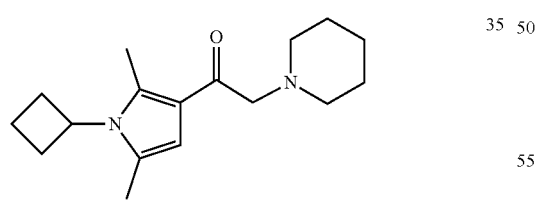

35

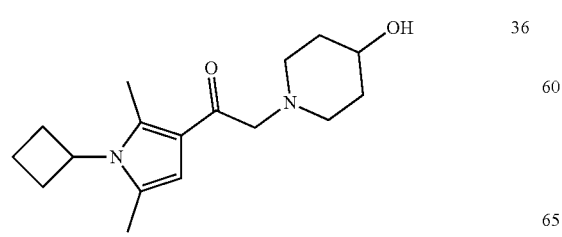

36

-continued

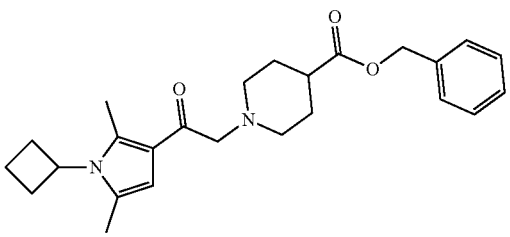 [SMILES: Cc1cc(C(=O)CN2CCC(C(=O)OCc3ccccc3)CC2)c(C)n1C1CCC1]

37

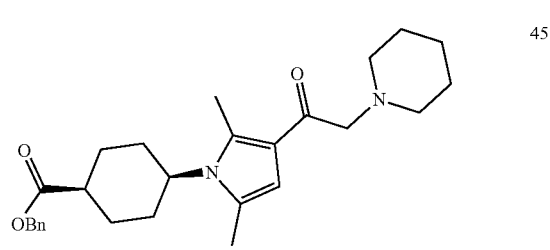

45

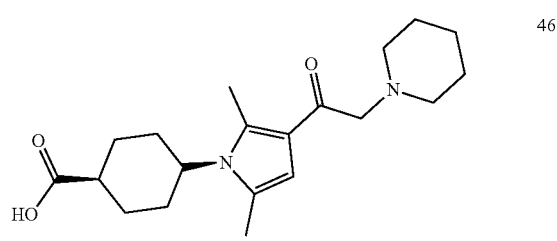

46

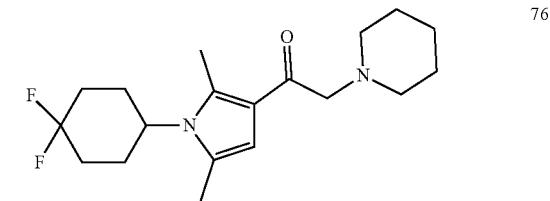

76

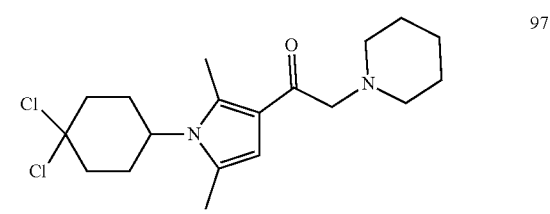

97

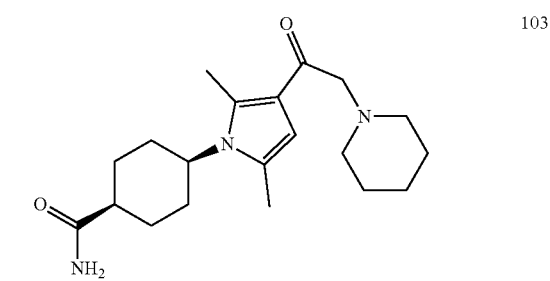

103

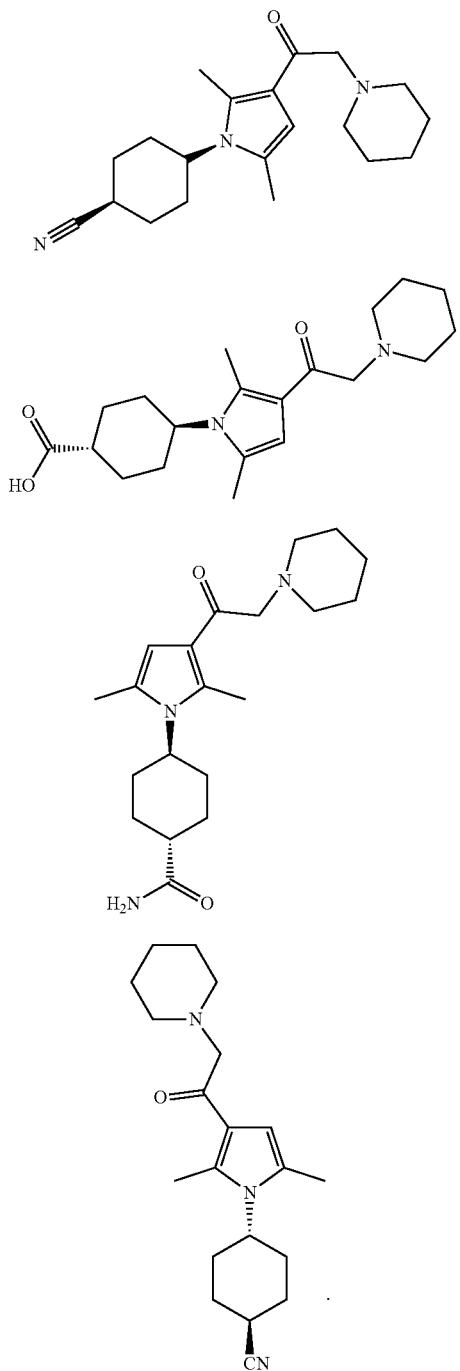

8. A compound having a structure of Formula (VIII):

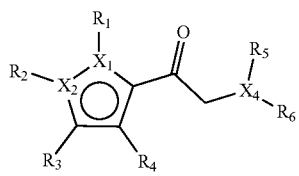

or a pharmaceutically acceptable salt or solvate thereof; wherein:

$X_1$ and $X_2$ are independently carbon or nitrogen, wherein one of $X_1$ and $X_2$ is nitrogen;

$X_4$ is N or $C(R_7)$;

$R_1$ is selected from the group consisting of substituted $C_{3-8}$ cycloalkyl, and phenyl substituted with at least one halogen;

$R_2$ is hydrogen or $C_{1-4}$ alkyl;

$R_3$ and $R_4$ are each independently selected from the group consisting of hydrogen, $C_{1-4}$ alkyl, and $C_{3-8}$ cycloalkyl;

$R_5$ and $R_6$ are each independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$cycloalkenyl, optionally substituted heterocyclic, optionally substituted aryl, and optionally substituted heteroaryl;

or $R_5$ and $R_6$ combine with $X_4$ to form an optionally substituted 5-6-membered heterocyclic, or an optionally substituted 5-6-membered heteroaryl; and $R_7$ is hydrogen or $C_{1-4}$alkyl;

wherein substituents of optionally substituted $R_1$, $R_5$, and $R_6$ are each independently selected from the group consisting of $C_{1-4}$ alkyl optionally substituted with $OR_c$ or $NR_dR_d$; CN; halo; $C_{1-4}$ haloalkyl; $C_{2-4}$ alkynyl; $C_{4-6}$ cycloalkyl; 5-membered heterocyclic optionally substituted with $C_{1-4}$ alkyl; $OR_c$; $COR_E$; $COOR_c$; $NR_dR_d$; $CONR_dR_d$; $OCONR_dR_d$; $S(O)_nR_c$ and $S(O)_nNR_dR_d$;

wherein each $R_c$ is independently selected form the group consisting of hydrogen, $C_{1-4}$ alkyl optionally substituted with phenyl or $CONR_dR_d$; $C_{1-4}$ haloalkyl; phenyl and heteroaryl optionally substituted with —$CH_3$ or phenyl; and each $R_d$ is independently selected from the group consisting of hydrogen, $C_{1-4}$ alkyl, $COOC_{1-4}$ alkyl, $C_3$-$C_{12}$ cycloalkyl, and heteroaryl optionally substituted with —$OC_{1-4}$ alkyl;

or two $R_d$ together with the nitrogen atom to which they are attached from a 3-6-membered heterocyclic;

each n is independently 0, 1 or 2.

9. The compound of claim 8, or a pharmaceutically acceptable salt or solvate thereof, wherein $X_1$ and $X_4$ are each nitrogen, and $X_2$ is carbon.

10. The compound of claim 8, or a pharmaceutically acceptable salt or solvate thereof, wherein $R_1$ is phenyl substituted with at least one halogen.

11. The compound of claim 10, or a pharmaceutically acceptable salt or solvate thereof, wherein the phenyl is substituted with at least one $C_{1-4}$ alkyl and at least one halogen.

12. The compound of claim 8, or a pharmaceutically acceptable salt or solvate thereof, wherein $R_2$, $R_3$ and $R_4$ are each hydrogen.

13. The compound of claim 8, or a pharmaceutically acceptable salt or solvate thereof, wherein $R_5$ and $R_6$ combine with $X_4$ to form an optionally substituted 5-6-membered heterocyclic, or an optionally substituted 5-6-membered heteroaryl.

14. The compound of claim 8, or a pharmaceutically acceptable salt or solvate thereof, wherein said compound is selected from the group consisting of

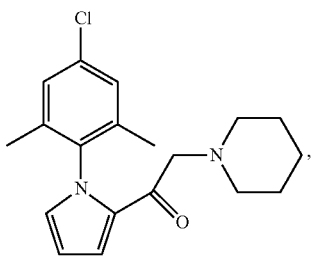 [SMILES: Cc1cc(Cl)cc(C)c1-n1cccc1C(=O)CN1CCCCC1]

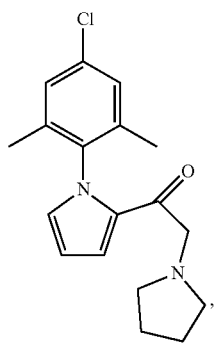 [SMILES: Cc1cc(Cl)cc(C)c1-n1cccc1C(=O)CN1CCCC1]

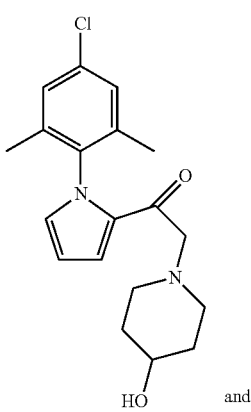 [SMILES: Cc1cc(Cl)cc(C)c1-n1cccc1C(=O)CN1CCC(O)CC1]

and

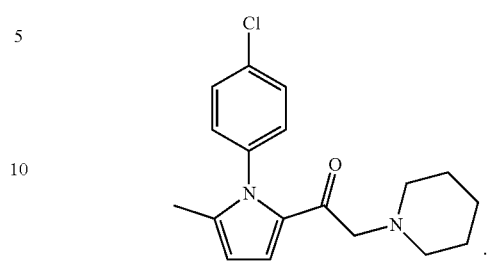

15. A compound having a structure of Formula (IX):

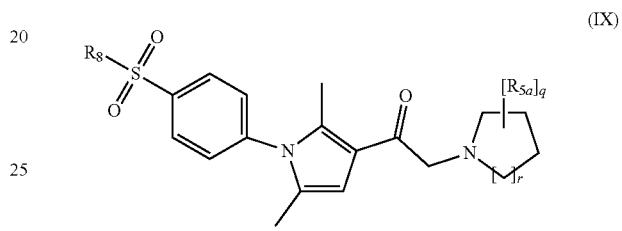

(IX)

or a pharmaceutically acceptable salt or solvate thereof; wherein:

$R_8$ is $NR_{8a}R_{8b}$, wherein $R_{8a}$ is selected from the group consisting of $C_{5-6}$ aryl and 5-6-membered heteroaryl, optionally substituted with —$OC_{1-4}$ alkyl, and wherein $R_{8b}$ is hydrogen;

each $R_{5a}$ is independently selected from the group consisting of hydrogen, $C_{1-4}$ alkyl optionally substituted with $OR_c$ or $NR_dR_d$, halo, $C_{1-4}$ haloalkyl, $OR_c$, $COOR_c$, $NR_dR_d$, $CONR_dR_d$, $OCONR_dR_d$, and $S(O)_nR_c$;

each $R_c$ is independently selected from the group consisting of hydrogen, $C_{1-4}$ alkyl optionally substituted with phenyl or $CONR_dR_d$, $C_{1-4}$ haloalkyl, phenyl, and heteroaryl optionally substituted with —$CH_3$ or phenyl;

each $R_d$ is independently selected from the group consisting of hydrogen, $C_{1-4}$ alkyl, $COOC_{1-4}$ alkyl, $C_3$-$C_{12}$ cycloalkyl, and heteroaryl optionally substituted with —$OCH_3$;

or two $R_d$ together form a heterocyclic;

each n is independently 0, 1 or 2;

q is 0, 1 or 2; and r is 1 or 2.

16. The compound of claim 15, or a pharmaceutically acceptable salt or solvate thereof, wherein $R_{8a}$ is pyrimidinyl.

17. The compound of claim 16, or a pharmaceutically acceptable salt or solvate thereof, wherein $R_{8a}$ is substituted with methoxy.

18. The compound of claim 15, or a pharmaceutically acceptable salt or solvate thereof, wherein r is 2.

19. A compound, or a pharmaceutically acceptable salt or solvate thereof, selected from the group consisting of:

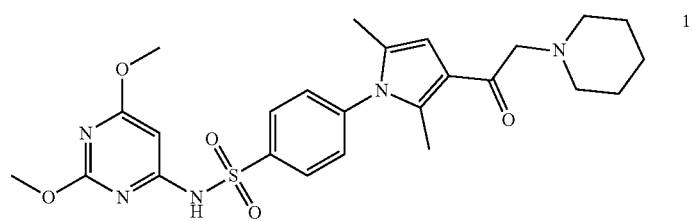
1
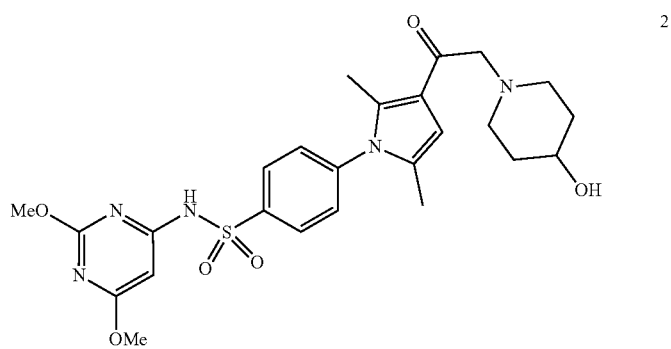
2
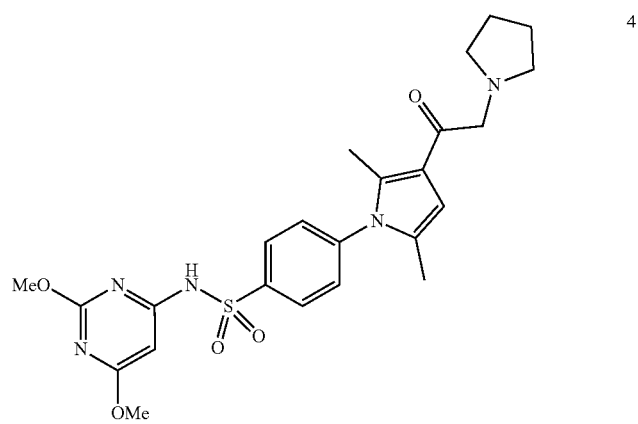
4
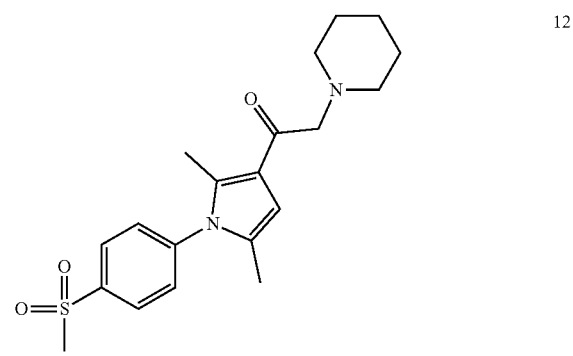
12

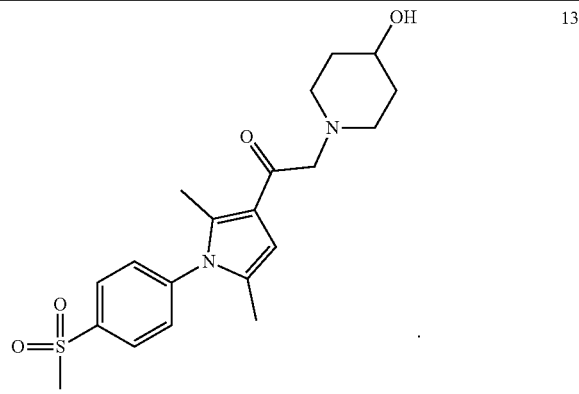
13

20. A compound having a structure of Formula (X):

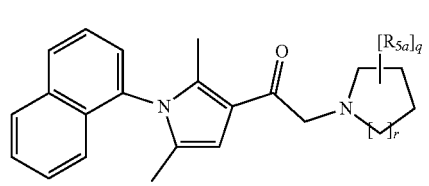
(X)

or a pharmaceutically acceptable salt or solvate thereof; wherein:
each $R_{5a}$ is independently selected from the group consisting of hydrogen, $C_{1-4}$ alkyl optionally substituted with $OR_c$ or $NR_dR_d$, halo, $C_{1-4}$ haloalkyl, $OR_c$, $COOR_c$, $NR_dR_d$, $CONR_dR_d$, $OCONR_dR_d$, and $S(O)_nR_c$;
each $R_c$ is independently selected from the group consisting of hydrogen, $C_{1-4}$ alkyl optionally substituted with phenyl or $CONR_dR_d$, $C_{1-4}$ haloalkyl, phenyl, and heteroaryl optionally substituted with —$CH_3$ or phenyl;
each $R_d$ is independently selected from the group consisting of hydrogen, $C_{1-4}$ alkyl, $COOC_{1-4}$ alkyl, $C_3$-$C_{12}$ cycloalkyl, and heteroaryl optionally substituted with —$OCH_3$;
or two $R_d$ together form a heterocyclic;
each n is independently 0, 1 or 2;
q is 0, 1 or 2; and
r is 1 or 2.

21. The compound of claim 20, or a pharmaceutically acceptable salt or solvate thereof, selected from the group consisting of:

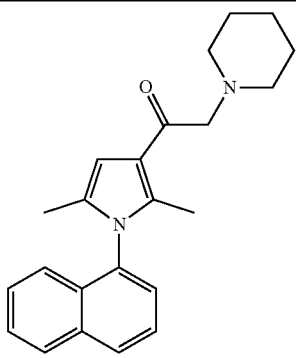
5

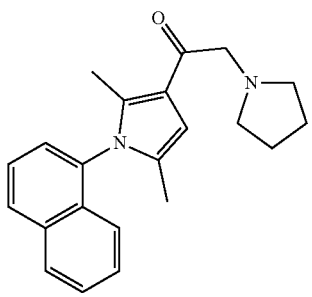 [SMILES: Cc1cc(C(=O)CN2CCCC2)c(C)n1-c1cccc2ccccc12]
8

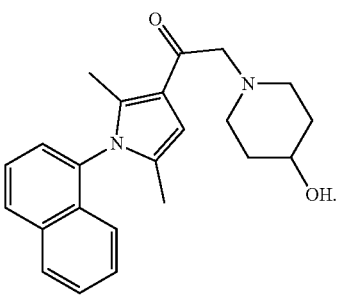 [SMILES: Cc1cc(C(=O)CN2CCC(O)CC2)c(C)n1-c1cccc2ccccc12]
9

22. The pharmaceutical composition comprising a compound of claim 1, or a pharmaceutically acceptable salt or solvate thereof, and a pharmaceutically acceptable carrier or excipient.

23. The pharmaceutical composition comprising a compound of claim 8, or a pharmaceutically acceptable salt or solvate thereof, and a pharmaceutically acceptable carrier or excipient.

24. The pharmaceutical composition comprising a compound of claim 15, or a pharmaceutically acceptable salt or solvate thereof, and a pharmaceutically acceptable carrier or excipient.

25. The pharmaceutical composition comprising a compound of claim 20, or a pharmaceutically acceptable salt or solvate thereof, and a pharmaceutically acceptable carrier or excipient.

* * * * *